US012516374B2

(12) United States Patent
Zheng et al.

(10) Patent No.: US 12,516,374 B2
(45) Date of Patent: Jan. 6, 2026

(54) CYANINE DERIVATIVES AND RELATED USES

(71) Applicant: Element Biosciences, Inc., San Diego, CA (US)

(72) Inventors: Genhua Zheng, San Diego, CA (US); Njoo Audrey Wibawa, San Diego, CA (US); Xi Zhang, San Diego, CA (US); Zhimin Yang, San Diego, CA (US); Marcus James Jellen, San Diego, CA (US); Gene Shen, San Diego, CA (US)

(73) Assignee: Element Biosciences, Inc., San Diego, CA (US)

( * ) Notice: Subject to any disclaimer, the term of this patent is extended or adjusted under 35 U.S.C. 154(b) by 0 days.

(21) Appl. No.: 18/424,417

(22) Filed: Jan. 26, 2024

(65) Prior Publication Data

US 2024/0240249 A1 Jul. 18, 2024

Related U.S. Application Data

(63) Continuation of application No. PCT/US2023/082907, filed on Dec. 7, 2023.

(60) Provisional application No. 63/430,993, filed on Dec. 7, 2022.

(51) Int. Cl.

| | |
|---|---|
| ***C09B 23/06*** | (2006.01) |
| ***C09B 23/10*** | (2006.01) |
| ***C12Q 1/48*** | (2006.01) |
| ***C12Q 1/68*** | (2018.01) |
| ***C12Q 1/6874*** | (2018.01) |

(52) U.S. Cl.

CPC ............ *C12Q 1/6874* (2013.01); *C09B 23/06* (2013.01); *C09B 23/105* (2013.01); *C12Q 1/485* (2013.01); *G01N 2333/91245* (2013.01)

(58) Field of Classification Search

CPC .............................. C09B 23/06; C09B 23/105

See application file for complete search history.

(56) References Cited

U.S. PATENT DOCUMENTS

| | | | |
|---|---|---|---|
| 5,558,991 | A | 9/1996 | Trainor |
| 6,974,873 | B2 | 12/2005 | Leung et al. |
| 7,170,050 | B2 | 1/2007 | Turner et al. |
| 7,302,146 | B2 | 11/2007 | Turner et al. |
| 7,405,281 | B2 | 7/2008 | Xu et al. |
| 7,968,702 | B2 | 6/2011 | Wegener et al. |
| 8,252,910 | B2 | 8/2012 | Korlach et al. |
| 8,388,982 | B2 | 3/2013 | Kong et al. |
| 8,637,650 | B2 | 1/2014 | Cherkasov et al. |
| 8,889,886 | B2 * | 11/2014 | Yue ...................... C09B 23/105 548/455 |
| 8,906,612 | B2 | 12/2014 | Shen et al. |
| 8,927,212 | B2 | 1/2015 | Kong et al. |
| 9,062,091 | B2 | 6/2015 | Bjornson et al. |
| 9,200,311 | B2 | 12/2015 | Otto et al. |
| 9,441,270 | B2 * | 9/2016 | Yue ...................... C12Q 1/6876 |

(Continued)

FOREIGN PATENT DOCUMENTS

| | | | |
|---|---|---|---|
| WO | WO-0226891 | A1 | 4/2002 |
| WO | WO-2005111240 | A2 | 11/2005 |

(Continued)

OTHER PUBLICATIONS

Lin et al. Guangpuxue Yu Guangpu Fenxi (2007), 27(9), 1775-1779.(abstract only) (Year: 2007).*

(Continued)

*Primary Examiner* — Jezia Riley

(74) *Attorney, Agent, or Firm* — Fenwick & West LLP; Heidi A. Erlacher; Daniel Manson

(57) ABSTRACT

The present disclosure provides a compound of Formula (I), (II), or (III):

(I)

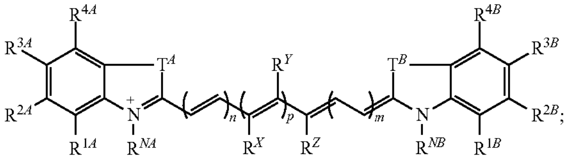

(II)

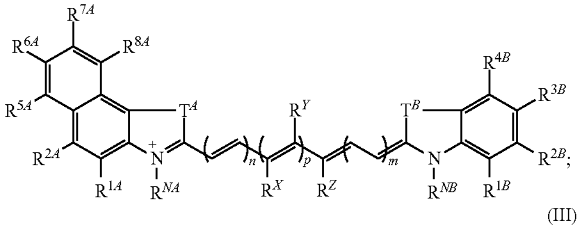

(III)

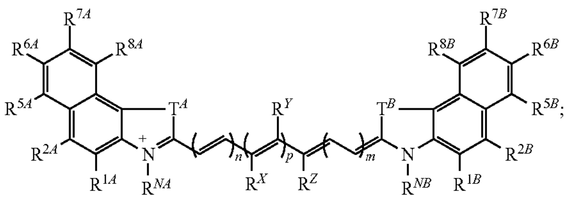

an ionic derivative thereof, an isomer thereof, or a salt thereof. The present disclosure also provides conjugates of the compounds, and methods of using the compounds and the conjugates. The disclosure also provides the use of the compounds and conjugates in methods of sequencing nucleic acids.

28 Claims, 15 Drawing Sheets

(56) References Cited

U.S. PATENT DOCUMENTS

| | | | | |
|---|---|---|---|---|
| 9,637,782 | B2 | 5/2017 | Shen et al. | |
| 9,957,291 | B2 | 5/2018 | Sebo et al. | |
| 10,233,490 | B2 | 3/2019 | Stapleton et al. | |
| 10,246,744 | B2 | 4/2019 | Vijayan et al. | |
| 10,669,299 | B2 | 6/2020 | Sebo et al. | |
| 10,731,141 | B2 | 8/2020 | Iyidogan | |
| 10,768,173 | B1 | 9/2020 | Arslan et al. | |
| 10,781,483 | B2 | 9/2020 | Sebo et al. | |
| 10,800,805 | B2 | 10/2020 | Sebo et al. | |
| 11,427,855 | B1 | 8/2022 | Arslan et al. | |
| 11,530,439 | B2 | 12/2022 | Francais et al. | |
| 11,624,089 | B2 | 4/2023 | Yue et al. | |
| 11,787,947 | B2 | 10/2023 | Knowlton et al. | |
| 11,859,171 | B2 | 1/2024 | Quake et al. | |
| 2002/0077487 | A1* | 6/2002 | Leung | A61K 41/0057 548/414 |
| 2009/0186343 | A1 | 7/2009 | Wang et al. | |
| 2012/0052506 | A1* | 3/2012 | Yue | C12Q 1/6876 435/6.12 |
| 2017/0145496 | A1* | 5/2017 | Sebo | C07H 19/10 |
| 2017/0313883 | A1* | 11/2017 | Park | C07D 209/10 |
| 2020/0231964 | A1 | 7/2020 | Ben-Yehezkel et al. | |
| 2020/0255668 | A1 | 8/2020 | Shin et al. | |
| 2022/0228063 | A1* | 7/2022 | Chappellet | C09K 19/3497 |
| 2022/0315614 | A1 | 10/2022 | Graham et al. | |

FOREIGN PATENT DOCUMENTS

| | | | |
|---|---|---|---|
| WO | WO-2008040994 | A2 | 4/2008 |
| WO | WO-2009105077 | A2 | 8/2009 |
| WO | WO 2010/096720 | A2 | 8/2010 |
| WO | WO-2010121163 | A2 | 10/2010 |
| WO | WO 2013/109859 | A1 | 7/2013 |
| WO | WO-2018045109 | A1 | 3/2018 |
| WO | WO-2019231568 | A1 | 12/2019 |
| WO | WO-2021146443 | A1 | 7/2021 |
| WO | WO-2021168155 | A1 | 8/2021 |
| WO | WO-2022129439 | A1 | 6/2022 |
| WO | WO-2022136402 | A1 | 6/2022 |
| WO | WO-2022155331 | A1 | 7/2022 |
| WO | WO-2022212280 | A1 | 10/2022 |
| WO | WO-2022243480 | A1 | 11/2022 |
| WO | WO-2024124008 | A2 | 6/2024 |

OTHER PUBLICATIONS

Eschenmoser, A., "Chemical Etiology of Nucleic Acid Structure," Science, Jun. 25, 1999, 284:2118-2124.

Ferraro, M. & Gotor, V., "Biocatalytic Selective Modifications of Conventional Nucleosides, Carbocyclic Nucleosides, and C-Nucleosides," Chem. Rev., 2000, 100:4319-4347.

Jeong, L.S. et al., "Structure-Activity Relationships of B-D-(2S,5R)- and α-D-(2S,5S)-1,3-Oxathiolanyl Nucleosides as Potential Anti-HIV Agents," J. Med. Chem., 1993, 36: 2627-2638.

Kim, H. O. et al., "1,3-Dioxolanylpurine Nucleosides (2R,4R) and (2R,4S) with Selective Anti-HIV-1 Activity in Human Lymphocytes," J. Med. Chem., 1993, 36:30-37.

Martinez, C. I. et al., "Acyclic Nucleoside Triphosphate Analogs as Terminators in Biocatalytic DNA Replication," Bioorganic & Medicinal Chemistry Letters, 1997, 7(23):3013-3016.

Martinez, C. I. et al., "An allylic/acyclic adenosine nucleoside triphosphate for termination of DNA synthesis by DNA template-dependent polymerases," Nucleic Acids Research, 1999, 27(5):1271-1274.

Wang, F. et al., "TEQUILA-seq: a versatile and low-cost method for targeted long-read RNA sequencing," Nat Commun., (2023); 14(1):4760, pp. 1-15.

Anderson, J.P. et al.; Fluorescent Structural DNA Nanoballs Functionalized with Phosphate-Linked Nucleotide Triphosphates. Nano Letters 10(3):788-792 (2010).

Chen, X., et al.; "Efficient in situ barcode sequencing using padlock probe-based BaristaSeq," Nucleic Acids Research; 46(4):e22 pp. 1-10 (2018).

Mignardi, M., et al.; "Fourth-generation sequencing in the cell and the clinic," Genome Med.; 6(4):31; pp. 1-4 (2014).

Altman, R. B. et al. "Cyanine Fluorophore Derivatives with Enhanced Photostability." Nature Methods, vol. 9, No. 1, Jan. 2012, pp. 68-73.

Altman, R. B. et al. "Enhanced Photostability of Cyanine Fluorophores Across the Visible Spectrum." Nature Methods, vol. 9, No. 5, May 2012, pp. 428-429.

Asher, W. B. et al. "Single-Molecule FRET Imaging of GPCR Dimers in Living Cells." Nature Methods, vol. 18, Apr. 2021, pp. 1-26.

Juette, M. F. et al. "The Bright Future of Single-Molecule Fluorescence Imaging." Current Opinion in Chemical Biology, vol. 20, Jun. 2014, pp. 103-111.

Martin, M. I. et al. "Leveraging Baird Aromaticity for Advancement of Bioimaging Applications." Journal of Physical Organic Chemistry, vol. 36, No. 1, Jan. 2023, pp. 1-7.

Zheng, Q. et al. "Ulta-Stable Organic Fluorophores for Single-Molecule Research." Chemical Society Reviews, vol. 43, No. 4, Feb. 2014, pp. 1044-1056.

* cited by examiner

Spacer:

Linkers:

11 atom Linker:

16 atom Linker:

23 atom Linker:

N3 Linker:

Linker 1:

Linker 2:

Linker 3:

Linker 4:

Linker 5:

Linker 6:

Molecular Weight: 352.35

Linker 7:

Molecular Weight: 449.42

Linker 8:

Molecular Weight: 518.57

Linker 9:

Molecular Weight: 615.64 dNTP-PA-$NH_2$:

dNTP-PA-11 Atom Linker-$NH_2$:

dNTP-PA-16 Atom Linker-$NH_2$:

dNTP-PA-23 Atom Linker-$NH_2$:

dNTP-PA-N3 Linker-$NH_2$:

dNTP-PA-Linker 1-$NH_2$:

dNTP-PA-Linker 2-$NH_2$:

dNTP-PA-Linker 3-$NH_2$:

dNTP-PA-Linker 4-$NH_2$:

dNTP-PA-N3 Linker-$NH_2$:

G-tetrad

CYANINE DERIVATIVES AND RELATED USES

CROSS REFERENCE TO RELATED APPLICATION

This application is a continuation of International Patent Application No. PCT/US2023/082907, filed Dec. 7, 2023, which claims priority to and the benefit of U.S. Provisional Application No. 63/430,993, filed on Dec. 7, 2022, which is incorporated by reference herein in its entirety for all purposes.

BACKGROUND

Cyanine dyes are particularly popular fluorophores and are widely used in many biological applications, including sequencing applications. There is thus a need to develop cyanine derivatives which may be useful in sequencing applications. The present disclosure addresses this need.

SUMMARY

In some aspects, the present disclosure provides a compound of Formula (I), (II), or (III):

(I)

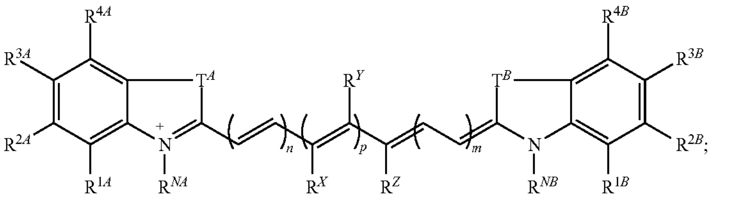

(II)

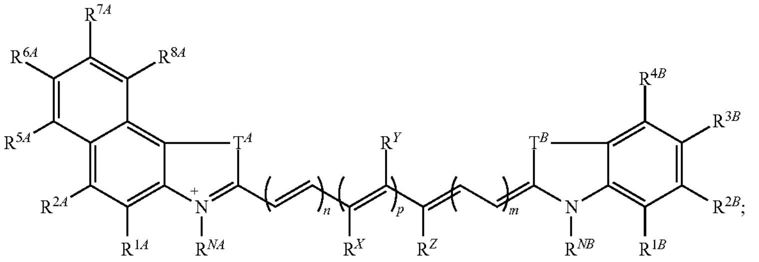

(III)

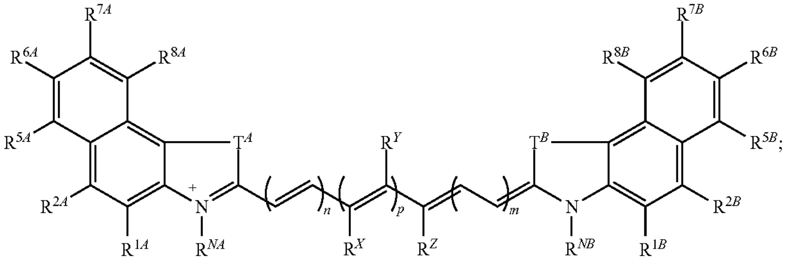

an ionic derivative thereof, an isomer thereof, or a salt thereof.

In some aspects, the present disclosure provides a sequencing method disclosed herein using a compound of the present disclosure (e.g., as a fluorescent dye).

In some aspects, the present disclosure provides a compound of the present disclosure for use (e.g., as a fluorescent dye) in a sequencing method disclosed herein.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION

Figure 1:
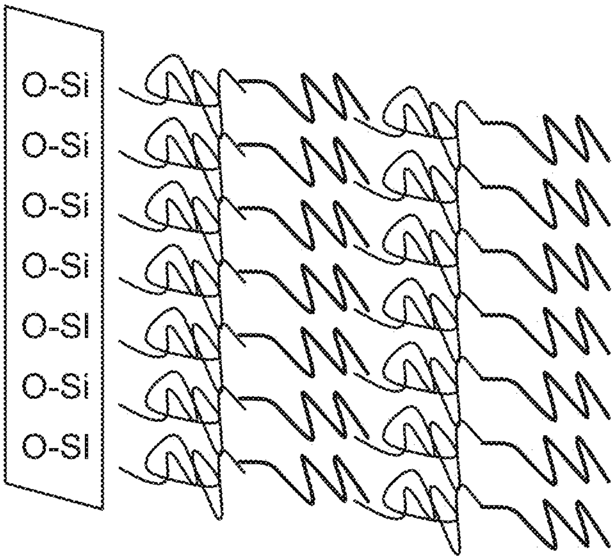
FIG. 1 is a schematic of an exemplary low binding support comprising a glass substrate and alternating layers of hydrophillic coatings which are covalently or non-covalently adhered to the glass, and which further comprises chemically-reactive functional groups that serve as attachment sites for oligonucleotide primers (e.g., capture oligonucleotides). In an alternative embodiment, the support can be made of any material such as glass, plastic or a polymer material.
Figure 2:
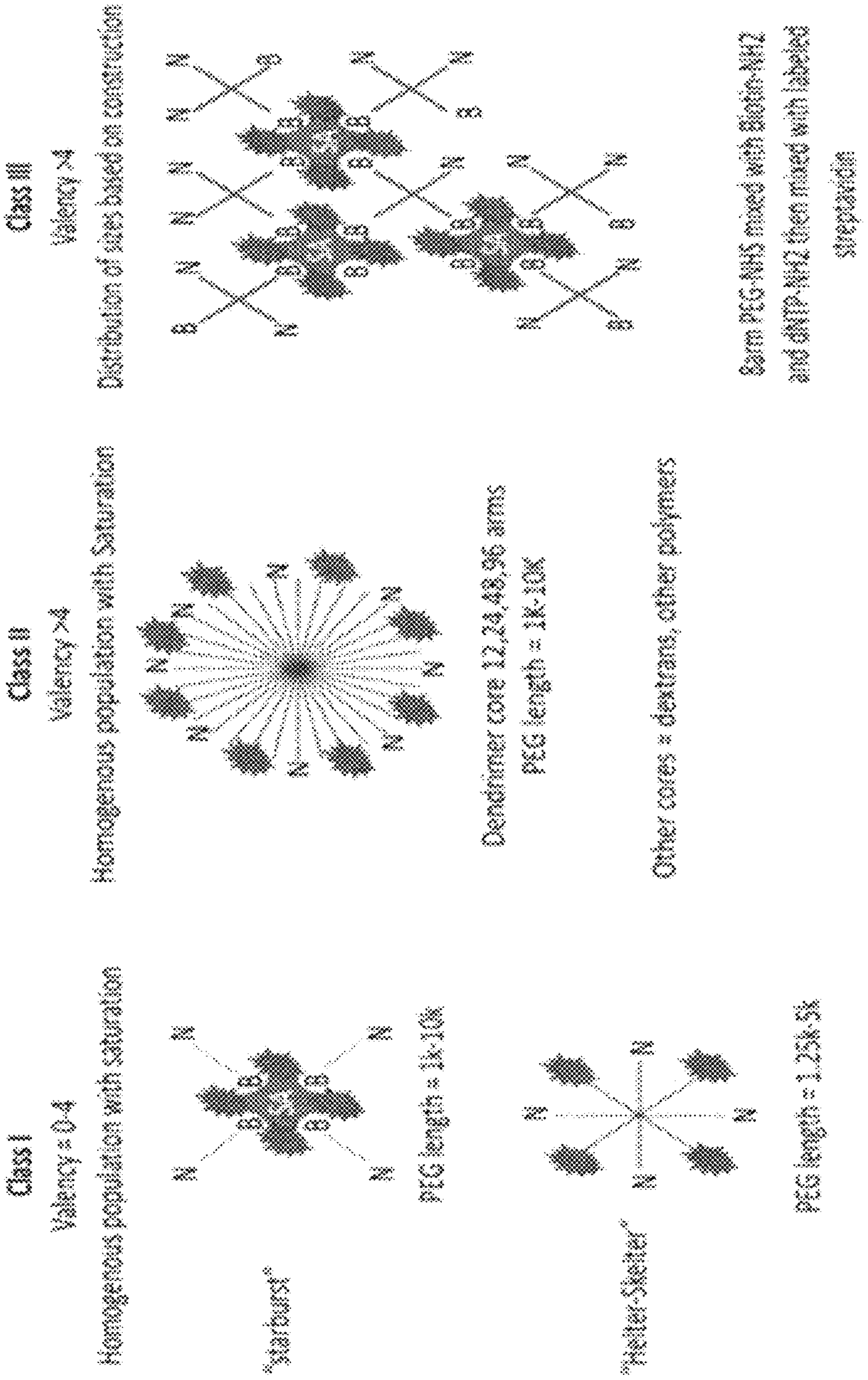
FIG. 2 is a schematic of various exemplary configurations of multivalent molecules. Left (Class I): schematics of multivalent molecules having a "starburst" or "helter-skelter" configuration. Center (Class II): a schematic of a multivalent molecule having a dendrimer configuration. Right (Class III): a schematic of multiple multivalent molecules formed by reacting streptavidin with 4-arm or 8-arm PEG-NHS with biotin and dNTPs. Nucleotide units are designated 'N', biotin is designated 'B', and streptavidin is designated 'SA'.
Figure 3:
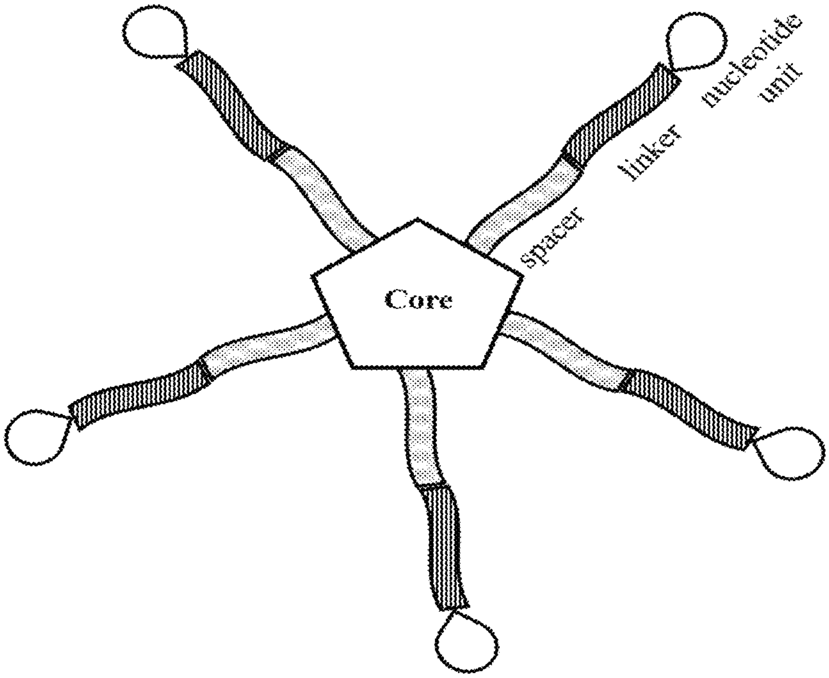
FIG. 3 is a schematic of an exemplary multivalent molecule comprising a generic core attached to a plurality of nucleotide-arms.
Figure 4:
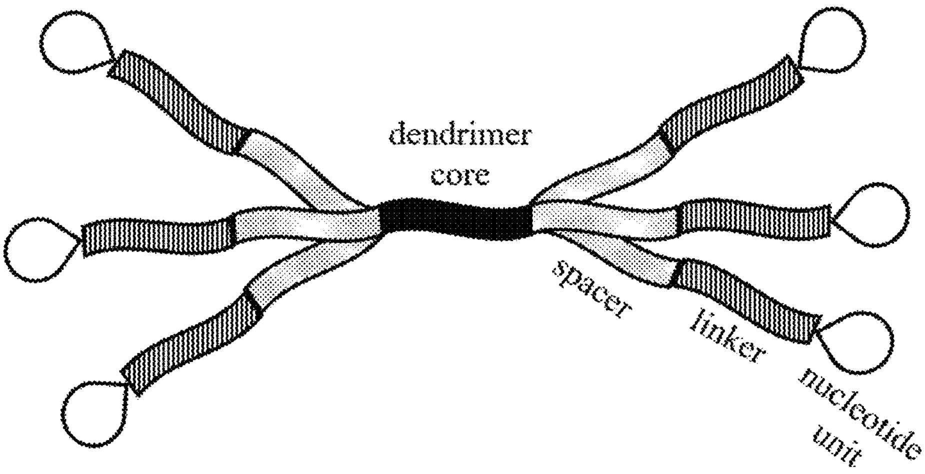
FIG. 4 is a schematic of an exemplary multivalent molecule comprising a dendrimer core attached to a plurality of nucleotide-arms.
Figure 5:
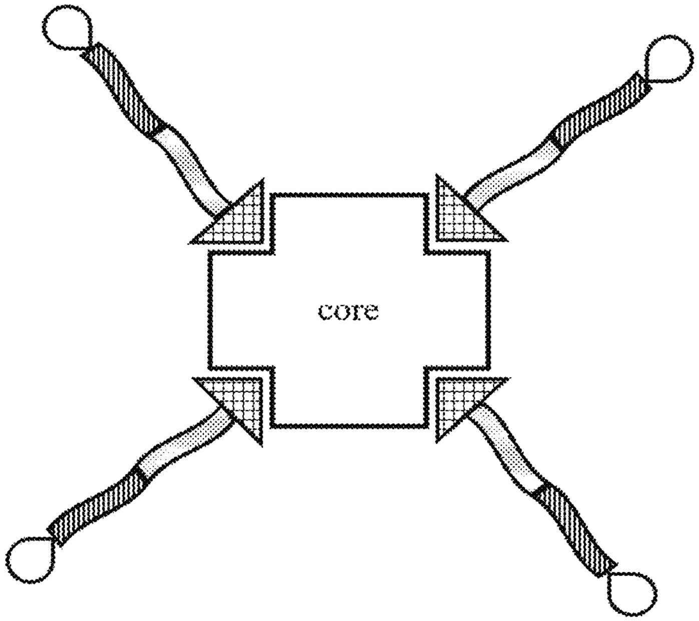
FIG. 5 shows a schematic of an exemplary multivalent molecule comprising a core attached to a plurality of nucleotide-arms, where the nucleotide arms comprise biotin, spacer, linker and a nucleotide unit.

The present disclosure relates to compounds of the Formulae disclosed herein, ionic derivatives thereof, isomers thereof, and salts thereof. Without wishing to be bound by theory, the compounds may be useful as dyes (e.g., fluorescent dyes), thereby may be useful in sequencing methods. The present disclosure also relates to conjugates of the dyes, methods of using the dyes and their conjugates.

Compounds of the Present Disclosure

In some aspects, the present disclosure provides a Compound of Formula (I), (II), or (III):

(I)

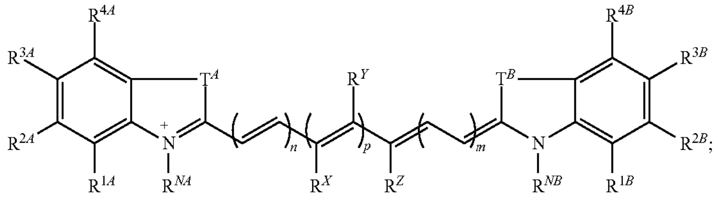

(II)

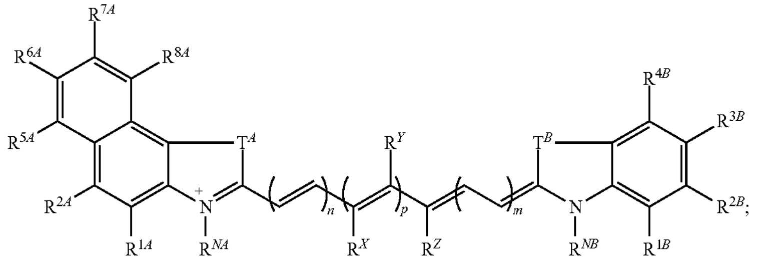

(III)

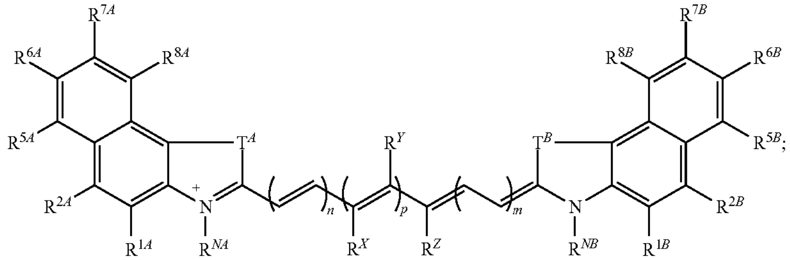

an ionic derivative thereof, an isomer thereof, or a salt thereof, wherein:

n is 0 or 1;

m is 0 or 1;

p is 0 or 1;

$R^X$ and $R^Z$ each independently are H, halogen, $C_{1-12}$ alkyl, $C_{1-12}$ alkenyl, $C_{1-12}$ alkynyl, $C_6$-$C_{10}$ aryl, or 5- to 10-membered heteroaryl; or $R^X$ and $R^Z$, together with the atoms to which they are attached, form $C_6$-$C_{10}$ arylene or $C_5$-$C_{10}$ cycloalkylene;

$R^Y$ is H, halogen, $C_{1-12}$ alkyl, $C_{1-12}$ alkenyl, $C_{1-12}$ alkynyl, $C_6$-$C_{10}$ aryl, or 5- to 10-membered heteroaryl;

$T^A$ is —S—, —O—, or —C($R^{TA}$)$_2$—;

each $R^{TA}$ independently is H, halogen, $C_{1-12}$ alkyl, $C_{1-12}$ alkenyl, $C_{1-12}$ alkynyl, $C_6$-$C_{10}$ aryl, or 5- to 10-membered heteroaryl; wherein the $C_{1-12}$ alkyl, $C_{1-12}$ alkynyl, $C_6$-$C_{10}$ aryl, or 5- to 10-membered heteroaryl is optionally substituted with one or more —S(═O)$_2$OH or —C(═O)OH;

$T^B$ is —S—, —O—, or —C($R^{TB}$)$_2$—;

each $R^{TB}$ independently is H, halogen, $C_{1-12}$ alkyl, $C_{1-12}$ alkenyl, $C_{1-12}$ alkynyl, $C_6$-$C_{10}$ aryl, or 5- to 10-membered heteroaryl; wherein the $C_{1-12}$ alkyl, $C_{1-12}$ alkynyl, $C_6$-$C_{10}$ aryl, or 5- to 10-membered heteroaryl is optionally substituted with one or more —S(═O)$_2$OH or —C(═O)OH;

$R^{NA}$ is $C_{1-12}$ alkyl, $C_{1-12}$ alkenyl, or $C_{1-12}$ alkynyl, wherein the $C_{1-12}$ alkyl, $C_{1-12}$ alkenyl, or $C_{1-12}$ alkynyl is optionally substituted with one or more $R^{NA1}$;

each $R^{NA1}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more $R^{NA2}$;

each $R^{NA2}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more $R^{NA3}$;

each $R^{NA3}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more —S(═O)$_2$OH or —C(═O)OH;

$R^{NB}$ is $C_{1-12}$ alkyl, $C_{1-12}$ alkenyl, or $C_{1-12}$ alkynyl, wherein the $C_{1-12}$ alkyl, $C_{1-12}$ alkenyl, or $C_{1-12}$ alkynyl is optionally substituted with one or more $R^{NB1}$;

each $R^{NB1}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more $R^{NB2}$;

each $R^{NB2}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more $R^{NB3}$;

each $R^{NB3}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more —S(═O)$_2$OH or —C(═O)OH;

$R^{1A}$, $R^{2A}$, $R^{3A}$, $R^{4A}$, $R^{5A}$, $R^{6A}$, $R^{7A}$, and $R^{8A}$ each independently are H, halogen, —S(═O)$_2$OH, —C(═O)OH, $C_{1-12}$ alkyl, $C_{1-12}$ alkenyl, $C_{1-12}$ alkynyl, —C(═O)—NH—($C_{1-12}$ alkyl), —C(═O)—NH—($C_{1-12}$ alkenyl), or —C(═O)—NH—($C_{1-12}$ alkynyl), wherein the $C_{1-12}$ alkyl, $C_{1-12}$ alkenyl, $C_{1-12}$ alkynyl, —C(═O)—NH—($C_{1-12}$ alkyl), —C(═O)—NH—($C_{1-12}$ alkenyl), or —C(═O)—NH—($C_{1-12}$ alkynyl) is optionally substituted with one or more $R^{AR}$;

each $R^{AR}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more $R^{AR1}$;

each $R^{AR1}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more —S(═O)$_2$OH or —C(═O)OH;

$R^{1B}$, $R^{2B}$, $R^{3B}$, $R^{4B}$, $R^{5B}$, $R^{6B}$, $R^{7B}$, and $R^{8B}$ each independently are H, halogen, —S(═O)$_2$OH, —C(═O)OH, $C_{1-12}$ alkyl, $C_{1-12}$ alkenyl, $C_{1-12}$ alkynyl, —C(═O)—NH—($C_{1-12}$ alkyl), —C(═O)—NH—($C_{1-12}$ alkenyl), or —C(═O)—NH—($C_{1-12}$ alkynyl), wherein the $C_{1-12}$ alkyl, $C_{1-12}$ alkenyl, $C_{1-12}$ alkynyl, —C(═O)—NH—($C_{1-12}$ alkyl), —C(═O)—NH—($C_{1-12}$ alkenyl), or —C(═O)—NH—($C_{1-12}$ alkynyl) is optionally substituted with one or more $R^{BR}$;

each $R^{AR}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more $R^{BR1}$; and each $R^{BR1}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more —S(═O)$_2$OH or —C(═O)OH.

In some embodiments, of Formula (I), (II), or (III), or an ionic derivative thereof, an isomer thereof, or a salt thereof:

an ionic derivative thereof, an isomer thereof, or a salt thereof, wherein:

n is 0 or 1;

m is 0 or 1;

p is 0 or 1;

$R^X$ and $R^Z$ each independently are H, halogen, $C_{1-12}$ alkyl, $C_{1-12}$ alkenyl, $C_{1-12}$ alkynyl, $C_6$-$C_{10}$ aryl, or 5- to 10-membered heteroaryl; or $R^Y$ and $R^Z$, together with the atoms to which they are attached, form $C_6$-$C_{10}$ arylene or $C_5$-$C_{10}$ cycloalkylene;

$R^Y$ is H, halogen, $C_{1-12}$ alkyl, $C_{1-12}$ alkenyl, $C_{1-2}$ alkynyl, $C_6$-$C_{10}$ aryl, or 5- to 10-membered heteroaryl;

$T^A$ is —S— or —C($R^{TA}$)$_2$—;

each $R^{TA}$ independently is H, halogen, $C_{1-12}$ alkyl, $C_{1-12}$ alkenyl, $C_{1-12}$ alkynyl, $C_6$-$C_{10}$ aryl, or 5- to 10-membered heteroaryl; wherein the $C_{1-12}$ alkyl, $C_{1-12}$ alkynyl, $C_6$-$C_{10}$ aryl, or 5- to 10-membered heteroaryl is optionally substituted with one or more —S(═O)$_2$OH or —C(═O)OH;

$T^B$ is —S— or —C($R^{TB}$)$_2$—;

each $R^{TB}$ independently is H, halogen, $C_{1-12}$ alkyl, $C_{1-12}$ alkenyl, $C_{1-12}$ alkynyl, $C_6$-$C_{10}$ aryl, or 5- to 10-membered heteroaryl; wherein the $C_{1-12}$ alkyl, $C_{1-12}$ alkynyl, $C_6$-$C_{10}$ aryl, or 5- to 10-membered heteroaryl is optionally substituted with one or more —S(═O)$_2$OH or —C(═O)OH;

$R^{NA}$ is $C_{1-12}$ alkyl, $C_{1-12}$ alkenyl, or $C_{1-12}$ alkynyl, wherein the $C_{1-12}$ alkyl, $C_{1-12}$ alkenyl, or $C_{1-12}$ alkynyl is optionally substituted with one or more RNAI.

each $R^{NA1}$ independently is —S(═O)$_2$OH, —C(═O)OH, —C(═O)—NH—($C_{1-12}$ alkyl). —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more $R^{NA2}$.

each $R^{NA2}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more $R^{NA3}$;

each $R^{NA3}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more —S(═O)$_2$OH or —C(═O)OH;

$R^{NB}$ is $C_{1-12}$ alkyl, $C_{1-12}$ alkenyl, or $C_{1-12}$ alkynyl, wherein the $C_{1-12}$ alkyl, $C_{1-12}$ alkenyl, or $C_{1-12}$ alkynyl is optionally substituted with one or more $R^{NB1}$.

each $R^{NB1}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more $R^{NB2}$.

each $R^{NB2}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more $R^{NB3}$.

each $R^{NB3}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more —S(═O)$_2$OH or —C(═O)OH;

$R^{1A}$, $R^{2A}$, $R^{3A}$, $R^{4A}$, $R^{5A}$, $R^{6A}$, $R^{7A}$, and $R^{8A}$ each independently are H, halogen, —S(═O)$_2$OH, —C(═O)OH, $C_{1-12}$ alkyl, $C_{1-12}$ alkenyl, $C_{1-12}$ alkynyl, —C(═O)—NH—($C_{1-12}$ alkyl), —C(═O)—NH—($C_{1-12}$ alkenyl), or —C(═O)—NH—($C_{1-12}$ alkynyl), wherein the $C_{1-12}$ alkyl, $C_{1-12}$ alkenyl, $C_{1-12}$ alkynyl, —C(═O)—NH—($C_{1-12}$ alkyl), —C(═O)—NH—($C_{1-12}$ alkenyl), or —C(═O)—NH—($C_{1-12}$ alkynyl) is optionally substituted with one or more $R^{AR}$.

each $R^{AR}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more $R^{AR1}$;

each $R^{AR1}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more —S(═O)$_2$OH or —C(═O)OH;

$R^{1B}$, $R^{2B}$, $R^{3B}$, $R^{4B}$, $R^{5B}$, $R^{6B}$, $R^{7B}$, and $R^{8B}$ each independently are H, halogen, —S(═O)$_2$OH, —C(═O)OH, $C_{1-12}$ alkyl, $C_{1-12}$ alkenyl, $C_{1-12}$ alkynyl, —C(═O)—NH—($C_{1-12}$ alkyl), —C(═O)—NH—($C_{1-12}$ alkenyl), or —C(═O)—NH—($C_{1-12}$ alkynyl), wherein the $C_{1-12}$ alkyl, $C_{1-12}$ alkenyl, $C_{1-12}$ alkynyl, —C(═O)—NH—($C_{1-12}$ alkyl), —C(═O)—NH—($C_{1-12}$ alkenyl), or —C(═O)—NH—($C_{1-12}$ alkynyl) is optionally substituted with one or more $R^{BR}$;

each $R^{AR}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more $R^{BR1}$; and each $R^{BR1}$ independently is —S(═O)$_2$OH, —C(═O)OH, —C(═O)—NH—($C_{1-12}$ alkyl), —C(═O)—NH—($C_{1-12}$ alkenyl), or —C(═O)—NH—($C_{1-12}$ alkynyl), wherein the —C(═O)—NH—($C_{1-12}$ alkyl), —C(═O)—NH—($C_{1-12}$ alkenyl), or —C(═O)—NH—($C_{1-12}$ alkynyl) is optionally substituted with one or more —S(═O)$_2$OH or —C(═O)OH.

In some embodiments, the compound is of Formula (I-A), (II-A), (III-A), or (IV-A):

(I-A)

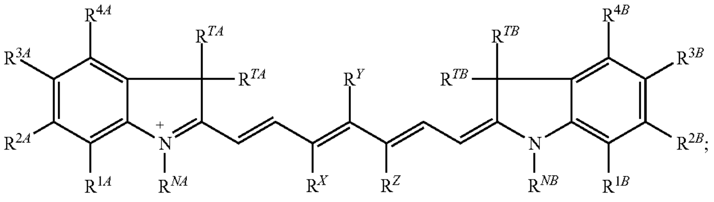

(II-A)

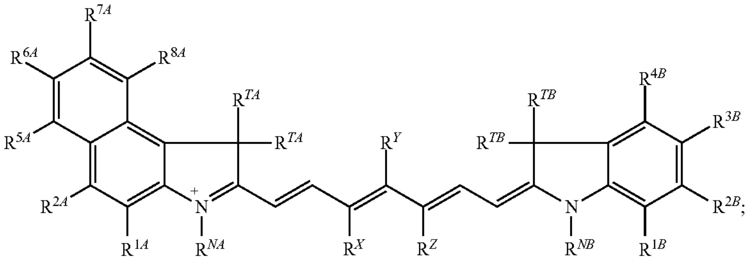

(III-A)

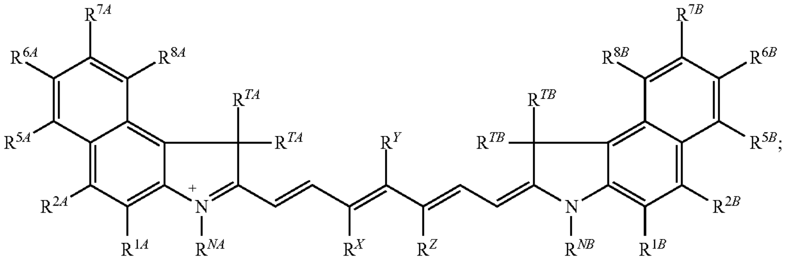

(IV-A)

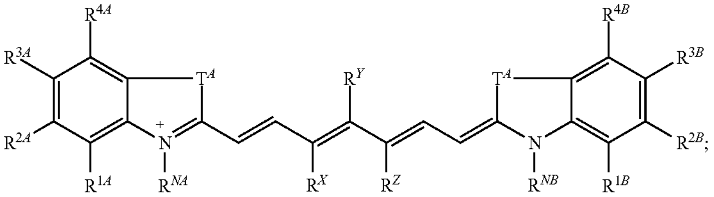

an ionic derivative thereof, an isomer thereof, or a salt thereof.

In some embodiments, the compound is of Formula (I-B), (II-B), (III-B) or (IV-b):

(I-B)

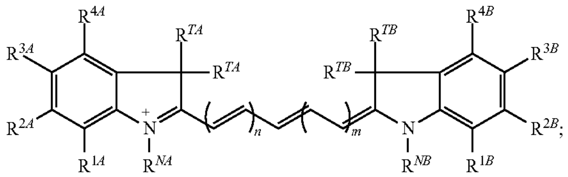

(II-B)

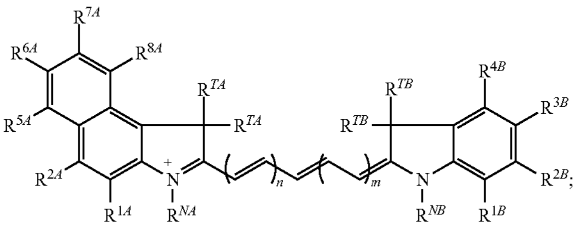

-continued (III-B)

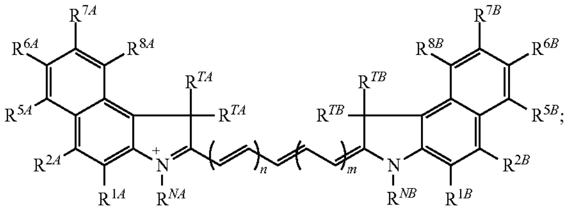

(IV-B)

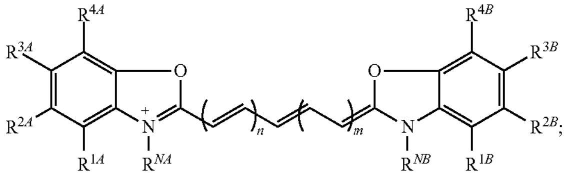

an ionic derivative thereof, an isomer thereof, or a salt thereof.

In some embodiments, the compound is of any one of the Formulae described herein, an ionic derivative thereof, an isomer thereof, or a salt thereof, wherein:

n is 0 or 1;

m is 0 or 1;

each $R^{TA}$ independently is $C_{1-12}$ alkyl optionally substituted with one or more —$S(=O)_2OH$ or —C(=O)OH;

each $R^{TB}$ independently is $C_{1-12}$ alkyl optionally substituted with one or more —$S(=O)_2OH$ or —C(=O)OH;

$R^{NA}$ is $C_{1-12}$ alkyl optionally substituted with one or more $R^{NA1}$;

each $R^{NA1}$ independently is —$S(=O)_2OH$, —C(=O)OH, or —C(=O)—NH—($C_{1-12}$ alkyl), wherein the —C(=O)—NH—($C_{1-12}$ alkyl) is optionally substituted with one or more —$S(=O)_2OH$, —C(=O)OH;

$R^{NB}$ is $C_{1-12}$ alkyl optionally substituted with one or more $R^{NB1}$;

each $R^{NB1}$ independently is —$S(=O)_2OH$, —C(=O)OH, or —C(=O)—NH—($C_{1-12}$ alkyl), wherein the —C(=O)—NH—($C_{1-12}$ alkyl) is optionally substituted with one or more —$S(=O)_2OH$, —C(=O)OH;

$R^{1A}$, $R^{3A}$, $R^{5A}$, $R^{6A}$, and $R^{8A}$ each independently are H, halogen, —$S(=O)_2OH$, or —C(=O)OH;

$R^{2A}$, $R^{4A}$, $R^{5A}$, and $R^{7A}$ each independently are H, halogen, —$S(=O)_2OH$, —C(=O)OH, $C_{1-12}$ alkyl, or —C(=O)—NH—($C_{1-12}$ alkyl), wherein the $C_{1-12}$ alkyl or —C(=O)—NH—($C_{1-12}$ alkyl) is optionally substituted with —$S(=O)_2OH$ or —C(=O)OH;

$R^{1B}$, $R^{3B}$, $R^{5B}$, $R^{6B}$, and $R^{8B}$ each independently are H, halogen, —$S(=O)_2OH$, or —C(=O)OH; and $R^{2B}$, $R^{4B}$, $R^{5B}$, and $R^{7B}$ each independently are H, halogen, —$S(=O)_2OH$, —C(=O)OH, $C_{1-12}$ alkyl, or —C(=O)—NH—($C_{1-12}$ alkyl), wherein the $C_{1-12}$ alkyl or —C(=O)—NH—($C_{1-12}$ alkyl) is optionally substituted with —$S(=O)_2OH$ or —C(=O)OH.

In some embodiments, the compound is of any one of the Formulae described herein, an ionic derivative thereof, an isomer thereof, or a salt thereof, wherein:

n is 0 or 1;

m is 0 or 1;

each $R^{TA}$ independently is $C_{1-12}$ alkyl optionally substituted with one or more —$S(=O)_2OH$ or —C(=O)OH;

each $R^{TB}$ independently is $C_{1-12}$ alkyl optionally substituted with one or more —$S(=O)_2OH$ or —C(=O)OH;

$R^{NA}$ is $C_{1-12}$ alkyl optionally substituted with one or more —$S(=O)_2OH$ or —C(=O)OH;

$R^{NB}$ is $C_{1-12}$ alkyl optionally substituted with one or more —$S(=O)_2OH$ or —C(=O)OH;

$R^{1A}$, $R^{3A}$, $R^{5A}$, $R^{6A}$, and $R^{8A}$ each independently are H or halogen;

$R^{2A}$, $R^{1A}$, $R^{5A}$, and $R^{7A}$ each independently are H, halogen, —$S(=O)_2OH$, —C(=O)OH, $C_{1-12}$ alkyl, or —C(=O)—NH—($C_{1-12}$ alkyl), wherein the $C_{1-12}$ alkyl or —C(=O)—NH—($C_{1-12}$ alkyl) is optionally substituted with —$S(=O)_2OH$ or —C(=O)OH;

$R^{1B}$, $R^{3B}$, $R^{5B}$, $R^{6B}$, and $R^{8B}$ each independently are H or halogen; and $R^{2B}$, $R^{4B}$, $R^{5B}$, and $R^{7B}$ each independently are H, halogen, —$S(=O)_2OH$, —C(=O)OH, $C_{1-12}$ alkyl, or —C(=O)—NH—($C_{1-12}$ alkyl), wherein the $C_{1-12}$ alkyl or —C(=O)—NH—($C_{1-12}$ alkyl) is optionally substituted with —$S(=O)_2OH$ or —C(=O)OH.

In some embodiments, the compound is of any one of the Formulae described herein, an ionic derivative thereof, an isomer thereof, or a salt thereof, wherein:

n is 0 or 1;

m is 0 or 1;

each $R^{TA}$ independently is $C_{1-12}$ alkyl;

each $R^{TB}$ independently is $C_{1-12}$ alkyl;

$R^{NA}$ is $C_{1-12}$ alkyl optionally substituted with one or more —$S(=O)_2OH$ or —C(=O)OH;

$R^{NB}$ is $C_{1-12}$ alkyl optionally substituted with one or more —$S(=O)_2OH$ or —C(=O)OH;

$R^{1A}$, $R^{3A}$, $R^{5A}$, $R^{6A}$, and $R^{8A}$ each independently are H or halogen;

$R^{2A}$, $R^{4A}$, $R^{5A}$, and $R^{7A}$ each independently are —$S(=O)_2OH$, —C(=O)OH, $C_{1-12}$ alkyl, or —C(=O)—NH—($C_{1-12}$ alkyl), wherein the $C_{1-12}$ alkyl or —C(=O)—NH—($C_{1-12}$ alkyl) is optionally substituted with —$S(=O)_2OH$ or —C(=O)OH;

$R^{1B}$, $R^{3B}$, $R^{5B}$, $R^{6B}$, and $R^{8B}$ each independently are H or halogen; and $R^{2B}$, $R^{4B}$, $R^{5B}$, and $R^{7B}$ each independently are —$S(=O)_2OH$, —C(=O)OH, $C_{1-12}$ alkyl, or —C(=O)—NH—($C_{1-12}$ alkyl), wherein the $C_{1-12}$ alkyl or —C(=O)—NH—($C_{1-12}$ alkyl) is optionally substituted with —$S(=O)_2OH$ or —C(=O)OH.

In some embodiments, the compound is of any one of the Formulae described herein, an ionic derivative thereof, an isomer thereof, or a salt thereof, wherein:

n is 0 or 1;

m is 0 or 1;

each $R^{TA}$ independently is $C_{1-12}$ alkyl;

each $R^{TB}$ independently is $C_{1-12}$ alkyl;

$R^{NA}$ is $C_{1-12}$ alkyl optionally substituted with one or more —$S(=O)_2OH$ or —C(=O)OH;

$R^{NB}$ is $C_{1-12}$ alkyl optionally substituted with one or more —$S(=O)_2OH$ or —C(=O)OH;

$R^{1A}$, $R^{3A}$, $R^{5A}$, $R^{6A}$, and $R^{8A}$ each independently are H;

$R^{2A}$, $R^{4A}$, $R^{5A}$, and $R^{1A}$ each independently are —$S(=O)_2OH$ or —C(=O)OH;

$R^{1B}$, $R^{3B}$, $R^{5B}$, $R^{6B}$, and $R^{8B}$ each independently are H; and $R^{2B}$, $R^{4B}$, $R^{5B}$, and $R^{7B}$ each independently are —$S(=O)_2OH$ or —C(=O)OH.

In some embodiments, at least one of $R^{TA}$, $R^{TB}$, $R^{NA}$, $R^{NB}$, $R^{1A}$, $R^{2A}$, $R^{3A}$, $R^{4A}$, $R^{3A}$, $R^{6A}$, $R^{7A}$, $R^{8A}$, $R^{1B}$, $R^{2B}$, $R^{3B}$, $R^{4B}$, $R^{5B}$, $R^{6B}$, $R^{7B}$, and $R^{8B}$ comprises —$SO_3H$.

In some embodiments, at least two, three, four, five, six, seven, or eight of $R^{TA}$, $R^{TB}$, $R^{NA}$, $R^{NB}$, $R^{1A}$, $R^{2A}$, $R^{3A}$, $R^{4A}$, $R^{5A}$, $R^{6A}$, $R^{2A}$, $R^{5A}$, $R^{1B}$, $R^{2B}$, $R^{3B}$, $R^{4B}$, $R^{5B}$, $R^{6B}$, $R^{7B}$, and R &B comprise —$SO_3H$.

In some embodiments, at least one of $R^{TA}$, $R^{TB}$, $R^{NA}$, $R^{NB}$, $R^{1A}$, $R^{2A}$, $R^{3A}$, $R^{4A}$, $R^{1B}$, $R^{2B}$, $R^{3B}$, and $R^{4B}$ comprises —$SO_3H$.

In some embodiments, at least two, three, four, five, six, seven, or eight of $R^{TA}$, $R^{TB}$, $R^{NA}$, $R^{NB}$, $R^{1A}$, $R^{2A}$, $R^{3A}$, $R^{4A}$, $R^{1B}$, $R^{2B}$, $R^{3B}$, and $R^{4B}$ comprise —$SO_3H$.

In some embodiments, at least one of $R^{TA}$, $R^{TB}$, $R^{NA}$, $R^{NB}$, $R^{1A}$, $R^{2A}$, $R^{5A}$, $R^{6A}$, $R^{7A}$, $R^{8A}$, $R^{1B}$, $R^{2B}$, $R^{3B}$, and $R^{4B}$ comprises —$SO_3H$.

In some embodiments, at least two, three, four, five, six, seven, or eight of $R^{TA}$, $R^{TB}$, $R^{NA}$, $R^{NB}$, $R^{1A}$, $R^{2A}$, $R^{5A}$, $R^{6A}$, $R^{7A}$, $R^{8A}$, $R^{1B}$, $R^{2B}$, $R^{3B}$, and $R^{4B}$ comprise —$SO_3H$.

In some embodiments, at least one of $R^{TA}$, $R^{TB}$, $R^{NA}$, $R^{NB}$, $R^{1A}$, $R^{2A}$, $R^{5A}$, $R^{6A}$, $R^{1A}$, $R^{8A}$, $R^{1B}$, $R^{2B}$, $R^{5B}$, $R^{6B}$, $R^{7B}$, and $R^{4B}$ comprises —$SO_3H$.

In some embodiments, at least two, three, four, five, six, seven, or eight of $R^{TA}$, $R^{TB}$, $R^{NA}$, $R^{NB}$, $R^{1A}$, $R^{2A}$, $R^{3A}$, $R^{4A}$, $R^{5A}$, $R^{6A}$, $R^{1A}$, $R^{5A}$, $R^{1B}$, $R^{2B}$, $R^{3B}$, $R^{4B}$, $R^{5B}$, $R^{6B}$, $R^{7B}$, and $R^{8B}$ comprise —$SO_3H$.

In some embodiments, at least one of $R^{TA}$, $R^{TB}$, $R^{1A}$, $R^{2A}$, $R^{3A}$, $R^{4A}$, $R^{5A}$, $R^{6A}$, $R^{7A}$, $R^{8A}$, $R^{1B}$, $R^{2B}$, $R^{3B}$, $R^{4B}$, $R^{5B}$, $R^{6B}$, $R^{7B}$, and $R^{8B}$ comprises —$SO_3H$.

In some embodiments, at least two, three, four, five, six, seven, or eight of $R^{TA}$, $R^{TB}$, $R^{1A}$, $R^{2A}$, $R^{3A}$, $R^{4A}$, $R^{5A}$, $R^{6A}$, $R^{1A}$, $R^{8A}$, $R^{1B}$, $R^{2B}$, $R^{3B}$, $R^{4B}$. $R^{5B}$, $R^{6B}$, $R^{7B}$, and $R^{8B}$ comprise —$SO_3H$.

In some embodiments, at least one of $R^{TA}$, $R^{TB}$, $R^{1A}$, $R^{2A}$, $R^{5A}$, $R^{4A}$, $R^{1B}$, $R^{2B}$, $R^{3B}$, and $R^{1B}$ comprises —$SO_3H$.

In some embodiments, at least two, three, four, five, six, seven, or eight of $R^{TA}$, $R^{TB}$, $R^{1A}$, $R^{2A}$, $R^{3A}$, $R^{4A}$, $R^{1B}$, $R^{2B}$, $R^{3B}$, and $R^{4B}$ comprise —$SO_3H$.

In some embodiments, at least one of $R^{TA}$, $R^{TB}$, $R^{1A}$, $R^{2A}$, $R^{5A}$, $R^{6A}$, $R^{1A}$, $R^{5A}$, $R^{1B}$, $R^{2B}$, $R^{3B}$, and $R^{4B}$ comprises —$SO_3H$.

In some embodiments, at least two, three, four, five, six, seven, or eight of $R^{TA}$, $R^{TB}$, $R^{1A}$, $R^{2A}$, $R^{5A}$, $R^{6A}$, $R^{2A}$, $R^{8A}$, $R^{1B}$, $R^{2B}$, $R^{4R}$, and $R^{4B}$ comprise —$SO_3H$.

In some embodiments, at least one of $R^{TA}$, $R^{1B}$, $R^{1A}$, $R^{2A}$, $R^{5A}$, $R^{6A}$, $R^{3A}$, $R^{8A}$, $R^{1B}$, $R^{2B}$, $R^{5B}$, $R^{6B}$, $R^{7B}$, and $R^{8B}$ comprises —$SO_3H$.

In some embodiments, at least two, three, four, five, six, seven, or eight of $R^{TA}$, $R^{TB}$, $R^{1A}$, $R^{2A}$, $R^{3A}$, $R^{4A}$, $R^{5A}$, $R^{6A}$, $R^{7A}$, $R^{8A}$, $R^{1B}$, $R^{2B}$, $R^{3B}$, $R^{4B}$, $R^{5B}$, $R^{6B}$, $R^{7B}$, and $R^{8B}$ comprise —$SO_3H$.

In some embodiments, at least one of $R^{1A}$, $R^{2A}$, $R^{3A}$, $R^{4A}$, $R^{5A}$, $R^{6A}$, $R^{7A}$, $R^{8A}$, $R^{1B}$, $R^{2B}$, $R^{3B}$, $R^{4B}$, $R^{5B}$, $R^{6B}$, $R^{7B}$, and $R^{8B}$ comprises —$SO_3H$.

In some embodiments, at least two, three, four, five, six, seven, or eight of $R^{1A}$, $R^{2A}$, $R^{3A}$, $R^{4A}$, $R^{5A}$, $R^{6A}$, $R^{7A}$, $R^{8A}$, $R^{1B}$, $R^{2B}$, $R^{3B}$, $R^{4B}$, $R^{5B}$, $R^{6B}$, $R^{7B}$, and $R^{8B}$ comprise —$SO_3H$.

In some embodiments, at least one of $R^{1A}$, $R^{2A}$, $R^{3A}$, $R^{4A}$, $R^{1B}$, $R^{2B}$, $R^{3B}$, and $R^{4B}$ comprises —$SO_3H$.

In some embodiments, at least two, three, four, five, six, seven, or eight of $R^{1A}$, $R^{2A}$, $R^{3A}$, $R^{4A}$, $R^{1B}$, $R^{2B}$, $R^{3B}$, and $R^{4B}$ comprise —$SO_3H$.

In some embodiments, at least one of $R^{1A}$, $R^{2A}$, $R^{5A}$, $R^{6A}$, $R^{7A}$, $R^{8A}$, $R^{1B}$, $R^{2B}$, $R^{3B}$, and RB comprises —$SO_3H$.

In some embodiments, at least two, three, four, five, six, seven, or eight of $R^{1A}$, $R^{2A}$, $R^{5A}$, $R^{6A}$, $R^{7A}$, $R^{8A}$, $R^{1B}$, $R^{2B}$, $R^{3B}$, and $R^{4B}$ comprise —$SO_3H$.

In some embodiments, at least one of $R^{1A}$, $R^{2A}$, $R^{5A}$, $R^{6A}$, $R^{7A}$, $R^{8A}$, $R^{1B}$, $R^{2B}$, $R^{5B}$, $R^{6B}$, $R^{7B}$, and $R^{8B}$ comprises —$SO_3H$.

In some embodiments, at least two, three, four, five, six, seven, or eight of $R^{1A}$, $R^{2A}$, $R^{3A}$, $R^{4A}$, $R^{5A}$, $R^{6A}$, $R^{7A}$, $R^{8A}$, $R^{1B}$, $R^{2B}$, $R^{3B}$, $R^{4B}$, $R^{5B}$, $R^{6B}$, $R^{7B}$, and $R^{8B}$ comprise —$SO_3H$.

In some embodiments, the compound is of any one of the Formulae described herein, an ionic derivative thereof, an isomer thereof, or a salt thereof, wherein:

(a) at least one of $R^{2A}$, $R^{5A}$, $R^{2A}$, $R^{TA}$, $R^{NB}$, $R^{NA}$, $R^{TB}$, $R^{2B}$, $R^{5B}$, $R^{6B}$, $R^{7B}$, $R^{4A}$, $R^{4B}$. $R^{8A}$, $R^{8B}$ comprises —$SO_3H$;

(b) when $T^A$ and $R^{TB}$ are $CH_3$, then (i) at least three of $R^{2A}$, $R^{4A}$, $R^{4B}$, $R^{2B}$, $R^{5B}$, and $R^{7B}$ are —$SO_3H$, (ii) n is 1, and (iii) the compound is not of Formula III (e.g., Formula III-A, Formula III-B, Formula III-C, Formula III-D, Formula III-E, or Formula III-F);

(c) when the compound is of Formula I (e.g., Formula I-A, Formula I-B, Formula I-C, Formula I-D, Formula I-E, or Formula I-F) and n is 1, then (i) at least one of $R^{2A}$, $R^{4A}$, $R^{4B}$ and $R^{2B}$ is C(=O)NH$CH_2CH_2SO_3H$, or (ii) three or of $R^{2A}$, $R^{2B}$, $R^{4A}$, $R^{4B}$, $R^{5B}$, $R^{5B}$, $R^{7A}$, and $R^{7B}$ are —$SO_3H$;

(d) when (i) the compound is of Formula III, (e.g., Formula III-A, Formula III-B, Formula III-C, Formula III-D, Formula III-E, or Formula III-F) (ii) $R^7$ is —($C_{2-12}$ alkylene)-$SO_3H$, and $R^{13}$ is —($C_{2-12}$ alkylene)-C(=O)OH, and (iii) n is 2, then (i) at least one of $R^{5A}$, $R^{7A}$, $R^{5B}$, and $R^{7B}$ is C(=O)OH or (ii) one of $R^{1A}$ and $R^{TB}$ is $CH_3$; and/or (e) when (i) the compound is of Formula III, (e.g., Formula III-A, Formula III-B, Formula III-C, Formula III-D, Formula III-E, or Formula III-F) (ii) $R^7$ is —($C_{2-12}$ alkylene)-$SO_3H$, and $R^{13}$ is —($C_{2-12}$ alkylene)-C(=O)OH, and (iii) n is 1, then (i) at least one of $R^{5A}$, $R^{7A}$, $R^{5B}$, and $R^{7B}$ is C(=O)OH, or (ii) both $R^{TA}$ and $R^{TB}$ are —($C_{1-12}$ alkylene)-$SO_3H$.

In some embodiments, the compound is of Formula (I-C), (II-C), or (III-C):

I-C)

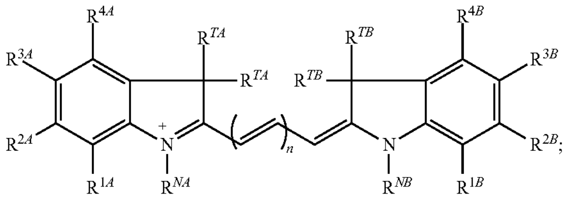

(II-C)

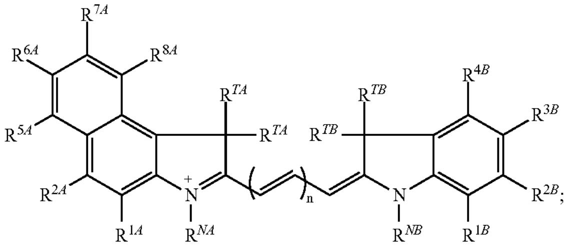

(III-C)

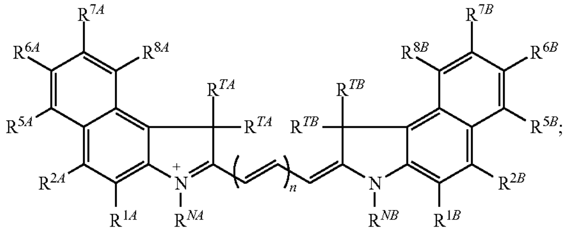

an ionic derivative thereof, an isomer thereof, or a salt thereof.

In some embodiments, the compound is of Formula (I-D), (II-D), or (III-D):

(I-D)

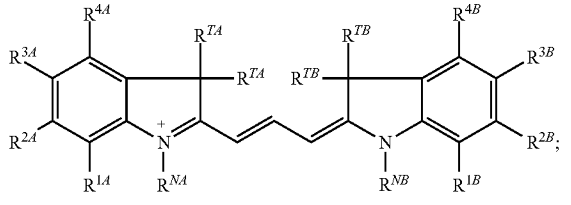

-continued (II-D)

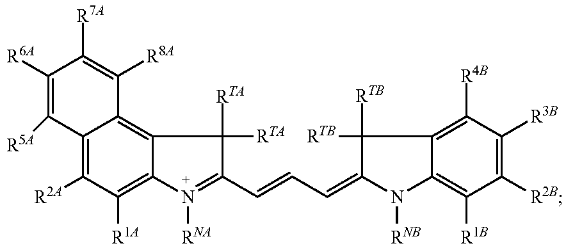

(III-D)

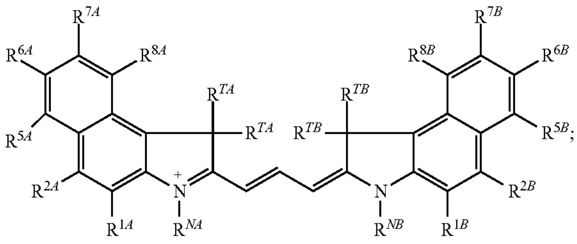

an ionic derivative thereof, an isomer thereof, or a salt thereof.

In some embodiments, the compound is of Formula (I-E), (II-E), or (III-E):

(I-E)

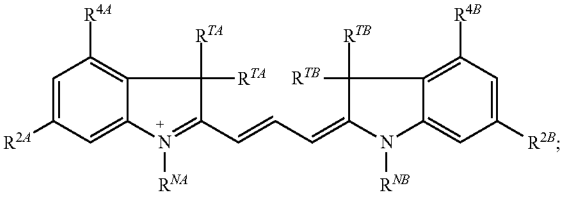

(II-E)

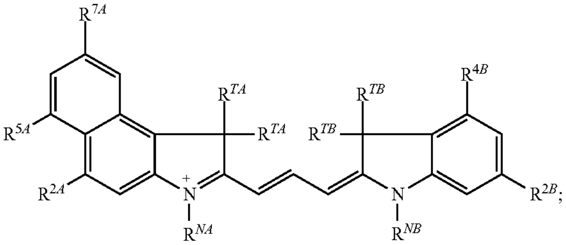

(III-E)

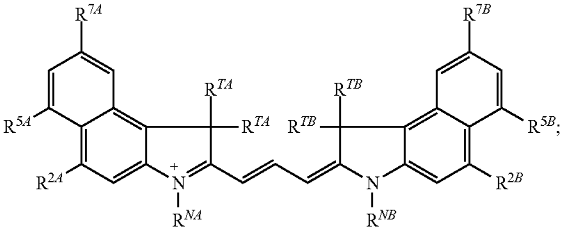

an ionic derivative thereof, an isomer thereof, or a salt thereof.

In some embodiments, the compound is of Formula (I-F), (II-F), or (III-F):

(I-F)

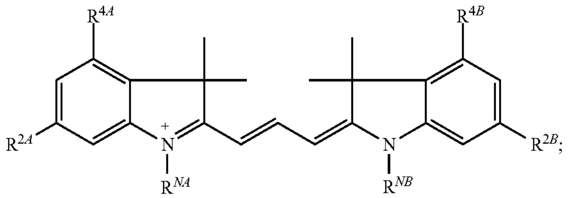

(II-F)

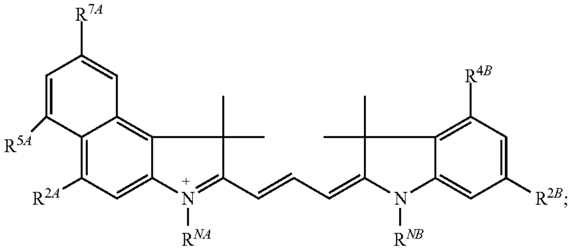

(III-F)

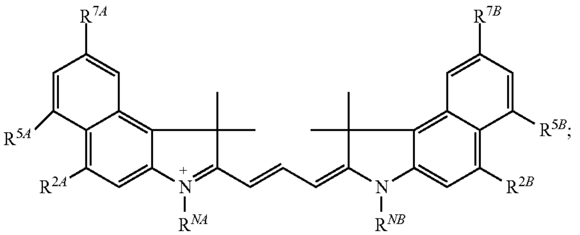

an ionic derivative thereof, an isomer thereof, or a salt thereof.

In some embodiments, the compound is of any one of the Formulae described herein, an ionic derivative thereof, an isomer thereof, or a salt thereof, wherein:

$R^{NA}$ is $C_{1-12}$ alkyl optionally substituted with one or more $—S(═O)_2OH$ or —C(═O)OH;

$R^{NB}$ is $C_{1-12}$ alkyl optionally substituted with one or more $—S(═O)_2OH$ or —C(═O)OH;

$R^{2A}$, $R^{4A}$, $R^{5A}$, and $R^{7A}$ each independently are $—S(═O)_2OH$, —C(═O)OH, $C_{1-12}$ alkyl, or —C(═O)—NH—($C_{1-12}$ alkyl), wherein the $C_{1-12}$ alkyl or —C(═O)—NH—($C_{1-12}$ alkyl) is optionally substituted with $—S(═O)_2OH$ or —C(═O)OH; and $R^{2B}$, $R^{4B}$, $R^{5B}$, and $R^{7B}$ each independently are $—S(═O)_2OH$, —C(═O)OH, $C_{1-12}$ alkyl, or —C(═O)—NH—($C_{1-12}$ alkyl), wherein the $C_{1-12}$ alkyl or —C(═O)—NH—($C_{1-12}$ alkyl) is optionally substituted with $—S(═O)_2OH$ or —C(═O)OH.

In some embodiments, the compound is of any one of the Formulae described herein, an ionic derivative thereof, an isomer thereof, or a salt thereof, wherein:

$R^{NA}$ is $C_{1-12}$ alkyl optionally substituted with one or more $—S(═O)_2OH$ or —C(═O)OH;

$R^{NB}$ is $C_{1-12}$ alkyl optionally substituted with one or more $—S(═O)_2OH$ or —C(═O)OH;

$R^{2A}$, $R^{4A}$, $R^{5A}$, and $R^{7A}$ each independently are $—S(═O)_2OH$ or —C(═O)OH; and $R^{2B}$, $R^{4B}$, $R^{5B}$, and $R^{7B}$ each independently are $—S(═O)_2OH$ or —C(═O)OH.

In some embodiments, at least one of $R^{TA}$, $R^{TB}$, $R^{2A}$, $R^{5A}$, $R^{1A}$, $R^{2B}$, $R^{5B}$, and $R^{7B}$ comprises $—SO_3H$.

In some embodiments, at least two, three, four, or five of $R^{TA}$, $R^{TB}$, $R^{2A}$, $R^{5A}$, $R^{7A}$, $R^{2B}$, $R^{5B}$, and $R^{7B}$ comprise $—SO_3H$.

In some embodiments, at least one of $R^{TA}$, $R^{TB}$, $R^{2A}$, $R^{4A}$, $R^{2B}$, and $R^{4B}$ comprises —$SO_3H$.

In some embodiments, at least two, three, four, or five of $R^{TA}$, $R^{TB}$, $R^{2A}$, $R^{4A}$, $R^{2B}$, and $R^{4B}$ comprise —$SO_3H$.

In some embodiments, one or more $R^{TA}$ and/or $R^{1B}$ is —$CH_2S$(═O)$_2$OH.

In some embodiments, one or more $R^{TA}$ and/or $R^{TB}$ is —$(CH_2)_3$—C(═O)OH.

In some embodiments, $R^{NA}$ and/or $R^{NB}$ is —$CH_3$.

In some embodiments, $R^X$ is H. In some embodiments, $R^X$ is halogen (e.g., F, $C_1$, Br, or I). In some embodiments, $R^X$ is $C_{1-12}$ alkyl (e.g., methyl, ethyl, propyl, butyl, pentyl, or hexyl). In some embodiments, $R^X$ is $C_{1-12}$ alkyl (e.g., methyl, ethyl, propyl, butyl, pentyl, or hexyl) optionally substituted with —S(═O)$_2$OH or —C(═O)OH.

In some embodiments, $R^Z$ is H. In some embodiments, $R^Z$ is halogen (e.g., F, Cl, Br, or I). In some embodiments, $R^Z$ is $C_{1-12}$ alkyl (e.g., methyl, ethyl, propyl, butyl, pentyl, or hexyl). In some embodiments, $R^Z$ is $C_{1-12}$ alkyl (e.g., methyl, ethyl, propyl, butyl, pentyl, or hexyl) optionally substituted with —S(═O)$_2$OH or —C(═O)OH.

In some embodiments, $R^X$ and $R^Z$, together with the atoms to which they are attached, form $C_{6-10}$ arylene (e.g., phenylene or napthylene). In some embodiments, $R^X$ and $R^Z$, together with the atoms to which they are attached, come together to form $C_5$-$C_{10}$ cycloalkylene (e.g., cyclopentylene, or cyclohexylene).

In some embodiments, $R^Y$ is H. In some embodiments, $R^Y$ is halogen (e.g., F, Cl, Br, or I). In some embodiments, $R^Y$ is $C_{1-12}$ alkyl (e.g., methyl, ethyl, propyl, butyl, pentyl, or hexyl). In some embodiments, $R^Y$ is $C_{1-12}$ alkyl (e.g., methyl, ethyl, propyl, butyl, pentyl, or hexyl) optionally substituted with —S(═O)$_2$OH or —C(═O)OH. In some embodiments, $R^Y$ is $C_{6-10}$ aryl (e.g., phenyl or napthyl). In some embodiments, $R^Y$ is $C_{6-10}$ aryl (e.g., phenyl or napthyl) optionally substituted with —S(═O)$_2$OH, —C(═O)OH, or —C(═O)O—$C_{1-12}$ alkyl. In some embodiments, $R^Y$ is 5-10 membered heteroaryl (e.g. pyrrolyl, thiophenyl, furanyl, thiazolyl, pyridinyl, pyrazinyl, or pyrimidinyl). In some embodiments, $R^Y$ is 5-10 membered heteroaryl (e.g. pyrrolyl, thiophenyl, furanyl, thiazolyl, pyridinyl, pyrazinyl, or pyrimidinyl) optionally substituted with —S(═O)$_2$OH, —C(═O)OH, or —C(═O)O—$C_{1-12}$ alkyl. In some embodiments, $R^Y$ is $C_{2-9}$ heterocyclyl (e.g., oxetanyl, azetidinyl, pyrrolidinyl, tetrahydrofuranyl, piperidinyl, or piperazinyl). In some embodiments, $R^Y$ is $C_{2-9}$ heterocyclyl (e.g., oxetanyl, azetidinyl, pyrrolidinyl, tetrahydrofuranyl, piperidinyl, or piperazinyl) optionally substituted with —S(═O)$_2$OH, —C(═O)OH, or —C(═O)O—$C_{1-12}$ alkyl. In some embodiments, $R^Y$ is amino (e.g., unsubstituted amino, monoalkyl amino, dialkyl amino, monoaryl amino, or diarylamino). In some embodiments. $R^Y$ is —S—$C_{1-6}$ alkyl or —S—$C_{6-10}$ aryl. In some embodiments, $R^Y$ is —S—$C_{1-6}$ alkyl or —S—$C_{6-10}$ aryl, wherein the $C_{1-6}$ alkyl or $C_{6-10}$ aryl is optionally substituted with —S(═O)$_2$OH, —C(═O)OH, or —C(═O)O—$C_{1-12}$ alkyl.

In some embodiments, $T^A$ is —S—. In some embodiments, T is —O—. In some embodiments. $T^A$ is —C($R^{1A}$)$_2$—. In some embodiments, each $R^{TA}$ independently is H. In some embodiments, each $R^{TA}$ independently is halogen (e.g., F, Cl, Br, or I). In some embodiments, each $R^{TA}$ independently is $C_{1-12}$ alkyl (e.g., methyl, ethyl, propyl, butyl, pentyl, or hexyl). In some embodiments, each $R^{TA}$ independently is a $C_{1-12}$ alkyl (e.g., methyl, ethyl, propyl, butyl, pentyl, or hexyl) optionally substituted with —S(═O)$_2$OH or —C(═O)OH. In some embodiments, each $R^{TA}$ independently is methyl, $C_5$ alkyl substituted with —C(═O)OH, or $C_3$ alkyl substituted with —S(═O)$_2$OH. In some embodiments, one $R^{TA}$ is CH; and one $R^{TA}$ is $C_5$ alkyl substituted with —C(═O)OH, or $C_5$ alkyl substituted with —S(═O)$_2$OH. In some embodiments, one $R^{TA}$ is $C_5$ alkyl substituted with —C(═O)OH and one $R^{1A}$ is $C_5$ alkyl substituted with —S(═O)$_2$OH. In some embodiments, each $R^{TA}$ independently is $C_{6-10}$ aryl (e.g., phenyl or napthyl). In some embodiments, each $R^{TA}$ independently is $C_{6-10}$ aryl (e.g., phenyl or napthyl) optionally substituted with —S(═O)$_2$OH, —C(═O)OH, or —C(═O)O—$C_{1-12}$ alkyl. In some embodiments, each $R^{TA}$ independently is 5-10 membered heteroaryl (e.g. pyrrolyl, thiophenyl, furanyl, thiazolyl, pyridinyl, pyrazinyl, or pyrimidinyl). In some embodiments, each $R^{TA}$ independently is 5-10 membered heteroaryl (e.g. pyrrolyl, thiophenyl, furanyl, thiazolyl, pyridinyl, pyrazinyl, or pyrimidinyl) optionally substituted, with —S(═O)$_2$OH, —C(═O)OH, or —C(═O)O—$C_{1-12}$ alkyl.

In some embodiments, $T^B$ is —S—. In some embodiments, $T^B$ is —O—. In some embodiments. $T^B$ is —C($R^{TB}$)$_2$—. In some embodiments, each $R^{TB}$ independently is H. In some embodiments, each $R^{TB}$ independently is halogen (e.g., F, Cl, Br, or I). In some embodiments, each $R^{1B}$ independently is $C_{1-12}$ alkyl (e.g., methyl, ethyl, propyl, butyl, pentyl, or hexyl). In some embodiments, each $R^{TB}$ independently is a $C_{1-12}$ alkyl (e.g., methyl, ethyl, propyl, butyl, pentyl, or hexyl) optionally substituted with —S(═O)$_2$OH or —C(═O)OH. In some embodiments, each $R^{TB}$ independently is methyl, $C_5$ alkyl substituted with —C(═O)OH, or $C_5$ alkyl substituted with —S(═O)$_2$OH. In some embodiments, one $R^{TB}$ is $CH_3$ and one $R^{TB}$ is $C_5$ alkyl substituted with —C(═O)OH, or $C_5$ alkyl substituted with —S(═O)$_2$OH. In some embodiments, one $R^{TB}$ is $C_5$ alkyl substituted with —C(═O)OH and one $R^{TB}$ is $C_5$ alkyl substituted with —S(═O)$_2$OH. In some embodiments, each $R^{TB}$ independently is $C_{6-10}$ aryl (e.g., phenyl or napthyl). In some embodiments, each $R^{TB}$ independently is $C_{6-10}$ aryl (e.g., phenyl or napthyl) optionally substituted with —S(═O)$_2$OH, —C(═O)OH, or —C(═O)O—$C_{1-12}$ alkyl. In some embodiments, each $R^{TB}$ independently is 5-10 membered heteroaryl (e.g. pyrrolyl, thiophenyl, furanyl, thiazolyl, pyridinyl, pyrazinyl, or pyrimidinyl). In some embodiments, each $R^{TB}$ independently is 5-10 membered heteroaryl (e.g. pyrrolyl, thiophenyl, furanyl, thiazolyl, pyridinyl, pyrazinyl, or pyrimidinyl) optionally substituted, with —S(═O)$_2$OH, —C(═O)OH, or —C(═O)O—$C_{1-12}$ alkyl.

In some embodiments, $R^{NA}$ is $C_{1-12}$ alkyl (e.g., methyl, ethyl, propyl, butyl, pentyl, or hexyl). In some embodiments, $R^{NA}$ is a $C_{1-12}$ alkyl (e.g., methyl, ethyl, propyl, butyl, pentyl, or hexyl) optionally substituted with —S(═O)$_2$OH or —C(═O)OH. In some embodiments, $R^{NA}$ is $C_5$ alkyl substituted with —C(═O)OH, or $C_5$ alkyl substituted with —S(═O)$_2$OH. In some embodiments, $R^{NA}$ is —($C_{1-12}$ alkylene)-C(═O)—NH—$(CH_2CH_2O)_q$—($C_{1-12}$ alkyl), wherein $C_{1-12}$ alkyl is optionally substituted with —S(═O)$_2$OH, —C(═O)OH and q is an integer from 20 to 30. In some embodiments, $R^{NA}$ is —($C_{1-12}$ alkylene)-C(═O)—NH—($C_{1-12}$ alkyl), wherein $C_{1-12}$ alkyl is optionally substituted with —S(═O)$_2$OH, —C(═O)OH. In some embodiments, $R^{NA}$ is $C_{6-10}$ aryl (e.g., phenyl or napthyl). In some embodiments, $R^{NA}$ is $C_{6-10}$ aryl (e.g., phenyl or napthyl) optionally substituted with —S(═O)$_2$OH, —C(═O)OH, or —C(═O)O—$C_{1-12}$ alkyl. In some embodiments, $R^{NA}$ is 5-10 membered heteroaryl (e.g. pyrrolyl, thiophenyl, furanyl, thiazolyl, pyridinyl, pyrazinyl, or pyrimidinyl). In some embodiments, $R^{NA}$ is 5-10 membered heteroaryl (e.g. pyrrolyl, thiophenyl, furanyl, thiazolyl, pyridinyl, pyrazinyl, or pyrimidinyl) optionally substituted with —S(═O)$_2$OH, —C(═O)OH, or —C(═O)O—$C_{1-12}$ alkyl.

In some embodiments, $R^{NB}$ is $C_{1-12}$ alkyl (e.g., methyl, ethyl, propyl, butyl, pentyl, or hexyl). In some embodiments, $R^{NB}$ is a $C_{1-12}$ alkyl (e.g., methyl, ethyl, propyl, butyl, pentyl, or hexyl) optionally substituted with —S(═O)$_2$OH or —C(═O)OH. In some embodiments, $R^{NB}$ is $C_5$ alkyl substituted with —C(═O)OH, or $C_5$ alkyl substituted with —S(═O)$_2$OH. In some embodiments, $R^{NB}$ is —($C_{1-12}$ alkylene)-C(═O)—NH—($CH_2CH_2O$)$_4$—($C_{1-12}$ alkyl), wherein $C_{1-12}$ alkyl is optionally substituted with —S(═O)$_2$OH, —C(═O)OH and q is an integer from 20 to 30. In some embodiments, $R^{NB}$ is —($C_{1-12}$ alkylene)-C(═O)—NH—($C_{1-12}$ alkyl), wherein $C_{1-12}$ alkyl is optionally substituted with —S(═O)$_2$OH, —C(═O)OH. In some embodiments, $R^{NB}$ is $C_{6-10}$ aryl (e.g., phenyl or napthyl). In some embodiments, $R^{4B}$ is $C_{6-10}$ aryl (e.g., phenyl or napthyl) optionally substituted with —S(═O)$_2$OH, —C(═O)OH, or —C(═O)O—$C_{1-12}$ alkyl. In some embodiments, $R^{NB}$ is 5-10 membered heteroaryl (e.g. pyrrolyl, thiophenyl, furanyl, thiazolyl, pyridinyl, pyrazinyl, or pyrimidinyl). In some embodiments, $R^{NB}$ is 5-10 membered heteroaryl (e.g. pyrrolyl, thiophenyl, furanyl, thiazolyl, pyridinyl, pyrazinyl, or pyrimidinyl) optionally substituted with —S(═O)$_2$OH, —C(═O)OH, or —C(═O)O—$C_{1-12}$ alkyl.

In some embodiments, $R^{1A}$ is H. In some embodiments, $R^{1A}$ is —C(═O)OH. In some embodiments, $R^{1A}$ is —S(═O)$_2$OH. In some embodiments, $R^{1A}$ is $C_{1-12}$ alkyl (e.g., methyl, ethyl, propyl, butyl, pentyl, or hexyl). In some embodiments, $R^{1A}$ is $C_{1-12}$ alkyl (e.g., methyl, ethyl, propyl, butyl, pentyl, or hexyl) optionally substituted with —S(═O)$_2$OH or —C(═O)OH. In some embodiments, $R^{1A}$ is —C(═O)—NH—($C_{1-12}$ alkyl) (e.g., —C(═O)—NH—$C_1$ alkyl, —C(═O)—NH—$C_2$ alkyl, —C(═O)—NH—$C_3$ alkyl, —C(═O)—NH—$C_4$ alkyl, —C(═O)—NH—$C_5$ alkyl, or —C(═O)—NH—$C_6$ alkyl). In some embodiments, $R^{1A}$ is —C(═O)—NH—($C_{1-12}$ alkyl), wherein the $C_{1-12}$ alkyl is optionally substituted with —S(═O)$_2$OH or —C(═O)OH. In some embodiments, $R^{1A}$ is —C(═O)—NH—$C_2$ alkyl-S(═O)$_2$OH.

In some embodiments, $R^{2A}$ is H. In some embodiments, $R^{2A}$ is —C(═O)OH. In some embodiments, $R^{2A}$ is —S(═O)$_2$OH. In some embodiments, $R^{2A}$ is $C_{1-12}$ alkyl (e.g., methyl, ethyl, propyl, butyl, pentyl, or hexyl). In some embodiments, $R^{2A}$ is $C_{1-12}$ alkyl (e.g., methyl, ethyl, propyl, butyl, pentyl, or hexyl) optionally substituted with —S(═O)$_2$OH or —C(═O)OH. In some embodiments, $R^{2A}$ is —C(═O)—NH—($C_{1-12}$ alkyl) (e.g., —C(═O)—NH—$C_1$ alkyl, —C(═O)—NH—$C_2$ alkyl, —C(═O)—NH—$C_3$ alkyl, —C(═O)—NH—$C_4$ alkyl, —C(═O)—NH—$C_5$ alkyl, or —C(═O)—NH—$C_6$ alkyl). In some embodiments, $R^{2A}$ is —C(═O)—NH—($C_{1-12}$ alkyl), wherein the $C_{1-12}$ alkyl is optionally substituted with —S(═O)$_2$OH or —C(═O)OH. In some embodiments, $R^{2A}$ is —C(═O)—NH—$C_2$ alkyl-S(═O)$_2$OH.

In some embodiments, $R^{3A}$ is H. In some embodiments, $R^{3A}$ is —C(═O)OH. In some embodiments, $R^{3A}$ is —S(═O)$_2$OH. In some embodiments, $R^{3A}$ is $C_{1-12}$ alkyl (e.g., methyl, ethyl, propyl, butyl, pentyl, or hexyl). In some embodiments, $R^{3A}$ is $C_{1-12}$ alkyl (e.g., methyl, ethyl, propyl, butyl, pentyl, or hexyl) optionally substituted with —S(═O)$_2$OH or —C(═O)OH. In some embodiments, $R^{3A}$ is —C(═O)—NH—($C_{1-12}$ alkyl) (e.g., —C(═O)—NH—$C_1$ alkyl, —C(═O)—NH—$C_2$ alkyl, —C(═O)—NH—$C_3$ alkyl, —C(═O)—NH—$C_4$ alkyl, —C(═O)—NH—$C_5$ alkyl, or —C(═O)—NH—$C_6$ alkyl). In some embodiments, $R^{3A}$ is —C(═O)—NH—($C_{1-12}$ alkyl), wherein the $C_{1-12}$ alkyl is optionally substituted with —S(═O)$_2$OH or —C(═O)OH. In some embodiments, $R^{3A}$ is —C(═O)—NH—$C_2$ alkyl-S(═O)$_2$OH.

In some embodiments, $R^{4A}$ is H. In some embodiments, $R^{4A}$ is —C(═O)OH. In some embodiments, $R^{4A}$ is —S(═O)$_2$OH. In some embodiments, $R^{4A}$ is $C_{1-12}$ alkyl (e.g., methyl, ethyl, propyl, butyl, pentyl, or hexyl). In some embodiments, $R^{4A}$ is $C_{1-12}$ alkyl (e.g., methyl, ethyl, propyl, butyl, pentyl, or hexyl) optionally substituted with —S(═O)$_2$OH or —C(═O)OH. In some embodiments, $R^{4A}$ is —C(═O)—NH—($C_{1-12}$ alkyl) (e.g., —C(═O)—NH—$C_1$ alkyl, —C(═O)—NH—$C_2$ alkyl, —C(═O)—NH—$C_3$ alkyl, —C(═O)—NH—$C_4$ alkyl, —C(═O)—NH—$C_5$ alkyl, or —C(═O)—NH—$C_6$ alkyl). In some embodiments, $R^{4A}$ is —C(═O)—NH—($C_{1-12}$ alkyl), wherein the $C_{1-12}$ alkyl is optionally substituted with —S(═O)$_2$OH or —C(═O)OH. In some embodiments, $R^{4A}$ is —C(═O)—NH—$C_2$ alkyl-S(═O)$_2$OH.

In some embodiments, $R^{5A}$ is H. In some embodiments, $R^{5A}$ is —C(═O)OH. In some embodiments, $R^{5A}$ is —S(═O)$_2$OH. In some embodiments, $R^{5A}$ is $C_{1-12}$ alkyl (e.g., methyl, ethyl, propyl, butyl, pentyl, or hexyl). In some embodiments, $R^{5A}$ is $C_{1-12}$ alkyl (e.g., methyl, ethyl, propyl, butyl, pentyl, or hexyl) optionally substituted with —S(═O)$_2$OH or —C(═O)OH. In some embodiments, $R^{5A}$ is —C(═O)—NH—($C_{1-12}$ alkyl) (e.g., —C(═O)—NH—$C_1$ alkyl, —C(═O)—NH—$C_2$ alkyl, —C(═O)—NH—$C_3$ alkyl, —C(═O)—NH—$C_4$ alkyl, —C(═O)—NH—$C_5$ alkyl, or —C(═O)—NH—$C_6$ alkyl). In some embodiments, $R^{5A}$ is —C(═O)—NH—($C_{1-12}$ alkyl), wherein the $C_{1-12}$ alkyl is optionally substituted with —S(═O)$_2$OH or —C(═O)OH. In some embodiments, $R^{5A}$ is —C(═O)—NH—$C_2$ alkyl-S(═O)$_2$OH.

In some embodiments, $R^{6A}$ is H. In some embodiments, $R^{6A}$ is —C(═O)OH. In some embodiments, $R^{6A}$ is —S(═O)$_2$OH. In some embodiments, $R^{6A}$ is $C_{1-12}$ alkyl (e.g., methyl, ethyl, propyl, butyl, pentyl, or hexyl). In some embodiments, $R^{6A}$ is $C_{1-12}$ alkyl (e.g., methyl, ethyl, propyl, butyl, pentyl, or hexyl) optionally substituted with —S(═O)$_2$OH or —C(═O)OH. In some embodiments, $R^{6A}$ is —C(═O)—NH—($C_{1-12}$ alkyl) (e.g., —C(═O)—NH—$C_1$ alkyl, —C(═O)—NH—$C_2$ alkyl, —C(═O)—NH—$C_3$ alkyl, —C(═O)—NH—$C_4$ alkyl, —C(═O)—NH—$C_5$ alkyl, or —C(═O)—NH—$C_6$ alkyl). In some embodiments, $R^{6A}$ is —C(═O)—NH—($C_{1-12}$ alkyl), wherein the $C_{1-12}$ alkyl is optionally substituted with —S(═O)$_2$OH or —C(═O)OH. In some embodiments, $R^{6A}$ is —C(═O)—NH—$C_2$ alkyl-S(═O)$_2$OH.

In some embodiments, $R^{7A}$ is H. In some embodiments, $R^{7A}$ is —C(═O)OH. In some embodiments, $R^{7A}$ is —S(═O)$_2$OH. In some embodiments, $R^{7A}$ is $C_{1-12}$ alkyl (e.g., methyl, ethyl, propyl, butyl, pentyl, or hexyl). In some embodiments, $R^{7A}$ is $C_{1-12}$ alkyl (e.g., methyl, ethyl, propyl, butyl, pentyl, or hexyl) optionally substituted with —S(═O)$_2$OH or —C(═O)OH. In some embodiments, $R^{7A}$ is —C(═O)—NH—($C_{1-12}$ alkyl) (e.g., —C(═O)—NH—$C_1$ alkyl, —C(═O)—NH—$C_2$ alkyl, —C(═O)—NH—$C_3$ alkyl, —C(═O)—NH—$C_4$ alkyl, —C(═O)—NH—$C_5$ alkyl, or —C(═O)—NH—$C_6$ alkyl). In some embodiments, $R^{7A}$ is —C(═O)—NH—($C_{1-12}$ alkyl), wherein the $C_{1-12}$ alkyl is optionally substituted with —S(═O)$_2$OH or —C(═O)OH. In some embodiments, $R^{7A}$ is —C(═O)—NH—$C_2$ alkyl-S(═O)$_2$OH.

In some embodiments, $R^{8A}$ is H. In some embodiments, $R^{8A}$ is —C(═O)OH. In some embodiments, $R^{8A}$ is —S(=O)$_2$OH. In some embodiments, $R^{8A}$ is $C_{1-12}$ alkyl (e.g., methyl, ethyl, propyl, butyl, pentyl, or hexyl). In some embodiments, $R^{8A}$ is $C_{1-12}$ alkyl (e.g., methyl, ethyl, propyl, butyl, pentyl, or hexyl) optionally substituted with —S(=O)$_2$OH or —C(=O)OH. In some embodiments, $R^{8A}$ is —C(=O)—NH—($C_{1-12}$ alkyl) (e.g., —C(=O)—NH—$C_1$ alkyl, —C(=O)—NH—$C_2$ alkyl, —C(=O)—NH—$C_3$ alkyl, —C(=O)—NH—$C_4$ alkyl, —C(=O)—NH—$C_5$ alkyl, or —C(=O)—NH—$C_6$ alkyl). In some embodiments, $R^{8A}$ is —C(=O)—NH—($C_{1-12}$ alkyl), wherein the $C_{1-12}$ alkyl is optionally substituted with —S(=O)$_2$OH or —C(=O)OH. In some embodiments, $R^{8A}$ is —C(=O)—NH—$C_2$ alkyl-S(=O)$_2$OH.

In some embodiments, $R^{1B}$ is H. In some embodiments, $R^{1B}$ is —C(=O)OH. In some embodiments, $R^{1B}$ is —S(=O)$_2$OH. In some embodiments, $R^{1B}$ is $C_{1-12}$ alkyl (e.g., methyl, ethyl, propyl, butyl, pentyl, or hexyl). In some embodiments, $R^{1B}$ is $C_{1-12}$ alkyl (e.g., methyl, ethyl, propyl, butyl, pentyl, or hexyl) optionally substituted with —S(=O)$_2$OH or —C(=O)OH. In some embodiments, $R^{1B}$ is —C(=O)—NH—($C_{1-12}$ alkyl) (e.g., —C(=O)—NH—$C_1$ alkyl, —C(=O)—NH—$C_2$ alkyl, —C(=O)—NH—$C_3$ alkyl, —C(=O)—NH—$C_4$ alkyl, —C(=O)—NH—$C_5$ alkyl, or —C(=O)—NH—$C_6$ alkyl). In some embodiments, $R^{1B}$ is —C(=O)—NH—($C_{1-12}$ alkyl), wherein the $C_{1-12}$ alkyl is optionally substituted with —S(=O)$_2$OH or —C(=O)OH. In some embodiments, $R^{1B}$ is —C(=O)—NH—$C_2$ alkyl-S(=O)$_2$OH.

In some embodiments, $R^{2B}$ is H. In some embodiments, $R^{2B}$ is —C(=O)OH. In some embodiments, $R^{2B}$ is —S(=O)$_2$OH. In some embodiments, $R^{2B}$ is $C_{1-12}$ alkyl (e.g., methyl, ethyl, propyl, butyl, pentyl, or hexyl). In some embodiments, $R^{2B}$ is $C_{1-12}$ alkyl (e.g., methyl, ethyl, propyl, butyl, pentyl, or hexyl) optionally substituted with —S(=O)$_2$OH or —C(=O)OH. In some embodiments, $R^{2B}$ is —C(=O)—NH—($C_{1-12}$ alkyl) (e.g., —C(=O)—NH—$C_1$ alkyl, —C(=O)—NH—$C_2$ alkyl, —C(=O)—NH—$C_3$ alkyl, —C(=O)—NH—$C_4$ alkyl, —C(=O)—NH—$C_5$ alkyl, or —C(=O)—NH—$C_6$ alkyl). In some embodiments, $R^{2B}$ is —C(=O)—NH—($C_{1-12}$ alkyl), wherein the $C_{1-12}$ alkyl is optionally substituted with —S(=O)$_2$OH or —C(=O)OH. In some embodiments, $R^{2B}$ is —C(=O)—NH—$C_2$ alkyl-S(=O)$_2$OH.

In some embodiments, $R^{3B}$ is H. In some embodiments, $R^{3B}$ is —C(=O)OH. In some embodiments, $R^{3B}$ is —S(=O)$_2$OH. In some embodiments, $R^{3B}$ is $C_{1-12}$ alkyl (e.g., methyl, ethyl, propyl, butyl, pentyl, or hexyl). In some embodiments, $R^{3B}$ is $C_{1-12}$ alkyl (e.g., methyl, ethyl, propyl, butyl, pentyl, or hexyl) optionally substituted with —S(=O)$_2$OH or —C(=O)OH. In some embodiments, $R^{3B}$ is —C(=O)—NH—($C_{1-12}$ alkyl) (e.g., —C(=O)—NH—$C_1$ alkyl, —C(=O)—NH—$C_2$ alkyl, —C(=O)—NH—$C_3$ alkyl, —C(=O)—NH—$C_4$ alkyl, —C(=O)—NH—$C_5$ alkyl, or —C(=O)—NH—$C_6$ alkyl). In some embodiments, $R^{3B}$ is —C(=O)—NH—($C_{1-12}$ alkyl), wherein the $C_{1-12}$ alkyl is optionally substituted with —S(=O)$_2$OH or —C(=O)OH. In some embodiments, $R^{3B}$ is —C(=O)—NH—$C_2$ alkyl-S(=O)$_2$OH.

In some embodiments, $R^{4B}$ is H. In some embodiments, $R^{4B}$ is —C(=O)OH. In some embodiments, $R^{4B}$ is —S(=O)$_2$OH. In some embodiments, $R^{4B}$ is $C_{1-12}$ alkyl (e.g., methyl, ethyl, propyl, butyl, pentyl, or hexyl). In some embodiments, $R^{4B}$ is $C_{1-12}$ alkyl (e.g., methyl, ethyl, propyl, butyl, pentyl, or hexyl) optionally substituted with —S(=O)$_2$OH or —C(=O)OH. In some embodiments, $R^{4B}$ is —C(=O)—NH—($C_{1-12}$ alkyl) (e.g., —C(=O)—NH—$C_1$ alkyl, —C(=O)—NH—$C_2$ alkyl, —C(=O)—NH—$C_3$ alkyl, —C(=O)—NH—$C_4$ alkyl, —C(=O)—NH—$C_5$ alkyl, or —C(=O)—NH—$C_6$ alkyl). In some embodiments, $R^{4B}$ is —C(=O)—NH—($C_{1-12}$ alkyl), wherein the $C_{1-12}$ alkyl is optionally substituted with —S(=O)$_2$OH or —C(=O)OH. In some embodiments, $R^{4B}$ is —C(=O)—NH—$C_2$ alkyl-S(=O)$_2$OH.

In some embodiments, $R^{5B}$ is H. In some embodiments, $R^{5B}$ is —C(=O)OH. In some embodiments, $R^{5B}$ is —S(=O)$_2$OH. In some embodiments, $R^{5B}$ is $C_{1-12}$ alkyl (e.g., methyl, ethyl, propyl, butyl, pentyl, or hexyl). In some embodiments, $R^{5B}$ is $C_{1-12}$ alkyl (e.g., methyl, ethyl, propyl, butyl, pentyl, or hexyl) optionally substituted with —S(=O)$_2$OH or —C(=O)OH. In some embodiments, $R^{5B}$ is —C(=O)—NH—($C_{1-12}$ alkyl) (e.g., —C(=O)—NH—$C_1$ alkyl, —C(=O)—NH—$C_2$ alkyl, —C(=O)—NH—$C_3$ alkyl, —C(=O)—NH—$C_4$ alkyl, —C(=O)—NH—$C_5$ alkyl, or —C(=O)—NH—$C_6$ alkyl). In some embodiments, $R^{5B}$ is —C(=O)—NH—($C_{1-12}$ alkyl), wherein the $C_{1-12}$ alkyl is optionally substituted with —S(=O)$_2$OH or —C(=O)OH. In some embodiments, $R^{5B}$ is —C(=O)—NH—$C_2$ alkyl-S(=O)$_2$OH.

In some embodiments, $R^{6B}$ is H. In some embodiments, $R^{6B}$ is —C(=O)OH. In some embodiments, $R^{6B}$ is —S(=O)$_2$OH. In some embodiments, $R^{6B}$ is $C_{1-12}$ alkyl (e.g., methyl, ethyl, propyl, butyl, pentyl, or hexyl). In some embodiments, $R^{6B}$ is $C_{1-12}$ alkyl (e.g., methyl, ethyl, propyl, butyl, pentyl, or hexyl) optionally substituted with —S(=O)$_2$OH or —C(=O)OH. In some embodiments, $R^{6B}$ is —C(=O)—NH—($C_{1-12}$ alkyl) (e.g., —C(=O)—NH—$C_1$ alkyl, —C(=O)—NH—$C_2$ alkyl, —C(=O)—NH—$C_3$ alkyl, —C(=O)—NH—$C_4$ alkyl, —C(=O)—NH—$C_5$ alkyl, or —C(=O)—NH—$C_6$ alkyl). In some embodiments, $R^{6B}$ is —C(=O)—NH—($C_{1-12}$ alkyl), wherein the $C_{1-12}$ alkyl is optionally substituted with —S(=O)$_2$OH or —C(=O)OH. In some embodiments, $R^{6B}$ is —C(=O)—NH—$C_2$ alkyl-S(=O)$_2$OH.

In some embodiments, $R^{7B}$ is H. In some embodiments, $R^{7B}$ is —C(=O)OH. In some embodiments, $R^{7B}$ is —S(=O)$_2$OH. In some embodiments, $R^{7B}$ is $C_{1-12}$ alkyl (e.g., methyl, ethyl, propyl, butyl, pentyl, or hexyl). In some embodiments, $R^{7B}$ is $C_{1-12}$ alkyl (e.g., methyl, ethyl, propyl, butyl, pentyl, or hexyl) optionally substituted with —S(=O)$_2$OH or —C(=O)OH. In some embodiments, $R^{7B}$ is —C(=O)—NH—($C_{1-12}$ alkyl) (e.g., —C(=O)—NH—$C_1$ alkyl, —C(=O)—NH—$C_2$ alkyl, —C(=O)—NH—$C_3$ alkyl, —C(=O)—NH—$C_4$ alkyl, —C(=O)—NH—$C_5$ alkyl, or —C(=O)—NH—$C_6$ alkyl). In some embodiments, $R^{7B}$ is —C(=O)—NH—($C_{1-12}$ alkyl), wherein the $C_{1-12}$ alkyl is optionally substituted with —S(=O)$_2$OH or —C(=O)OH. In some embodiments, $R^{7B}$ is —C(=O)—NH—$C_2$ alkyl-S(=O)$_2$OH.

In some embodiments, $R^{8B}$ is H. In some embodiments, $R^{8B}$ is —C(=O)OH. In some embodiments, $R^{8B}$ is —S(=O)$_2$OH. In some embodiments, $R^{8B}$ is $C_{1-12}$ alkyl (e.g., methyl, ethyl, propyl, butyl, pentyl, or hexyl). In some embodiments, $R^{8B}$ is $C_{1-12}$ alkyl (e.g., methyl, ethyl, propyl, butyl, pentyl, or hexyl) optionally substituted with —S(=O)$_2$OH or —C(=O)OH. In some embodiments, $R^{8B}$ is —C(=O)—NH—($C_{1-12}$ alkyl) (e.g., —C(=O)—NH—$C_1$ alkyl, —C(=O)—NH—$C_2$ alkyl, —C(=O)—NH—$C_3$ alkyl, —C(=O)—NH—$C_4$ alkyl, —C(=O)—NH—$C_5$ alkyl, or —C(=O)—NH—$C_6$ alkyl). In some embodiments, $R^{8B}$ is —C(=O)—NH—($C_{1-12}$ alkyl), wherein the $C_{1-12}$ alkyl is optionally substituted with —S(=O)$_2$OH or —C(=O)OH. In some embodiments, $R^{8B}$ is —C(=O)—NH—$C_2$ alkyl-S(=O)$_2$OH.

Exemplary Embodiments of the Compounds

In some embodiments, the compound is selected from the compounds described in Table 1, ionic derivatives thereof, isomers thereof, and salts thereof.

In some embodiments, the compound is selected from the compounds described in Table 1.

TABLE 1
| Compound No. | Structure |
| --- | --- |
| 1 | 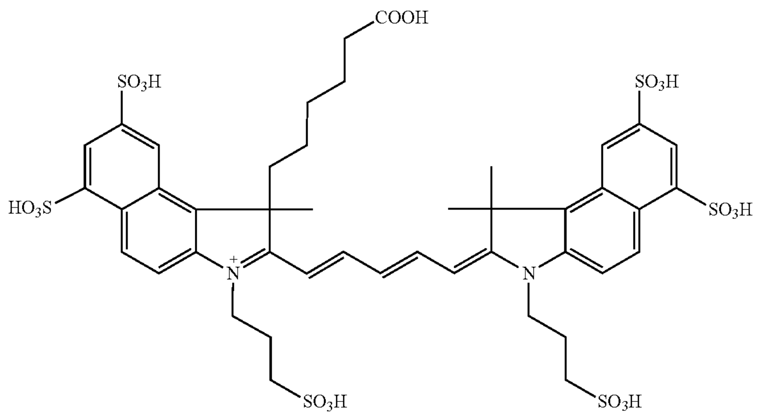 |
| 2 | 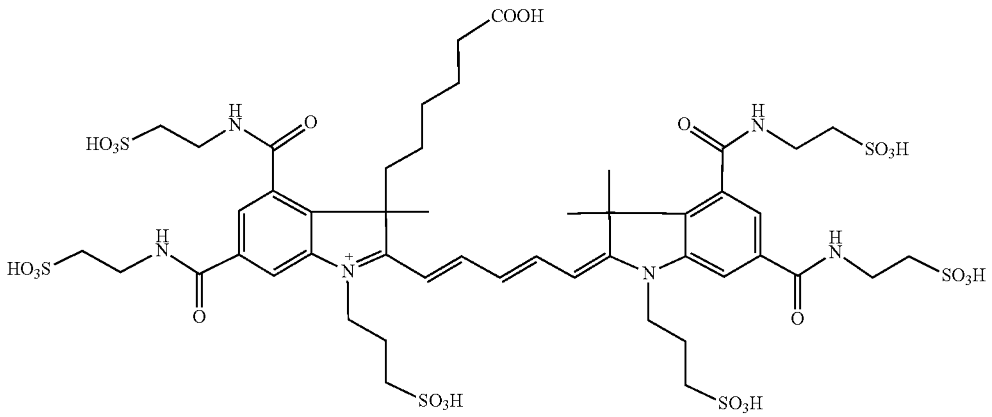 |
| 3 | 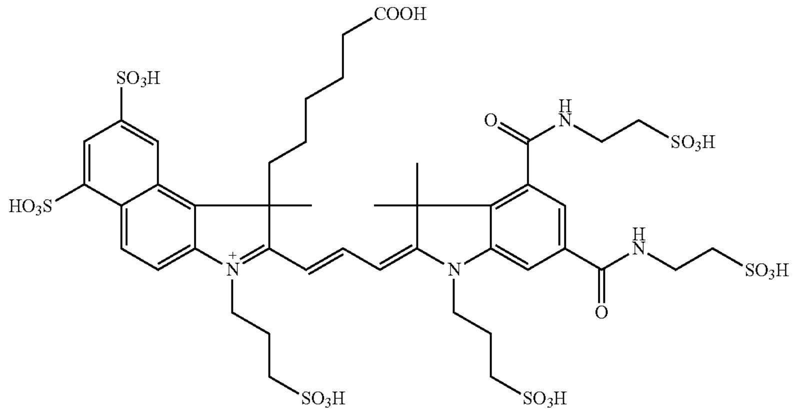 |
| 4 | 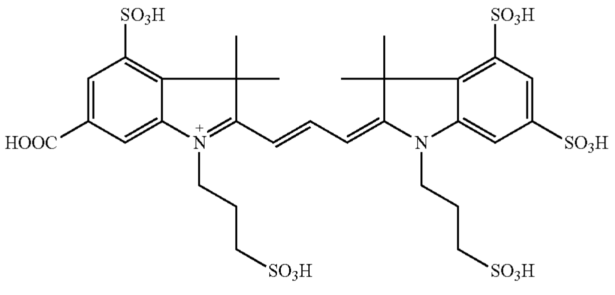 |

TABLE 1-continued
| Compound No. | Structure |
| --- | --- |
| 9 | 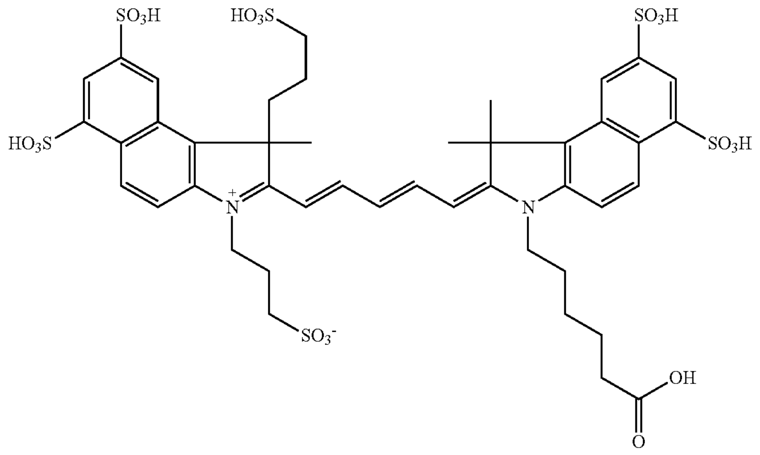 |
| 10 | 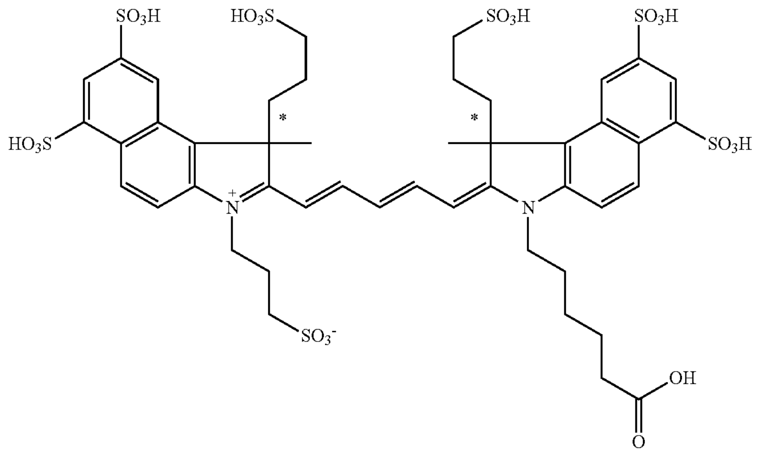 |
| 11 | 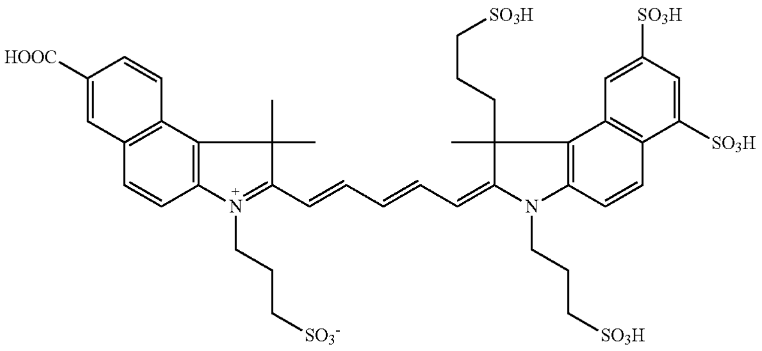 |

TABLE 1-continued
| Compound No. | Structure |
| --- | --- |
| 12 | 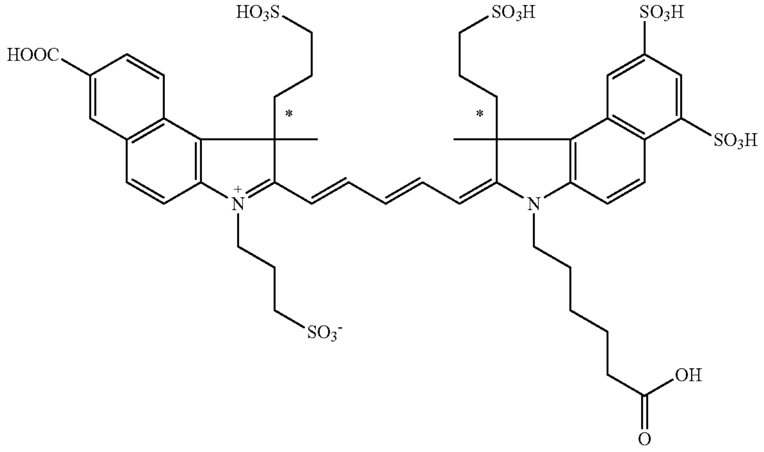 |
| 13 | 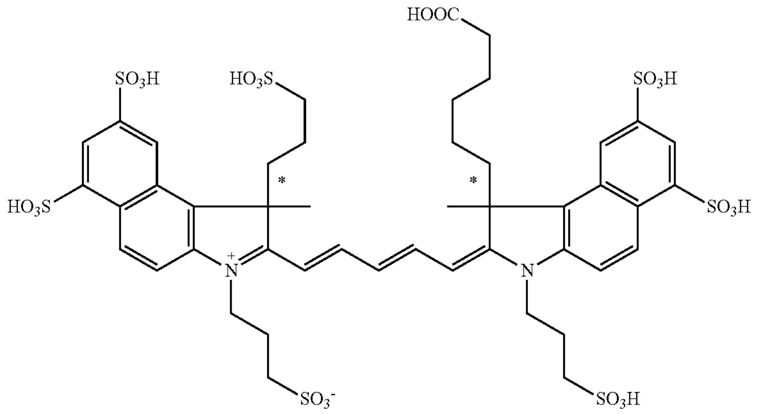 |
| 14 | 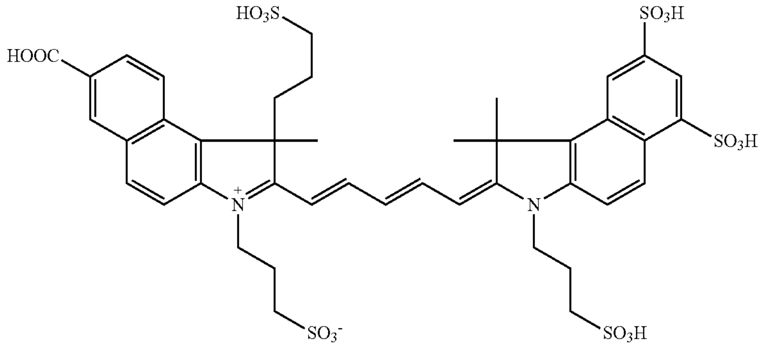 |
| 15 | 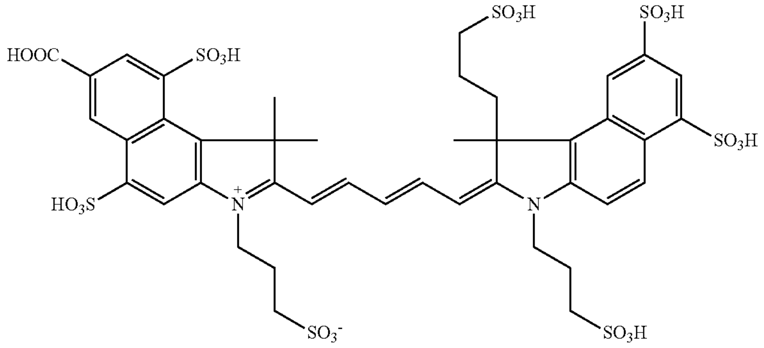 |

TABLE 1-continued
| Compound No. | Structure |
| --- | --- |
| 16 | 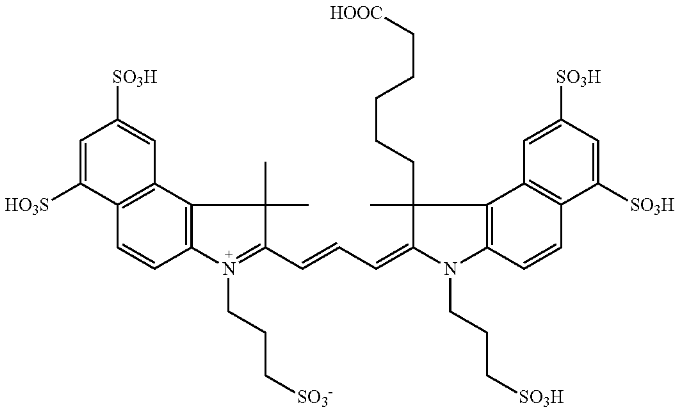 |
| 17 | 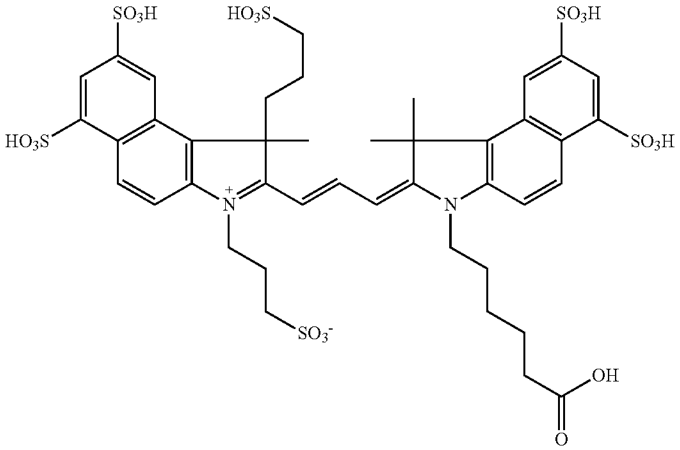 |
| 18 | 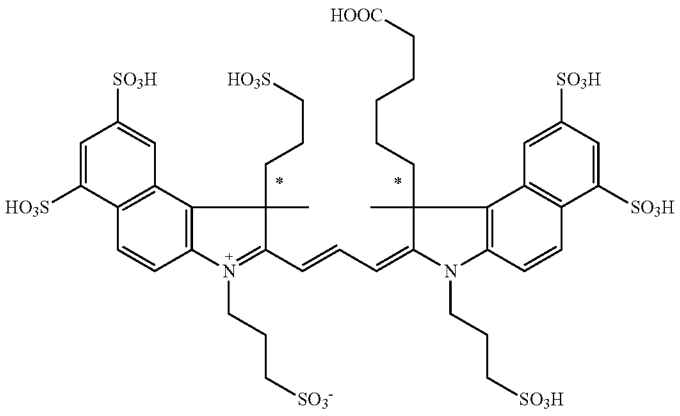 |

TABLE 1-continued
| Compound No. | Structure |
|---|---|
| 19 | 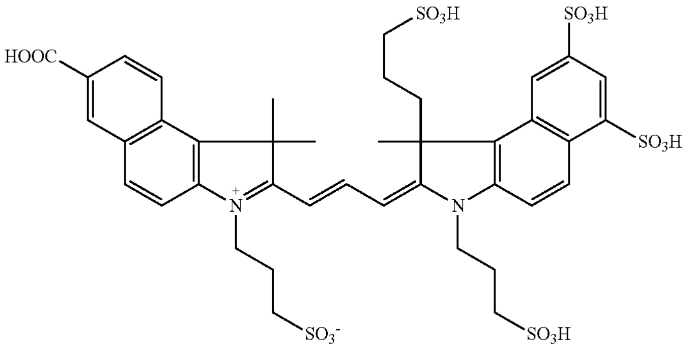 |
| 20 | 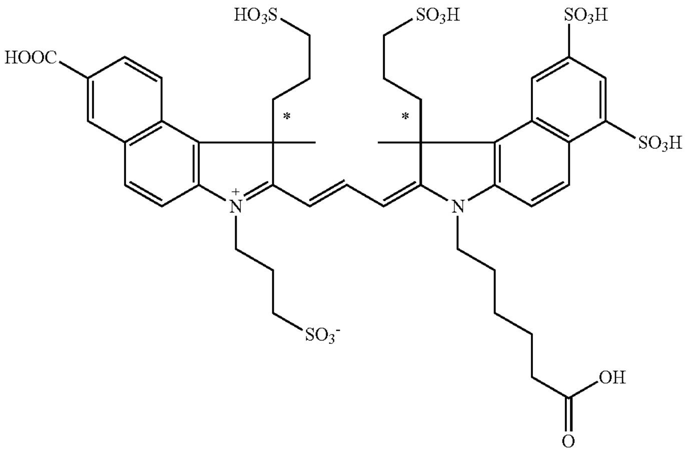 |
| 21 | 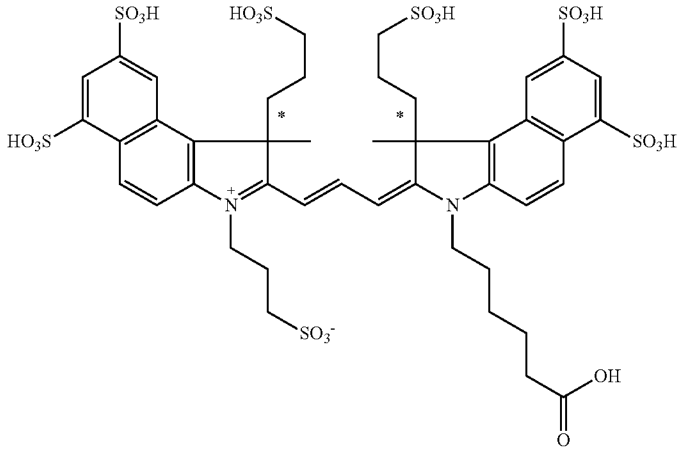 |
| 22 | 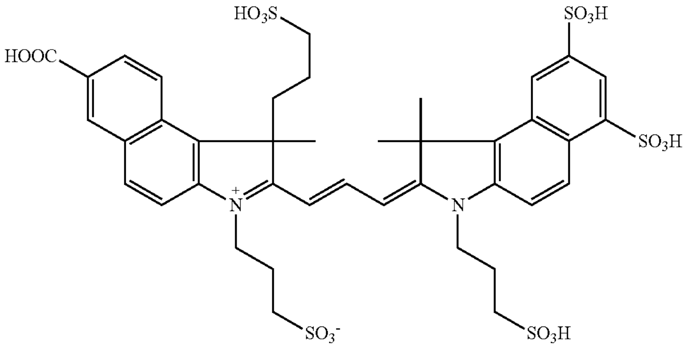 |

TABLE 1-continued
| Compound No. | Structure |
| --- | --- |
| 23 | 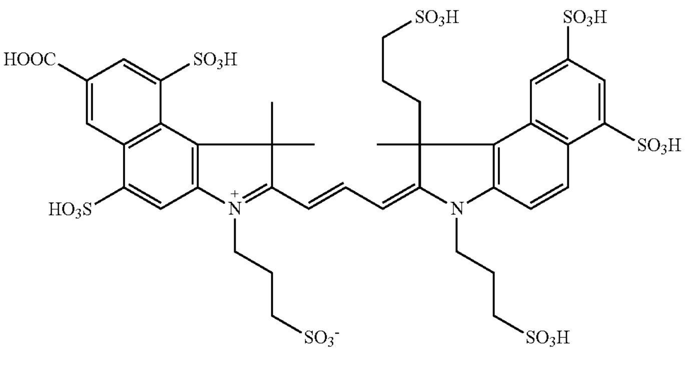 |
| 24 | 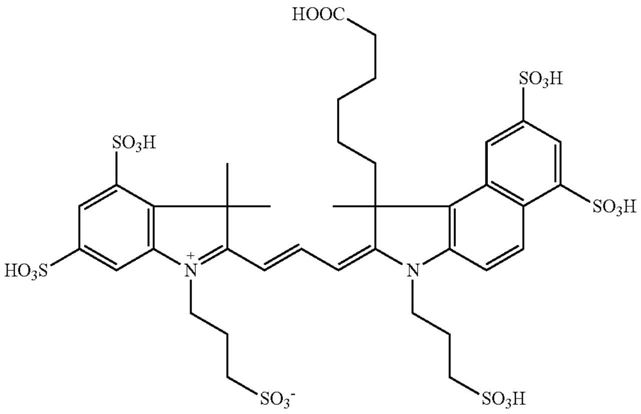 |
| 25 | 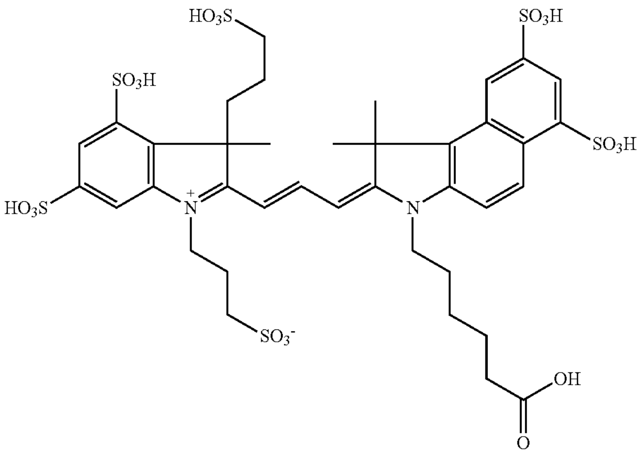 |

TABLE 1-continued
| Compound No. | Structure |
| --- | --- |
| 26 | 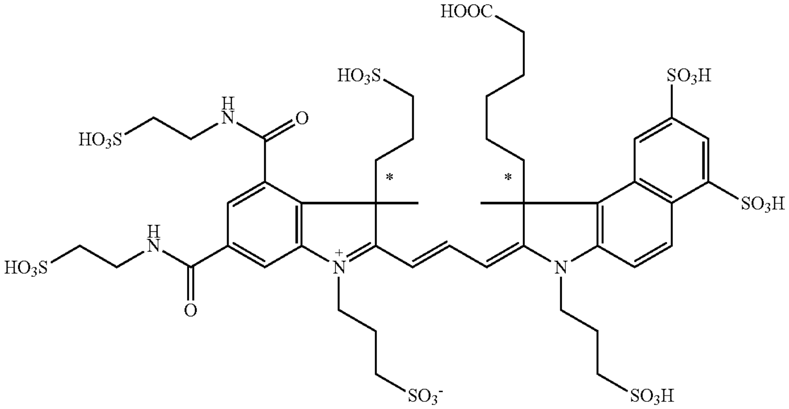 |
| 27 | 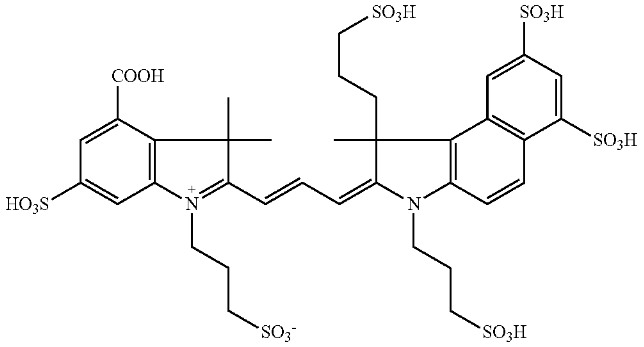 |
| 28 | 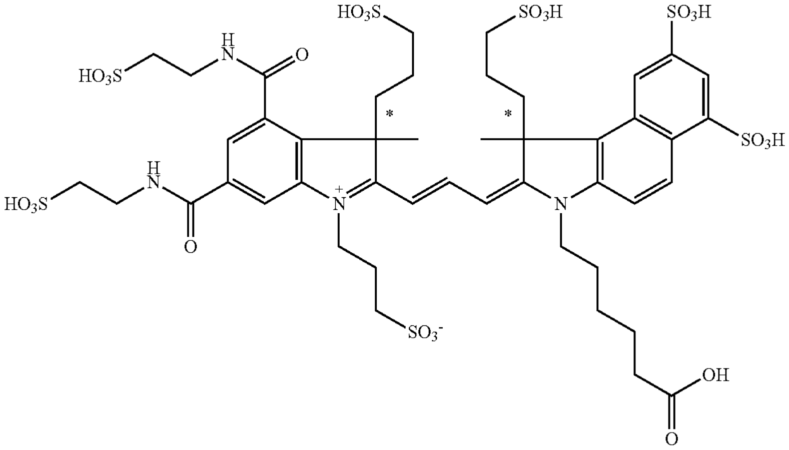 |
| 29 | 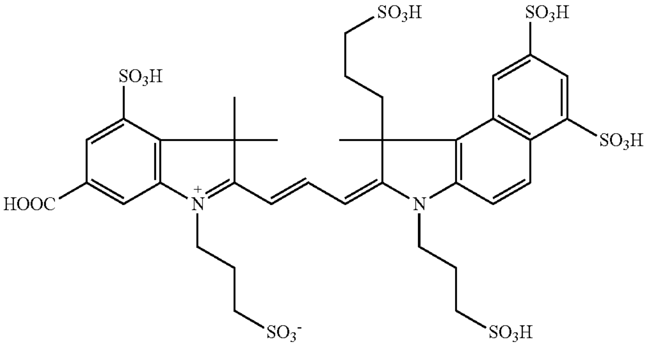 |

TABLE 1-continued
| Compound No. | Structure |
| --- | --- |
| 30 | 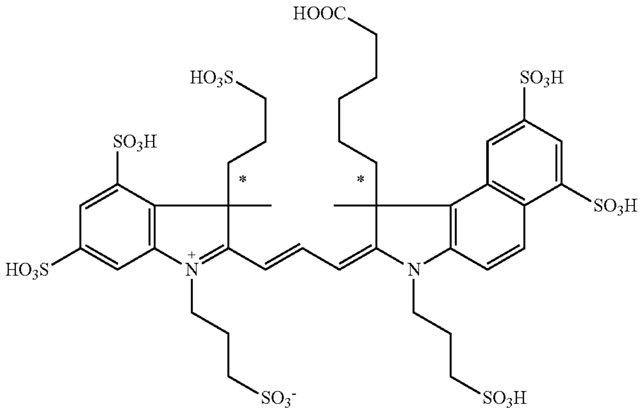 |
| 31 | 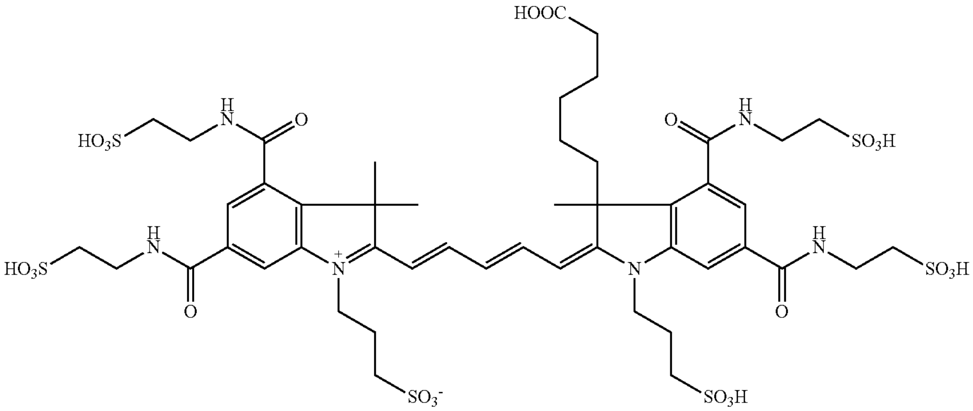 |
| 32 | 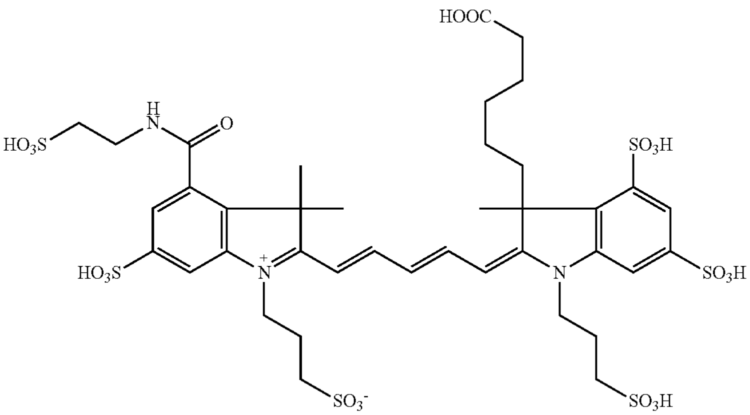 |

TABLE 1-continued
| Compound No. | Structure |
|---|---|
| 33 | 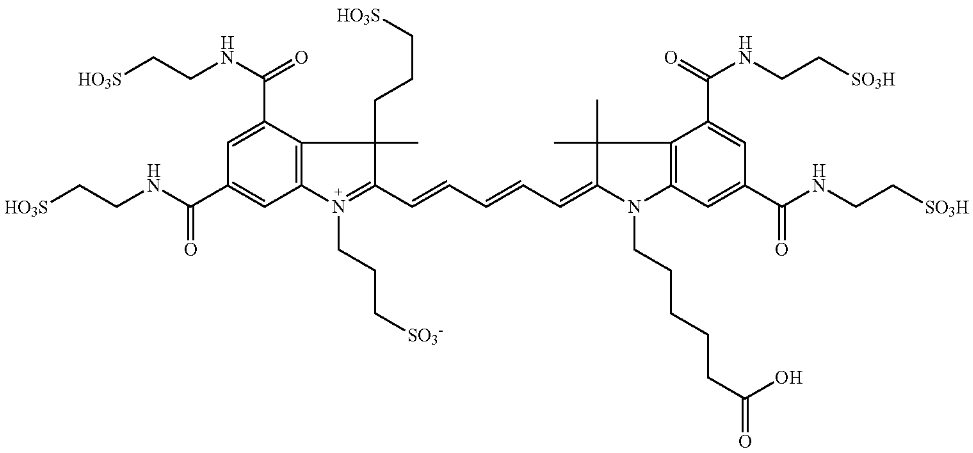 |
| 34 | 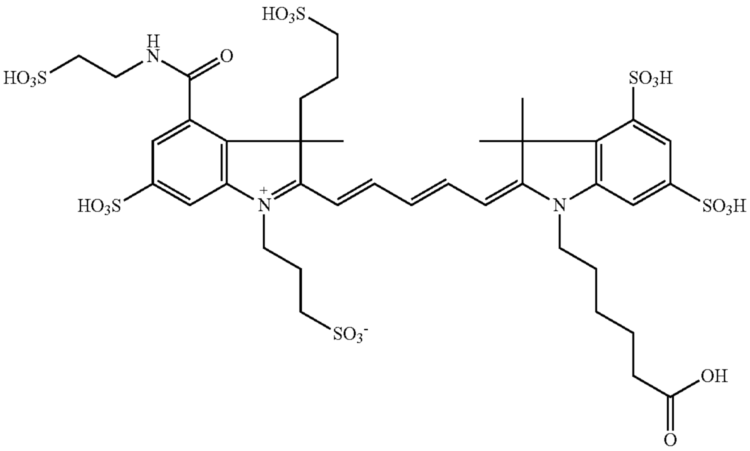 |
| 35 | 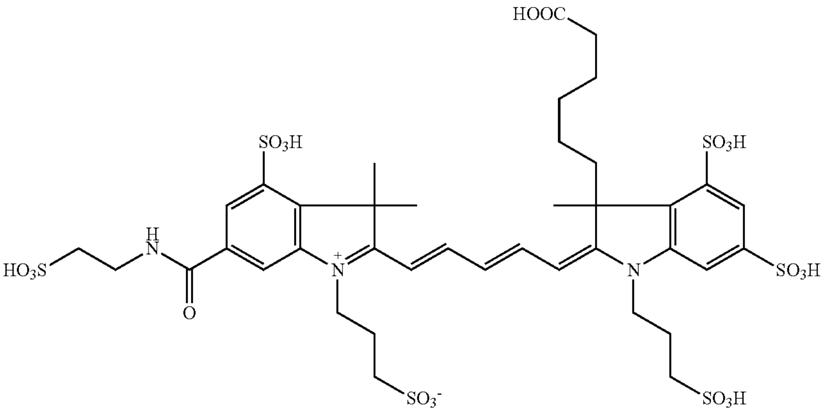 |

TABLE 1-continued
| Compound No. | Structure |
|---|---|
| 36 | 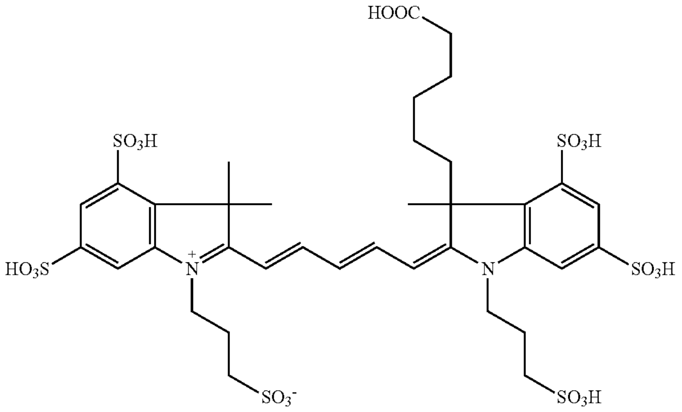 |
| 37 | 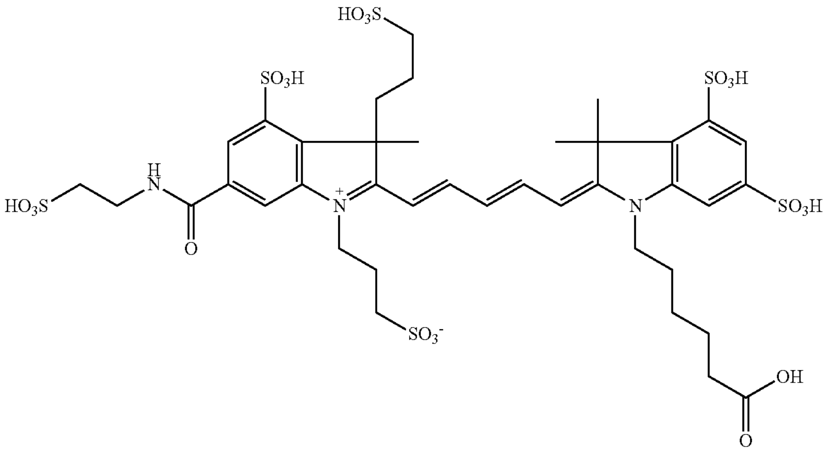 |
| 38 | 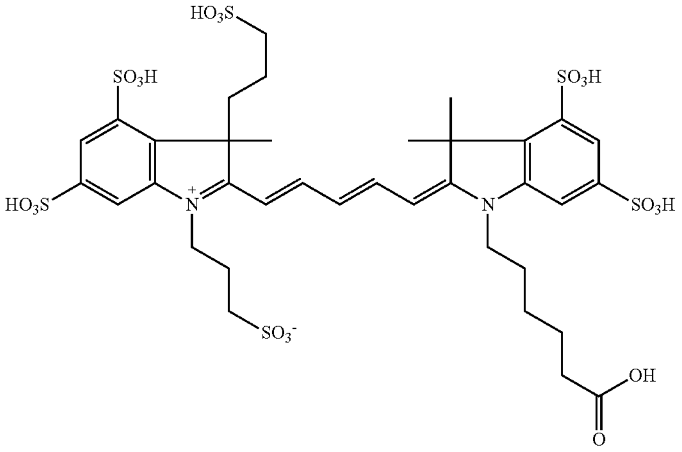 |

TABLE 1-continued
| Compound No. | Structure |
|---|---|
| 39 | 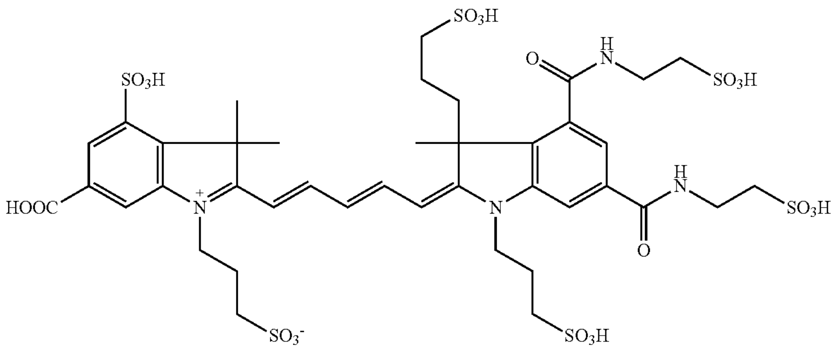 |
| 40 | 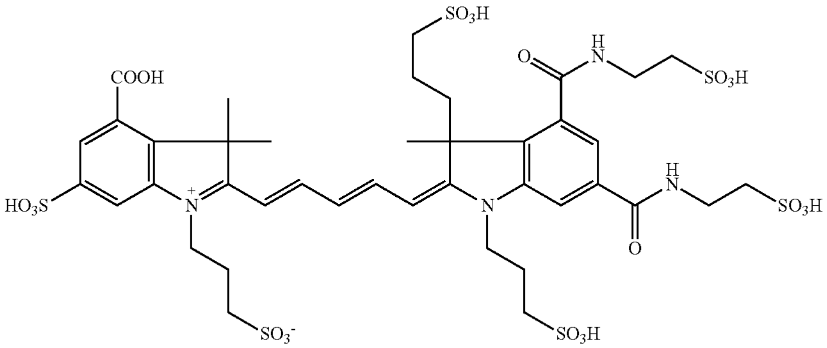 |
| 41 | 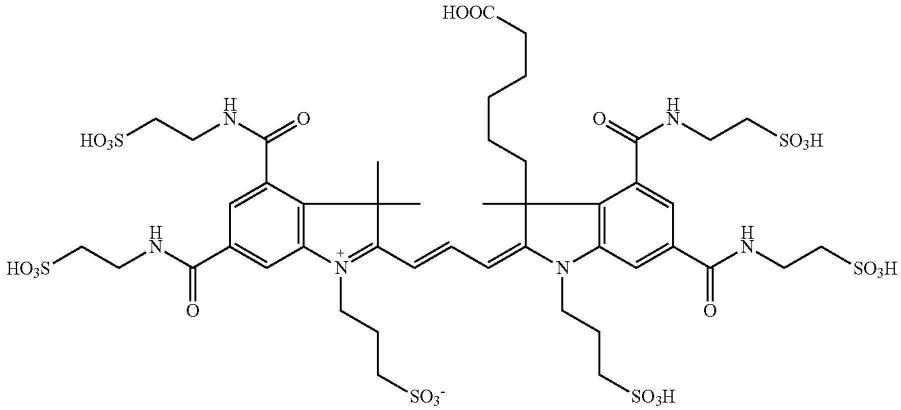 |
| 42 | 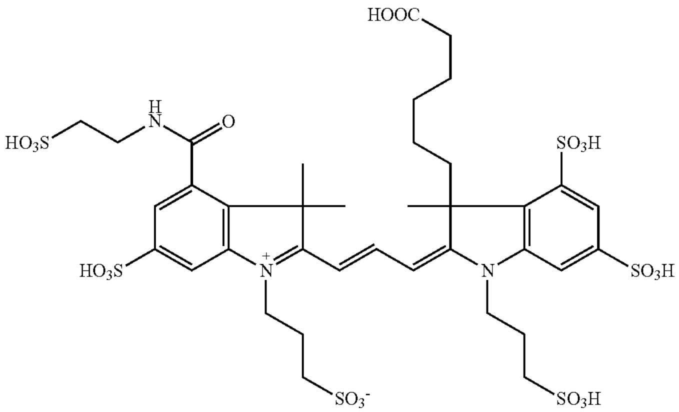 |

TABLE 1-continued
| Compound No. | Structure |
| --- | --- |
| 43 | 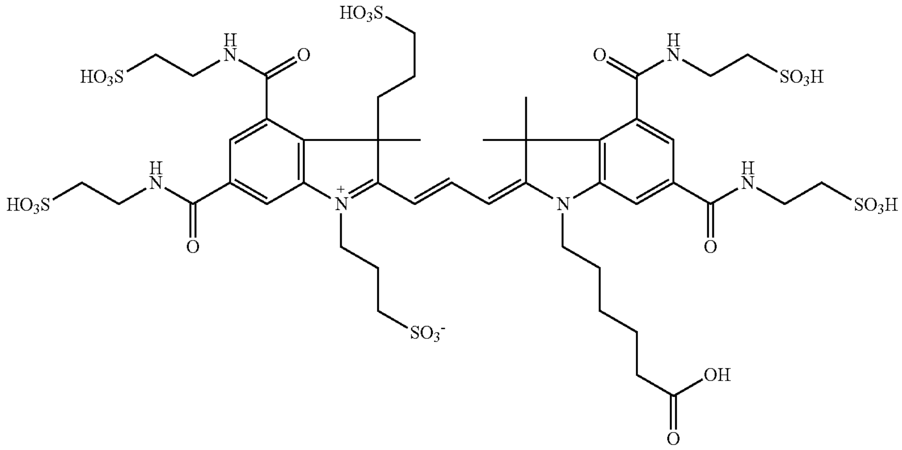 |
| 44 | 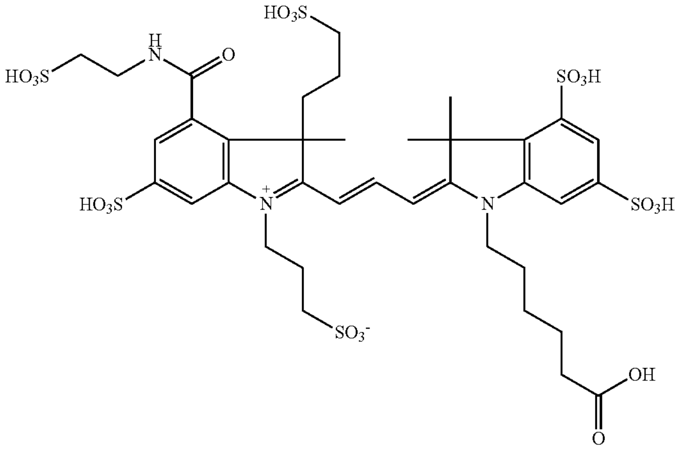 |
| 45 | 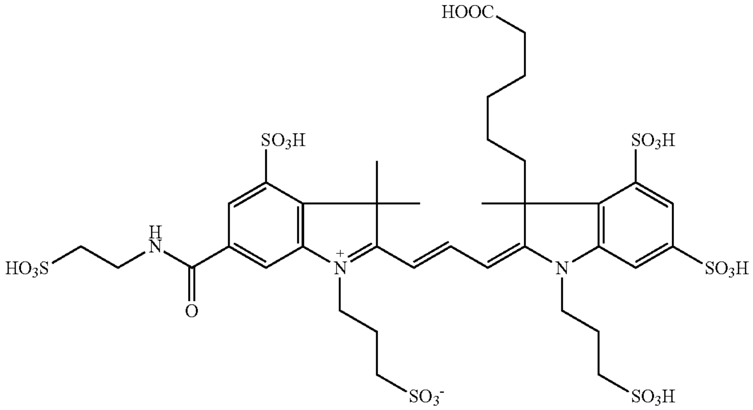 |

TABLE 1-continued
| Compound No. | Structure |
| --- | --- |
| 46 | 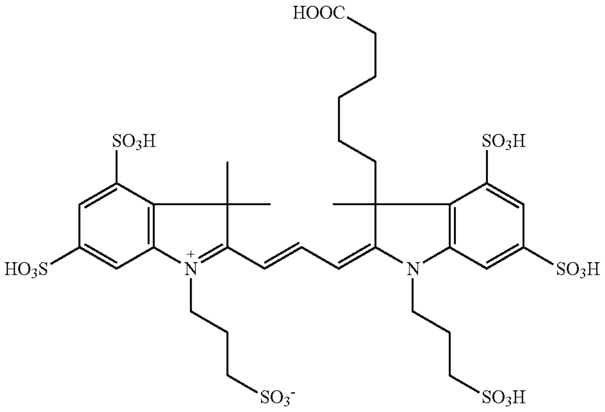 |
| 47 | 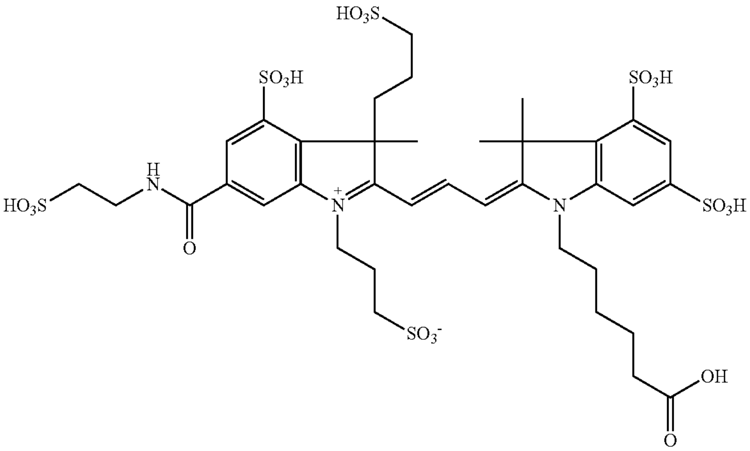 |
| 48 | 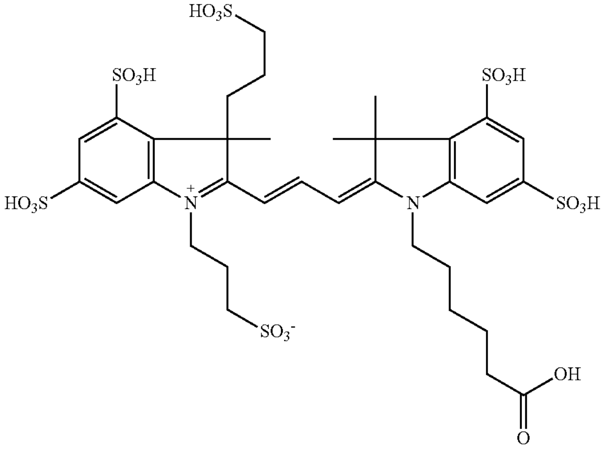 |

TABLE 1-continued
| Compound No. | Structure |
|---|---|
| 49 | 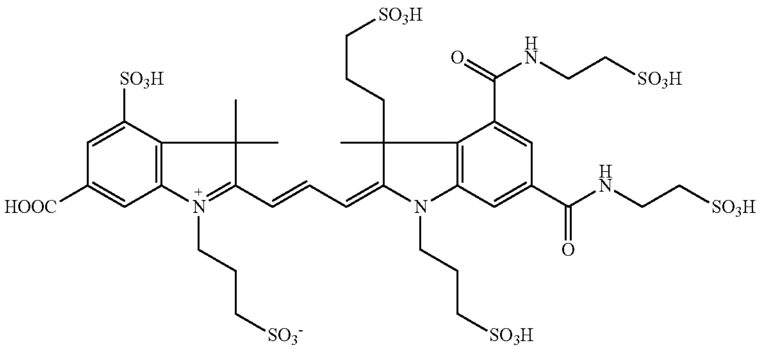 |
| 50 | 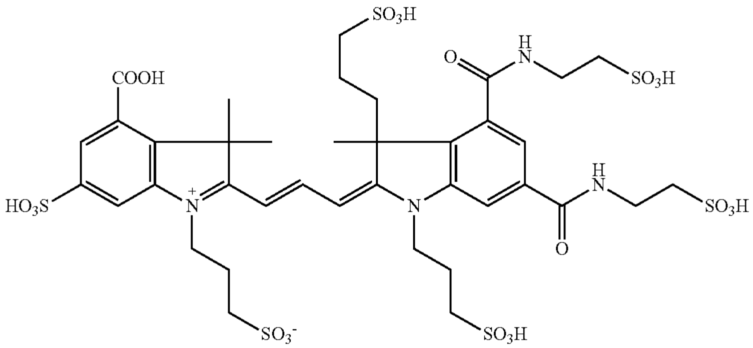 |
TABLE 2
| Compound No. | Structure |
|---|---|
| 51 | 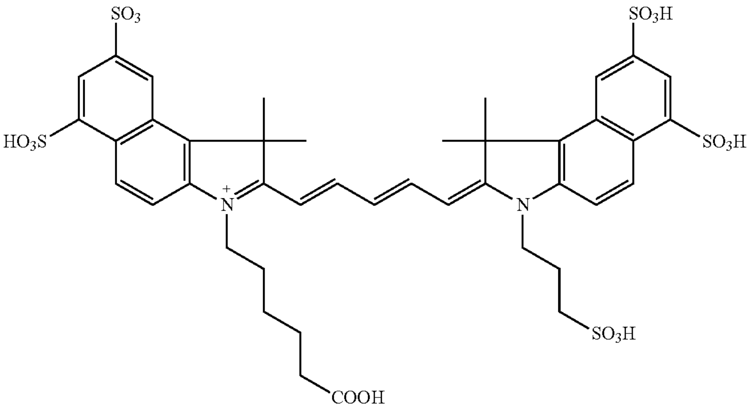 |

TABLE 2-continued
| Compound No. | Structure |
| --- | --- |
| 52 | 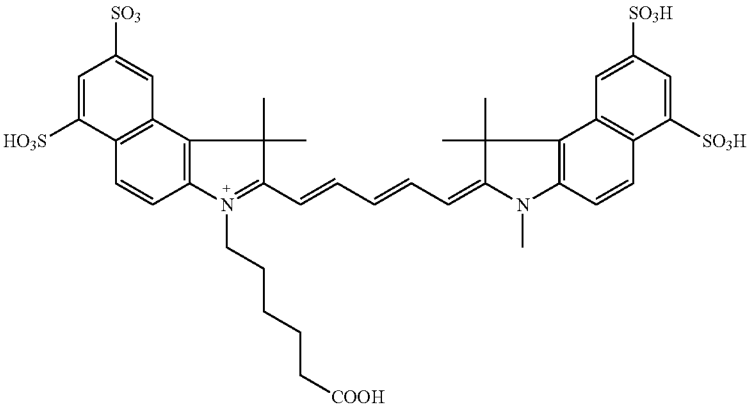 |
| 53 | 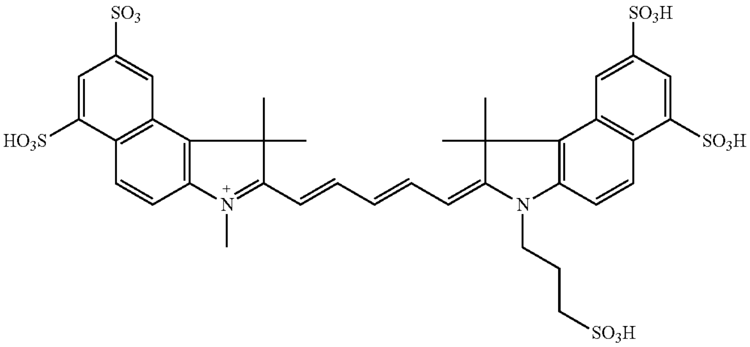 |
| 54 | 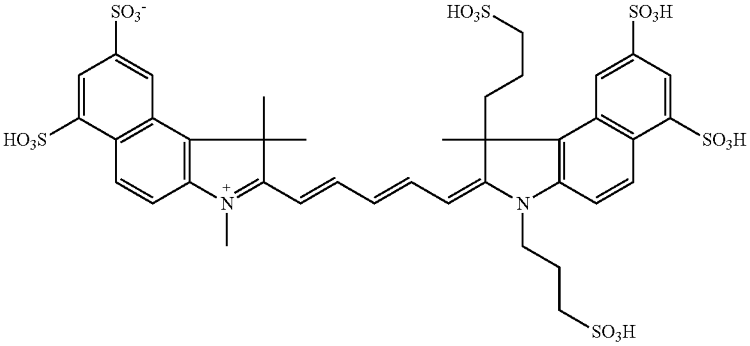 |
| 55 | 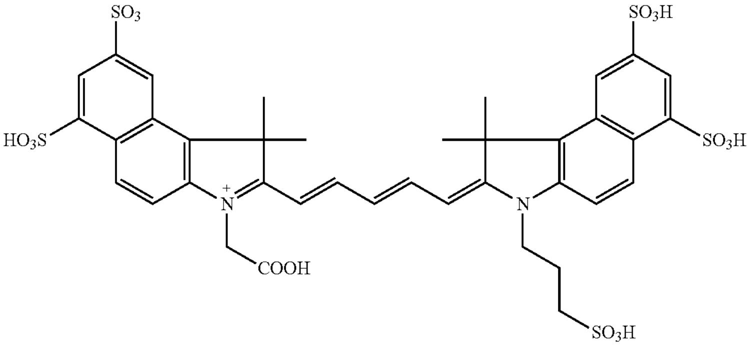 |

TABLE 2-continued
| Compound No. | Structure |
|---|---|
| 56 | 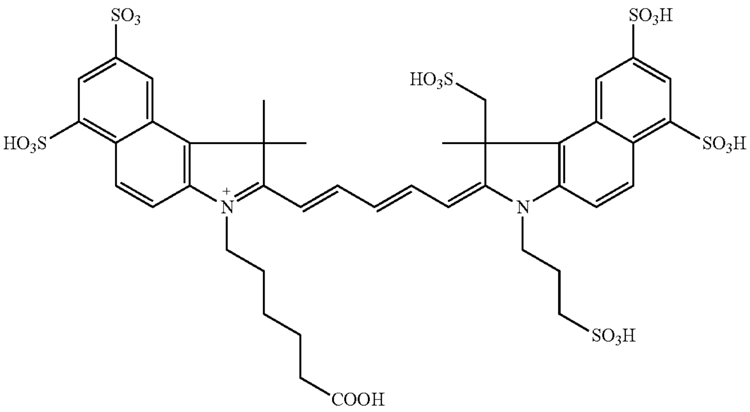 |
| 57 | 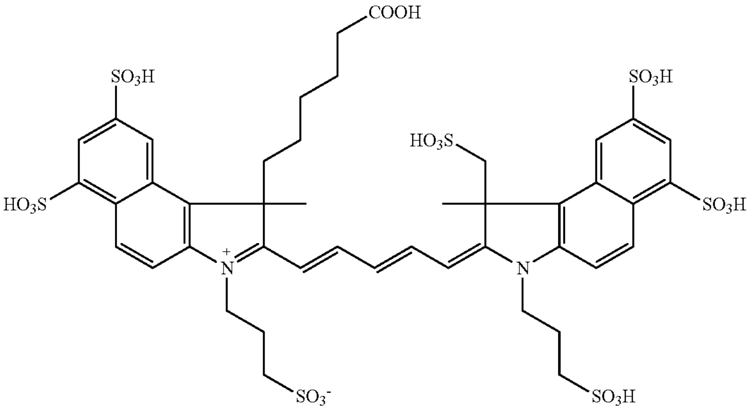 |
| 57a | 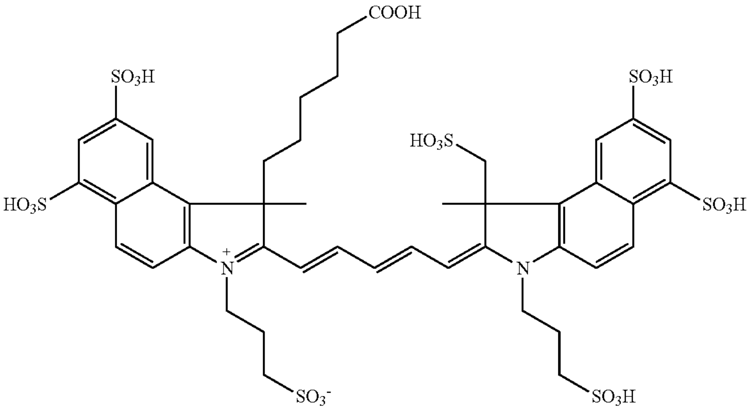 |

TABLE 2-continued
| Compound No. | Structure |
| --- | --- |
| 58 | 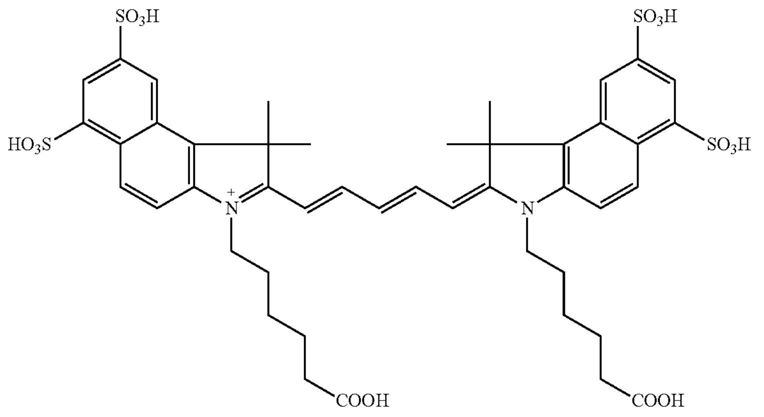 |
| 59 | 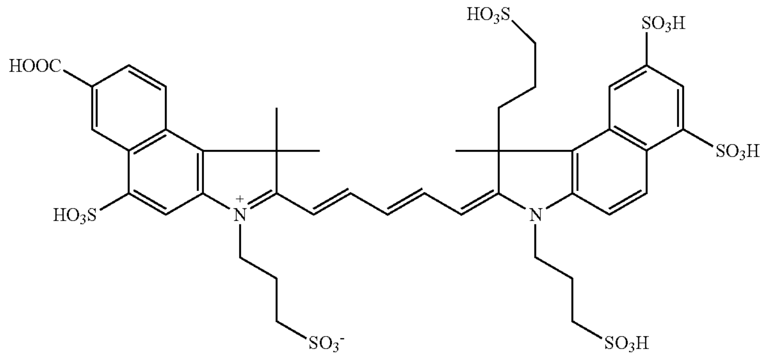 |
| 60 | 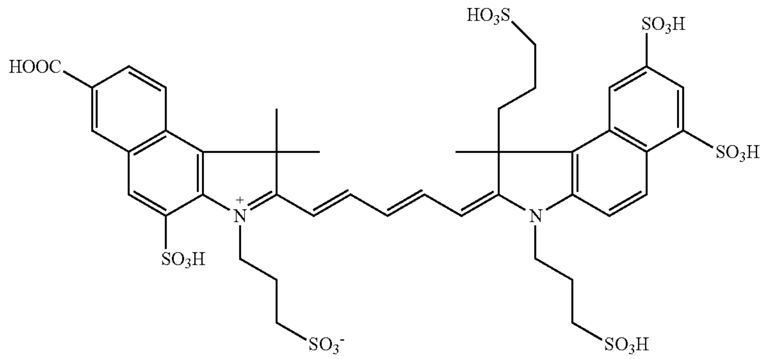 |
| 61 | 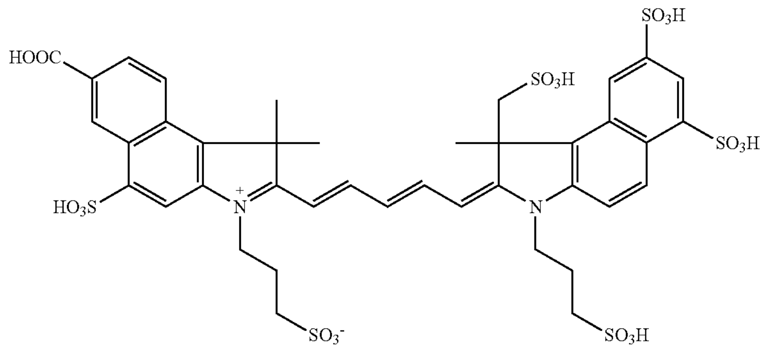 |

TABLE 2-continued
| Compound No. | Structure |
|---|---|
| 62 | 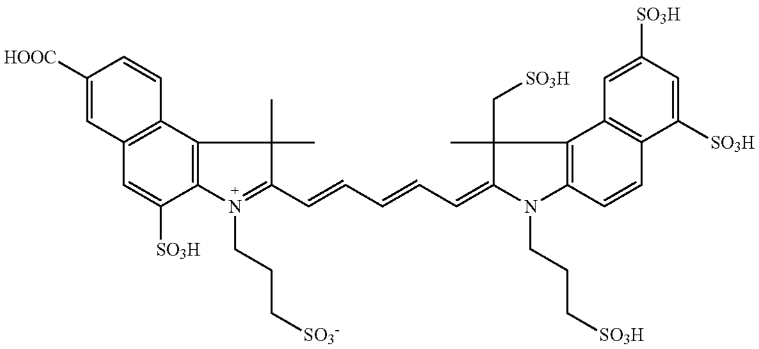 |
| 63 | 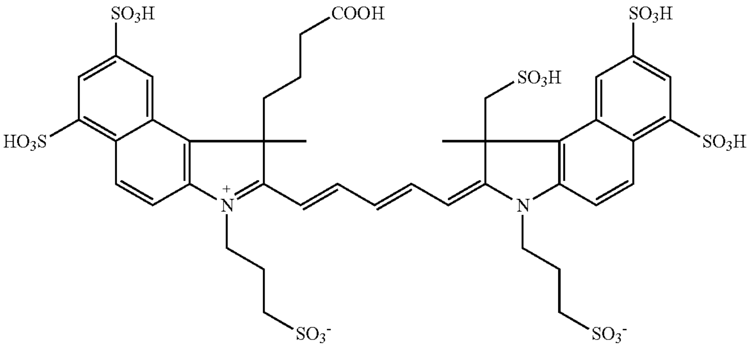 |
| 64 | 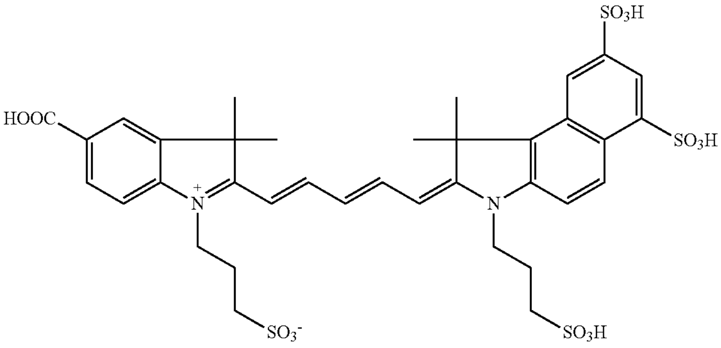 |
| 65 | 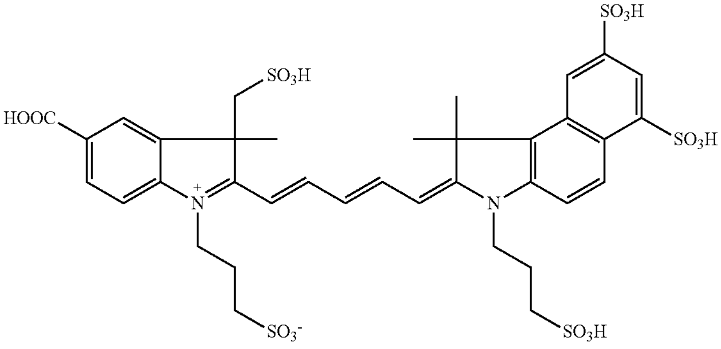 |

TABLE 2-continued
| Compound No. | Structure |
| --- | --- |
| 66 | 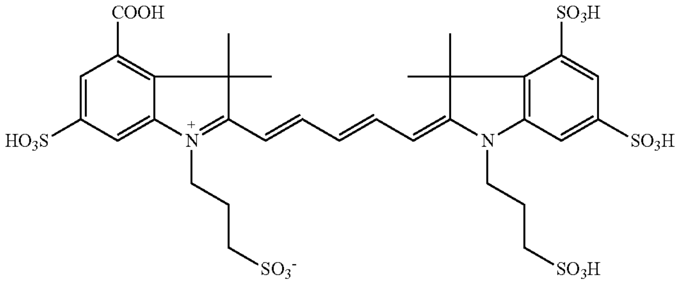 |
| 67 | 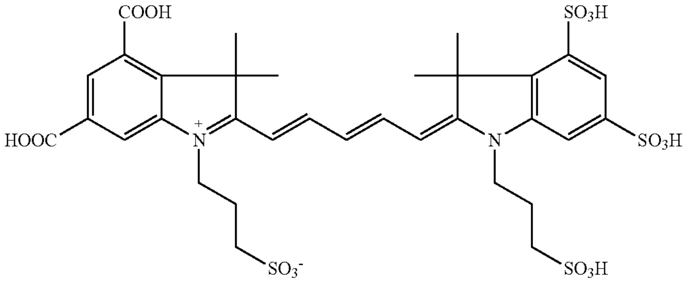 |
| 68 | 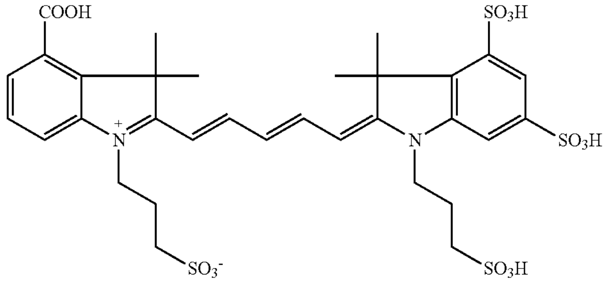 |
| 69 | 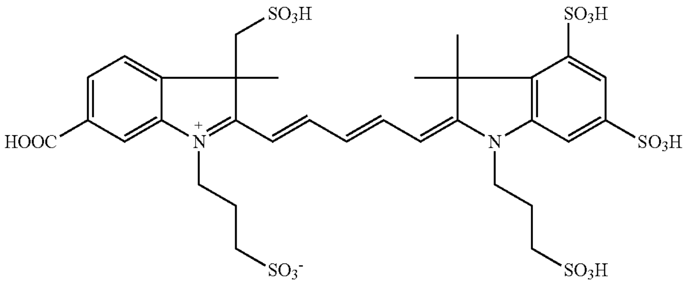 |
| 70 | 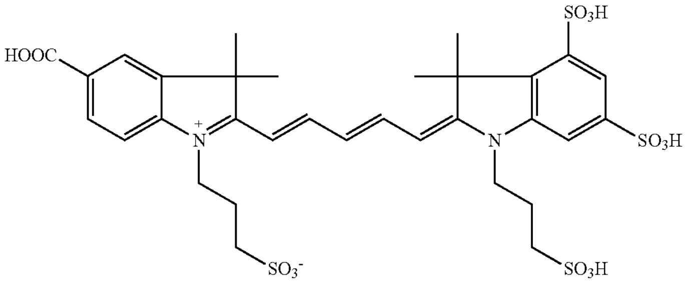 |

TABLE 2-continued
| Compound No. | Structure |
|---|---|
| 71 | 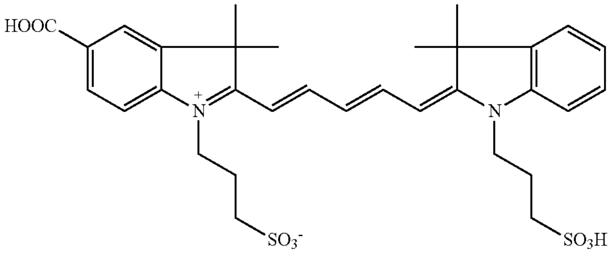 |
| 72 | 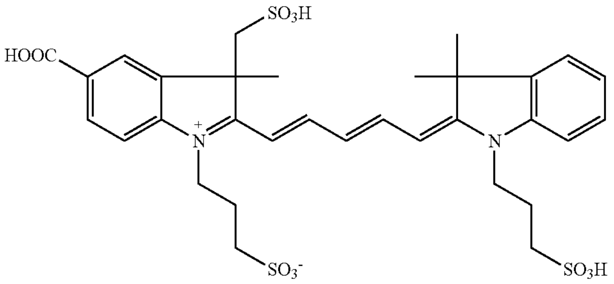 |
| 73 | 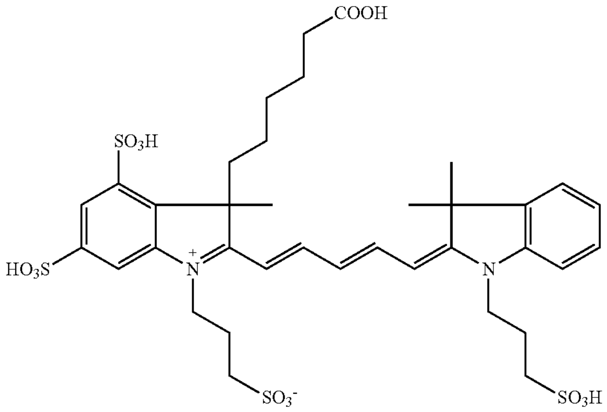 |
| 74 | 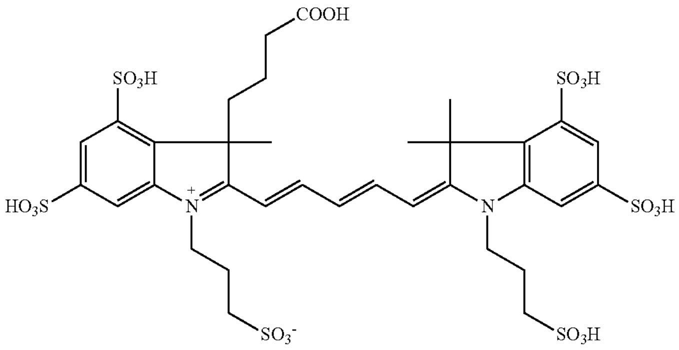 |

TABLE 2-continued
| Compound No. | Structure |
| --- | --- |
| 75 | 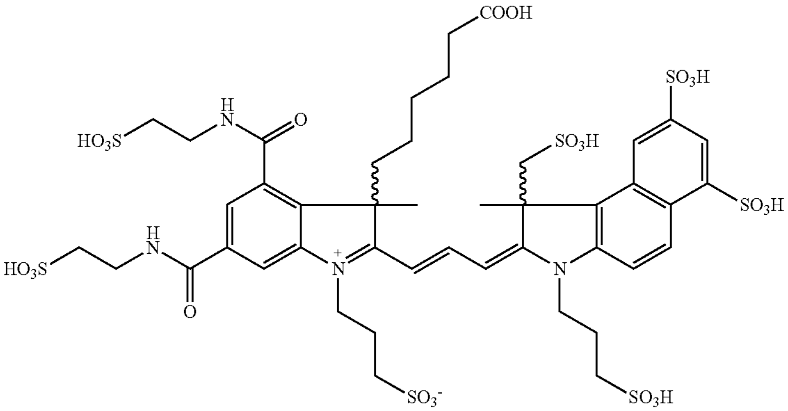 |
| 76 | 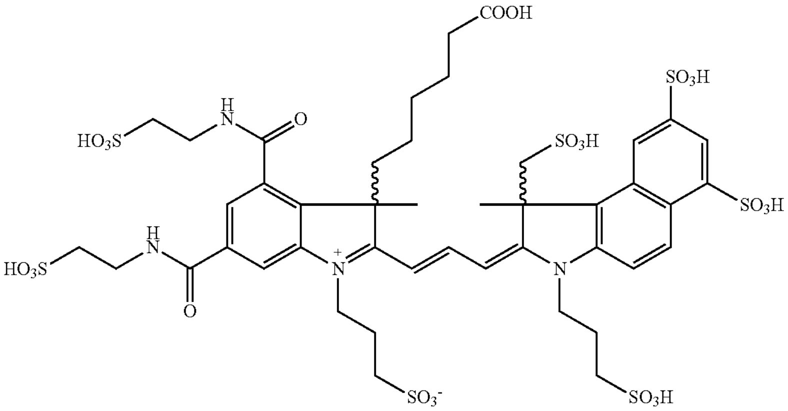 |
| 77 | 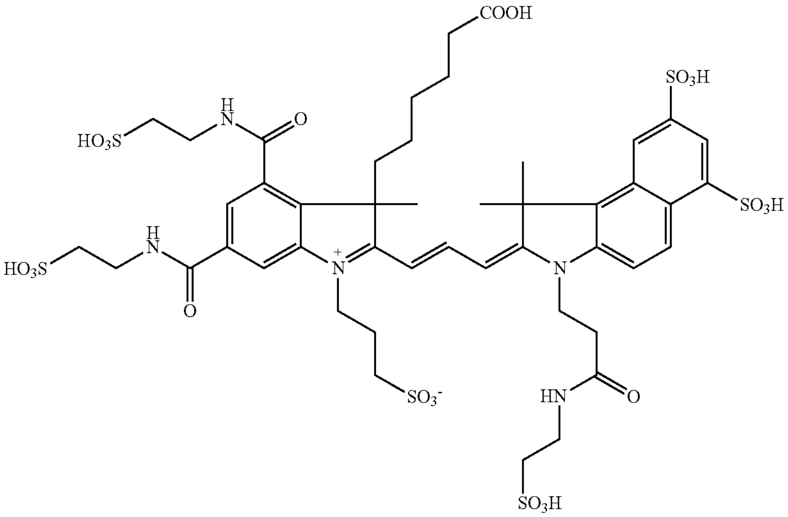 |

TABLE 2-continued
| Compound No. | Structure |
|---|---|
| 78 | 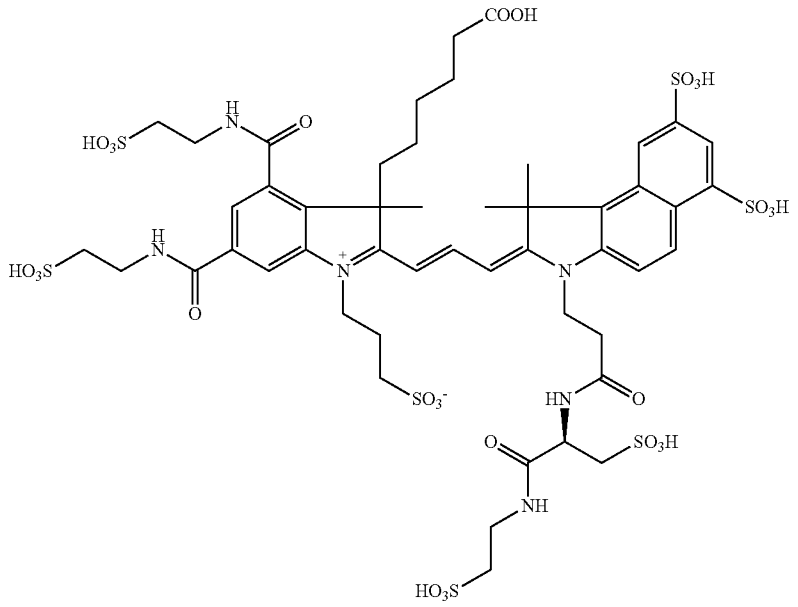 |
| 79 | 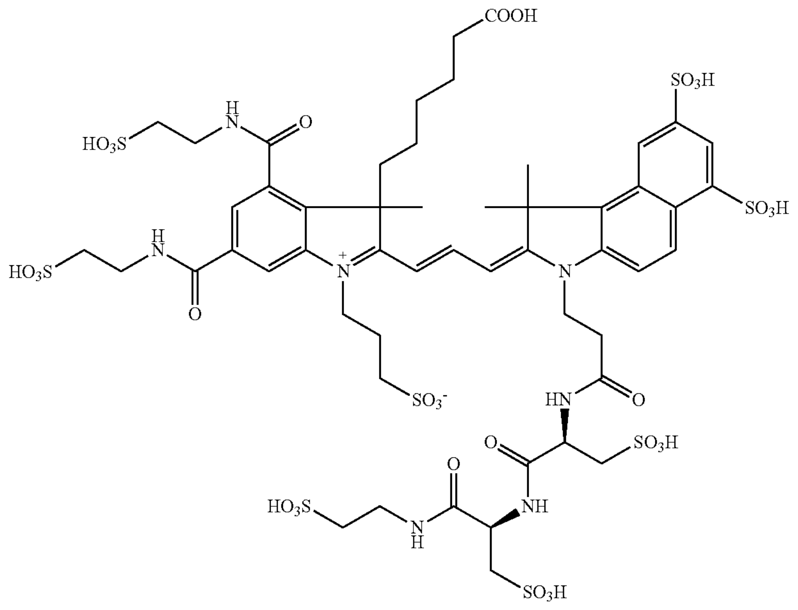 |

TABLE 2-continued
| Compound No. | Structure |
|---|---|
| 80 | 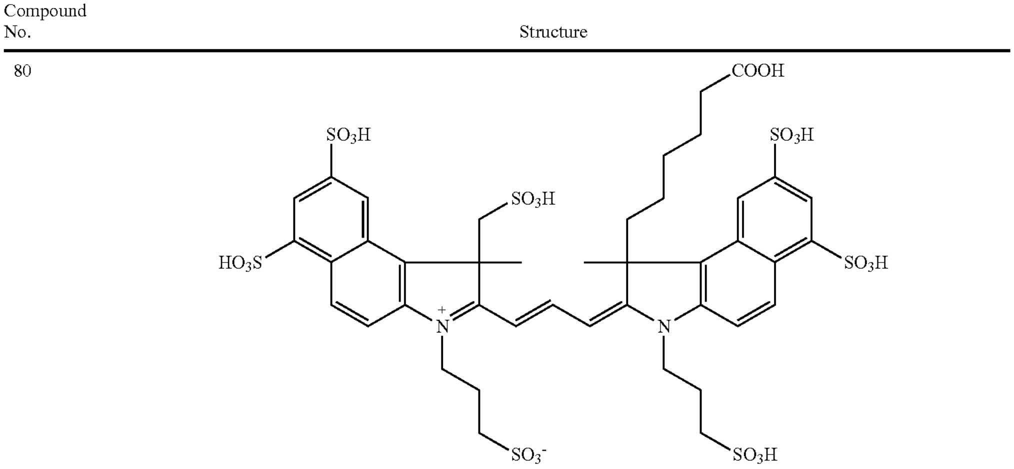 |
| 81 | 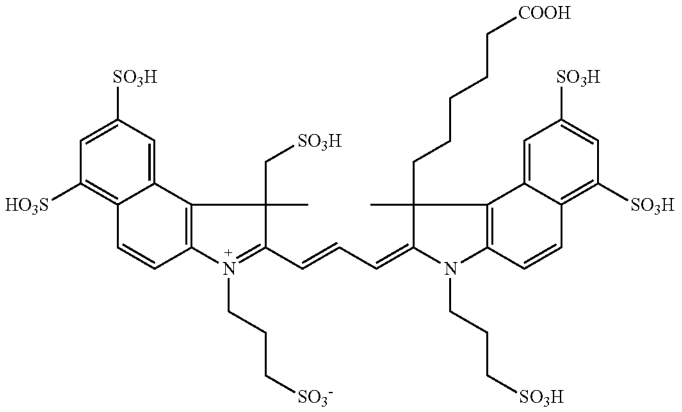 |
| 82 | 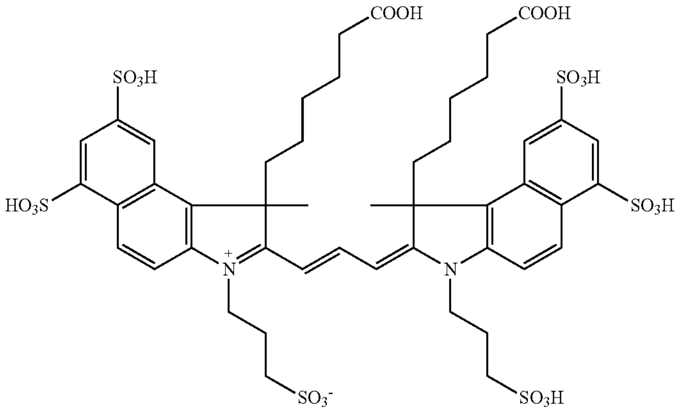 |
| 83 | 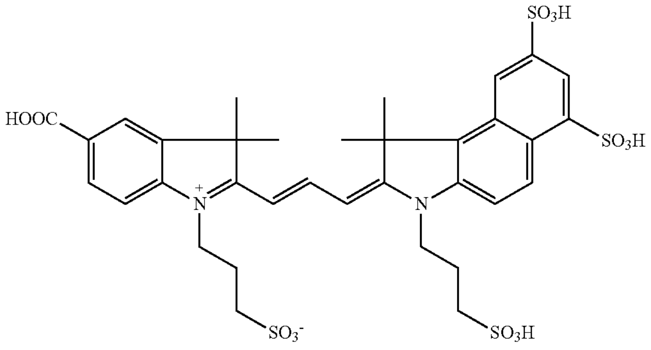 |

TABLE 2-continued
| Compound No. | Structure |
| --- | --- |
| 84 | 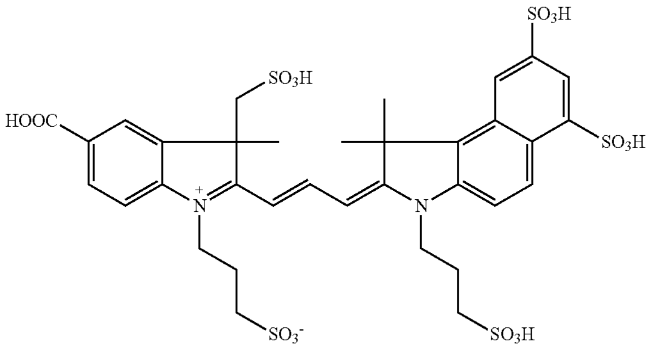 |
| 85 | 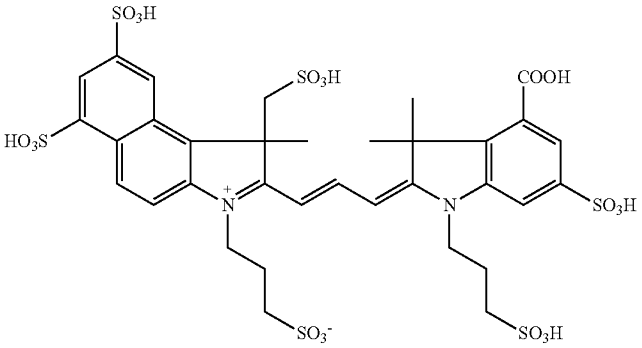 |
| 86 | 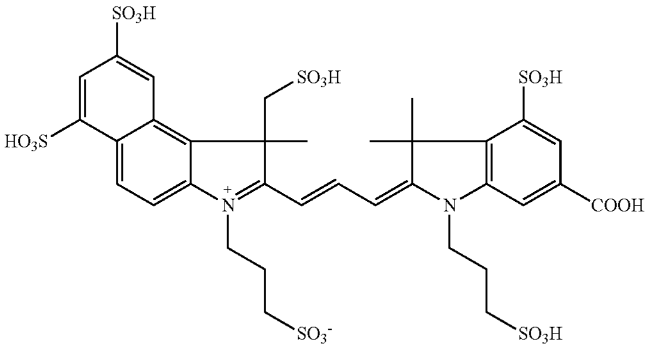 |
| 87 | 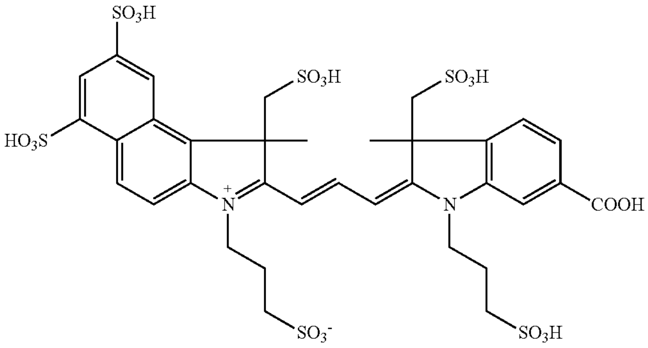 |

TABLE 2-continued
| Compound No. | Structure |
|---|---|
| 88 | 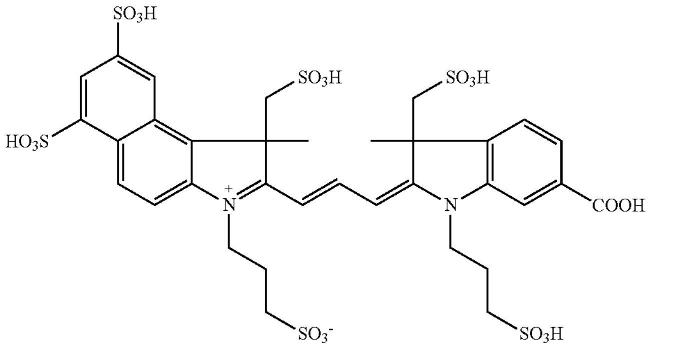 |
| 89 | 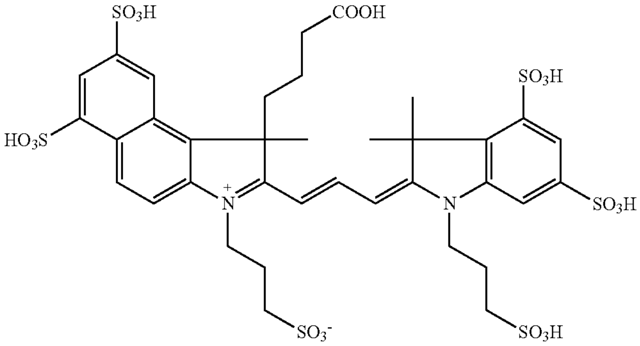 |
| 90 | 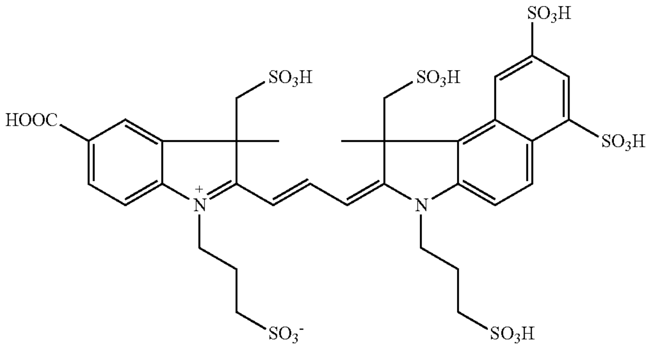 |
| 91 | 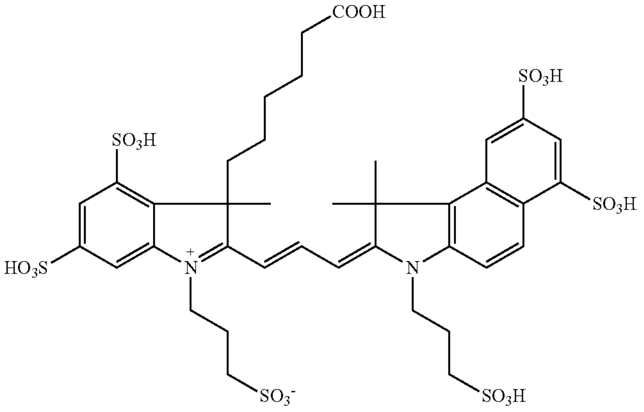 |

TABLE 2-continued
| Compound No. | Structure |
| --- | --- |
| 92 | 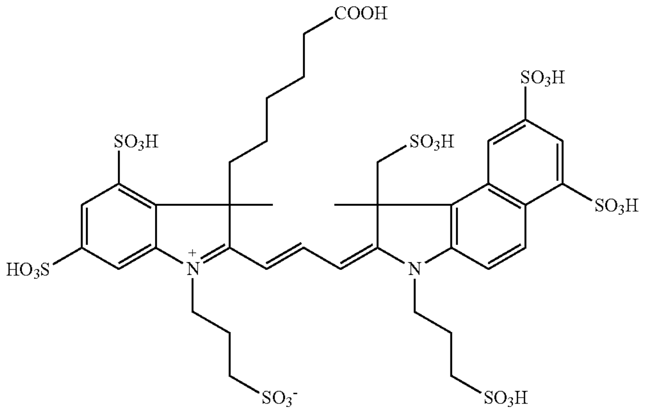 |
| 93 | 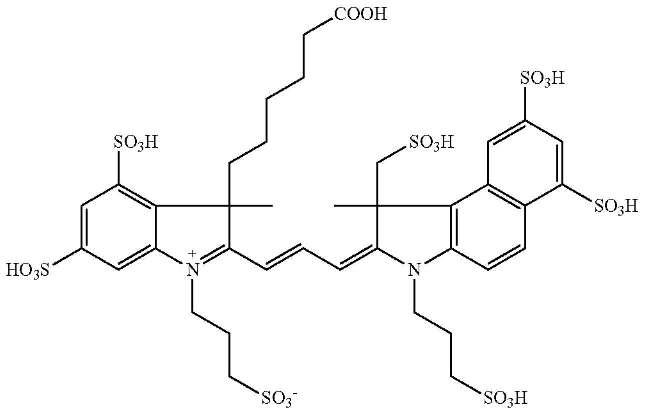 |
| 94 | 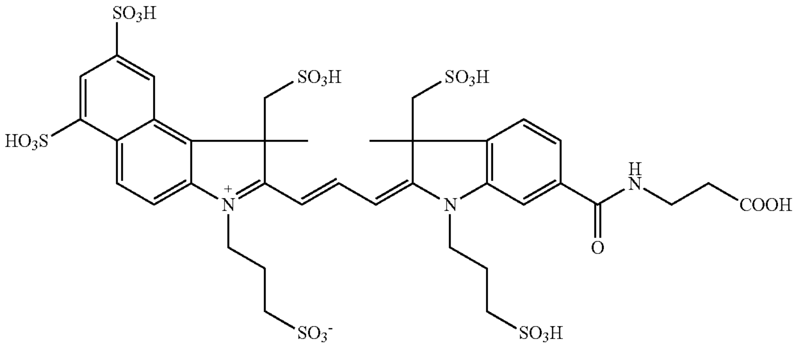 |
| 95 | 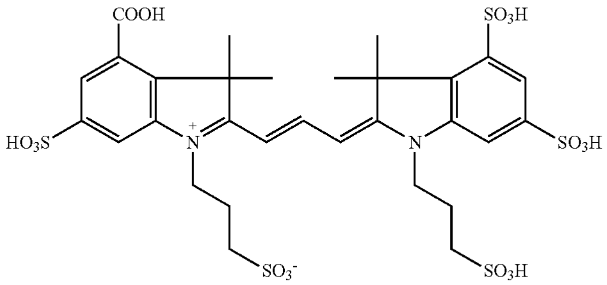 |

TABLE 2-continued
| Compound No. | Structure |
|---|---|
| 96 | 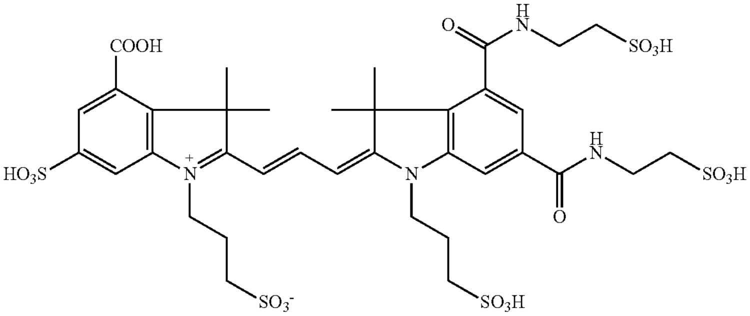 |
| 97 | 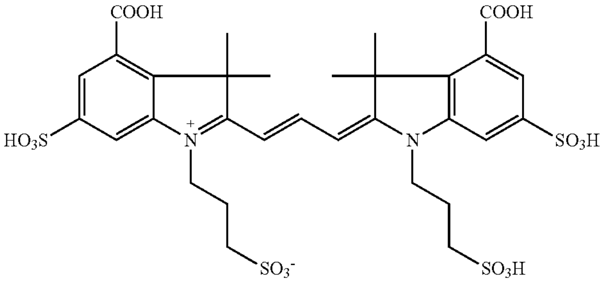 |
| 98 | 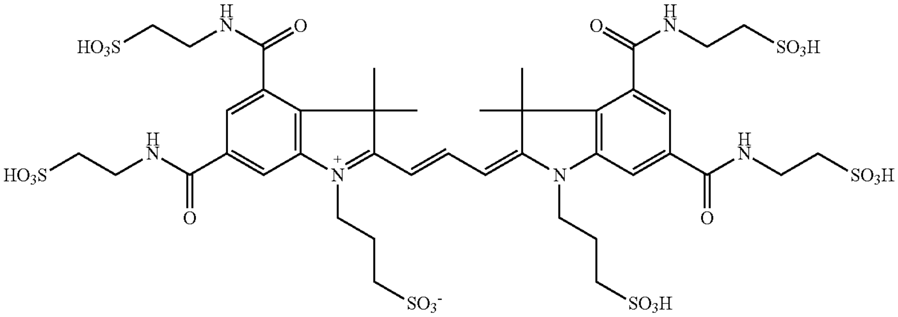 |
| 99 | 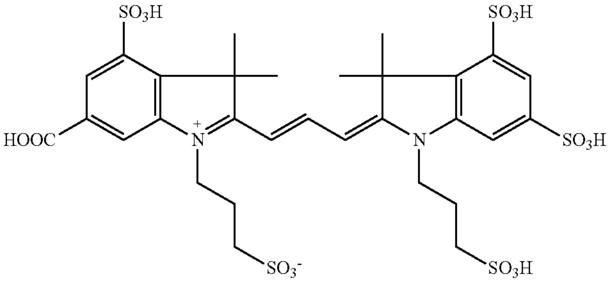 |
| 100 | 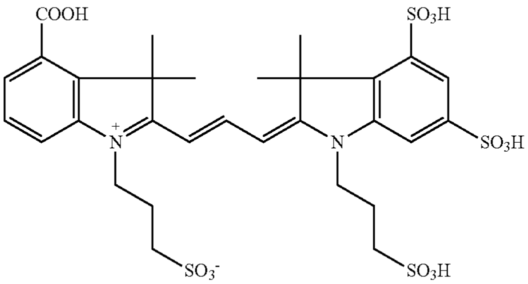 |

TABLE 2-continued
| Compound No. | Structure |
| --- | --- |
| 101 | 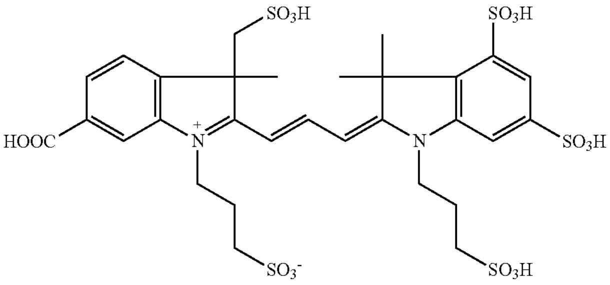 |
| 102 | 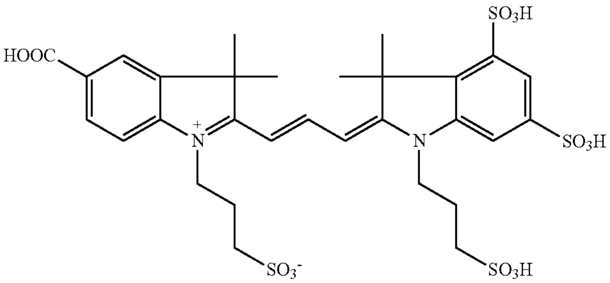 |
| 103 | 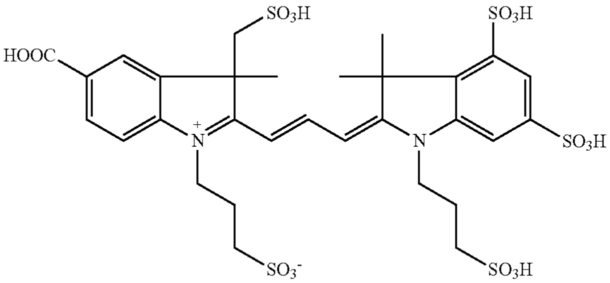 |
| 104 | 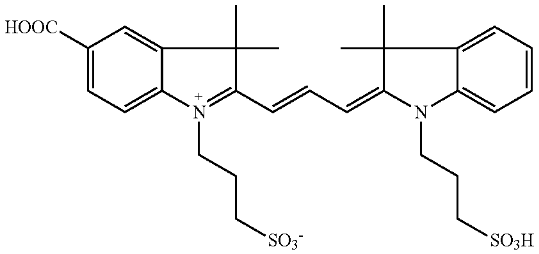 |
| 105 | 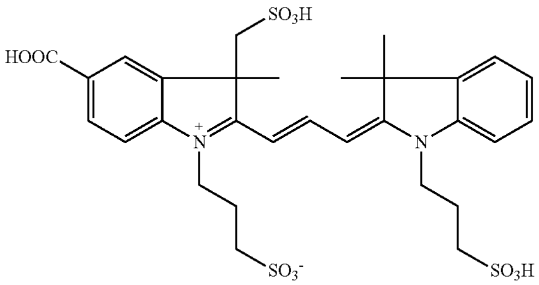 |

TABLE 2-continued
| Compound No. | Structure |
|---|---|
| 106 | 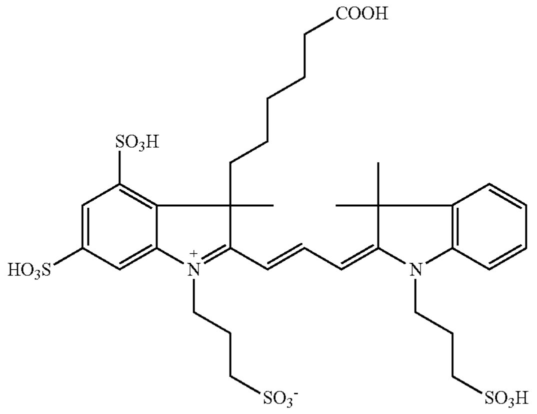 |
| 107 | 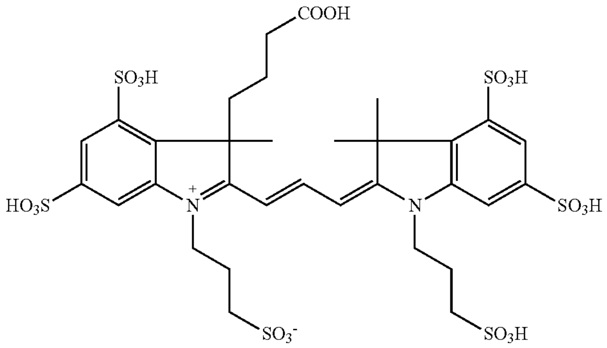 |
| 108 | 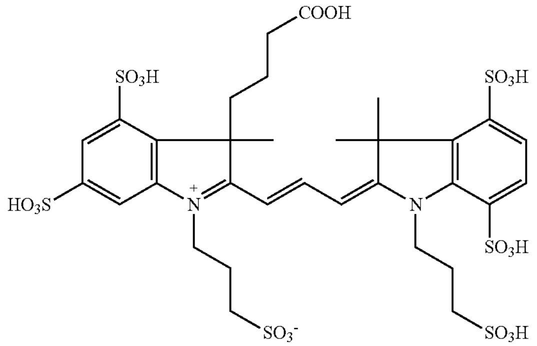 |
| 109 | 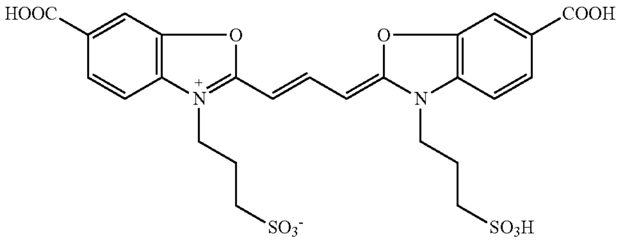 |

TABLE 2-continued

| Compound No. | Structure |
|---|---|
| 110 | 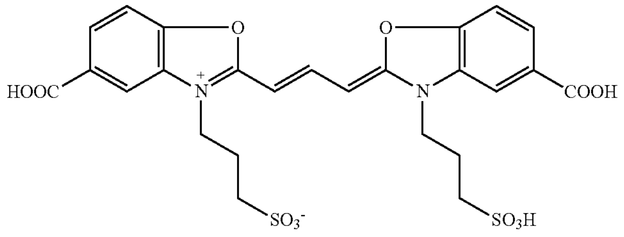 |
| 111 | 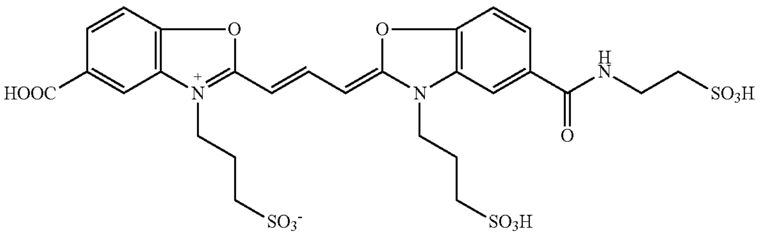 |
| 112 | 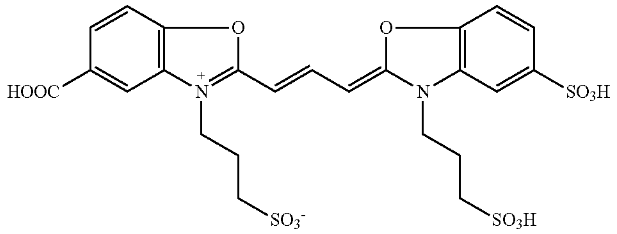 |
| 113 | 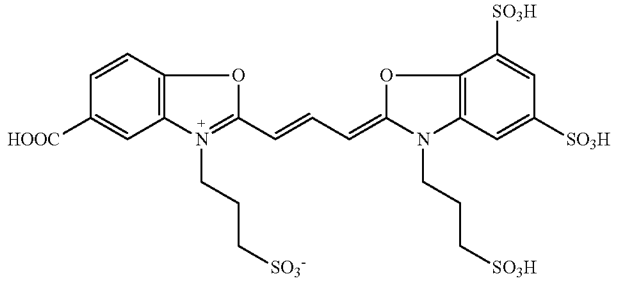 |
| 114 | 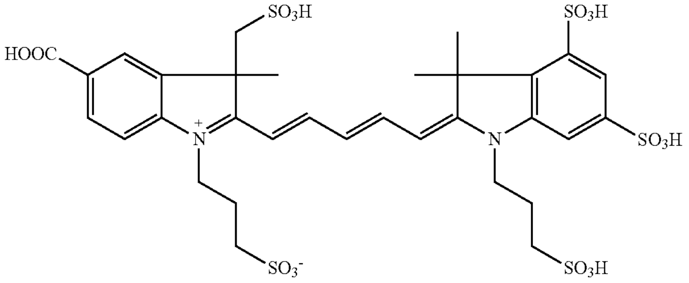 |

For the avoidance of doubt it is to be understood that, where in this specification a group is qualified by "described herein", the said group encompasses the first occurring and broadest definition as well as each and all of the particular definitions for that group.

A suitable salt of a compound of the disclosure is, for example, an acid-addition salt of a compound of the disclosure which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable salt of a compound of the disclosure which is sufficiently acidic is an alkali metal salt, for example a sodium or potassium salt, an alkaline earth metal salt, for example a calcium or magnesium salt, an ammonium salt or a salt with an organic base which affords a cation, for example a salt with methylamine, dimethylamine, diethylamine, trimethylamine, piperidine, morpholine or tris-(2-hydroxyethyl)amine.

It will be understood that the compounds of the present disclosure and any salts thereof, comprise stereoisomers, mixtures of stereoisomers, polymorphs of all isomeric forms of said compounds.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral center" refers to a carbon atom bonded to four nonidentical substituents.

As used herein, the term "chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerisation is possible, a chemical equilibrium of the tautomers will be reached. The exact ratio of the tautomers depends on several factors, including temperature, solvent and pH. The concept of tautomers that are interconvertible by tautomerisations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarised light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this disclosure may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March. John Wiley and Sons, New York, 2001), for example by synthesis from optically active starting materials or by resolution of a racemic form. Some of the compounds of the disclosure may have geometric isomeric centers (E- and Z-isomers). It is to be understood that the present disclosure encompasses all optical, diastereoisomers and geometric isomers and mixtures thereof that possess inflammasome inhibitory activity.

The present disclosure also encompasses compounds of the disclosure as defined herein which comprise one or more isotopic substitutions.

It is to be understood that the compounds of any Formula described herein include the compounds themselves, as well as their salts, and their solvates, if applicable. A salt, for example, can be formed between an anion and a positively charged group (e.g., amino) on a substituted compound disclosed herein. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As used herein, the term "derivative" refers to compounds that have a common core structure and are substituted with various groups as described herein.

As used herein, the term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonamides, tetrazoles, sulfonates and phosphonates. See, e.g., Patani and LaVoie, *Chem. Rev.* 96, 3147-3176, 1996.

It is also to be understood that certain compounds of the present disclosure may exist in solvated as well as unsolvated forms such as, for example, hydrated forms. A suitable solvate is, for example, a hydrate such as hemi-hydrate, a mono-hydrate, a di-hydrate or a tri-hydrate. It is to be understood that the disclosure encompasses all such solvated forms that possess inflammasome inhibitory activity.

It is also to be understood that certain compounds of the present disclosure may exhibit polymorphism, and that the disclosure encompasses all such forms, or mixtures thereof, which possess inflammasome inhibitory activity. It is generally known that crystalline materials may be analysed using conventional techniques such as X-Ray Powder Diffraction analysis, Differential Scanning calorimetry, Thermal Gravimetric Analysis. Diffuse Reflectance Infrared Fourier Transform (DRIFT) spectroscopy. Near Infrared (NIR) spectroscopy, solution and/or solid state nuclear magnetic resonance spectroscopy. The water content of such crystalline materials may be determined by Karl Fischer analysis.

Compounds of the present disclosure may exist in a number of different tautomeric forms and references to compounds of the present disclosure include all such forms. For the avoidance of doubt, where a compound can exist in one of several tautomeric forms, and only one is specifically described or shown, all others are nevertheless embraced by the Formulae disclosed. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

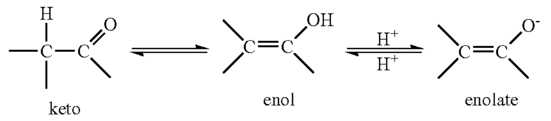

Compounds of the present disclosure containing an amine function may also form N-oxides. A reference herein to a compound disclosed herein that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-oxides can be formed by treatment of the corresponding amine with an oxidising agent such as hydrogen peroxide or a peracid (e.g. a peroxycarboxylic acid), see for example Advanced Organic Chemistry, by Jerry March, 4th Edition. Wiley Interscience, pages. More particularly, N-oxides can be made by the procedure of L. W. Deady (Syn. Comm. 1977, 7, 509-514) in which the amine compound is reacted with meta-chloroperoxybenzoic acid (mCPBA), for example, in an inert solvent such as dichloromethane.

Combinations of the Compounds

Without wishing to be bound by theory, it is understood that compounds of the present disclosure may be useful as fluorescent dyes, e.g., in sequencing methods. In some embodiments, a combination of the compounds is used, e.g., to produce differentiated signals in a sequencing method.

In some aspects, the present disclosure provides a combination comprising two or more of the compounds disclosed herein.

In some embodiments, the combination comprises two compounds disclosed herein.

In some embodiments, the two compounds are selected from the compounds described in Table 1, ionic derivatives thereof, isomers thereof, and salts thereof.

In some embodiments, the two compounds are selected from the compounds described in Table 2, ionic derivatives thereof, isomers thereof, and salts thereof.

In some embodiments, the two compounds are selected from the compounds described in Table 1 and Table 2, ionic derivatives thereof, isomers thereof, and salts thereof.

In some embodiments, the two compounds are selected from Compound Nos. 1-4, ionic derivatives thereof, isomers thereof, and salts thereof.

In some embodiments, the combination comprises three or more of the compounds disclosed herein.

In some embodiments, the combination comprises three compounds disclosed herein.

In some embodiments, the three compounds are selected from the compounds described in Table 1, ionic derivatives thereof, isomers thereof, and salts thereof.

In some embodiments, the three compounds are selected from Compound Nos. 1-4, ionic derivatives thereof, isomers thereof, and salts thereof.

In some embodiments, the combination comprises four or more of the compounds disclosed herein.

In some embodiments, the combination comprises four compounds disclosed herein.

In some embodiments, the four compounds are selected from the compounds described in Table 1, ionic derivatives thereof, isomers thereof, and salts thereof.

In some embodiments, the four compounds are selected from Compound Nos. 1-4, ionic derivatives thereof, isomers thereof, and salts thereof.

In some embodiments, the combination comprises:

Compound No. 1, an ionic derivative thereof, an isomer thereof, or a salt thereof;

Compound No. 2, an ionic derivative thereof, an isomer thereof, or a salt thereof;

Compound No. 3, an ionic derivative thereof, an isomer thereof, or a salt thereof; and Compound No. 4, an ionic derivative thereof, an isomer thereof, or a salt thereof.

In some embodiments, the combination comprises:

Compound No. 1, an ionic derivative thereof, an isomer thereof, or a salt thereof;

Compound No. 2, an ionic derivative thereof, an isomer thereof, or a salt thereof;

Compound No. 3, an ionic derivative thereof, an isomer thereof, or a salt thereof; and Compound No. 95, an ionic derivative thereof, an isomer thereof, or a salt thereof.

Methods of Using the Compounds

It is understood that compounds of the present disclosure may be useful in various sequencing methods, including the sequencing methods described herein.

In some aspects, the present disclosure provides a sequencing method disclosed herein using a compound of the present disclosure (e.g., as a fluorescent dye).

In some aspects, the present disclosure provides a compound of the present disclosure for use (e.g., as a fluorescent dye) in a sequencing method disclosed herein.

Nucleic Acid Template Molecules Immobilized to a Support or Coated Support

The present disclosure provides methods for sequencing a plurality of nucleic acid template molecules that are immobilized to a support (or immobilized to a coating on the support). In some embodiments, the individual template molecules comprise single-stranded nucleic acid molecules.

In some embodiments, the support is passivated/coated with at least one polymer layer (e.g., FIG. 1). In some embodiments, at least one of the polymer layers comprises a plurality of capture primers tethered to the polymer layer. In some embodiments, individual capture primers serve to attach a template molecule to the polymer layer. In some embodiments, the 5' or 3' end of individual template molecules are covalently attached to a capture primer. In some embodiments, the 5' or 3' region of individual template molecules are hybridized to a capture primer. In some embodiments, the at least one polymer layers can further comprise a plurality of pinning primers tethered to the polymer layer. In some embodiments, individual pinning primers serve to hybridize to a portion of a template molecule thereby pinning down a portion of the template molecule to the polymer layer.

In some embodiments, the nucleic acid template molecule can be generated by a clonal amplification workflow. In some embodiments, the nucleic acid template molecule was not generated by a clonal amplification workflow.

In some embodiments, the template molecule comprises one copy of the sequence-of-interest. For example, the one-copy template molecule can be generated by bridge amplification. In some embodiments, bridge amplification can be conducted with any combination of dATP, dGTP, dCTP, dTTP and/or dUTP. In some embodiments, the one-copy template molecule includes at least one uridine nucleotide or lacks a uridine nucleotide.

In some embodiments, the template molecule comprises a concatemer which includes two or more tandem copies of a polynucleotide unit. In some embodiments, individual polynucleotide unit of a concatemer comprises a sequence-of-interest (e.g., an insert region) and at least one universal adaptor sequence including any one or any combination of: a capture primer binding site sequence; a pinning primer binding site sequence; a forward sequencing primer binding site sequence; a reverse sequencing primer binding site sequence; an amplification primer binding site sequence; a first sample index sequence; a second sample index sequence; a first unique molecular tag sequence, a second unique molecular tag sequence; a first compaction oligonucleotide binding site; and/or a second compaction oligonucleotide binding site. In some embodiments, the concatemer can be generated by conducting rolling circle amplification (RCA) using a circularized library molecule, an amplification primer (e.g., immobilized to a support or soluble), a strand-displacing polymerase, and a plurality of nucleotides. For example, the rolling circle amplification reaction can be conducted in a template-directed manner to generate a concatemer having sequences that are complementary to the circularized library molecule. The rolling circle amplification reaction can be conducted under isothermal amplification conditions. In some embodiments, rolling circle amplification can be conducted with any combination of dATP, dGTP, dCTP, dTTP and/or dUTP. In some embodiments, the concatemer template molecule includes at least one uridine nucleotide or lacks a uridine nucleotide.

In some embodiments, each polynucleotide unit of a concatemer comprises a sequence-of-interest (e.g., an insert region) and at least one universal adaptor sequence including any one or any combination of: a capture primer binding site sequence; a pinning primer binding site sequence; a forward sequencing primer binding site sequence; a reverse sequencing primer binding site sequence; an amplification primer binding site sequence; a first sample index sequence; a second sample index sequence; a first unique molecular tag sequence; a second unique molecular tag sequence; a first compaction oligonucleotide binding site; and/or a second compaction oligonucleotide binding site.

Figure 11:
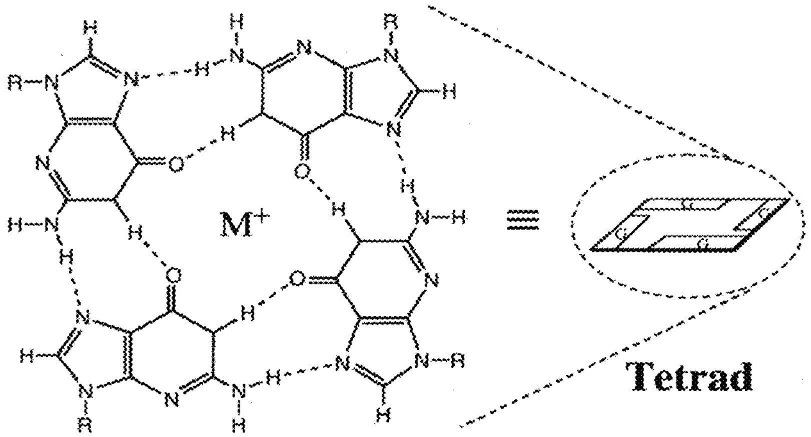
FIG. 11 is a schematic of a guanine tetrad (e.g., G-tetrad).

The concatemer can self-collapse to form a DNA nanoball. The shape and size of the DNA nanoball can be further compacted by including a pair of inverted repeat sequences in the circular template molecule, or by conducting the rolling circle amplification reaction in the presence of one or more compaction oligonucleotides. In some embodiments, the compaction oligonucleotides comprise at least four consecutive guanines. The rolling circle amplification reaction generates concatemers comprising repeat copies of the universal binding sequence for the compaction oligonucleotide. At least one compaction oligonucleotide can form a guanine tetrad (e.g., FIG. 11) and hybridize to the universal binding sequences for the compaction oligonucleotide, and the resulting concatemer can fold to form an intramolecular G-quadruplex structure. The concatemers can self-collapse to form compact nanoballs. Formation of the guanine tetrads and G-quadruplexes in the nanoballs may increase the stability of the nanoballs to retain their compact size and shape which can withstand repeated flows of reagents for conducting any of the sequencing workflows described herein.

Figure 12:
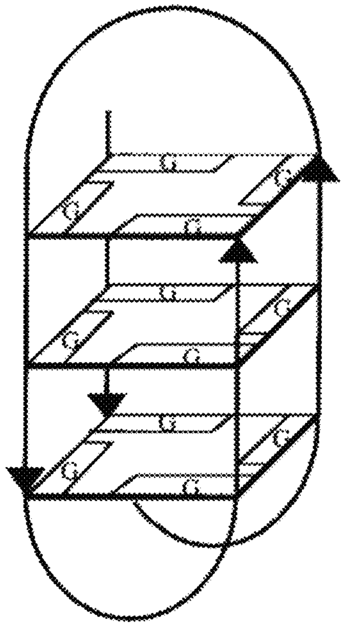
FIG. 12 is a schematic of an exemplary intramolecular G-quadruplex structure.

In some embodiments, the compaction oligonucleotides can include at least one region having consecutive guanines. For example, the compaction oligonucleotides can include at least one region having 2, 3, 4, 5, 6 or more consecutive guanines. In some embodiments, the compaction oligonucleotides comprise four consecutive guanines which can form a guanine tetrad structure (see FIG. 12). The guanine tetrad structure can be stabilized via Hoogsteen hydrogen bonding. The guanine tetrad structure can be stabilized by a central cation including potassium, sodium, lithium, rubidium or cesium.

In some embodiments, rolling circle amplification (RCA) can be conducted with compaction oligonucleotides to generate single stranded concatemer molecules having multiple copies of a polynucleotide unit arranged in tandem, where each polynucleotide unit comprises a sequence-of-interest and at least one binding site for a compaction oligonucleotide. In some embodiments, the compaction oligonucleotides include a 5' region, an optional internal region (intervening region), and a 3' region. The 5' and 3' regions of the compaction oligonucleotide can hybridize to binding sites in the concatemer to pull together distal portions of the concatemer causing compaction of the concatemer to form a DNA nanoball. For example, the 5' region of the compaction oligonucleotide is designed to hybridize to a first portion of the concatemer molecule, and the 3' region of the compaction oligonucleotide is designed to hybridized to a second portion of the concatemer molecule. Inclusion of compaction oligonucleotides during RCA can promote formation of DNA nanoballs having tighter size and shape compared to concatemers generated in the absence of the compaction oligonucleotides. The compact and stable characteristics of the DNA nanoballs improves sequencing accuracy by increasing signal intensity and they retain their shape and size during multiple sequencing cycles.

Methods for Sequencing

The present disclosure provides methods for sequencing a plurality of nucleic acid template molecules. In some embodiments, the nucleic acid template molecules comprise one copy of the sequence-of-interest, or the nucleic acid template molecules comprise concatemers. In some embodiments, the sequencing reactions employ nucleotide reagents comprising any one or any combination of nucleotides and/or multivalent molecules. In some embodiments, the nucleotide reagents comprise canonical nucleotides. In some embodiments, the nucleotide reagents comprise nucleotide analogs comprise detectably labeled nucleotides. In some embodiments, the nucleotide reagents comprise nucleotides carrying a removable or non-removable chain terminating moiety. In some embodiments, the nucleotide reagents comprise multivalent molecules each comprising a central core attached to multiple polymer arms each having a nucleotide unit at the end of the arms. In some embodiments, the sequencing reactions employ binding non-labeled nucleotides without incorporation. In some embodiments, the sequencing reactions employ incorporating non-labeled nucleotide analogs. In some embodiments, the sequencing reactions employ incorporating detectably labeled nucleotides having removable chain terminating moiety. In some embodiments, the sequencing reactions employ a two-stage sequencing reaction comprising binding detectably labeled multivalent molecules without incorporation, and incorporating nucleotide analogs.

Methods for Sequencing Using Nucleotide Analogs

The present disclosure provides methods for sequencing nucleic acid template molecules, comprising step (a): contacting (i) a plurality of sequencing polymerases, (ii) a plurality of nucleic acid template molecules and (iii) a plurality of nucleic acid sequencing primers, where the contacting is conducted under a condition suitable to form a plurality of complexed sequencing polymerases each complex comprising a sequencing polymerase bound to a nucleic acid duplex wherein the nucleic acid duplex comprises a nucleic acid template molecule hybridized to a nucleic acid sequencing primer. In some embodiments, the sequencing polymerases comprise a recombinant mutant sequencing polymerase that can bind and incorporate nucleotide analogs. In some embodiments, the sequencing primers comprise 3' extendible ends or 3' non-extendible ends.

In some embodiments, the methods for sequencing nucleic acid template molecules further comprise step (b): contacting the plurality of sequencing polymerases with a plurality of nucleotides under a condition suitable for binding at least one nucleotide to one of the sequencing polymerases which is bound to a nucleic acid duplex, and the condition is suitable for promoting polymerase-catalyzed nucleotide incorporation. In some embodiments, the sequencing polymerase is contacted with the plurality of nucleotides in the presence of at least one catalytic cation comprising magnesium and/or manganese. In some embodiments, the plurality of nucleotides comprises at least one nucleotide analog having a chain terminating moiety at the sugar 2' or 3' position. In some embodiments, the chain terminating moiety is removable from the sugar 2' or 3' position to convert the chain terminating moiety to an OH or H group. In some embodiments, the plurality of nucleotides comprises at least one nucleotide that lacks a chain terminating moiety. In some embodiments, at least one nucleotide is labeled with a detectable reporter moiety (e.g., fluorescent dye such as a compound of the present disclosure). In some embodiments, the plurality of nucleotides comprise one type of nucleotides selected from a group consisting of dATP, dGTP, dCTP, dTTP or dUTP. In some embodiments, the plurality of nucleotides comprise a mixture of any two or more types of nucleotides comprising dATP, dGTP, dCTP, dTTP and/or dUTP.

In some embodiments, the methods for sequencing nucleic acid template molecules further comprise step (c): incorporating at least one nucleotide into the 3' end of an extendible sequencing primer of at least one complexed sequencing polymerase. In some embodiments, the nucleotide incorporation reaction of step (c) comprises a primer extension reaction.

In some embodiments, the methods for sequencing nucleic acid template molecules further comprise step (d): repeating steps (b) and (c) at least once.

In some embodiments, in step (b), the dye is attached to the nucleotide base. In some embodiments, the dye is attached to the nucleotide base with a linker which is cleavable/removable from the base. In some embodiments, at least one of the nucleotides in the plurality is not labeled with a detectable reporter moiety. In some embodiments, a particular detectable reporter moiety (e.g., fluorescent dye) that is attached to the nucleotide can correspond to the nucleotide base (e.g., dATP, dGTP, dCTP, dTTP or dUTP) to permit detection and identification of the nucleotide base. In some embodiments, the nucleotide analog comprises a dye attached to the nucleotide base with a linker which is cleavable/removable from the base, and the nucleotide analog further comprises a chain terminating moiety attached to the 2' or 3' sugar position by a linker which is cleavable/removable using the same condition (e.g., chemical cleaving condition) that cleaves the dye from the base.

In some embodiments, the method further comprises detecting the at least one incorporated nucleotide at step (c) and/or (d). In some embodiments, the method further comprises identifying the at least one incorporated nucleotide at step (c) and/or (d). In some embodiments, the sequence of the template molecule can be determined by detecting and identifying the nucleotide that binds the sequencing polymerase, thereby determining the sequence of the template molecule. In some embodiments, the sequence of the nucleic acid template molecule can be determined by detecting and identifying the nucleotide that incorporates into the 3' end of the primer, thereby determining the sequence of the template molecule.

Two-Stage Methods for Nucleic Acid Sequencing

The present disclosure provides a two-stage method for sequencing nucleic acid template molecules. In some embodiments, the first stage generally comprises binding multivalent molecules to complexed polymerases to form multivalent-complexed polymerases, and detecting the multivalent-complexed polymerases.

In some embodiments, the first stage comprises step (a): contacting (i) a first plurality of sequencing polymerases, (ii) a plurality of nucleic acid template molecules and (iii) a plurality of nucleic acid sequencing primers, where the contacting is conducted under a condition suitable to form a first plurality of complexed sequencing polymerases each complex comprising a first sequencing polymerase bound to a nucleic acid duplex wherein the nucleic acid duplex comprises a nucleic acid template molecule hybridized to a nucleic acid sequencing primer. In some embodiments, the sequencing primers comprise 3' extendible ends or 3' non-extendible ends.

In some embodiments, the methods for sequencing nucleic acid template molecules further comprise step (b): contacting the first plurality of complexed polymerases with a plurality of multivalent molecules to form a plurality of multivalent-complexed polymerases (e.g., binding complexes). In some embodiments, individual multivalent molecules in the plurality of multivalent molecules comprise a core attached to multiple nucleotide arms and each nucleotide arm is attached to a nucleotide unit (e.g., nucleotide moiety) (e.g., FIGS. 2-5). In some embodiments, the contacting of step (b) is conducted under a condition suitable for binding complementary nucleotide units of the multivalent molecules to at least two of the complexed polymerases in the first plurality thereby forming a plurality of multivalent-complexed polymerases. In some embodiments, the condition is suitable for inhibiting polymerase-catalyzed incorporation of the complementary nucleotide units into the primers of the plurality of multivalent-complexed polymerases. In some embodiments, the contacting of step (b) is conducted in the presence of at least one non-catalytic cation which inhibits polymerase-catalyzed nucleotide incorporation. In some embodiments, the at least one non-catalytic cation comprises strontium, barium and/or calcium.

In some embodiments, in the method of step (b), at least one of the multivalent molecules in the plurality of multivalent molecules is labeled with a detectable reporter moiety. In some embodiments, the detectable reporter moiety comprises a dye.

In some embodiments, in the method of step (b), individual nucleotide arms of a multivalent molecule comprise (i) a core attachment moiety, (ii) a spacer comprising a PEG moiety, (iii) a linker, and (iv) a nucleotide unit, wherein the core is attached to the plurality of nucleotide arms, wherein the spacer is attached to the linker, wherein the linker is attached to the nucleotide unit. In some embodiments, the labeled multivalent molecules comprise a dye attached to the core, spacer, linker and/or nucleotide unit of the multivalent molecules.

In some embodiments, in the method of step (b), the plurality of multivalent molecules comprise at least one multivalent molecule having multiple nucleotide arms (e.g., FIGS. 2-5) each attached with a nucleotide analog (e.g., nucleotide analog unit), where the nucleotide analog includes a chain terminating moiety at the sugar 2' and/or 3' position. In some embodiments, the plurality of multivalent molecules comprises at least one multivalent molecule comprising multiple nucleotide arms each attached with a nucleotide unit that lacks a chain terminating moiety.

In some embodiments, the methods for sequencing further comprise step (c): detecting the plurality of multivalent-complexed polymerases. In some embodiments, the detecting includes detecting the multivalent molecules that are bound to the complexed polymerases in the first plurality, where the complementary nucleotide units of the multivalent molecules are bound to the primers but incorporation of the complementary nucleotide units is inhibited. In some embodiments, the multivalent molecules are labeled with a detectable reporter moiety to permit detection.

In some embodiments, the methods for sequencing further comprise step (d): identifying the nucleo-base of the complementary nucleotide units that are bound to the first plurality of complexed polymerases, thereby determining the sequence of the nucleic acid template molecule. In some embodiments, the multivalent molecules are labeled with a detectable reporter moiety that corresponds to the particular nucleotide units attached to the nucleotide arms to permit identification of the complementary nucleotide units (e.g., nucleotide base adenine, guanine, cytosine, thymine or uracil) that are bound to the first plurality of complexed polymerases.

In some embodiments, the second stage of the two-stage sequencing method generally comprises nucleotide incorporation. In some embodiments, the methods for sequencing further comprise step (e): dissociating the plurality of multivalent-complexed polymerases and removing the first plurality of sequencing polymerases and their bound multivalent molecules, and retaining the plurality of nucleic acid duplexes.

In some embodiments, the methods for sequencing further comprises step (f): contacting the plurality of the retained nucleic acid duplexes of step (e) with a second plurality of sequencing polymerases, wherein the contacting is conducted under a condition suitable for binding the second plurality of sequencing polymerases to the plurality of the retained nucleic acid duplexes, thereby forming a second plurality of complexed polymerases each complex comprising a second sequencing polymerase bound to a nucleic acid duplex. In some embodiments, the second sequencing polymerase comprises a recombinant mutant sequencing polymerase.

In some embodiments, the plurality of first sequencing polymerases of step (a) have an amino acid sequence that is 100% identical to the amino acid sequence as the plurality of the second sequencing polymerases of step (f). In some embodiments, the plurality of first sequencing polymerases of step (a) have an amino acid sequence that differs from the amino acid sequence of the plurality of the second sequencing polymerases of step (f).

In some embodiments, the methods for sequencing further comprise step (g): contacting the second plurality of complexed polymerases with a plurality of nucleotides, wherein the contacting is conducted under a condition suitable for binding complementary nucleotides from the plurality of nucleotides to at least two of the second complexed polymerases thereby forming a plurality of nucleotide-complexed polymerases. In some embodiments, the contacting of step (g) is conducted under a condition that is suitable for promoting polymerase-catalyzed incorporation of the bound complementary nucleotides into the primers of the nucleotide-complexed polymerases. In some embodiments, the incorporating the nucleotide into the 3' end of the primer in step (g) comprises a primer extension reaction. In some embodiments, the contacting of step (g) is conducted in the presence of at least one catalytic cation which promotes nucleotide incorporation. In some embodiments, the at least one catalytic cation comprises magnesium and/or manganese. In some embodiments, the plurality of nucleotides comprise native nucleotides (e.g., non-analog nucleotides) or nucleotide analogs. In some embodiments, the plurality of nucleotides comprise a 2' and/or 3' chain terminating moiety which is removable or is not removable. In some embodiments, the plurality of nucleotides comprises a plurality of nucleotides labeled with detectable reporter moiety. The detectable reporter moiety comprises a dye. In some embodiments, the dye is attached to the nucleotide base. In some embodiments, the dye is attached to the nucleotide base with a linker which is cleavable/removable from the base or is not removable from the base. In some embodiments, at least one of the nucleotides in the plurality is not labeled with a detectable reporter moiety. In some embodiments, the plurality of nucleotides are non-labeled nucleotides. In some embodiments, a particular detectable reporter moiety (e.g., fluorescent dye) that is attached to the nucleotide can correspond to the nucleotide base (e.g., dATP, dGTP, dCTP, dTTP or dUTP) to permit detection and identification of the nucleotide base.

In some embodiments, when the plurality of nucleotides in steps (g) comprises labeled nucleotides, the methods for sequencing further comprise step (h): detecting the complementary nucleotides which are incorporated into the primers of the nucleotide-complexed polymerases. In some embodiments, the plurality of nucleotides are labeled with a detectable reporter moiety to permit detection. In some embodiments, when the plurality of nucleotides in steps (g) comprises non-labeled nucleotides, the detecting of step (h) is omitted.

In some embodiments, when the plurality of nucleotides in steps (g) comprises labeled nucleotides, the methods for sequencing further comprise step (i): identifying the bases of the complementary nucleotides which are incorporated into the primers of the nucleotide-complexed polymerases. In some embodiments, the identification of the incorporated complementary nucleotides in step (i) can be used to confirm the identity of the complementary nucleotides of the multivalent molecules that are bound to the first plurality of complexed polymerases in step (d). In some embodiments, the identifying of step (i) can be used to determine the sequence of the nucleic acid template molecules. In some embodiments, when the plurality of nucleotides in steps (g) comprises non-labeled nucleotides, the identifying of step (1) is omitted.

In some embodiments, when the plurality of nucleotides in step (g) comprise 2' and/or 3' chain terminating nucleotides, the methods for sequencing further comprise step (j): removing the chain terminating moiety from the incorporated nucleotides.

In some embodiments, the methods for sequencing further comprise step (k): repeating steps (a)-(j) at least once. In some embodiments, the sequence of the nucleic acid template molecules can be determined by detecting and identifying the multivalent molecules that bind the sequencing polymerases but do not incorporate into the 3' end of the primer at steps (c) and (d). In some embodiments, the sequence of the nucleic acid template molecule can be determined (or confirmed) by detecting and identifying the nucleotide that incorporates into the 3' end of the primer at steps (h) and (i).

Forming Avidity Complexes

In some embodiments, in any of the methods for sequencing template molecules, the binding of the first plurality of complexed polymerases with the plurality of multivalent molecules forms at least one avidity complex, the method comprising the steps: (1) binding a first sequencing primer, a first sequencing polymerase, and a first multivalent molecule to a first portion of a concatemer template molecule thereby forming a first binding complex, wherein a first nucleotide unit of the first multivalent molecule binds to the first sequencing polymerase; and (2) binding a second sequencing primer, a second sequencing polymerase, and the first multivalent molecule to a second portion of the same concatemer template molecule thereby forming a second binding complex, wherein a second nucleotide unit of the first multivalent molecule binds to the second sequencing polymerase, wherein the first and second binding complexes which include the same multivalent molecule forms an avidity complex. The concatemer template molecule comprises tandem repeat sequences of a sequence of interest and at least one universal site for binding a sequencing primer. The first and second sequencing primers can bind to a sequencing primer binding site along the concatemer template molecule. Exemplary multivalent molecules are shown in FIGS. 2-5.

Forming Avidity Complexes with Detecting and Identifying

In some embodiments, in any of the methods for sequencing template molecules, wherein the method includes binding the first plurality of complexed polymerases with the plurality of multivalent molecules to form at least one avidity complex, the method comprising the steps: (1) contacting the plurality of sequencing polymerases and the plurality of sequencing primers with different portions of a concatemer template molecule to form at least first and second complexed polymerases on the same concatemer template molecule; (2) contacting a plurality of multivalent molecules to the at least first and second complexed polymerases on the same concatemer template molecule, under conditions suitable to bind a single multivalent molecule from the plurality to the first and second complexed polymerases, wherein at least a first nucleotide unit of the single multivalent molecule is bound to the first complexed polymerase which includes a first sequencing primer hybridized to a first portion of the concatemer template molecule thereby forming a first binding complex (e.g., first ternary complex), and wherein at least a second nucleotide unit of the single multivalent molecule is bound to the second complexed polymerase which includes a second sequencing primer hybridized to a second portion of the concatemer template molecule thereby forming a second binding complex (e.g., second ternary complex), wherein the contacting is conducted under a condition suitable to inhibit polymerase-catalyzed incorporation of the bound first and second nucleotide units in the first and second binding complexes, and wherein the first and second binding complexes which are bound to the same multivalent molecule forms an avidity complex; and (3) detecting the first and second binding complexes on the same concatemer template molecule, and (4) identifying the first nucleotide unit in the first binding complex thereby determining the sequence of the first portion of the concatemer template molecule, and identifying the second nucleotide unit in the second binding complex thereby determining the sequence of the second portion of the concatemer template molecule.

The concatemer template molecule comprises tandem repeat sequences of a sequence of interest and at least one universal site for binding a sequencing primer. The plurality of nucleic acid primers can bind to a sequencing primer binding site along the concatemer template molecule. Exemplary multivalent molecules are shown in FIGS. 2-5.

Sequencing-by-Binding

The present disclosure provides methods for sequencing nucleic acid template molecules comprising a sequencing-by-binding (SBB) procedure which employs non-labeled chain-terminating nucleotides. In some embodiments, the sequencing-by-binding (SBB) method comprises the steps of (a) sequentially contacting a primed template nucleic acid (e.g., template molecule hybridized to a sequencing primer) with at least two separate mixtures under ternary complex stabilizing conditions, wherein the at least two separate mixtures each include a polymerase and a nucleotide, whereby the sequentially contacting results in the primed template nucleic acid being contacted, under the ternary complex stabilizing conditions, with nucleotide cognates for first, second and third base type base types in the template; (b) examining the at least two separate mixtures to determine whether a ternary complex formed; and (c) identifying the next correct nucleotide for the primed template nucleic acid molecule, wherein the next correct nucleotide is identified as a cognate of the first, second or third base type if ternary complex is detected in step (b), and wherein the next correct nucleotide is imputed to be a nucleotide cognate of a fourth base type based on the absence of a ternary complex in step (b); (d) adding a next correct nucleotide to the primer of the primed template nucleic acid after step (b), thereby producing an extended primer, and (e) repeating steps (a) through (d) at least once on the primed template nucleic acid that comprises the extended primer. Exemplary sequencing-by-binding methods are described in U.S. Pat. Nos. 10,246,744 and 10,731,141 (where the contents of both patents are hereby incorporated by reference in their entireties).

In some embodiments, in step (a) of all of the sequencing methods described herein, the plurality of nucleic acid template molecules are immobilized to a support at a density of about $10^2$-$10^{15}$ per $mm^2$.

In some embodiments, in step (a) of all of the sequencing methods described herein, the plurality of nucleic acid template molecules are immobilized to a support at pre-determined positions on the support, or immobilized to random positions on the support.

In some embodiments, in step (a) of all of the sequencing methods described herein, the support is passivated/coated with at least one polymer layer. In some embodiments, at least one of the polymer lavers comprises a plurality of capture primers tethered to the polymer laver. In some embodiments, individual capture primers serve to attach a template molecule to the polymer layer. In some embodiments, the plurality of nucleic acid template molecules are immobilized to the at least one polymer layer at pre-determined positions on the polymer layer, or immobilized to random positions on the polymer layer.

In some embodiments, in step (a) of all of the sequencing methods described herein, the plurality of nucleic acid template molecules comprise a plurality of one-copy template molecule which can be generated by bridge amplification. In some embodiments, the one-copy template molecules comprise the same target sequence of interest or different target sequences of interest.

In some embodiments, in step (a) of all of the sequencing methods described herein, the plurality of nucleic acid template molecules comprise a plurality of concatemer molecules, wherein individual concatemer molecules comprise two or more tandem copies of a polynucleotide unit. In some embodiments, each polynucleotide unit of a concatemer comprises a sequence-of-interest (e.g., an insert region) and at least one universal adaptor sequence including any one or any combination of: a capture primer binding site sequence; a pinning primer binding site sequence; a forward sequencing primer binding site sequence; a reverse sequencing primer binding site sequence; an amplification primer binding site sequence; a first sample index sequence; a second sample index sequence; a first unique molecular tag sequence; a second unique molecular tag sequence; a first compaction oligonucleotide binding site; and/or a second compaction oligonucleotide binding site. In some embodiments, the concatemer template molecules comprise the same target sequence of interest or different target sequences of interest.

Methods for Sequencing Using Phosphate-Chain Labeled Nucleotides

The present disclosure provides methods for sequencing using immobilized sequencing polymerases which bind non-immobilized template molecules, wherein the sequencing reactions are conducted with phosphate-chain labeled nucleotides. In some embodiments, the sequencing methods comprise step (a): providing a support having a plurality of sequencing polymerases immobilized thereon. In some embodiments, the sequencing polymerase comprises a processive DNA polymerase. In some embodiments, the sequencing polymerase comprises a wild type or mutant DNA polymerase, including for example a Phi29 DNA polymerase. In some embodiments, the support comprise a plurality of separate compartments and a sequencing polymerase is immobilized to the bottom of a compartment. In some embodiments, the separate compartments comprise a silica bottom through which light can penetrate. In some embodiments, the separate compartments comprise a silica bottom configured with a nanophotonic confinement structure comprising a hole in a metal cladding film (e.g., aluminum cladding film). In some embodiments, the hole in the metal cladding has a small aperture, for example, approximately 70 nm. In some embodiments, the height of the nanophotonic confinement structure is approximately 100 nm. In some embodiments, the nanophotonic confinement structure comprises a zero mode waveguide (ZMW). In some embodiments, the nanophotonic confinement structure contains a liquid.

In some embodiments, the sequencing method further comprises step (b): contacting the plurality of immobilized sequencing polymerases with a plurality of single stranded circular nucleic acid template molecules and a plurality of oligonucleotide sequencing primers, under a condition suitable for individual immobilized sequencing polymerases to bind a single stranded circular template molecule, and suitable for individual sequencing primers to hybridize to individual single stranded circular template molecules, thereby generating a plurality of polymerase/template/primer complexes. In some embodiments, the individual sequencing primers hybridize to a universal sequencing primer binding site on the single stranded circular template molecule.

In some embodiments, the sequencing method further comprises step (c): contacting the plurality of polymerase/ template/primer complexes with a plurality of phosphate chain labeled nucleotides each comprising an aromatic base, a five carbon sugar (e.g., ribose or deoxyribose), and phosphate chain comprising 3-20 phosphate groups, where the terminal phosphate group is linked to a detectable reporter moiety (e.g., a fluorescent dye). The first, second and third phosphate groups can be referred to as alpha, beta and gamma phosphate groups. In some embodiments, a particular detectable reporter moiety which is attached to the terminal phosphate group corresponds to the nucleotide base (e.g., dATP, dGTP, dCTP, dTTP or dUTP) to permit detection and identification of the nucleo-base. In some embodiments, the plurality of polymerase/template/primer complexes are contacted with the plurality of phosphate chain labeled nucleotides under a condition suitable for polymerase-catalyzed nucleotide incorporation. In some embodiments, the sequencing polymerases are capable of binding a complementary phosphate chain labeled nucleotide and incorporating the complementary nucleotide opposite a nucleotide in a template molecule. In some embodiment, the polymerase-catalyzed nucleotide incorporation reaction cleaves between the alpha and beta phosphate groups thereby releasing a multi-phosphate chain linked to a dye.

In some embodiments, the sequencing method further comprises step (d): detecting the fluorescent signal emitted by the phosphate chain labeled nucleotide that is bound by the sequencing polymerase, and incorporated into the terminal end of the sequencing primer. In some embodiments, step (d) further comprises identifying the phosphate chain labeled nucleotide that is bound by the sequencing polymerase, and incorporated into the terminal end of the sequencing primer.

In some embodiments, the sequencing method further comprises step (d): repeating steps (c)-(d) at least once. In some embodiments, sequencing methods that employ phosphate chain labeled nucleotides can be conducted according to the methods described in U.S. Pat. Nos. 7,170,050; 7,302,146; and/or 7,405,281.

Sequencing Polymerases

The present disclosure provides methods for sequencing nucleic acid template molecules, wherein the sequencing polymerase(s) is/are capable of incorporating a complementary nucleotide opposite a nucleotide in a concatemer template molecule. The present disclosure provides methods for sequencing nucleic acid template molecules, wherein, the sequencing polymerase(s) is/are capable of binding a complementary nucleotide unit of a multivalent molecule opposite a nucleotide in a nucleic acid template molecule. In some embodiments, the plurality of sequencing polymerases comprise recombinant mutant polymerases.

Examples of suitable polymerases for use in sequencing with nucleotides and/or multivalent molecules include but are not limited to: Klenow DNA polymerase; *Thermus aquaticus* DNA polymerase I (Taq polymerase); KlenTaq polymerase; Candidatus altiarchaeales archaeon; Candidatus Hadarchaeum Yellowstonense; Hadesarchaea archaeon; Euryarchaeota archaeon, Thermoplasmata archaeon; *Thermococcus* polymerases such as *Thermococcus litoralis*, bacteriophage T7 DNA polymerase; human alpha, delta and epsilon DNA polymerases; bacteriophage polymerases such as T4, RB69 and phi29 bacteriophage DNA polymerases; *Pyrococcus furiosus* DNA polymerase (Pfu polymerase); *Bacillus subtilis* DNA polymerase III; *E. coli* DNA polymerase III alpha and epsilon; 9 degree N polymerase; reverse transcriptases such as HIV type M or O reverse transcriptases; avian myeloblastosis virus reverse transcriptase; Moloney Murine Leukemia Virus (MMLV) reverse transcriptase; or telomerase. Further non-limiting examples of DNA polymerases include those from various Archaea genera, such as, *Aeropyrum, Archaeglobus, Desulfurococcus, Pyrobaculum, Pyrococcus, Pyrolobus, Pyrodictium, Staphylothermus, Stetteria, Sulfolobus, Thermococcus*, and *Vulcanisaeta* and the like or variants thereof, including such polymerases as are known in the art such as 9 degrees N, VENT, DEEP VENT, THERMINATOR, Pfu, KOD, Pfx, Tgo and RB69 polymerases.

Nucleotides

The present disclosure provides methods for sequencing nucleic acid template molecules, where any of the sequencing methods described herein employ at least one nucleotide. The nucleotides comprise a base, sugar and at least one phosphate group. In some embodiments, at least one nucleotide in the plurality comprises an aromatic base, a five carbon sugar (e.g., ribose or deoxyribose), and one or more phosphate groups (e.g., 1-10 phosphate groups). The plurality of nucleotides can comprise at least one type of nucleotide selected from a group consisting of dATP, dGTP, dCTP, dTTP and dUTP. The plurality of nucleotides can comprise at a mixture of any combination of two or more types of nucleotides selected from a group consisting of dATP, dGTP, dCTP, dTTP and/or dUTP. In some embodiments, at least one nucleotide in the plurality is not a nucleotide analog. In some embodiments, at least one nucleotide in the plurality comprises a nucleotide analog.

In some embodiments, in any of the methods for sequencing nucleic acid template molecules described herein, at least one nucleotide in the plurality of nucleotides comprise a chain of one, two or three phosphorus atoms where the chain is typically attached to the 5" carbon of the sugar moiety via an ester or phosphoramide linkage. In some embodiments, at least one nucleotide in the plurality is an analog having a phosphorus chain in which the phosphorus atoms are linked together with intervening O, S, NH, methylene or ethylene. In some embodiments, the phosphorus atoms in the chain include substituted side groups including O, S or $BH_3$. In some embodiments, the chain includes phosphate groups substituted with analogs including phosphoramidate, phosphorothioate, phosphordithioate, and O-methylphosphoroamidite groups.

In some embodiments, in any of the methods for sequencing nucleic acid template molecules described herein, at least one nucleotide in the plurality of nucleotides comprises a terminator nucleotide analog having a chain terminating moiety (e.g., blocking moiety) at the sugar 2' position, at the sugar 3' position, or at the sugar 2' and 3' position. In some embodiments, the chain terminating moiety can inhibit polymerase-catalyzed incorporation of a subsequent nucleotide unit or free nucleotide in a nascent strand during a primer extension reaction. In some embodiments, the chain terminating moiety is attached to the 3' sugar hydroxyl position where the sugar comprises a ribose or deoxyribose sugar moiety. In some embodiments, the chain terminating moiety is removable/cleavable from the 3' sugar hydroxyl position to generate a nucleotide having a 3'OH sugar group which is extendible with a subsequent nucleotide in a polymerase-catalyzed nucleotide incorporation reaction. In some embodiments, the chain terminating moiety comprises an alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group. In some embodiments, the chain terminating moiety is cleavable/removable from the nucleotide, for example by reacting the chain terminating moiety with a chemical agent, pH change, light or heat. In some embodiments, the chain terminating moieties alkyl, alkenyl, alkynyl and allyl are cleavable with tetrakis(triphenylphosphine)palladium(0) ($Pd(PPh_3)_4$) with piperidine, or with 2,3-Dichloro-5,6-dicyano-1,4-benzo-quinone (DDQ). In some embodiments, the chain terminating moieties aryl and benzyl are cleavable with H2 Pd/C. In some embodiments, the chain terminating moieties amine, amide, keto, isocyanate, phosphate, thio, disulfide are cleavable with phosphine or with a thiol group including beta-mercaptoethanol or dithiothritol (DTT). In some embodiments, the chain terminating moiety carbonate is cleavable with potassium carbonate ($K_2CO_3$) in MeOH, with triethylamine in pyridine, or with Zn in acetic acid (AcOH). In some embodiments, the chain terminating moieties urea and silyl are cleavable with tetrabutylammonium fluoride, pyridine-HF, with ammonium fluoride, or with triethylamine trihydrofluoride.

In some embodiments, in any of the methods for sequencing nucleic acid template molecules described herein, at least one nucleotide in the plurality of nucleotides comprises a terminator nucleotide analog having a chain terminating moiety (e.g., blocking moiety) at the sugar 2' position, at the sugar 3' position, or at the sugar 2' and 3' position. In some embodiments, the chain terminating moiety comprises an azide, azido or azidomethyl group. In some embodiments, the chain terminating moiety comprises a 3'-O-azido or 3'-O-azidomethyl group. In some embodiments, the chain terminating moieties azide, azido and azidomethyl group are cleavable/removable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP) or Tri (hydroxyproyl)phosphine (THPP). In some embodiments, the cleaving agent comprises 4-dimethylaminopyridine (4-DMAP).

In some embodiments, in any of the methods for sequencing nucleic acid template molecules described herein, the nucleotide comprises a chain terminating moiety which is selected from a group consisting of 3-deoxy nucleotides, 2',3'-dideoxynucleotides, 3'-methyl, 3'-azido, 3'-azidomethyl, 3'-O-azidoalkyl, 3'-O-ethynyl, 3'-O-aminoalkyl, 3'-O-fluoroalkyl, 3'-fluoromethyl, 3'-difluoromethyl, 3'-trifluoromethyl, 3'-sulfonyl, 3'-malonyl, 3'-amino, 3"-O-amino, 3'-sulfhydral, 3'-aminomethyl, 3'-ethyl, 3'butyl, 3'-tert butyl, 3'-Fluorenylmethyloxycarbonyl, 3' tert-Butyloxycarbonyl, 3'-O-alkyl hydroxylamino group, 3'-phosphorothioate, and 3-O-benzyl, or derivatives thereof.

In some embodiments, in any of the methods for sequencing nucleic acid template molecules described herein, the plurality of nucleotides comprises a plurality of nucleotides labeled with detectable reporter moiety. The detectable reporter moiety comprises a dye. In some embodiments, the dye is attached to the nucleotide base. In some embodiments, the dye is attached to the nucleotide base with a linker which is cleavable/removable from the base. In some embodiments, at least one of the nucleotides in the plurality is not labeled with a detectable reporter moiety. In some embodiments, a particular detectable reporter moiety (e.g., fluorescent dye) that is attached to the nucleotide can correspond to the nucleotide base (e.g., dATP, dGTP, dCTP, dTTP or dUTP) to permit detection and identification of the nucleotide base.

In some embodiments, in any of the methods for sequencing nucleic acid template molecules described herein, the cleavable linker on the nucleotide base comprises a cleavable moiety comprising an alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group. In some embodiments, the cleavable linker on the base is cleavable/removable from the base by reacting the cleavable moiety with a chemical agent, pH change, light or heat. In some embodiments, the cleavable moieties alkyl, alkenyl, alkynyl and allyl are cleavable with tetrakis(triphenylphosphine)palladium(0) ($Pd(PPh_3)_4$) with piperidine, or with 2,3-Dichloro-5,6-dicyano-1,4-benzo-quinone (DDQ). In some embodiments, the cleavable moieties aryl and benzyl are cleavable with H2 Pd/C. In some embodiments, the cleavable moieties amine, amide, keto, isocyanate, phosphate, thio, disulfide are cleavable with phosphine or with a thiol group including beta-mercaptoethanol or dithiothritol (DTT). In some embodiments, the cleavable moiety carbonate is cleavable with potassium carbonate ($K_2CO_3$) in MeOH, with triethylamine in pyridine, or with Zn in acetic acid (AcOH). In some embodiments, the cleavable moieties urea and silyl are cleavable with tetrabutylammonium fluoride, pyridine-HF, with ammonium fluoride, or with triethylamine trihydrofluoride.

In some embodiments, in any of the methods for sequencing nucleic acid template molecules described herein, the cleavable linker on the nucleotide base comprises cleavable moiety including an azide, azido or azidomethyl group. In some embodiments, the cleavable moieties azide, azido and azidomethyl group are cleavable/removable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP) or Tri(hydroxyproyl)phosphine (THPP). In some embodiments, the cleaving agent comprises 4-dimethylaminopyridine (4-DMAP).

In some embodiments, in any of the methods for sequencing nucleic acid template molecules described herein, the chain terminating moiety (e.g., at the sugar 2' and/or sugar 3" position) and the cleavable linker on the nucleotide base have the same or different cleavable moieties. In some embodiments, the chain terminating moiety (e.g., at the sugar 2' and/or sugar 3' position) and the detectable reporter moiety linked to the base are chemically cleavable/removable with the same chemical agent. In some embodiments, the chain terminating moiety (e.g., at the sugar 2' and/or sugar 3' position) and the detectable reporter moiety linked to the base are chemically cleavable/removable with different chemical agents.

Multivalent Molecules

Figure 6:
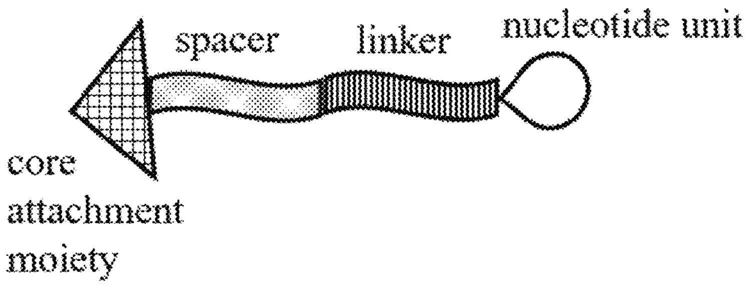
FIG. 6 is a schematic of an exemplary nucleotide-arm comprising a core attachment moiety, spacer, linker and nucleotide unit.
Figure 7:
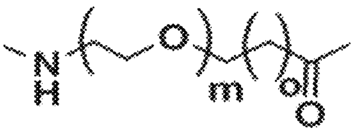
FIG. 7 shows the chemical structure of an exemplary spacer (TOP), and the chemical structures of various exemplary linkers, including an 11-atom Linker, 16-atom Linker, 23-atom Linker and an N3 Linker (BOTTOM).
Figure 7:
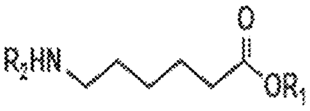
Figure 7:
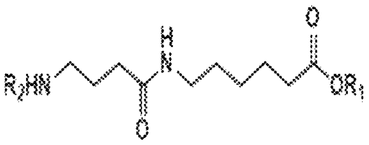
Figure 7:
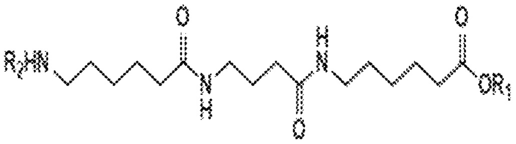
Figure 7:
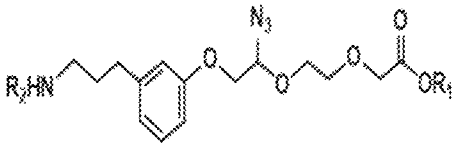
Figure 8:
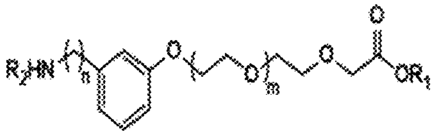
FIG. 8 shows the chemical structures of various exemplary linkers, including Linkers 1-9.
Figure 8:
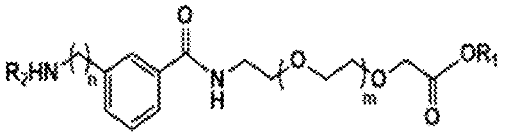
Figure 8:
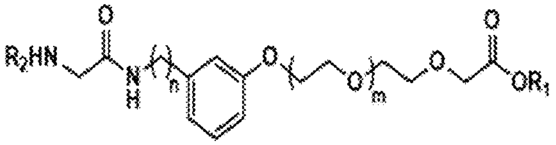
Figure 8:
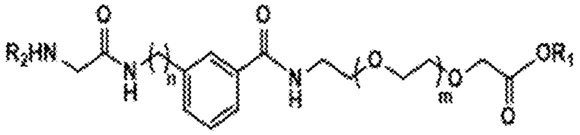
Figure 8:
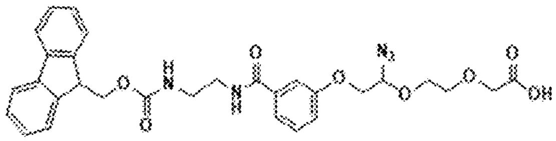
Figure 8:
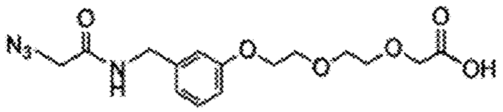
Figure 8:
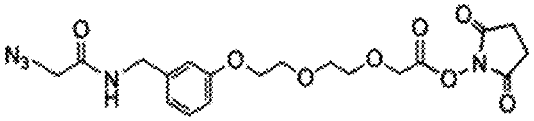
Figure 8:
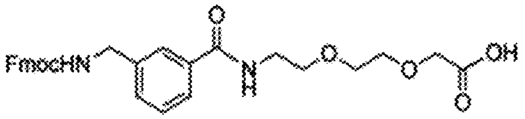
Figure 8:
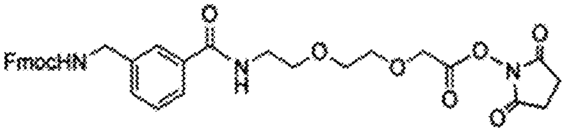
Figure 9A:
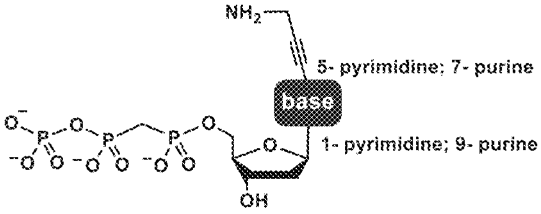
FIG. 9A shows the chemical structures of various exemplary linkers joined/attached to nucleotide units.
Figure 9A:
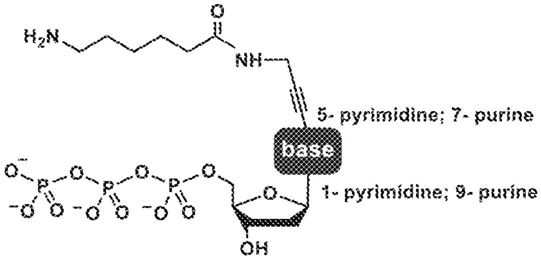
Figure 9A:
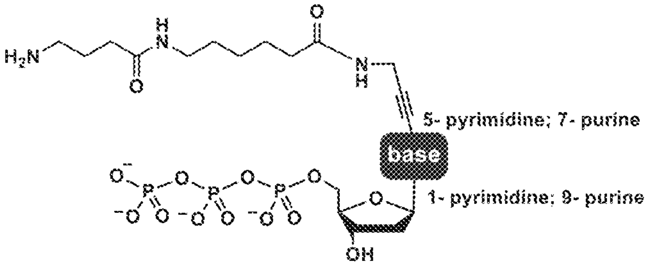
Figure 9B:
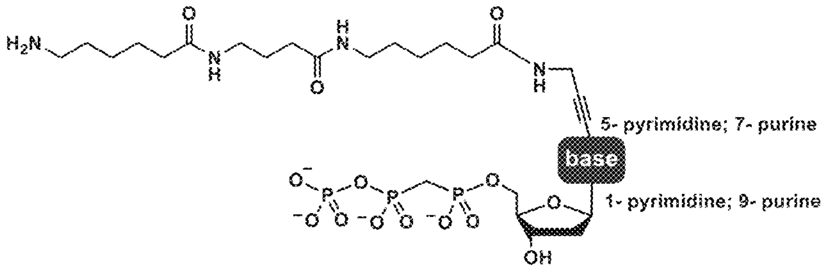
FIG. 9B shows the chemical structures of various exemplary linkers joined/attached to nucleotide units.
Figure 9B:
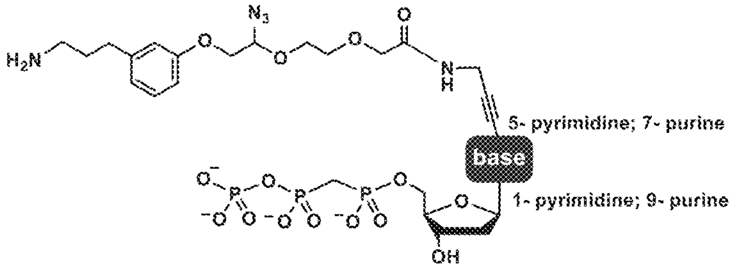
Figure 9B:
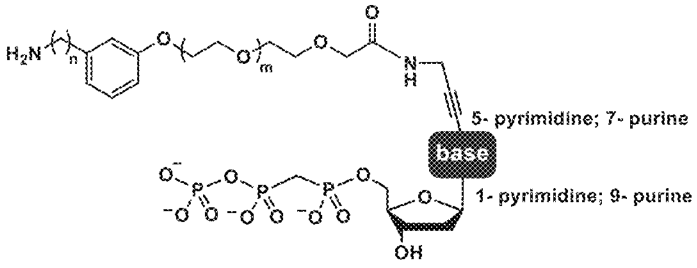
Figure 9C:
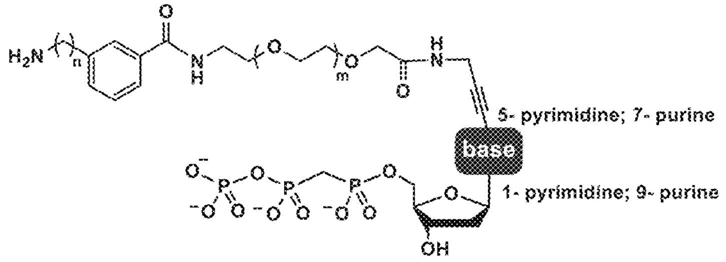
FIG. 9C shows the chemical structures of various exemplary linkers joined/attached to nucleotide units.
Figure 9C:
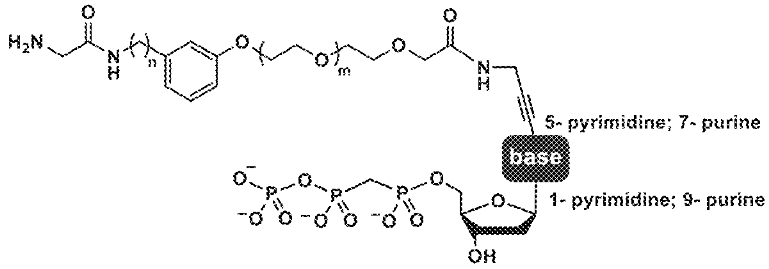
Figure 9D:
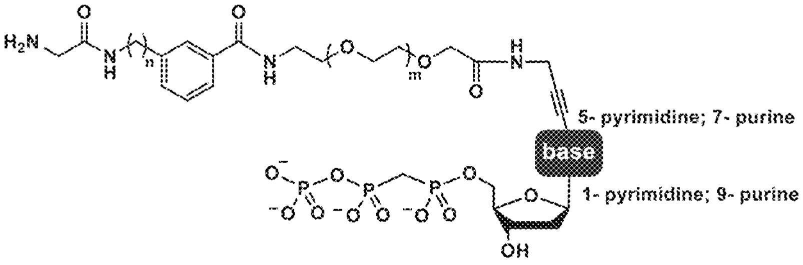
FIG. 9D shows the chemical structures of various exemplary linkers joined/attached to nucleotide units.
Figure 9D:
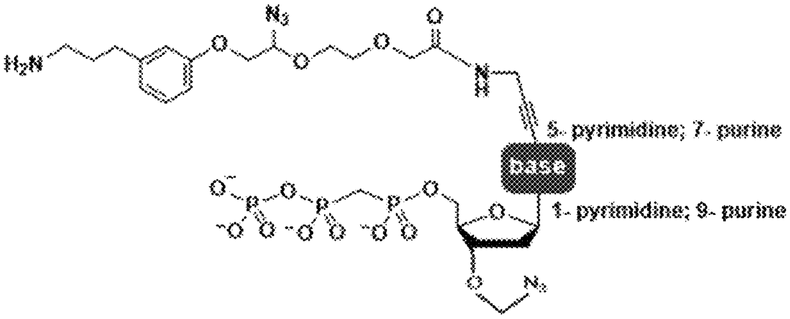
Figure 10:
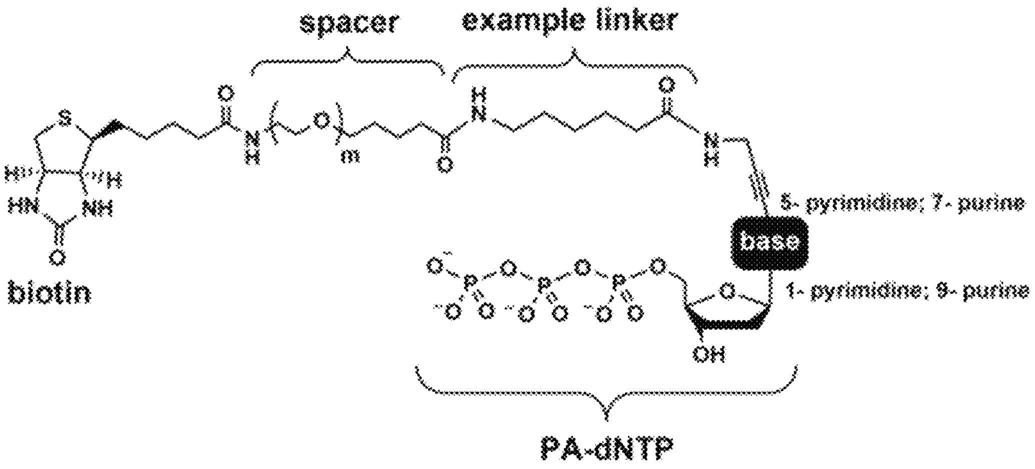
FIG. 10 shows the chemical structure of an exemplary biotinylated nucleotide-arm. In this example, the nucleotide unit is connected to the linker via a propargyl amine attachment at the 5 position of a pyrimidine base or the 7 position of a purine base.

The present disclosure provides methods for sequencing nucleic acid template molecules, where any of the sequencing methods described herein employ at least one multivalent molecule. In some embodiments, the multivalent molecule comprises a plurality of nucleotide arms attached to a core and having any configuration including a starburst, helter skelter, or bottle brush configuration (e.g., FIG. 2). The multivalent molecule comprises: (1) a core; and (2) a plurality of nucleotide arms which comprise (i) a core attachment moiety. (ii) a spacer comprising a PEG moiety, (iii) a linker, and (iv) a nucleotide unit, wherein the core is attached to the plurality of nucleotide arms, wherein the spacer is attached to the linker, wherein the linker is attached to the nucleotide unit. In some embodiments, the nucleotide unit comprises a base, sugar and at least one phosphate group, and the linker is attached to the nucleotide unit through the base. In some embodiments, the linker comprises an aliphatic chain or an oligo ethylene glycol chain where both linker chains having 2-6 subunits. In some embodiments, the linker also includes an aromatic moiety. An exemplary nucleotide arm is shown in FIG. 6. Exemplary multivalent molecules are shown in FIGS. 2-5. An exemplary spacer is shown in FIG. 7 (top) and exemplary linkers are shown in FIG. 7 (bottom) and FIG. 8. Exemplary nucleotides attached to a linker are shown in FIGS. 9A-D. An exemplary biotinylated nucleotide arm is shown in FIG. 10.

In some embodiments, a multivalent molecule comprises a core attached to multiple nucleotide arms, and wherein the multiple nucleotide arms have the same type of nucleotide unit which is selected from a group consisting of dATP, dGTP, dCTP, dTTP and dUTP.

In some embodiments, a multivalent molecule comprises a core attached to multiple nucleotide arms, where each arm includes a nucleotide unit. The nucleotide unit comprises an aromatic base, a five carbon sugar (e.g., ribose or deoxyribose), and one or more phosphate groups (e.g., 1-10 phosphate groups). The plurality of multivalent molecules can comprise one type multivalent molecule having one type of nucleotide unit selected from a group consisting of dATP, dGTP, dCTP, dTTP and dUTP. The plurality of multivalent molecules can comprise at a mixture of any combination of two or more types of multivalent molecules, where individual multivalent molecules in the mixture comprise nucleotide units selected from a group consisting of dATP, dGTP, dCTP, dTTP and/or dUTP.

In some embodiments, the nucleotide unit comprises a chain of one, two or three phosphorus atoms where the chain is typically attached to the 5' carbon of the sugar moiety via an ester or phosphoramide linkage. In some embodiments, at least one nucleotide unit is a nucleotide analog having a phosphorus chain in which the phosphorus atoms are linked together with intervening O, S, NH, methylene or ethylene. In some embodiments, the phosphorus atoms in the chain include substituted side groups including O, S or $BH_3$. In some embodiments, the chain includes phosphate groups substituted with analogs including phosphoramidate, phosphorothioate, phosphordithioate, and O-methylphosphoroamidite groups.

In some embodiments, the multivalent molecule comprises a core attached to multiple nucleotide arms, and wherein individual nucleotide arms comprise a nucleotide unit which is a nucleotide analog having a chain terminating moiety (e.g., blocking moiety) at the sugar 2' position, at the sugar 3° position, or at the sugar 2' and 3' position. In some embodiments, the nucleotide unit comprises a chain terminating moiety (e.g., blocking moiety) at the sugar 2' position, at the sugar 3' position, or at the sugar 2' and 3' position. In some embodiments, the chain terminating moiety can inhibit polymerase-catalyzed incorporation of a subsequent nucleotide unit or free nucleotide in a nascent strand during a primer extension reaction. In some embodiments, the chain terminating moiety is attached to the 3' sugar hydroxyl position where the sugar comprises a ribose or deoxyribose sugar moiety. In some embodiments, the chain terminating moiety is removable/cleavable from the 3' sugar hydroxyl position to generate a nucleotide having a 3'OH sugar group which is extendible with a subsequent nucleotide in a polymerase-catalyzed nucleotide incorporation reaction. In some embodiments, the chain terminating moiety comprises an alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group. In some embodiments, the chain terminating moiety is cleavable/removable from the nucleotide unit, for example by reacting the chain terminating moiety with a chemical agent, pH change, light or heat. In some embodiments, the chain terminating moieties alkyl, alkenyl, alkynyl and allyl are cleavable with tetrakis(triphenylphosphine) palladium(0) ($Pd(PPh_3)_4$) with piperidine, or with 2,3-Dichloro-5,6-dicyano-1,4-benzo-quinone (DDQ). In some embodiments, the chain terminating moieties aryl and benzyl are cleavable with H2 Pd/C. In some embodiments, the chain terminating moieties amine, amide, keto, isocyanate, phosphate, thio, disulfide are cleavable with phosphine or with a thiol group including beta-mercaptoethanol or dithiothritol (DTT). In some embodiments, the chain terminating moiety carbonate is cleavable with potassium carbonate ($K_2CO_3$) in MeOH, with triethylamine in pyridine, or with Zn in acetic acid (AcOH). In some embodiments, the chain terminating moieties urea and silyl are cleavable with tetrabutylammonium fluoride, pyridine-HF, with ammonium fluoride, or with triethylamine trihydrofluoride.

In some embodiments, the nucleotide unit comprises a chain terminating moiety (e.g., blocking moiety) at the sugar 2' position, at the sugar 3' position, or at the sugar 2' and 3' position. In some embodiments, the chain terminating moiety comprises an azide, azido or azidomethyl group. In some embodiments, the chain terminating moiety comprises a 3'-O-azido or 3'-O-azidomethyl group. In some embodiments, the chain terminating moieties azide, azido and azidomethyl group are cleavable/removable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP) or Tri(hydroxyproyl)phosphine (THPP). In some embodiments, the cleaving agent comprises 4-dimethylaminopyridine (4-DMAP).

In some embodiments, the nucleotide unit comprising a chain terminating moiety which is selected from a group consisting of 3'-deoxy nucleotides, 2',3-dideoxynucleotides, 3'-methyl, 3'-azido, 3'-azidomethyl, 3'-O-azidoalkyl, 3'-O-ethynyl, 3'-O-aminoalkyl, 3'-O-fluoroalkyl, 3-fluoromethyl, 3'-difluoromethyl, 3'-trifluoromethyl, 3-sulfonyl, 3'-malonyl, 3'-amino, 3'-O-amino, 3'-sulfhydral, 3'-aminomethyl, 3"-ethyl, 3 butyl, 3'-tert butyl, 3'-Fluorenylmethyloxycarbonyl, 3" tert-Butyloxycarbonyl, 3'-O-alkyl hydroxylamino group, 3'-phosphorothioate, and 3-O-benzyl, or derivatives thereof.

In some embodiments, the multivalent molecule comprises a core attached to multiple nucleotide arms, wherein the nucleotide arms comprise a spacer, linker and nucleotide unit, and wherein the core, linker and/or nucleotide unit is labeled with detectable reporter moiety. In some embodiments, the detectable reporter moiety comprises a dye. In some embodiments, a particular detectable reporter moiety (e.g., fluorescent dye) that is attached to the multivalent molecule can correspond to the base (e.g., dATP, dGTP, dCTP, dTTP or dUTP) of the nucleotide unit to permit detection and identification of the nucleotide base.

In some embodiments, at least one nucleotide arm of a multivalent molecule has a nucleotide unit that is attached to a detectable reporter moiety. In some embodiments, the detectable reporter moiety is attached to the nucleotide base. In some embodiments, the detectable reporter moiety comprises a dye. In some embodiments, a particular detectable reporter moiety (e.g., fluorescent dye) that is attached to the multivalent molecule can correspond to the base (e.g. dATP, dGTP, dCTP, dTTP or dUTP) of the nucleotide unit to permit detection and identification of the nucleotide base.

In some embodiments, the core of a multivalent molecule comprises an avidin-like or streptavidin-like moiety and the core attachment moiety comprises biotin. In some embodiments, the core comprises an streptavidin-type or avidin-type moiety which includes an avidin protein, as well as any derivatives, analogs and other non-native forms of avidin that can bind to at least one biotin moiety. Other forms of avidin moieties include native and recombinant avidin and streptavidin as well as derivatized molecules, e.g. non-glycosylated avidin and truncated streptavidins. For example, avidin moiety includes de-glycosylated forms of avidin, bacterial streptavidin produced by *Streptomyces* (e.g., *Streptomyces avidinii*), as well as derivatized forms, for example, N-acyl avidins, e.g., N-acetyl, N-phthalyl and N-succinyl avidin, and the commercially-available products EXTRAVIDIN, CAPTAVIDIN, NEUTRAVIDIN and NEUTRALITE AVIDIN.

In some embodiments, any of the methods for sequencing nucleic acid molecules described herein can include forming a binding complex, where the binding complex comprises (i) a polymerase, a nucleic acid concatemer molecule duplexed with a primer, and a nucleotide, or the binding complex comprises (ii) a polymerase, a nucleic acid concatemer molecule duplexed with a primer, and a nucleotide unit of a multivalent molecule. In some embodiments, the binding complex has a persistence time of greater than about 0, 1, 0.2, 0.3, 0.4, 0.5, 0.6, 0.7, 0.8, 0.9 or 1 second. The binding complex has a persistence time of greater than about 0.1-0.25 seconds, or about 0.25-0.5 seconds, or about 0.5-0.75 seconds, or about 0.75-1 second, or about 1-2 seconds, or about 2-3 seconds, or about 3-4 second, or about 4-5 seconds, and/or wherein the method is or may be carried out at a temperature of at or above 15° C. at or above 20° C. at or above 25° C., at or above 35° C., at or above 37° ° C., at or above 42° ° C. at or above 55° C. at or above 60° C., or at or above 72° C., or at or above 80° C., or within a range defined by any of the foregoing. The binding complex (e.g., ternary complex) remains stable until subjected to a condition that causes dissociation of interactions between any of the polymerase, template molecule, primer and/or the nucleotide unit or the nucleotide. For example, a dissociating condition comprises contacting the binding complex with any one or any combination of a detergent. EDTA and/or water. In some embodiments, the present disclosure provides said method wherein the binding complex is deposited on, attached to, or hybridized to, a surface showing a contrast to noise ratio in the detecting step of greater than 20. In some embodiments, the present disclosure provides said method wherein the contacting is performed under a condition that stabilizes the binding complex when the nucleotide or nucleotide unit is complementary to a next base of the template nucleic acid, and destabilizes the binding complex when the nucleotide or nucleotide unit is not complementary to the next base of the template nucleic acid.

Coated Support

The present disclosure provides methods for sequencing nucleic acid template molecules, where the template molecules are immobilized to a support. In some embodiments, at least one surface of the support can be modified with a chemical compound that enables attachment of a polymer coating to the support. For example, the support can be modified with a silane compound. In some embodiments, the silane compound can bind a polymer coating. In some embodiments, at least one surface of the support is passivated with at least one polymer coating layer (e.g., FIG. 1). In some embodiments, the support is passivated with 1, 2, 3, 4, 5, 6, 7, 8, 9, 10 or more polymer coating layers. In some embodiments, the coating forms a continuous layer on the support wherein the coating forms no pre-determined pattern.

In some embodiments, the surface coating may be patterned, such that the chemical modification layers are confined to one or more discrete regions of the support. For example, the coating may be patterned using photolithographic techniques to create an ordered array or random pattern of chemically-modified regions on the support. Alternately or in combination, the coating may be patterned using, e.g., contact printing and/or ink-jet printing techniques. In some embodiments, the coating is distributed on the support in a pre-determined pattern, for example the pre-determined pattern comprises or spots arranged in rows and/or columns or other pre-determined patterns. In some embodiments, the coating having a pre-determined pattern comprises at least one interstitial region that lacks a polymer coating. In some embodiments, the passivated layer forms a porous or semi-porous layer.

In some embodiments, at least one of the polymer coating layers comprises a hydrophilic polymer layer. In some embodiments, at least one polymer coating layer comprises polymer molecules having a molecular weight of at least 1000 Daltons. The hydrophilic polymer coating layer can comprise polyethylene glycol (PEG). The hydrophilic polymer layer can comprise unbranched PEG. The hydrophilic polymer layer can comprise branched PEG having at least 4 branches, for example the branched PEG comprises 4-16 branches. In some embodiments, the hydrophilic polymer layer comprises cross-linking or lacks cross-linking. In some embodiments, the hydrophilic polymer layer comprises cross-linking to form a hydrogel.

In some embodiments, the hydrophilic polymer layer comprises a monolayer having unbranched polymers which can form a brush monolayer. In some embodiments, the brush monolayer can form an extended brush monolayer. In some embodiments, the brush monolayer comprises a plurality of unbranched polymers where one end of a given unbranched polymer is attached to the support and the other end of the same given unbranched polymer is attached to an oligonucleotide primer (e.g., capture primer or pinning primer). In some embodiments, the density of the plurality of oligonucleotide primers attached to the brush monolayer is about $10^2$-$10^{15}$ per $um^2$.

In some embodiments, the coating layer has a degree of hydrophilicity which can be measured as a water contact angle, where the water contact angle is no more than 45 degrees.

In some embodiments, any layer of the polymer coating includes a plurality of oligonucleotide primers covalently tethered to the polymer layer. In some embodiments, the plurality of oligonucleotide primers are distributed at a plurality of depths throughout any of the polymer layers. In some embodiments, the density of the plurality of oligonucleotide primers in any of the polymer layers is about $10^2$-$10^{15}$ per $um^2$. In some embodiments, individual oligonucleotide primers comprise nucleic acid molecules comprising DNA, RNA, DNA/RNA chimeric or analogs thereof. In some embodiments, the plurality of oligonucleotide primers are about 10-100 nucleotides in length. In some embodiments, individual oligonucleotide primers in the plurality comprise 3' extendible ends or 3' non-extendible ends. In some embodiments, the 3' non-extendible ends comprise a 3' chain terminating moiety. In some embodiments, individual oligonucleotide primers have their 5' or 3' ends or an internal region attached to the polymer layer. In some embodiments, the 5' ends of the plurality of oligonucleotide primers are attached to the polymer laver. In some embodiments, the plurality of oligonucleotide primer are randomly distributed throughout and embedded within at least one of the polymer layers. In some embodiments, the plurality of oligonucleotide primer are distributed in or on at least one of the polymer layers in a random manner or a pre-determined pattern. In some embodiments, the plurality of oligonucleotide primers are distributed in or on at least one of the polymer layers in a non-random pre-determined pattern, for example the pre-determined pattern comprises stripes or spots arranged in rows and/or columns or other pre-determined patterns.

In some embodiments, the support comprises a first layer comprising a first monolayer having hydrophilic polymer molecules tethered to the support. In some embodiments, at least some of the polymer molecules in the first layer are covalently tethered to oligonucleotide primers. In some embodiments, the tethered oligonucleotide primers in the first monolayer are arranged in a random manner or in a pre-determined pattern. In some embodiments, the polymer molecules in the first layer are not tethered to oligonucleotide primers.

In some embodiments, the support further comprises a second layer comprising a second monolayer having hydrophilic polymer molecules tethered to the first monolayer. In some embodiments, at least some of the polymer molecules in the second layer are covalently tethered to oligonucleotide primers. In some embodiments, the tethered oligonucleotide primers in the second monolayer are arranged in a random manner or in a pre-determined pattern. In some embodiments, the polymer molecules in the second layer are not tethered to oligonucleotide primers.

In some embodiments, the support further comprises a third layer comprising a third monolayer having hydrophilic polymer molecules tethered to the second monolayer. In some embodiments, at least some of the polymer molecules in the third layer are covalently tethered to oligonucleotide primers. In some embodiments, the tethered oligonucleotide primers in the third monolayer are arranged in a random manner or in a pre-determined pattern. In some embodiments, the polymer molecules in the third layer are not tethered to oligonucleotide primers.

In some embodiments, the support comprises a functionalized polymer coating layer covalently bound at least to a portion of the support via a chemical group on the support, a primer grafted to the functionalized polymer coating, and a water-soluble protective coating on the primer and the functionalized polymer coating. In some embodiments, the functionalized polymer coating comprises a poly(N-(5-azidoacetamidylpentyl)acrylamide-co-acrylamide (PAZAM).

In some embodiments, at least one of the polymer layers comprise oligonucleotide primers including capture primers, pinning primers, or a mixture of capture and pinning primers. In some embodiments, the plurality of oligonucleotide primers comprise one type of capture primer (e.g., having that same batch capture primer sequence) or a mixture of 2-50 different types of capture primers (e.g., having 2-50 different batch capture primer sequences). In some embodiments, the plurality of oligonucleotide primers comprise one type of pinning primer (e.g., having that same batch pinning primer sequence) or a mixture of 2-50 different types of pinning primers (e.g., having 2-50 different batch pinning primer sequences).

In some embodiments, individual capture primers (e.g., which are tethered to and/or embedded in a polymer layer) can be used in an on-support amplification reaction wherein individual capture primers hybridize to a capture primer binding site in a circularized library molecule, and rolling circle amplification can be conducted to generate a concatemer template molecule which is tethered and/or embedded in the polymer layer.

In some embodiments, individual capture primers (e.g., which are tethered to and/or embedded in a polymer layer) can be used in an in-solution amplification workflow wherein individual capture primers can hybridize to a capture primer binding site in a nascent concatemer molecule, and rolling circle amplification can continue on the polymer layer to generate a concatemer template molecule which is tethered and/or embedded in the polymer laver.

In some embodiments, the density of the capture primers in a polymer layer can be modulated (e.g., increased or decreased) to achieve a desired density of immobilized concatemer template molecules on a support. Generally, a polymer layer having a high density of capture primers will generate concatemer template molecules that are tightly packed and immobilized to the support at a density of about $10^5$-$10^{15}$ per $mm^2$ which cannot be achieved using supports fabricated to include nano-scale features for attachment of template molecules.

In some embodiments, a single pinning primer (e.g., which is tethered to or embedded in a polymer layer) can hybridize to a pinning primer binding site in a concatemer molecule to generate a concatemer template molecule which is tethered or embedded (e.g., pinned down) in the polymer layer.

Nucleotide Compositions

The present disclosure provide a composition comprising a plurality of nucleotides wherein at least one nucleotide in the plurality is labeled with any of the dyes described herein. In some embodiments, the plurality of nucleotides comprises a mixture of different types of nucleotides having nucleo-bases adenine, guanine, cytosine, thymine and/or uracil, wherein all of the different types of nucleotides are dye labeled or wherein one type of nucleotide is not labeled. In some embodiments, a dye is joined to the nucleo-base of a nucleotide. In some embodiments, the dye is joined to one of the phosphate groups in the phosphate chain. For example, the dye is joined to the terminal phosphate group. In some embodiments, the dye is joined to the nucleo-base or the phosphate group by a linker. In some embodiments, the linker is cleavable with a chemical, enzyme, heat or light.

Multivalent Compositions

The present disclosure provide a composition comprising a plurality of multivalent molecules, wherein at least one multivalent molecule in the plurality is labeled with a dye. In some embodiments, individual multivalent molecules in the plurality comprise a core attached to multiple nucleotide arms and each nucleotide arm is attached to a nucleotide unit (e.g., nucleotide moiety) (e.g., FIGS. 2-5). In some embodiments, the multivalent molecule comprises: (1) a core; and (2) a plurality of nucleotide arms which comprise (1) a core attachment moiety, (ii) a spacer comprising a PEG moiety, (iii) a linker, and (iv) a nucleotide unit, wherein the core is attached to the plurality of nucleotide arms, wherein the spacer is attached to the linker, wherein the linker is attached to the nucleotide unit. In some embodiments, the nucleotide unit comprises a base, sugar and at least one phosphate group, and the linker is attached to the nucleotide unit through the base. In some embodiments, the linker comprises an aliphatic chain or an oligo ethylene glycol chain where both linker chains having 2-6 subunits. In some embodiments, the linker also includes an aromatic moiety.

In some embodiments, a multivalent molecule comprises a core attached to multiple nucleotide arms, and wherein the multiple nucleotide arms have the same type of nucleotide unit which is selected from a group consisting of dATP, dGTP, dCTP, dTTP and dUTP.

In some embodiments, a multivalent molecule comprises a core attached to multiple nucleotide arms, where each arm includes a nucleotide unit. The nucleotide unit comprises an aromatic base, a five carbon sugar (e.g., ribose or deoxyribose), and one or more phosphate groups (e.g., 1-10) phosphate groups). The plurality of multivalent molecules can comprise one type multivalent molecule having one type of nucleotide unit selected from a group consisting of dATP, dGTP, dCTP, dTTP and dUTP. The plurality of multivalent molecules can comprise at a mixture of any combination of two or more types of multivalent molecules, where individual multivalent molecules in the mixture comprise nucleotide units selected from a group consisting of dATP, dGTP, dCTP, dTTP and/or dUTP.

In some embodiments, the nucleotide unit comprises a chain of one, two or three phosphorus atoms where the chain is typically attached to the 5' carbon of the sugar moiety via an ester or phosphoramide linkage. In some embodiments, at least one nucleotide unit is a nucleotide analog having a phosphorus chain in which the phosphorus atoms are linked together with intervening O, S, NH, methylene or ethylene. In some embodiments, the phosphorus atoms in the chain include substituted side groups including O, S or $BH_3$. In some embodiments, the chain includes phosphate groups substituted with analogs including phosphoramidate, phosphorothioate, phosphordithioate, and O-methylphosphoroamidite groups.

In some embodiments, the plurality of multivalent molecules comprises a mixture of different types of multivalent molecules (e.g., any combination of dATP, dGTP, dCTP, dTTP and/or dUTP) wherein all of the different types of multivalent molecules are dye labeled. In some embodiments, at least one type of multivalent molecule in the mixture is not labeled.

In some embodiments, the multivalent molecule comprises a core attached to multiple nucleotide arms, wherein the nucleotide arms comprise a spacer, linker and nucleotide unit. In some embodiments, the core, linker and/or nucleotide unit is labeled with detectable reporter moiety. In some embodiments, the detectable reporter moiety comprises any of the fluorescent dyes described herein. In some embodiments, a particular dye that is attached to the multivalent molecule can correspond to the base (e.g., dATP, dGTP, dCTP, dTTP or dUTP) of the nucleotide unit to permit detection and identification of the nucleotide base.

In some embodiments, at least one nucleotide arm of a multivalent molecule has a nucleotide unit that is attached to a detectable reporter moiety. In some embodiments, the dye is attached to the nucleo-base or one of the phosphate groups. In some embodiments, a particular dye that is attached to the multivalent molecule can correspond to the base (e.g., dATP, dGTP, dCTP, dTTP or dUTP) of the nucleotide unit to permit detection and identification of the nucleotide base.

In some embodiments, the core of a multivalent molecule comprises an avidin-like or streptavidin-like moiety and the core attachment moiety comprises biotin. In some embodiments, the core is labeled with one or more dyes. In some embodiments, the core comprises an streptavidin-type or avidin-type moiety which includes an avidin protein, as well as any derivatives, analogs and other non-native forms of avidin that can bind to at least one biotin moiety. Other forms of avidin moieties include native and recombinant avidin and streptavidin as well as derivatized molecules. e.g. non-glycosylated avidin and truncated streptavidins. For example, avidin moiety includes de-glycosylated forms of avidin, bacterial streptavidin produced by *Streptomyces* (e.g., *Streptomyces avidinii*), as well as derivatized forms, for example, N-acyl avidins, e.g., N-acetyl, N-phthalyl and N-succinyl avidin, and the commercially-available products EXTRAVIDIN, CAPTAVIDIN, NEUTRAVIDIN and NEUTRALITE AVIDIN. In some embodiments, one or more lysine residues in the core can be dye labeled.

In some embodiments, the composition comprises a plurality of multivalent molecules and a plurality of polymerases. In some embodiments, individual multivalent molecules are not bound to individual polymerases. In some embodiments, at least one multivalent molecule is bound to at least one polymerase. In some embodiments, the composition further comprises a plurality of nucleic acid template molecules and/or a plurality of nucleic acid primer molecules. In some embodiments, the multivalent molecules, polymerases, template molecules and primer molecules may or may not be bound together.

In some embodiments, the composition comprises an avidity complex labeled with one or more dyes, wherein the avidity complex comprises (i) a first sequencing primer, a first sequencing polymerase, and a first multivalent molecule bound to a first portion of a concatemer template molecule thereby forming a first binding complex, wherein a first nucleotide unit of the first multivalent molecule binds to the first sequencing polymerase; and (ii) a second sequencing primer, a second sequencing polymerase, and the first multivalent molecule bound to a second portion of the same concatemer template molecule thereby forming a second binding complex, wherein a second nucleotide unit of the first multivalent molecule binds to the second sequencing polymerase, wherein the first and second binding complexes which include the same multivalent molecule forms an avidity complex. In some embodiments, the first and/or the second multivalent molecule(s) can be dye labeled. In some embodiments, the concatemer template molecule comprises tandem repeat sequences of a sequence of interest and at least one universal site for binding a sequencing primer. The first and second sequencing primers can bind to different sequencing primer binding sites along the concatemer template molecule.

Compositions and methods for preparing and using the multivalent molecules (also called polymer-nucleotide conjugates) are described in U.S. Ser. No. 16/579,794, filed on Sep. 23, 2019, the contents of which is hereby expressly incorporated by reference in its entirety.

Additional Suitable Sequencing Methods

Additional sequencing methods and/or devices suitable for use with the compounds disclosed herein are disclosed in International Application Nos. PCT/EP2022/063647, filed May 19, 2022, PCT/US2022/022184, filed Mar. 28, 2022, PCT/US2022/169972, filed Feb. 3, 2022, PCT/EP2021/087044, filed Dec. 21, 2021, PCT/EP2021/086349, filed Dec. 16, 2021, PCT/US2021/018631, filed Feb. 18, 2021, PCT/US2022/012306, filed Jan. 13, 2022, PCT/US2021/013465, filed Jan. 14, 2021, PCT/US2019/027292, filed Apr. 12, 2019, and PCT/US2017/049496, filed Aug. 30, 2017, U.S. Pat. No. 11,427,855, issued Aug. 30, 2022, U.S. Pat. No. 10,233,490, issued Mar. 19, 2019, and U.S. patent application Ser. No. 16/783,301, filed Feb. 6, 2022, and Ser. No. 14/784,605, filed Apr. 17, 2014, which are hereby incorporated by reference.

Definitions

The headings provided herein are not limitations of the various aspects of the disclosure, which aspects can be understood by reference to the specification as a whole.

As used herein, the term "ionic derivative" refers to an ionic form of the referenced structure. The ionic form may be a cation, an anion, or a zwitterion. In some embodiments, the ionic form is zwitterion (i.e., a structure containing an equal number of positively- and negatively-charged functional groups). For example, when a structure is described herein as an anion, the disclosure intends to cover the corresponding zwitterion of the structure (e.g., wherein one $—S(=O)_2OH$ forms $—S(=O)_2O^-$).

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_2$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, arylovycarbonyloxy, carboxylate, alkylcarbonyl, arvlcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "cycloalkyl" refers to a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. In the case of polycyclic cycloalkyl, only one of the rings in the cycloalkyl needs to be non-aromatic.

As used herein, the term "cycloalkylene" refers to a bivalent moiety for which the corresponding monovalent moiety is cycloalkyl. It is understood that cycloalkylene can be saturated or partially unsaturated.

As used herein, the term "heterocycloalkyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperdinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydroimidazo[1,2-a]pyridinyl, 6,7,8,9-tetrahydro-5H-imidazo[1,2-a]azepinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like. In the case of multicyclic heterocycloalkyl, only one of the rings in the heterocycloalkyl needs to be non-aromatic (e.g., 4,5,6,7-tetrahydrobenzo[c]isoxazolyl).

As used herein, the term "aryl" includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like. Conveniently, an aryl is phenyl.

As used herein, the term "arylene" refers to a bivalent moiety for which the corresponding monovalent moiety is aryl.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidised (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like. Heteroaryl groups can also be fused or bridged with alicyclic or heterocyclic rings, which are not aromatic so as to form a multicyclic system (e.g., 4,5,6,7-tetrahydrobenzo[c]isoxazolyl).

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthyridine, indole, benzofuran, purine, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonylovy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or $—O^-$.

As used herein, the term "halo" or "halogen" refers to fluoro, chloro, bromo and iodo.

The term "haloalkyl" or "haloalkoxyl" refers to an alkyl or alkoxyl substituted with one or more halogen atoms.

As used herein, the term "optionally substituted haloalkyl" refers to unsubstituted haloalkyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxy late, alkylcarbonyl, arylcarbonyl, alkoxycarbonyl, aminocarbonyl, alkylaminocarbonyl, dialkylaminocarbonyl, alkylthiocarbonyl, alkoxyl, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March. J., *March's Advanced Organic Chemistry: Reactions, Mechanisms, and Structure,* 5th edition, John Wiley & Sons: New York, 2001; Greene, T. W., Wuts. P. G. M., *Protective Groups in Organic Synthesis,* 3rd edition, John Wiley & Sons: New York, 1999; R. Larock, Comprehensive Organic Transformations, VCH Publishers (1989); L. Fieser and M. Fieser, *Fieser and Fieser's Reagents for Organic Synthesis*, John Wiley and Sons (1994), and L. Paquette, ed., *Encyclopedia of Reagents for Organic Synthesis*, John Wiley and Sons (1995), incorporated by reference herein, are useful and recognized reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts. P. G. M., *Protective Groups in Organic Synthesis,* 3rd edition, John Wiley & Sons: New York, 1999.

Unless defined otherwise, technical and scientific terms used herein have meanings that are commonly understood by those of ordinary skill in the art unless defined otherwise. Generally, terminologies pertaining to techniques of molecular biology, nucleic acid chemistry, protein chemistry, genetics, microbiology, transgenic cell production, and hybridization described herein are those well-known and commonly used in the art. Techniques and procedures described herein are generally performed according to conventional methods well known in the art and as described in various general and more specific references that are cited and discussed throughout the instant specification. For example, see Sambrook et al., Molecular Cloning: A Laboratory Manual (Third ed., Cold Spring Harbor Laboratory Press, Cold Spring Harbor, N.Y. 2000). See also Ausubel et al., Current Protocols in Molecular Biology. Greene Publishing Associates (1992). The nomenclatures utilized in connection with, and the laboratory procedures and techniques described herein are those well-known and commonly used in the art.

Unless otherwise required by context herein, singular terms shall include pluralities and plural terms shall include the singular. Singular forms "a", "an" and "the", and singular use of any word, include plural referents unless expressly and unequivocally limited on one referent.

It is understood the use of the alternative term (e.g., "or") is taken to mean either one or both or any combination thereof of the alternatives.

The term "and/or" used herein is to be taken mean specific disclosure of each of the specified features or components with or without the other. For example, the term "and/or" as used in a phrase such as "A and/or B" herein is intended to include: "A and B"; "A or B"; "A" (A alone); and "B" (B alone). In a similar manner, the term "and/or" as used in a phrase such as "A, B, and/or C" is intended to encompass each of the following aspects. "A, B, and C"; "A, B, or C";

"A or C"; "A or B"; "B or C"; "A and B"; "B and C"; "A and C"; "A" (A alone); "B" (B alone); and "C" (C alone).

As used herein and in the appended claims, terms "comprising", "including", "having" and "containing", and their grammatical variants, as used herein are intended to be non-limiting so that one item or multiple items in a list do not exclude other items that can be substituted or added to the listed items. It is understood that wherever aspects are described herein with the language "comprising." otherwise analogous aspects described in terms of "consisting of" and/or "consisting essentially of" are also provided.

As used herein, the terms "about" and "approximately" refer to a value or composition that is within an acceptable error range for the particular value or composition as determined by one of ordinary skill in the art, which will depend in part on how the value or composition is measured or determined, i.e., the limitations of the measurement system. For example, "about" or "approximately" can mean within one or more than one standard deviation per the practice in the art. Alternatively. "about" or "approximately" can mean a range of up to 10% (i.e., +10%) or more depending on the limitations of the measurement system. For example, about 5 mg can include any number between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "approximately" should be assumed to be within an acceptable error range for that particular value or composition. Also, where ranges and/or subranges of values are provided, the ranges and/or subranges can include the endpoints of the ranges and/or subranges.

The term "biological sample" refers to a single cell, a plurality of cells, a tissue, an organ, an organism, or section of any of these biological samples. The biological sample can be extracted (e.g., biopsied) from an organism, or obtained from a cell culture grown in liquid or in a culture dish. The biological sample comprises a sample that is fresh, frozen, fresh frozen, or archived (e.g., formalin-fixed paraffin-embedded; FFPE). The biological sample can be embedded in a wax, resin, epoxy or agar. The biological sample can be fixed, for example in any one or any combination of two or more of acetone, ethanol, methanol, formaldehyde, paraformaldehyde-Triton or glutaraldehyde. The biological sample can be sectioned or non-sectioned. The biological sample can be stained, de-stained or non-stained.

The nucleic acids of interest can be extracted from biological samples using any of a number of techniques known to those of skill in the art. For example, a typical DNA extraction procedure comprises (i) collection of the cell sample or tissue sample from which DNA is to be extracted, (ii) disruption of cell membranes (i.e., cell lysis) to release DNA and other cytoplasmic components, (iii) treatment of the lysed sample with a concentrated salt solution to precipitate proteins, lipids, and RNA, followed by centrifugation to separate out the precipitated proteins, lipids, and RNA, and (iv) purification of DNA from the supernatant to remove detergents, proteins, salts, or other reagents used during the cell membrane lysis. A variety of suitable commercial nucleic acid extraction and purification kits are consistent with the disclosure herein. Examples include, but are not limited to, the QIAamp kits (for isolation of genomic DNA from human samples) and DNAeasy kits (for isolation of genomic DNA from animal or plant samples) from Qiagen (Germantown, MD), or the Maxwell® and ReliaPrep™ series of kits from Promega (Madison, WI).

The terms "nucleic acid", "polynucleotide" and "oligonucleotide" and other related terms used herein are used interchangeably and refer to polymers of nucleotides and are not limited to any particular length. Nucleic acids include recombinant and chemically-synthesized forms. Nucleic acids can be isolated. Nucleic acids include DNA molecules (e.g., cDNA or genomic DNA), RNA molecules (e.g., mRNA), analogs of the DNA or RNA generated using nucleotide analogs (e.g., peptide nucleic acids (PNA) and non-naturally occurring nucleotide analogs), and chimeric forms containing DNA and RNA. Nucleic acids can be single-stranded or double-stranded. Nucleic acids comprise polymers of nucleotides, where the nucleotides include natural or non-natural bases and/or sugars. Nucleic acids comprise naturally-occurring internucleosidic linkages, for example phosphdiester linkages. Nucleic acids can lack a phosphate group. Nucleic acids comprise non-natural internucleoside linkages, including phosphorothioate, phosphorothiolate, or peptide nucleic acid (PNA) linkages. In some embodiments, nucleic acids comprise a one type of polynucleotides or a mixture of two or more different types of polynucleotides.

The term "universal sequence", "universal adaptor sequences" and related terms refers to a sequence in a nucleic acid molecule that is common among two or more polynucleotide molecules. For example, adaptors having the same universal sequence can be joined to a plurality of polynucleotides so that the population of co-joined molecules carry the same universal adaptor sequence. Examples of universal adaptor sequences include an amplification primer sequence, a sequencing primer sequence or a capture primer sequence (e.g., soluble or support-immobilized capture primers).

The term "operably linked" and "operably joined" or related terms as used herein refers to juxtaposition of components. The juxtapositioned components can be linked together covalently. For example, two nucleic acid components can be enzymatically ligated together where the linkage that joins together the two components comprises phosphodiester linkage. A first and second nucleic acid component can be linked together, where the first nucleic acid component can confer a function on a second nucleic acid component. For example, linkage between a primer binding sequence and a sequence of interest forms a nucleic acid library molecule having a portion that can bind to a primer. In another example, a transgene (e.g., a nucleic acid encoding a polypeptide or a nucleic acid sequence of interest) can be ligated to a vector where the linkage permits expression or functioning of the transgene sequence contained in the vector. In some embodiments, a transgene is operably linked to a host cell regulatory sequence (e.g., a promoter sequence) that affects expression of the transgene. In some embodiments, the vector comprises at least one host cell regulatory sequence, including a promoter sequence, enhancer, transcription and/or translation initiation sequence, transcription and/or translation termination sequence, polypeptide secretion signal sequences, and the like. In some embodiments, the host cell regulatory sequence controls expression of the level, timing and/or location of the transgene.

The terms "linked", "joined", "attached", "appended" and variants thereof comprise any type of fusion, bond, adherence or association between any combination of compounds or molecules that is of sufficient stability to withstand use in the particular procedure. The procedure can include but are not limited to: nucleotide binding; nucleotide incorporation; de-blocking (e.g., removal of chain-terminating moiety); washing; removing; flowing; detecting; imaging and/or identifying. Such linkage can comprise, for example, covalent, ionic, hydrogen, dipole-dipole, hydrophilic, hydrophobic, or affinity bonding, bonds or associations involving van der Waals forces, mechanical bonding, and the like. In some embodiments, such linkage occurs intramolecularly, for example linking together the ends of a single-stranded or double-stranded linear nucleic acid molecule to form a circular molecule. In some embodiments, such linkage can occur between a combination of different molecules, or between a molecule and a non-molecule, including but not limited to: linkage between a nucleic acid molecule and a solid surface; linkage between a protein and a detectable reporter moiety; linkage between a nucleotide and detectable reporter moiety; and the like. Some examples of linkages can be found, for example, in Hermanson, G., "Bioconjugate Techniques", Second Edition (2008); Aslam. M., Dent. A., "Bioconjugation: Protein Coupling Techniques for the Biomedical Sciences", London: Macmillan (1998); Aslam, M., Dent, A., "Bioconjugation: Protein Coupling Techniques for the Biomedical Sciences", London: Macmillan (1998).

The term "adaptor" and related terms refers to oligonucleotides that can be operably linked (appended) to a target polynucleotide, where the adaptor confers a function to the co-joined adaptor-target molecule. Adaptors comprise DNA, RNA, chimeric DNA/RNA, or analogs thereof. Adaptors can include at least one ribonucleoside residue. Adaptors can be single-stranded, double-stranded, or have single-stranded and/or double-stranded portions. Adaptors can be configured to be linear, stem-looped, hairpin, or Y-shaped forms. Adaptors can be any length, including 4-100 nucleotides or longer. Adaptors can have blunt ends, overhang ends, or a combination of both. Overhang ends include 5' overhang and 3' overhang ends. The 5' end of a single-stranded adaptor, or one strand of a double-stranded adaptor, can have a 5' phosphate group or lack a 5' phosphate group. Adaptors can include a 5' tail that does not hybridize to a target polynucleotide (e.g., tailed adaptor), or adaptors can be non-tailed. An adaptor can include a sequence that is complementary to at least a portion of a primer, such as an amplification primer, a sequencing primer, or a capture primer (e.g., soluble or immobilized capture primers). Adaptors can include a random sequence or degenerate sequence. Adaptors can include at least one inosine residue. Adaptors can include at least one phosphorothioate, phosphorothiolate and/or phosphoramidate linkage. Adaptors can include a barcode sequence which can be used to distinguish polynucleotides (e.g., insert sequences) from different sample sources in a multiplex assay. Adaptors can include a unique identification sequence (e.g., unique molecular index, UMI; or a unique molecular tag) that can be used to uniquely identify a nucleic acid molecule to which the adaptor is appended. In some embodiments, a unique identification sequence can be used to increase error correction and accuracy, reduce the rate of false-positive variant calls and/or increase sensitivity of variant detection. Adaptors can include at least one restriction enzyme recognition sequence, including any one or any combination of two or more selected from a group consisting of type I, type II, type III, type IV, type Hs or type IIB.

The term "nucleic acid template", "template polynucleotide", "nucleic acid target" "target polynucleotide", "template strand" and other variations refer to a nucleic acid strand that serves as the basis nucleic acid molecule for any of the analysis methods describe herein (e.g., primer extension, amplifying and/or sequencing). The template nucleic acid can be single-stranded or double-stranded, or the template nucleic acid can have single-stranded or double-stranded portions. The template nucleic acid can be obtained from a naturally-occurring source, recombinant form, or chemically synthesized to include any type of nucleic acid analog. The template nucleic acid can be linear, circular, or other forms. The template nucleic acids can include an insert region having an insert sequence which is also known as a sequence of interest. The template nucleic acids can also include at least one adaptor sequence. The template nucleic acid can be a concatemer having two or tandem copies of a sequence of interest and at least one adaptor sequence. The insert region can be isolated in any form, including chromosomal, genomic, organellar (e.g., mitochondrial, chloroplast or ribosomal), recombinant molecules, cloned, amplified, cDNA, RNA such as precursor mRNA or mRNA, oligonucleotides, whole genomic DNA, obtained from fresh frozen paraffin embedded tissue, needle biopsies, circulating tumor cells, cell free circulating DNA, or any type of nucleic acid library. The insert region can be isolated from any source including from organisms such as prokaryotes, eukaryotes (e.g., humans, plants and animals), fungus, viruses cells, tissues, normal or diseased cells or tissues, body fluids including blood, urine, serum, lymph, tumor, saliva, anal and vaginal secretions, amniotic samples, perspiration, semen, environmental samples, culture samples, or synthesized nucleic acid molecules prepared using recombinant molecular biology or chemical synthesis methods. The insert region can be isolated from any organ, including head, neck, brain, breast, ovary, cervix, colon, rectum, endometrium, gallbladder, intestines, bladder, prostate, testicles, liver, lung, kidney, esophagus, pancreas, thyroid, pituitary, thymus, skin, heart, larynx, or other organs. The template nucleic acid can be subjected to nucleic acid analysis, including sequencing and composition analysis.

The term "polymerase" and its variants, as used herein, comprises an enzyme comprising a domain that binds a nucleotide (or nucleoside) where the polymerase can form a complex having a template nucleic acid and a complementary nucleotide. The polymerase can have one or more activities including, but not limited to, base analog detection activities, DNA polymerization activity, reverse transcriptase activity. DNA binding, strand displacement activity, and nucleotide binding and recognition. A polymerase can be any enzyme that can catalyze polymerization of nucleotides (including analogs thereof) into a nucleic acid strand. Typically but not necessarily such nucleotide polymerization can occur in a template-dependent fashion. Typically, a polymerase comprises one or more active sites at which nucleotide binding and/or catalysis of nucleotide polymerization can occur. In some embodiments, a polymerase includes other enzymatic activities, such as for example, 3' to 5' exonuclease activity or 5' to 3' exonuclease activity. In some embodiments, a polymerase has strand displacing activity. A polymerase can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze nucleotide polymerization (e.g., catalytically active fragment). The polymerase includes catalytically inactive polymerases, catalytically active polymerases, reverse transcriptases, and other enzymes comprising a nucleotide binding domain. In some embodiments, a polymerase can be isolated from a cell, or generated using recombinant DNA technology or chemical synthesis methods. In some embodiments, a polymerase can be expressed in prokaryote, eukaryote, viral, or phage organisms. In some embodiments, a polymerase can be post-translationally modified proteins or fragments thereof. A polymerase can be derived from a prokaryote, eukaryote, virus or phage. A polymerase comprises DNA-directed DNA polymerase and RNA-directed DNA polymerase.

The term "strand displacing" refers to the ability of a polymerase to locally separate strands of double-stranded nucleic acids and synthesize a new strand in a template-based manner. Strand displacing polymerases displace a complementary strand from a template strand and catalyze new strand synthesis. Strand displacing polymerases include mesophilic and thermophilic polymerases. Strand displacing polymerases include wild type enzymes, and variants including exonuclease minus mutants, mutant versions, chimeric enzymes and truncated enzymes. Examples of strand displacing polymerases include phi29 DNA polymerase, large fragment of Bst DNA polymerase, large fragment of Bsu DNA polymerase (exo-), Bca DNA polymerase (exo-), Klenow fragment of *E. coli* DNA polymerase, T5 polymerase. M-MuLV reverse transcriptase, HIV viral reverse transcriptase, Deep Vent DNA polymerase and KOD DNA polymerase. The phi29 DNA polymerase can be wild type phi29 DNA polymerase (e.g., MagniPhi from Expedeon), or variant EquiPhi29 DNA polymerase (e.g., from Thermo Fisher Scientific), or chimeric QualiPhi DNA polymerase (e.g., from 4basebio).

As used herein, the term "DNA primase-polymerase" and related terms refers to enzymes having activities of a DNA polymerase and an RNA primase. A DNA primase-polymerase enzyme can utilize deoxyribonucleotide triphosphates to synthesize a DNA primer on a single-stranded DNA template in a template-sequence dependent manner, and can extend the primer strand via nucleotide polymerization (e.g., primer extension), in the presence of a catalytic divalent cation (e.g., magnesium and/or manganese). The DNA primase-polymerase include enzymes that are members of DnaG-like primases (e.g., bacteria) and AEP-like primases (Archaea and Eukaryotes). An exemplary DNA primase-polymerase enzyme is Tth PrimPol from *Thermus thermophilus* HB27.

As used herein, the term "fidelity" refers to the accuracy of DNA polymerization by template-dependent DNA polymerase. The fidelity of a DNA polymerase is typically measured by the error rate (the frequency of incorporating an inaccurate nucleotide, i.e., a nucleotide that is not complementary to the template nucleotide). The accuracy or fidelity of DNA polymerization is maintained by both the polymerase activity and the 3'-5' exonuclease activity of a DNA polymerase.

As used herein, the term "binding complex" refers to a complex formed by binding together a nucleic acid duplex, a polymerase, and a free nucleotide or a nucleotide unit of a multivalent molecule, where the nucleic acid duplex comprises a nucleic acid template molecule hybridized to a nucleic acid primer. In the binding complex, the free nucleotide or nucleotide unit may or may not be bound to the 3' end of the nucleic acid primer at a position that is opposite a complementary nucleotide in the nucleic acid template molecule. A "ternary complex" is an example of a binding complex which is formed by binding together a nucleic acid duplex, a polymerase, and a free nucleotide or nucleotide unit of a multivalent molecule, where the free nucleotide or nucleotide unit is bound to the 3' end of the nucleic acid primer (as part of the nucleic acid duplex) at a position that is opposite a complementary nucleotide in the nucleic acid template molecule.

The term "persistence time" and related terms refers to the length of time that a binding complex remains stable without dissociation of any of the components, where the components of the binding complex include a nucleic acid template and nucleic acid primer, a polymerase, a nucleotide unit of a multivalent molecule or a free (e.g., unconjugated) nucleotide. The nucleotide unit or the free nucleotide can be complementary or non-complementary to a nucleotide residue in the template molecule. The nucleotide unit or the free nucleotide can bind to the 3' end of the nucleic acid primer at a position that is opposite a complementary nucleotide residue in the nucleic acid template molecule. The persistence time is indicative of the stability of the binding complex and strength of the binding interactions. Persistence time can be measured by observing the onset and/or duration of a binding complex, such as by observing a signal from a labeled component of the binding complex. For example, a labeled nucleotide or a labeled reagent comprising one or more nucleotides may be present in a binding complex, thus allowing the signal from the label to be detected during the persistence time of the binding complex. One exemplary label is a fluorescent label. The binding complex (e.g., ternary complex) remains stable until subjected to a condition that causes dissociation of interactions between any of the polymerase, template molecule, primer and/or the nucleotide unit or the nucleotide. For example, a dissociating condition comprises contacting the binding complex with any one or any combination of a detergent. EDTA and/or water.

The term "primer" and related terms used herein refers to an oligonucleotide that is capable of hybridizing with a DNA and/or RNA polynucleotide template to form a duplex molecule. Primers comprise natural nucleotides and/or nucleotide analogs. Primers can be recombinant nucleic acid molecules. Primers may have any length, but typically range from 4-50 nucleotides. A typical primer comprises a 5' end and 3' end. The 3' end of the primer can include a 3' OH moiety which serves as a nucleotide polymerization initiation site in a polymerase-catalyzed primer extension reaction. Alternatively, the 3' end of the primer can lack a 3' OH moiety, or can include a terminal 3' blocking group that inhibits nucleotide polymerization in a polymerase-catalyzed reaction. Any one nucleotide, or more than one nucleotide, along the length of the primer can be labeled with a detectable reporter moiety. A primer can be in solution (e.g., a soluble primer) or can be immobilized to a support (e.g., a capture primer).

When used in reference to nucleic acid molecules, the terms "hybridize" or "hybridizing" or "hybridization" or other related terms refers to hydrogen bonding between two different nucleic acids to form a duplex nucleic acid. Hybridization also includes hydrogen bonding between two different regions of a single nucleic acid molecule to form a self-hybridizing molecule having a duplex region. Hybridization can comprise Watson-Crick or Hoogstein binding to form a duplex double-stranded nucleic acid, or a double-stranded region within a nucleic acid molecule. The double-stranded nucleic acid, or the two different regions of a single nucleic acid, may be wholly complementary, or partially complementary. Complementary nucleic acid strands need not hybridize with each other across their entire length. The complementary base pairing can be the standard A-T or C-G base pairing, or can be other forms of base-pairing interactions. Duplex nucleic acids can include mismatched base-paired nucleotides.

When used in reference to nucleic acids, the terms "extend", "extending", "extension" and other variants, refers to incorporation of one or more nucleotides into a nucleic acid molecule. Nucleotide incorporation comprises polymerization of one or more nucleotides into the terminal 3' OH end of a nucleic acid strand (e.g., a nucleic acid primer), resulting in extension of the nucleic acid strand (e.g., extended primer). Nucleotide incorporation can be conducted with natural nucleotides and/or nucleotide analogs. Typically, but not necessarily, nucleotide incorporation occurs in a template-dependent fashion. Any suitable method of extending a nucleic acid molecule may be used, including primer extension catalyzed by a DNA polymerase or RNA polymerase.

In some embodiments, any of the amplification primer sequences, sequencing primer sequences, capture primer sequences (capture oligonucleotides), target capture sequences, circularization anchor sequences, sample barcode sequences, spatial barcode sequences, or anchor region sequences can be about 3-50 nucleotides in length, or about 5-40 nucleotides in length, or about 5-25 nucleotides in length.

The term "nucleotides" and related terms refers to a molecule comprising an aromatic base, a five carbon sugar (e.g., ribose or deoxyribose), and at least one phosphate group. Canonical or non-canonical nucleotides are consistent with use of the term. The phosphate in some embodiments comprises a monophosphate, diphosphate, or triphosphate, or corresponding phosphate analog. The term "nucleoside" refers to a molecule comprising an aromatic base and a sugar. Nucleotides and nucleosides can be non-labeled or labeled with a detectable reporter moiety.

Nucleotides (and nucleosides) typically comprise a hetero cyclic base including substituted or unsubstituted nitrogen-containing parent heteroaromatic ring which are commonly found in nucleic acids, including naturally-occurring, substituted, modified, or engineered variants, or analogs of the same. The base of a nucleotide (or nucleoside) is capable of forming Watson-Crick and/or Hoogstein hydrogen bonds with an appropriate complementary base. Exemplary bases include, but are not limited to, purines and pyrimidines such as: 2-aminopurine, 2,6-diaminopurine, adenine (A), ethenoadenine, $N^6$-$\Delta^2$-isopentenyladenine (6iA), $N^6$-$\Delta^2$-isopentenyl-2-methylthioadenine (2ms6iA), $N^6$-methyladenine, guanine (G), isoguanine. $N^2$-dimethylguanine (dmG), 7-methylguanine (7mG), 2-thiopyrimidine, 6-thioguanine (6sG), hypoxanthine and $O^6$-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, $O^4$-methylthymine, uracil (U), 4-thiouracil (4sU) and 5,6-dihydrouracil (dihydrouracil; D); indoles such as nitroindole and 4-methylindole; pyrroles such as nitropyrrole; nebularine; inosines; hydroxymethylcytosines; 5-methycytosines; base (Y); as well as methylated, glycosylated, and acylated base moieties; and the like. Additional exemplary bases can be found in Fasman, 1989, in "Practical Handbook of Biochemistry and Molecular Biology", pp 385-394, CRC Press, Boca Raton, Fla.

Nucleotides (and nucleosides) typically comprise a sugar moiety, such as carbocyclic moiety (Ferraro and Gotor 2000 Chem. Rev. 100: 4319-48), acyclic moieties (Martinez, et al., 1999 Nucleic Acids Research 27: 1271-1274; Martinez, et al., 1997 Bioorganic & Medicinal Chemistry Letters vol. 7: 3013-3016), and other sugar moieties (Joeng, et al., 1993 J. Med. Chem. 36: 2627-2638; Kim, et al., 1993 J. Med. Chem. 36: 30-7; Eschenmosser 1999 Science 284:2118-2124; and U.S. Pat. No. 5,558,991). The sugar moiety comprises: ribosyl; 2'-deoxyribosyl; 3'-deoxyribosyl; 2',3'-dideoxyribosyl; 2',3'-didehydrodideoxyribosyl; 2'-alkoxyribosyl; 2'-azidoribosyl; 2'-aminoribosyl; 2'-fluororibosyl; 2'-mercaptoriboxyl; 2'-alkylthioribosvl; 3'-alkoxyribosyl, 3'-azidoribosyl; 3'-aminoribosyl; 3'-fluororibosyl; 3'-mercaptoriboxyl; 3'-alkylthioribosyl carbocyclic; acyclic or other modified sugars.

In some embodiments, nucleotides comprise a chain of one, two or three phosphorus atoms where the chain is typically attached to the 5' carbon of the sugar moiety via an ester or phosphoramide linkage. In some embodiments, the nucleotide is an analog having a phosphorus chain in which the phosphorus atoms are linked together with intervening O. S. NH, methylene or ethylene. In some embodiments, the phosphorus atoms in the chain include substituted side groups including O, S or $BH_3$. In some embodiments, the chain includes phosphate groups substituted with analogs including phosphoramidate, phosphorothioate, phosphordithioate, and O-methylphosphoroamidite groups.

The term "reporter moiety", "reporter moieties" or related terms refers to a compound that generates, or causes to generate, a detectable signal. A reporter moiety is sometimes called a "label". Any suitable reporter moiety may be used, including luminescent, photoluminescent, electroluminescent, bioluminescent, chemiluminescent, fluorescent, phosphorescent, chromophore, radioisotope, electrochemical, mass spectrometry, Raman, hapten, affinity tag, atom, or an enzyme. A reporter moiety generates a detectable signal resulting from a chemical or physical change (e.g., heat, light, electrical, pH, salt concentration, enzymatic activity, or proximity events). A proximity event includes two reporter moieties approaching each other, or associating with each other, or binding each other. It is well known to one skilled in the art to select reporter moieties so that each absorbs excitation radiation and/or emits fluorescence at a wavelength distinguishable from the other reporter moieties to permit monitoring the presence of different reporter moieties in the same reaction or in different reactions. Two or more different reporter moieties can be selected having spectrally distinct emission profiles, or having minimal overlapping spectral emission profiles. Reporter moieties can be linked (e.g., operably linked) to nucleotides, nucleosides, nucleic acids, enzymes (e.g., polymerases or reverse transcriptases), or support (e.g., surfaces).

A reporter moiety (or label) comprises a fluorescent label or a fluorophore. Exemplary fluorescent moieties which may serve as fluorescent labels or fluorophores include, but are not limited to fluorescein and fluorescein derivatives such as carboxyfluorescein, tetrachlorofluorescein, hexachlorofluorescein, carboxynapthofluorescein, fluorescein isothiocyanate, NHS-fluorescein, iodoacetamidofluorescein, fluorescein maleimide, SAMSA-fluorescein, fluorescein thiosemicarbazide, carbohydrazinomethylthioacetyl-amino fluorescein, rhodamine and rhodamine derivatives such as TRITC, TMR, lissamine rhodamine, Texas Red, rhodamine B, rhodamine 6G, rhodamine 10. NHS-rhodamine, TMR-iodoacetamide, lissamine rhodamine B sulfonyl chloride, lissamine rhodamine B sulfonyl hydrazine. Texas Red sulfonyl chloride. Texas Red hydrazide, coumarin and coumarin derivatives such as AMCA, AMCA-NHS, AMCA-sulfo-NHS, AMCA-HPDP, DCIA, AMCE-hydrazide, BODIPY and derivatives such as BODIPY FL C3-SE, BODIPY 530/550 C3, BODIPY 530/550 C3-SE, BODIPY 530/550

C3 hydrazide, BODIPY 493/503 C3 hydrazide, BODIPY FL C3 hydrazide, BODIPY FL IA, BODIPY 530/551 IA, Br-BODIPY 493/503. Cascade Blue and derivatives such as Cascade Blue acetyl azide. Cascade Blue cadaverine, Cascade Blue ethylenediamine, Cascade Blue hydrazide, Lucifer Yellow and derivatives such as Lucifer Yellow iodoacetamide, Lucifer Yellow CH, cyanine and derivatives such as indolium based cyanine dyes, benzo-indolium based cyanine dyes, pyridium based cyanine dyes, thiozolium based cyanine dyes, quinolinium based cyanine dyes, imidazolium based cyanine dyes, Cy 3, Cy5, Ianthanide chelates and derivatives such as BCPDA, TBP, TMT, BHHCT, BCOT, Europium chelates, Terbium chelates, Alexa Fluor dyes, DyLight dyes, Atto dyes, LightCycler Red dyes, CAL Flour dyes, JOE and derivatives thereof, Oregon Green dyes, WellRED dyes, IRD dyes, phycoerythrin and phycobilin dyes, Malachite green, stilbene, DEG dyes, NR dyes, near-infrared dyes and others known in the art such as those described in Haugland, Molecular Probes Handbook, (Eugene, Oreg.) 6th Edition; Lakowicz, Principles of Fluorescence Spectroscopy, 2nd Ed., Plenum Press New York (1999), or Hermanson, Bioconjugate Techniques, 2nd Edition, or derivatives thereof, or any combination thereof. Cyanine dyes may exist in either sulfonated or non-sulfonated forms, and consist of two indolenin, benzo-indolium, pyridium, thiozolium, and/or quinolinium groups separated by a polymethine bridge between two nitrogen atoms. Commercially available cyanine fluorophores include, for example. Cy3, (which may comprise 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-1,3-dihydro-2H-indol-2-ylidene}prop-1-en-1-yl)-3,3-dimethyl-3H-indolium or 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-5-sulfo-1,3-dihydro-2H-indol-2-ylidene}prop-1-en-1-yl)-3,3-dimethyl-3H-indolium-5-sulfonate), Cy5 (which may comprise 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-indolin-2-ylidene)penta-1,3-dien-1-yl)-3,3-dimethyl-3H-indol-1-ium or 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-sulfoindolin-2-ylidene)penta-1,3-dien-1-yl)-3,3-dimethyl-3H-indol-1-ium-5-sulfonate), and Cy7 (which may comprise 1-(5-carboxypentyl)-2-[(1E,3E,5E,7Z)-7-(1-ethyl-1,3-dihydro-2H-indol-2-ylidene)hepta-1,3,5-trien-1-yl]-3H-indolium or 1-(5-carboxypentyl)-2-[(1E,3E,5E,7Z)-7-(1-ethyl-5-sulfo-1,3-dihydro-2H-indol-2-ylidene)hepta-1,3,5-trien-1-yl]-3H-indolium-5-sulfonate), where "Cy" stands for 'cyanine', and the first digit identifies the number of carbon atoms between two indolenine groups. Cy2 which is an oxazole derivative rather than indolenin, and the benzo-derivatized Cy3.5, Cy5.5 and Cy7.5 are exceptions to this rule.

In some embodiments, the reporter moiety can be a FRET pair, such that multiple classifications can be performed under a single excitation and imaging step. As used herein, FRET may comprise excitation exchange (Forster) transfers, or electron-exchange (Dexter) transfers.

The term "support" as used herein refers to a substrate that is designed for deposition of biological molecules or biological samples for assays and/or analyses. Examples of biological molecules to be deposited onto a support include nucleic acids (e.g., DNA, RNA), polypeptides, saccharides, lipids, a single cell or multiple cells. Examples of biological samples include but are not limited to saliva, phlegm, mucus, blood, plasma serum, urine, stool, sweat, tears and fluids from tissues or organs.

In some embodiments, the support is solid, semi-solid, or a combination of both. In some embodiments, the support is porous, semi-porous, non-porous, or any combination of porosity. In some embodiments, the support can be substantially planar, concave, convex, or any combination thereof. In some embodiments, the support can be cylindrical, for example comprising a capillary or interior surface of a capillary.

In some embodiments, the surface of the support can be substantially smooth. In some embodiments, the support can be regularly or irregularly textured, including bumps, etched, pores, three-dimensional scaffolds, or any combination thereof.

In some embodiments, the support comprises a bead having any shape, including spherical, hemi-spherical, cylindrical, barrel-shaped, toroidal, disc-shaped, rod-like, conical, triangular, cubical, polygonal, tubular or wire-like.

The support can be fabricated from any material, including but not limited to glass, fused-silica, silicon, a polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET)), or any combination thereof. Various compositions of both glass and plastic substrates are contemplated.

The support can have a plurality (e.g., two or more) of nucleic acid templates immobilized thereon. The plurality of immobilized nucleic acid templates have the same sequence or have different sequences. In some embodiments, individual nucleic acid template molecules in the plurality of nucleic acid templates are immobilized to a different site on the support. In some embodiments, two or more individual nucleic acid template molecules in the plurality of nucleic acid templates are immobilized to a site on the support.

The term "array" refers to a support comprising a plurality of sites located at pre-determined locations on the support to form an array of sites. The sites can be discrete and separated by interstitial regions. In some embodiments, the pre-determined sites on the support can be arranged in one dimension in a row or a column, or arranged in two dimensions in rows and columns. In some embodiments, the plurality of pre-determined sites is arranged on the support in an organized fashion. In some embodiments, the plurality of pre-determined sites is arranged in any organized pattern, including rectilinear, hexagonal patterns, grid patterns, patterns having reflective symmetry, patterns having rotational symmetry, or the like. The pitch between different pairs of sites can be that same or can vary. In some embodiments, the support comprises at least $10^2$ sites, at least $10^3$ sites, at least $10^4$ sites, at least $10^5$ sites, at least $10^6$ sites, at least $10^7$ sites, at least $10^8$ sites, at least $10^9$ sites, at least $10^{10}$ sites, at least $10^{11}$ sites, at least $10^{12}$ sites, at least $10^{13}$ sites, at least $10^{14}$ sites, at least $10^{15}$ sites, or more, where the sites are located at pre-determined locations on the support. In some embodiments, a plurality of pre-determined sites on the support (e.g., $10^2$-$10^{15}$ sites or more) are immobilized with nucleic acid templates to form a nucleic acid template array. In some embodiments, the nucleic acid templates that are immobilized at a plurality of pre-determined sites by hybridization to immobilized surface capture primers, or the nucleic acid templates are covalently attached to the surface capture primer. In some embodiments, the nucleic acid templates that are immobilized at a plurality of pre-determined sites, for example immobilized at $10^2$-$10^{15}$ sites or more. In some embodiments, the immobilized nucleic acid templates are clonally-amplified to generate immobilized nucleic acid polonies at the plurality of pre-determined sites. In some embodiments, individual immobilized nucleic acid polonies comprise single-stranded or double-stranded concatemers.

In some embodiments, a support comprising a plurality of sites located at random locations on the support is referred to herein as a support having randomly located sites thereon. The location of the randomly located sites on the support are not pre-determined. The plurality of randomly-located sites is arranged on the support in a disordered and/or unpredictable fashion. In some embodiments, the support comprises at least $10^2$ sites, at least $10^3$ sites, at least $10^4$ sites, at least $10^5$ sites, at least $10^6$ sites, at least $10^7$ sites, at least $10^8$ sites, at least $10^9$ sites, at least $10^{10}$ sites, at least $10^{11}$ sites, at least $10^{12}$ sites, at least $10^{13}$ sites, at least $10^{14}$ sites, at least $10^{15}$ sites, or more, where the sites are randomly located on the support. In some embodiments, a plurality of randomly located sites on the support (e.g., $10^2$-$10^{15}$ sites or more) are immobilized with nucleic acid templates to form a support immobilized with nucleic acid templates. In some embodiments, the nucleic acid templates that are immobilized at a plurality of randomly located sites by hybridization to immobilized surface capture primers, or the nucleic acid templates are covalently attached to the surface capture primer. In some embodiments, the nucleic acid templates that are immobilized at a plurality of randomly located sites, for example immobilized at $10^2$-$10^{15}$ sites or more. In some embodiments, the immobilized nucleic acid templates are clonally-amplified to generate immobilized nucleic acid polonies at the plurality of randomly located sites. In some embodiments, individual immobilized nucleic acid polonies comprise single-stranded or double-stranded concatemers.

When used in reference to a low binding surface coating, one or more layers of a multi-layered surface coating may comprise a branched polymer or may be linear. Examples of suitable branched polymers include, but are not limited to, branched PEG, branched poly(vinyl alcohol) (branched PVA), branched poly(vinyl pyridine), branched poly(vinyl pyrrolidone) (branched PVP), branched), poly(acrylic acid) (branched PAA), branched polyacrylamide, branched poly (N-isopropylacrylamide) (branched PNIPAM), branched poly(methyl methacrylate) (branched PMA), branched poly (2-hydroxylethyl methacrylate) (branched PHEMA), branched poly(oligo(ethylene glycol) methyl ether methacrylate) (branched POEGMA), branched polyglutamic acid (branched PGA), branched poly-lysine, branched poly-glucoside, and dextran.

In some embodiments, the branched polymers used to create one or more layers of any of the multi-layered surfaces disclosed herein may comprise at least 4 branches, at least 5 branches, at least 6 branches, at least 7 branches, at least 8 branches, at least 9 branches, at least 10 branches, at least 12 branches, at least 14 branches, at least 16 branches, at least 18 branches, at least 20 branches, at least 22 branches, at least 24 branches, at least 26 branches, at least 28 branches, at least 30 branches, at least 32 branches, at least 34 branches, at least 36 branches, at least 38 branches, or at least 40 branched.

Linear, branched, or multi-branched polymers used to create one or more layers of any of the multi-layered surfaces disclosed herein may have a molecular weight of at least 500, at least 1,000, at least 2,000, at least 3,000, at least 4,000, at least 5,000, at least 10,000, at least 15.000, at least 20.000, at least 25,000, at least 30,000, at least 35,000, at least 40,000, at least 45,000, or at least 50,000 daltons.

In some embodiments, e.g., wherein at least one layer of a multi-layered surface comprises a branched polymer, the number of covalent bonds between a branched polymer molecule of the layer being deposited and molecules of the previous layer may range from about one covalent linkage per molecule and about 32 covalent linkages per molecule. In some embodiments, the number of covalent bonds between a branched polymer molecule of the new layer and molecules of the previous layer may be at least 1, at least 2, at least 3, at least 4, at least 5, at least 6, at least 7, at least 8, at least 9, at least 10, at least 12, at least 14, at least 16, at least 18, at least 20, at least 22, at least 24, at least 26, at least 28, at least 30, or at least 32 covalent linkages per molecule.

Any reactive functional groups that remain following the coupling of a material layer to the surface may optionally be blocked by coupling a small, inert molecule using a high yield coupling chemistry. For example, in the case that amine coupling chemistry is used to attach a new material layer to the previous one, any residual amine groups may subsequently be acetylated or deactivated by coupling with a small amino acid such as glycine.

The number of layers of low non-specific binding material, e.g., a hydrophilic polymer material, deposited on the surface, may range from 1 to about 10. In some embodiments, the number of layers is at least 1, at least 2, at least 3, at least 4, at least 5, at least 6, at least 7, at least 8, at least 9, or at least 10. In some embodiments, the number of layers may be at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some embodiments the number of layers may range from about 2 to about 4. In some embodiments, all of the layers may comprise the same material. In some embodiments, each layer may comprise a different material. In some embodiments, the plurality of layers may comprise a plurality of materials. In some embodiments at least one layer may comprise a branched polymer. In some embodiment, all of the layers may comprise a branched polymer.

One or more layers of low non-specific binding material may in some cases be deposited on and/or conjugated to the substrate surface using a polar protic solvent, a polar or polar aprotic solvent, a nonpolar solvent, or any combination thereof. In some embodiments the solvent used for layer deposition and/or coupling may comprise an alcohol (e.g., methanol, ethanol, propanol, etc.), another organic solvent (e.g., acetonitrile, dimethyl sulfoxide (DMSO), dimethyl formamide (DMF), etc.), water, an aqueous buffer solution (e.g., phosphate buffer, phosphate buffered saline, 3-(N-morpholino)propanesulfonic acid (MOPS), etc.), or any combination thereof. In some embodiments, an organic component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, with the balance made up of water or an aqueous buffer solution. In some embodiments, an aqueous component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, with the balance made up of an organic solvent. The pH of the solvent mixture used may be less than 6, about 6, 6.5, 7, 7.5, 8, 8.5, 9, or greater than pH 9.

The term "branched polymer" and related terms refers to a polymer having a plurality of functional groups that help conjugate a biologically active molecule such as a nucleotide, and the functional group can be either on the side chain of the polymer or directly attaches to a central core or central backbone of the polymer. The branched polymer can have linear backbone with one or more functional groups coming off the backbone for conjugation. The branched polymer can also be a polymer having one or more sidechains, wherein the side chain has a site suitable for conjugation. Examples of the functional group include but are limited to hydroxyl, ester, amine, carbonate, acetal, aldehyde, aldehyde hydrate, alkenyl, acrylate, methacrylate, acrylamide, active sulfone, hydrazide, thiol, alkanoic acid, acid halide, isocyanate, isothiocyanate, maleimide, vinylsulfone, dithiopyridine, vinylpyridine, iodoacetamide, epoxide, glyoxal, dione, mesylate, tosylate, and tresylate.

When used in reference to immobilized nucleic acids, the term "immobilized" and related terms refer to nucleic acid molecules that are attached to a support through covalent bond or non-covalent interaction, or attached to a coating on the support, or buried within a matrix formed by a coating on the support, where the nucleic acid molecules include surface capture primers, nucleic acid template molecules and extension products of capture primers. Extension products of capture primers includes nucleic acid concatemers that can form nucleic acid polonies.

In some embodiments, one or more nucleic acid templates are immobilized on the support, for example immobilized at the sites on the support. In some embodiments, the one or more nucleic acid templates are clonally-amplified. In some embodiments, the one or more nucleic acid templates are clonally-amplified off the support (e.g., in-solution) and then deposited onto the support and immobilized on the support. In some embodiments, the clonal amplification reaction of the one or more nucleic acid templates is conducted on the support resulting in immobilization on the support. In some embodiments, the one or more nucleic acid templates are clonally-amplified (e.g., in solution or on the support) using a nucleic acid amplification reaction, including any one or any combination of: polymerase chain reaction (PCR), multiple displacement amplification (MDA), transcription-mediated amplification (TMA), nucleic acid sequence-based amplification (NASBA), strand displacement amplification (SDA), real-time SDA, bridge amplification, isothermal bridge amplification, rolling circle amplification (RCA), circle-to-circle amplification, helicase-dependent amplification, recombinase-dependent amplification, and/or single-stranded binding (SSB) protein-dependent amplification.

The term "surface primer", "surface capture primer" and related terms refers to single-stranded oligonucleotides that are immobilized to a support and comprise a sequence that can hybridize to at least a portion of a nucleic acid template molecule. Surface primers can be used to immobilize template molecules to a support via hybridization. Surface primers can be immobilized to a support in a manner that resists primer removal during flowing, washing, aspirating, and changes in temperature. pH, salts, chemical and/or enzymatic conditions. Typically, but not necessarily, the 5' end of a surface primer can be immobilized to a support. Alternatively, an interior portion or the 3' end of a surface primer can be immobilized to a support.

The surface primers comprise DNA, RNA, or analogs thereof. The surface primers can include a combination of DNA and RNA. The sequence of surface primers can be wholly complementary or partially complementary along their length to at least a portion of the nucleic acid template molecule (e.g., linear or circular template molecules). A support can include a plurality of immobilized surface primers having the same sequence, or having two or more different sequences. Surface primers can be any length, for example 4-50 nucleotides, or 50-100 nucleotides, or 100-150 nucleotides, or longer lengths.

A surface primer can include a terminal 3' nucleotide having a sugar 3' OH moiety which is extendible for nucleotide polymerization (e.g., polymerase catalyzed polymerization). A surface primer can include a terminal 3' nucleotide having a moiety that blocks polymerase-catalyzed extension. A surface primer can include a terminal 3' nucleotide having the 3' sugar position linked to a chain-terminating moiety that inhibits nucleotide polymerization. The 3" chain-terminating moiety can be removed (e.g., de-blocked) to convert the 3' end to an extendible 3' OH end using a de-blocking agent. Examples of chain terminating moieties include alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group. Azide type chain terminating moieties including azide, azido and azidomethyl groups. Examples of de-blocking agents include a phosphine compound, such as Tris(2-carboxyethyl)phosphine (TCEP) and bis-sulfo triphenyl phosphine (BS-TPP), for chain-terminating groups azide, azido and azidomethyl groups. Examples of de-blocking agents include tetrakis(triphenylphosphine) palladium(0) ($Pd(PPh_3)_4$) with piperidine, or with 2,3-Dichloro-5,6-dicyano-1,4-benzo-quinone (DDQ), for chain-terminating groups alkyl, alkenyl, alkynyl and allyl. Examples of a de-blocking agent includes Pd/C for chain-terminating groups aryl and benzyl. Examples of de-blocking agents include phosphine, beta-mercaptoethanol or dithiothritol (DTT), for chain-terminating groups amine, amide, keto, isocyanate, phosphate, thio and disulfide. Examples of de-blocking agents include potassium carbonate ($K_2CO_3$) in MeOH, triethylamine in pyridine, and Zn in acetic acid (AcOH), for carbonate chain-terminating groups. Examples of de-blocking agents include tetrabutylammonium fluoride, pyridine-HF, with ammonium fluoride, and triethylamine trihydrofluoride, for chain-terminating groups urea and silyl.

In some embodiment, the plurality of immobilized surface capture primers on the support are in fluid communication with each other to permit flowing a solution of reagents (e.g., linear or circular nucleic acid template molecules, soluble primers, enzymes, nucleotides, divalent cations, buffers, reagents and the like) onto the support so that the plurality of immobilized surface capture primers on the support can be essentially simultaneously reacted with the reagents in a massively parallel manner. In some embodiments, the fluid communication of the plurality of immobilized surface capture primers can be used to conduct nucleic acid amplification reactions (e.g., RCA. MDA, PCR and bridge amplification) essentially simultaneously on the plurality of immobilized surface capture primers.

In some embodiment, the plurality of immobilized single stranded nucleic acid concatemer template molecules on the support are in fluid communication with each other to permit flowing a solution of reagents (e.g., soluble primers, enzymes, nucleotides, divalent cations, buffers, reagents and the like) onto the support so that the plurality of immobilized concatemer template molecules on the support can be essentially simultaneously reacted with the reagents in a massively parallel manner. In some embodiments, the fluid communication of the plurality of immobilized single stranded nucleic acid concatemer template molecules can be used to conduct nucleotide binding assays and/or conduct nucleotide polymerization reactions (e.g., primer extension or sequencing) essentially simultaneously on the plurality of immobilized single stranded nucleic acid concatemer template molecules, and optionally to conduct detection and imaging for massively parallel sequencing.

When used in reference to nucleic acids, the terms “amplify”, “amplifying”, “amplification”, and other related terms include producing multiple copies of an original polynucleotide template molecule, where the copies comprise a sequence that is complementary to the template sequence, or the copies comprise a sequence that is the same as the template sequence. In some embodiments, the copies comprise a sequence that is substantially identical to a template sequence, or is substantially identical to a sequence that is complementary to the template sequence.

The present disclosure provides various pH buffering agents. The full name of the pH buffering agents is listed herein.

The term “Tris” refers to a pH buffering agent Tris (hydroxymethyl)-aminomethane. The term “Tris-HCl” refers to a pH buffering agent Tris(hydroxymethyl)-aminomethane hydrochloride. The term “Tricine” refers to buffering agent N-[tris(hydroxymethyl)methyl]glycine. The term “Bicine” refers to a pH buffering agent N,N-bis(2-hydroxyethyl)glycine. The term “Bis-Tris propane” refers to a pH buffering agent 1,3 Bis[tris(hydroxymethyl)methylamino]propane. The term “HEPES” refers to a pH buffering agent 4-(2-hydroxyethyl)-1-piperazineethanesulfonic acid. The term “MES” refers to a pH buffering agent 2-(N-morpholino)ethanesulfonic acid). The term “MOPS” refers to a pH buffering agent 3-(N-morpholino)propanesulfonic acid. The term “MOPSO” refers to a pH buffering agent 3-(N-morpholino)-2-hydroxypropanesulfonic acid. The term “BES” refers to a pH buffering agent N. N-bis(2-hydroxyethyl)-2-aminoethanesulfonic acid. The term “TES” refers to a pH buffering agent 2-[(2-Hydroxy-1,1bis(hydroxymethyl)ethyl)amino]ethanesulfonic acid). The term “CAPS” refers to a pH buffering agent 3-(cyclohexylamino)-1-propanesulfonic acid. The term “TAPS” refers to a pH buffering agent N-[Tris(hydroxymethyl)methyl]-3-amino propane sulfonic acid. The term “TAPSO” refers to a pH buffering agent N-[Tris(hydroxymethyl)methyl]-3-amino-2-hydroxypropansulfonic acid. The term “ACES” refers to a pH buffering agent N-(2-Acetamido)-2-aminoethanesulfonic acid. The term “PIPES” refers to a pH buffering agent piperazine-1,4-bis(2-ethanesulfonic acid.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Unless otherwise specified, the values reported here are approximate values subject to normal instrumental and experimental variation.

Example 1. Synthesis of Exemplary Compounds

Exemplary compounds of the present disclosure, e.g., compounds 85-88, may be synthesized according to methods described below, e.g., in Schemes 1A-1D.

Scheme 1A

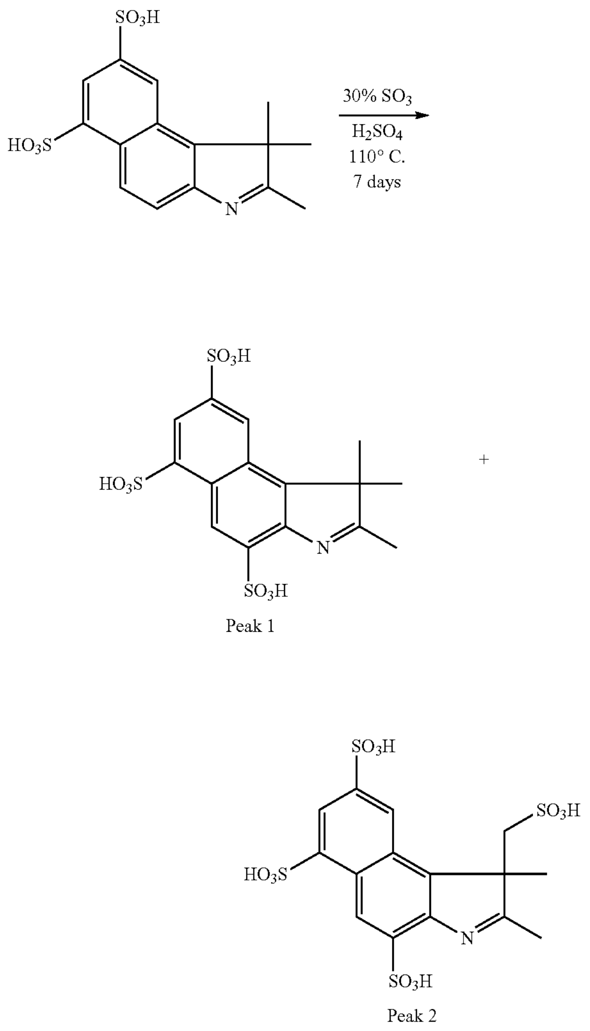

Scheme 1B

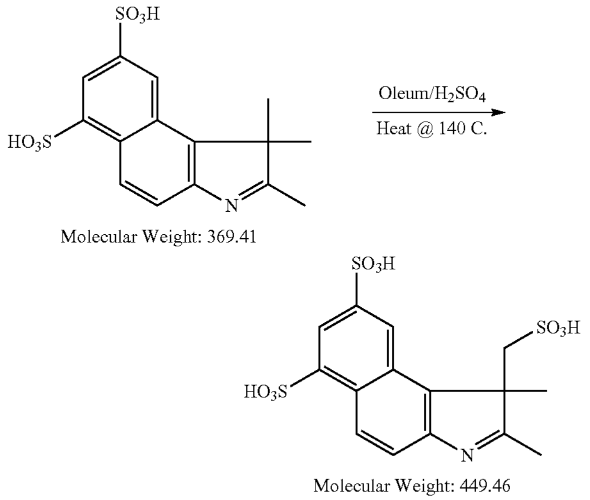

Scheme 1C.
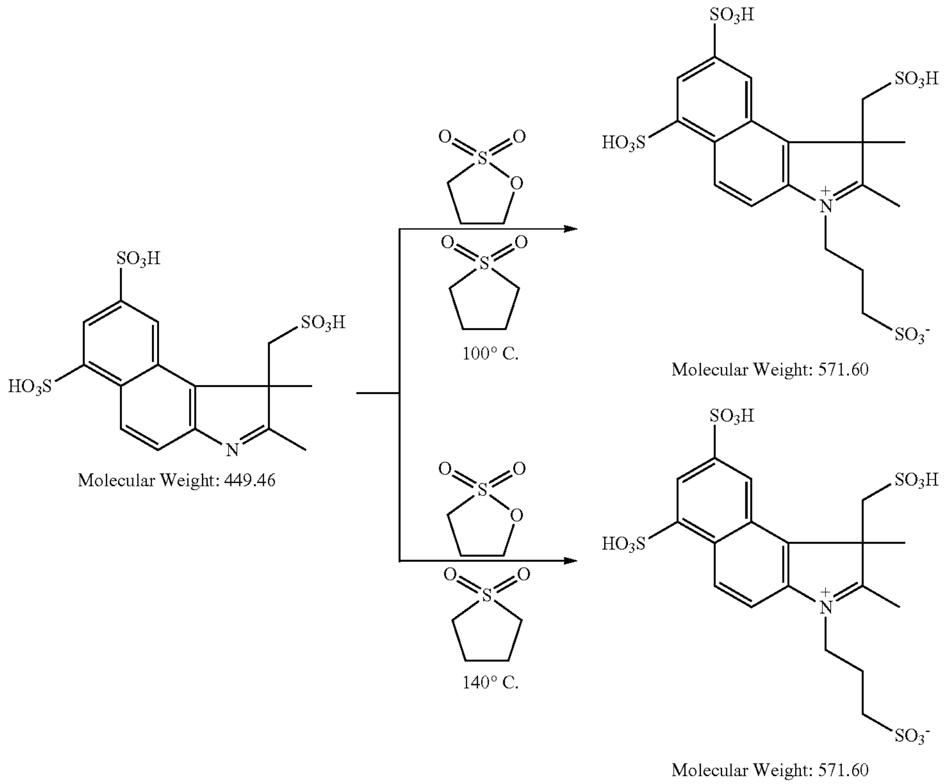

Scheme 1D
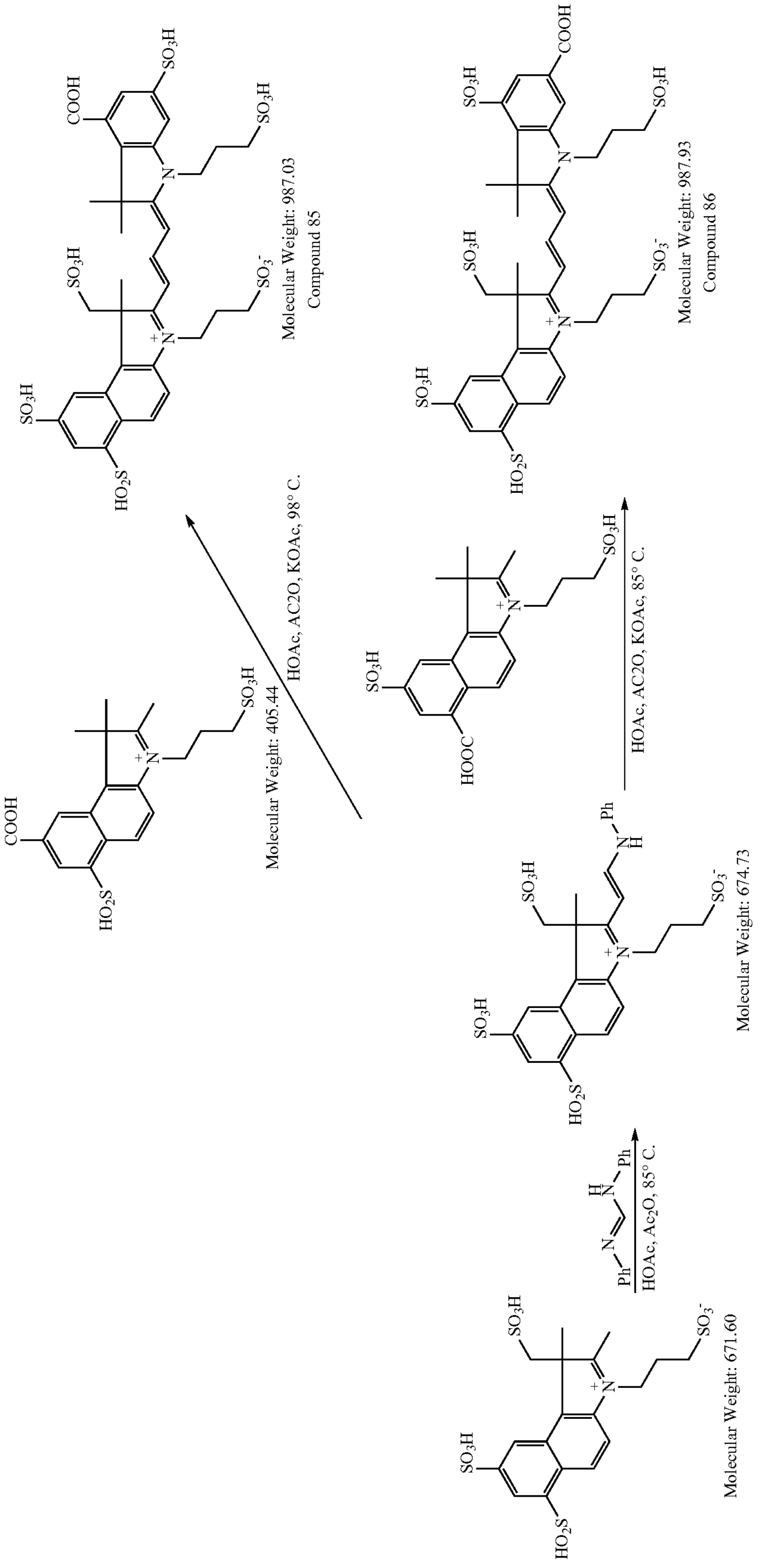

-continued
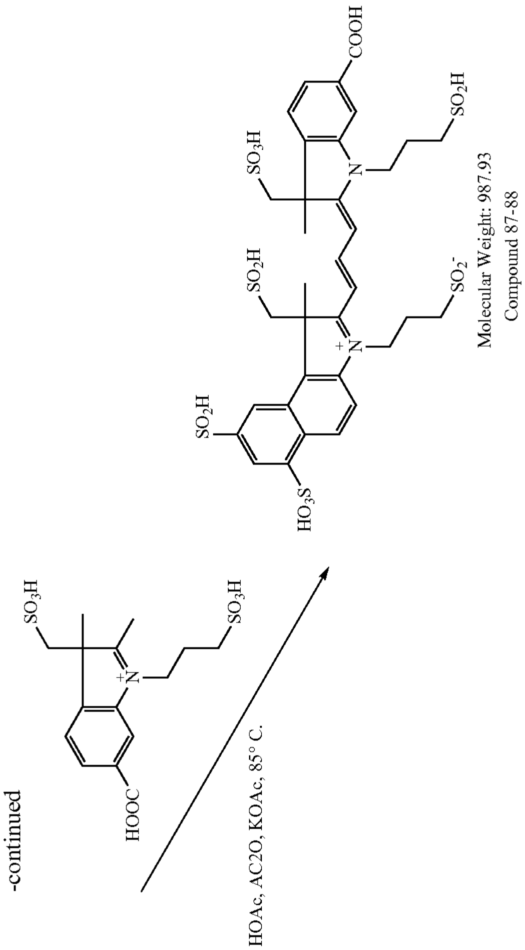
Molecular Weight: 987.93
Compound 87-88

Example 2. Properties of Exemplary Compounds

The compounds disclosed herein are useful as dye molecules. Absorption and emission data for representative compounds of the disclosure are reported below in Table 3. Laser condition 1 refers to a laser at 638±7 nm and an emission range of 719.5±32.5 nm. Laser condition 2 refers to a laser at 638±7 nm and an emission range of 674±17 nm. Laser condition 3 refers to a laser at 520±7 nm and an emission range of 595.5±24.5 nm. Laser condition 4 refers to a laser at 520±7 nm and an emission range of 555±20 nm.

TABLE 3

| Compound # | Abs/Em λ in aqueous (nm) | Abs/Em λ in MeOH (nm) | A280/Amax (CF) in 1x PBS | A280/Amax (CF) in MeOH | Laser Condition |
|---|---|---|---|---|---|
| 51 | 675/694 | 681/701 | 0.10 | 0.10 | 1 |
| 9 | 678/696 | 684/705 | 0.10 | 0.09 | 1 |
| 52 | 673/692 | 678/701 | 0.09 | 0.10 | 1 |
| 1 | 678/696 (in-house Ex/Em: 677/696) | 682/702 (in-house Ex/Em: 681/702) | 0.11 | 0.10 | 1 |
| 11 | 684/702 | 685/706 | 0.07 | 0.08 | 1 |
| 22 | 683/703 | 684/707 | 0.07 | 0.09 | 1 |
| 12 | 688/705 | 687/708 | 0.12 | 0.14 | 1 |
| 12 | 688/706 | 686/708 | 0.07 | 0.08 | 1 |
| 56 | 680/701 | 682.5/707 | 0.11 | 0.1 | 1 |
| 57 | 683.5/702 | 684/705 | 0.23 | 0.23 | 1 |
| 57a | 683.5/703 | 685/708 | 0.11 | 0.11 | 3 |
| 59 | 686/705 | 686.5/711 | 0.09 | 0.0 | 1 |
| 60 | 681.5/701 | 683/705 | 0.1 | 0.09 | 1 |
| 61 | 688.5/706 | 687/711 | 0.07 | ? | 3 |
| 62 | 683.5/704 | 683/707 | 0.09 | 0.09 | 1 |
| 63 | 684.5/702 | 684/709 | 0.09 | 0.1 | 1 |
| 64 | 665/684 | 666/688 | | | 1 |
| 65 | 670/689 | 671/693 | | | 1 |
| 2 | 645/666 recent meas: 645/664 (in-house Ex/Em: 639/664) | 645/663 (in-house Ex/Em: 639/666) | 0.02 | 0.02 | 2 |
| 66 | 645/659 | 640/660 | 0.03 | 0.02 | 2 |
| 67 | 639/657 | 641.5/663 | 0.02 | 0.02 | 2 |
| 69 | 645/663 | 645/665 | 0.07 | 0.06 | 2 |
| 70 | 641/665 | 641/667 | | | 2 |
| 114 | 649/671 | 649/672 | | | 2 |
| 71 | 643/668 | 643/671 | | | 2 |
| 72 | 649/673 | 653/677 | | | 2 |
| 73 | 637/660 | 639/665 | | | 2 |
| 36 | 637/659 | 639/664 | | | 2 |
| 74 | 637/660 | 639/665 | | | 2 |
| 16 | 582/596 | 588/604 | 0.23 | 0.22 | 3 |
| 3 | 564/580 (in-house Ex/Em: 562/580) | 570/600 (in-house Ex/Em: 568/586) | 0.17 | 0.17 | 3 |
| 24 | 562/580 | 567/587 | 0.20 | 0.20 | 3 |
| 75 | 570.5/588 | 573/593 | 0.16 | 0.18 | 3 |
| 76 | 570/587 | 573/593 | 0.11 | 0.12 | 3 |
| 77 | 568.5/580 | 566/586 | 0.12 | 0.13 | 3 |
| 78 | 569/579 | 567/585 | 0.16 | 0.13 | 3 |
| 80 | 587.5/602 | 592/610 | 0.22 Due to impurities at low wavelength, use 0.15 for caculation | 0.21 Due to impurities at low wavelength, use 0.15 for caculation | 3 |
| 81 | 587.5/601.5 | 591.5/609 | 0.26 Due to impurities at low wavelength, use 0.15 for caculation | 0.26 Due to impurities at low wavelength, use 0.15 for caculation | 3 |
| 83 | 565/582 | 571/590 | | | 3 |
| 84 | 571/589 | 575/595 | | | 3 |
| 85 | 568/585 | 570.5/591 | 0.12 | 0.12 | 3 |
| 86 | 565.5/583 | 567/590 | 0.12 | 0.13 | 3 |
| 87 | 574.5/590 | 574/594 | 0.2 Due to impurities at low wavelength, use 0.15 for caculation | 0.19 Due to impurities at low wavelength, use 0.15 for caculation | 3 |
| 88 | 575.5/591 | 576/596 | 0.14 | 0.14 | 3 |
| 89 | 564/580 | 569/587 | 0.11 | 0.12 | 3 |

TABLE 3-continued

| Compound # | Abs/Em λ in aqueous (nm) | Abs/Em λ in MeOH (nm) | A280/Amax (CF) in 1x PBS | A280/Amax (CF) in MeOH | Laser Condition |
|---|---|---|---|---|---|
| 90 | 577/597 | 580/600 | | | 3 |
| 91 | 560/578 | 565/585 | | | 3 |
| 92 | 567/586 | 571/592 | | | 3 |
| 93 | 566/586 | 571/592 | | | 3 |
| 94 | 566.6/ | | | | 3 |
| 4 | 546/561 | 548/563 | 0.09 | 0.07 | 4 |
| 95 | 542/556 (in-house Ex/Em: 540/556) | 545/562 (in-house Ex/Em: 542/561) | 0.06 | 0.06 | 4 |
| 96 | 544/559 | 545/561 | 0.15 | 0.15 | 4 |
| 97 | 544/NA | 546/NA | 0.07 | 0.10 | 4 |
| 98 | 545/NA | 547/NA | 0.14 | 0.13 | 4 |
| 99 | 540/555 | 544/560 | 0.05 | 0.06 | 4 |
| 100 | 542.5/558 | 543.5/561 | 0.1 | 0.09 | 4 |
| 102 | 546/564 | 550/568 | | | 4 |
| 103 | 554/570 | 557/574 | 0.07 | | 4 |
| 104 | 548/565 | 554/571 | | | 4 |
| 105 | 554/571 | 557/575 | | | 4 |
| 106 | 542/560 | 546/564 | | | 4 |
| 46 | 540/557 | 545/561 | | | 4 |
| 107 | 542/557 | 545/562 | | | 4 |
| 108 | 549/564 | 552/569 | | | 4 |
| 109 | 494/509 | 496.5/511 | 0.04 | 0.05 | |
| 110 | 486/502 | 488/505 | 0.04 | 0.05 | |
| 111 | 486.5/502 | 488.5/505 | 0.06 | 0.06 | |
| 112 | 486/502 | 488/505 | 0.05 | 0.04 | |
| 113 | 489/505 | 490/507 | 0.07 | 0.06 | |

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:

1. A compound, wherein the compound is

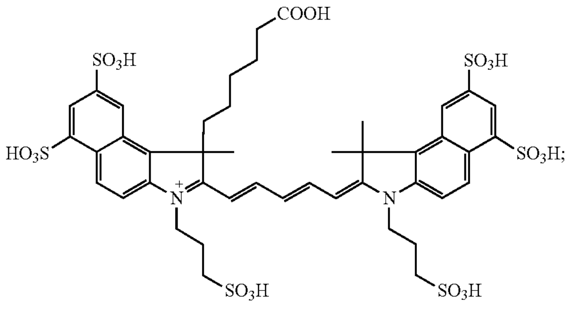

-continued

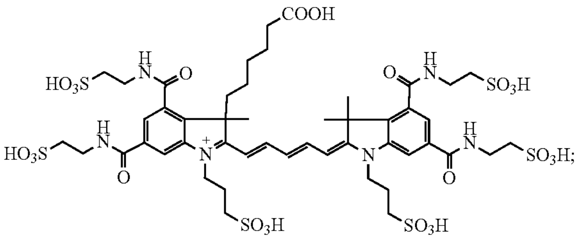

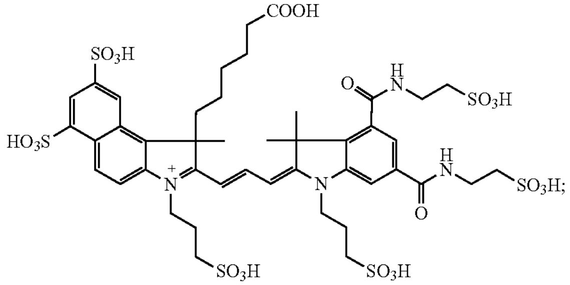

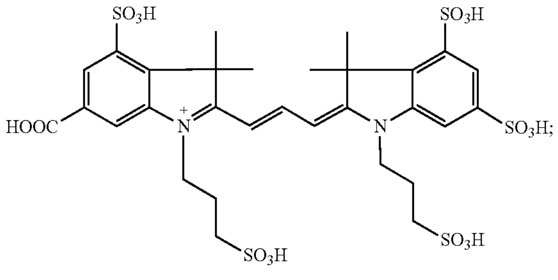

-continued
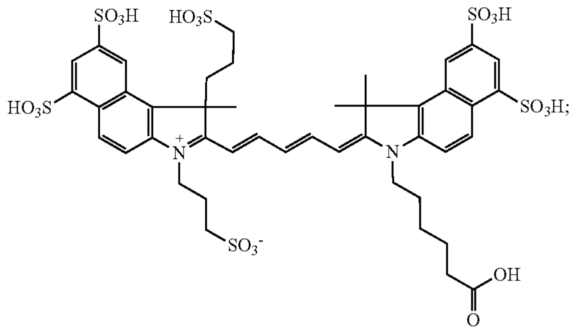
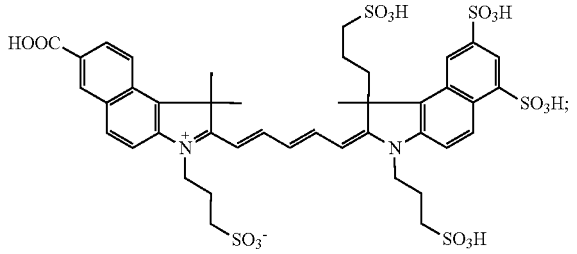
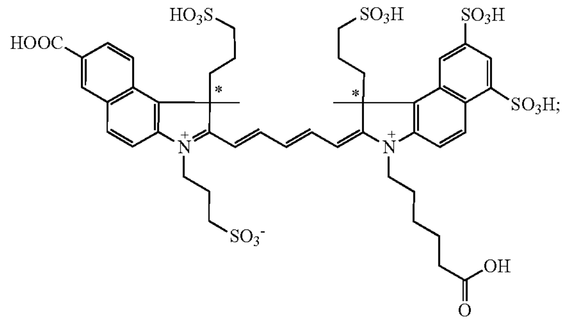
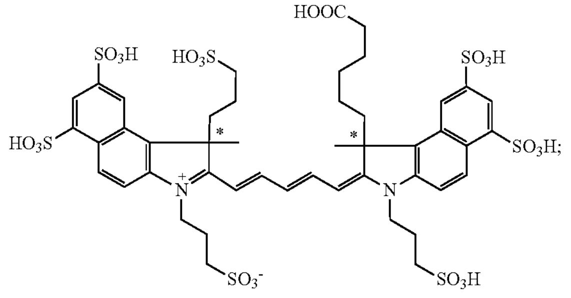
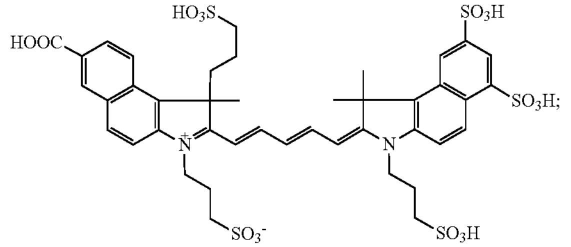
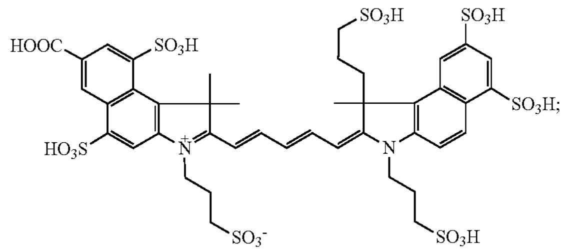
-continued
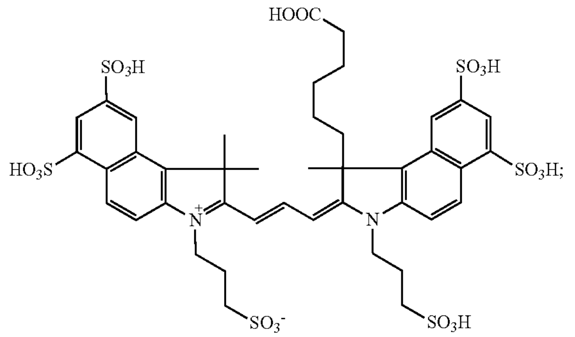
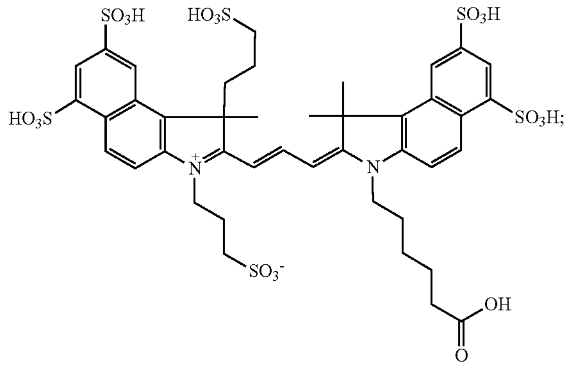
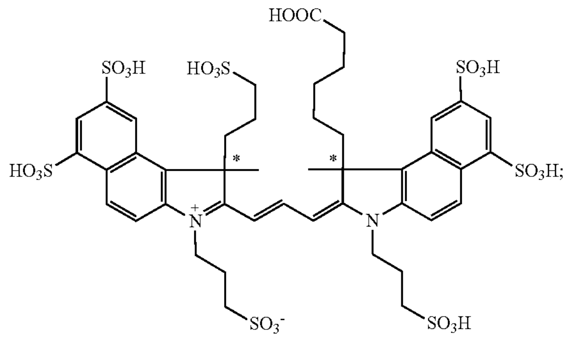
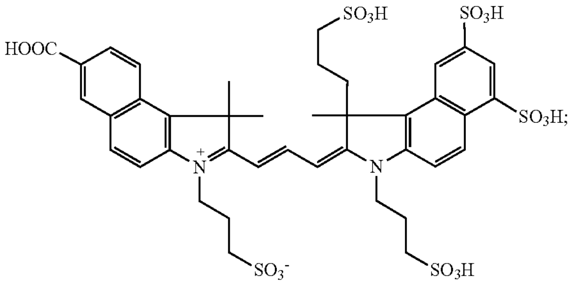
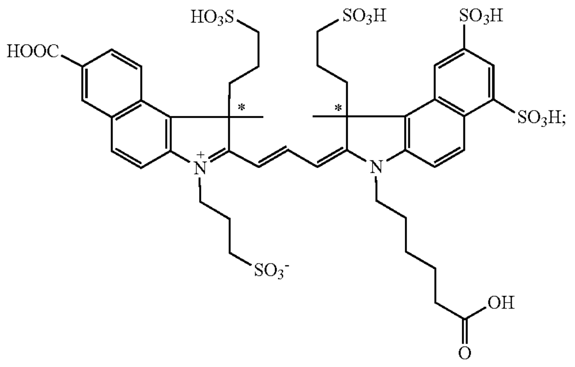

-continued
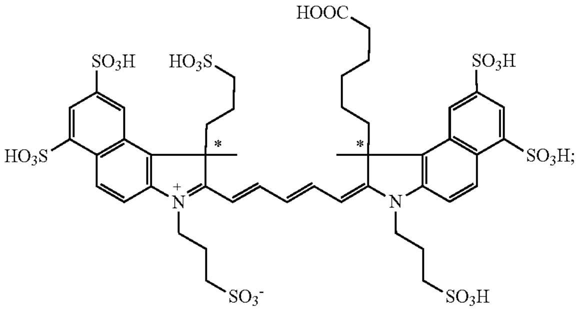
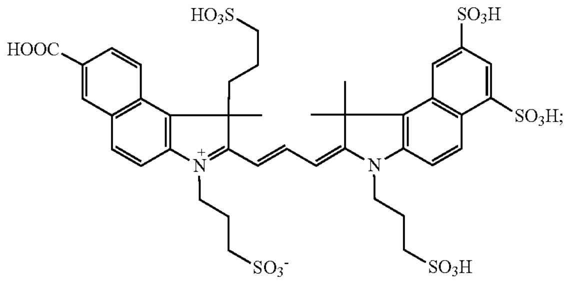
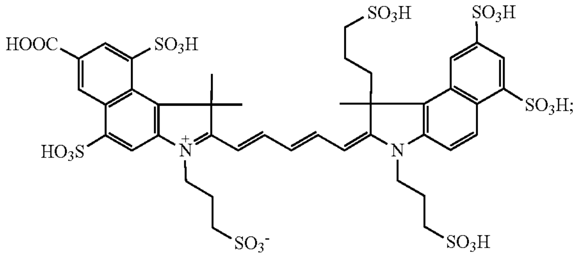
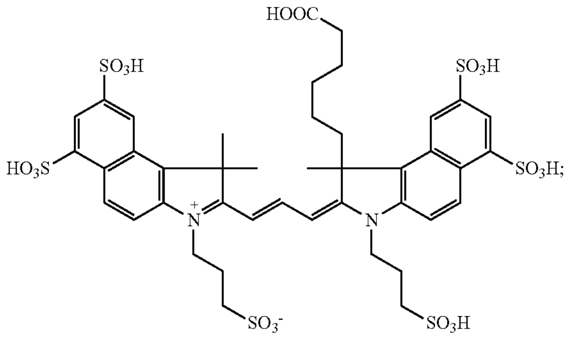
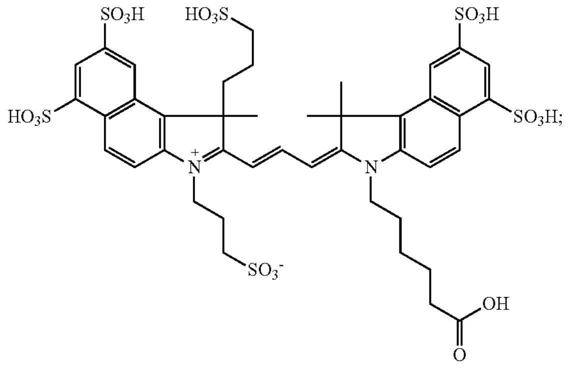
-continued
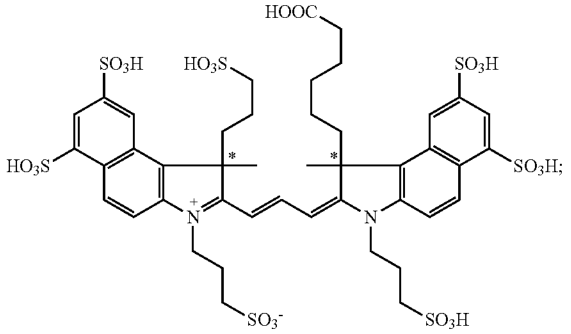
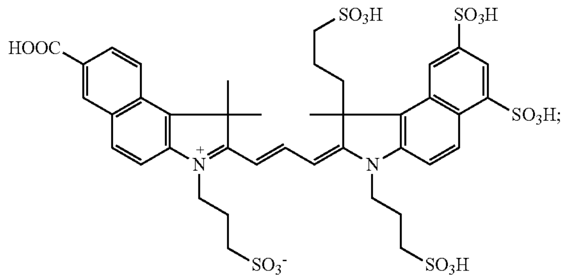
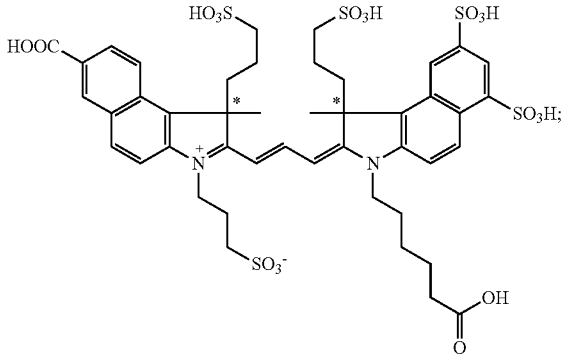
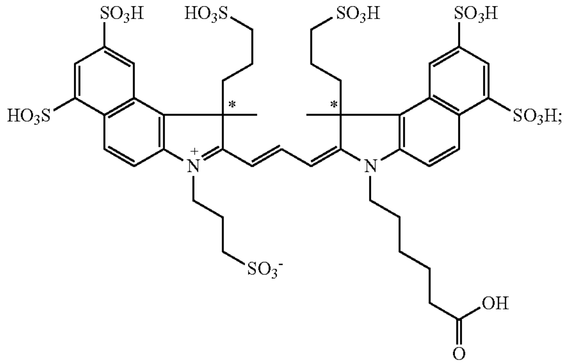
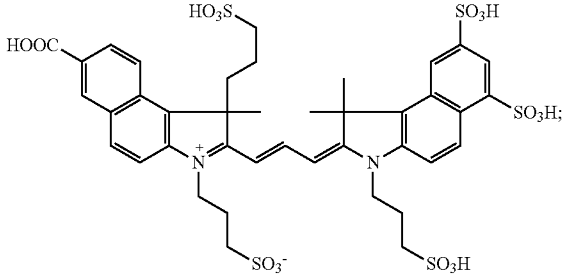

-continued
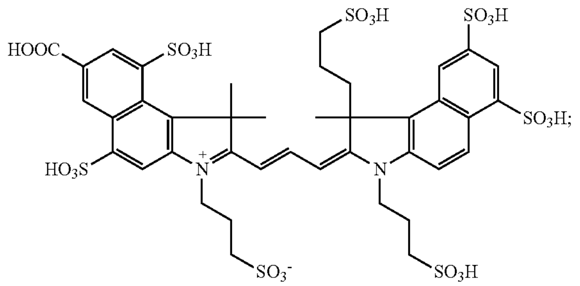
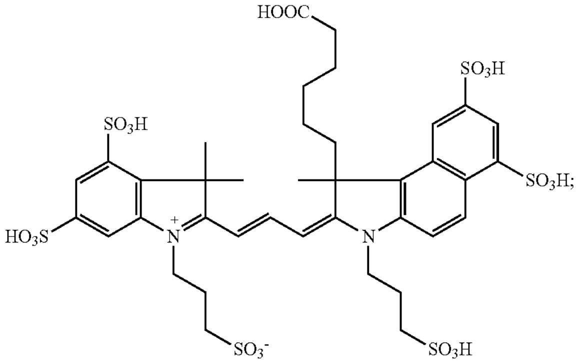
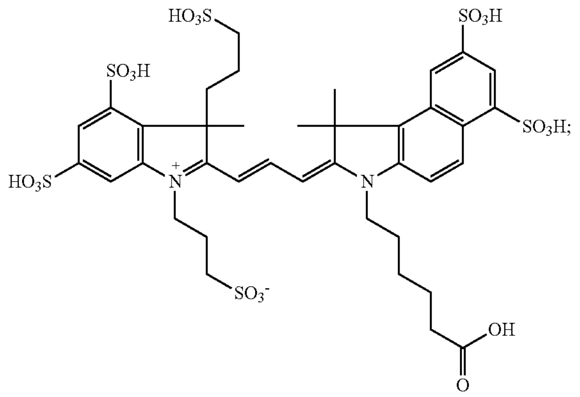
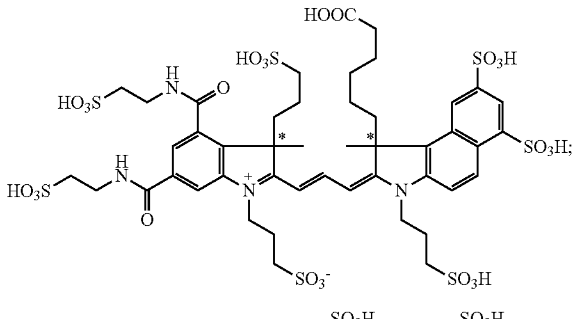
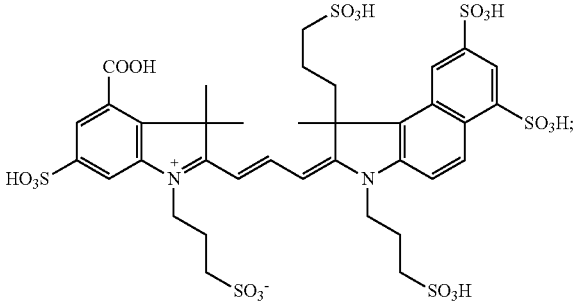
-continued
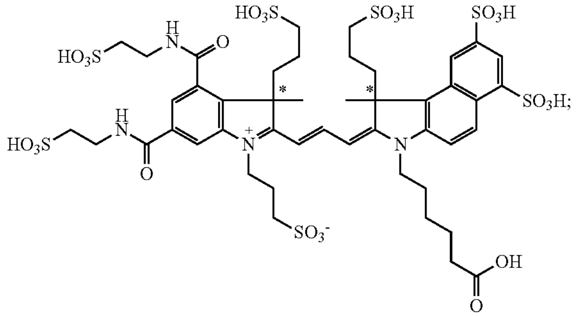
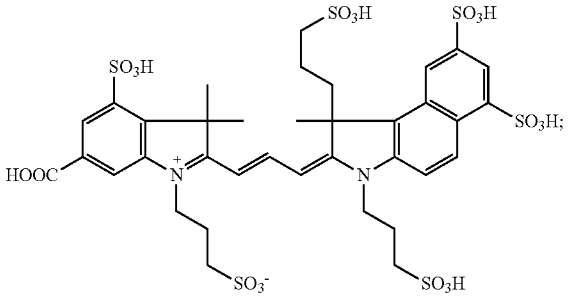
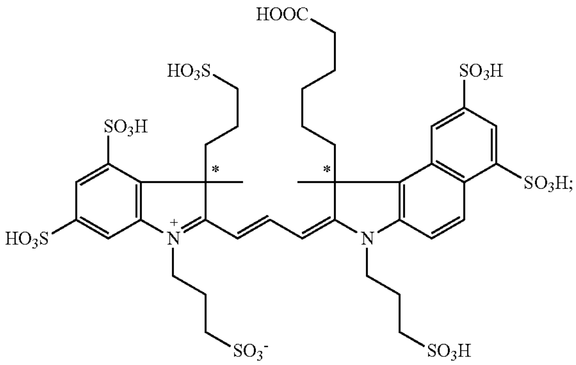
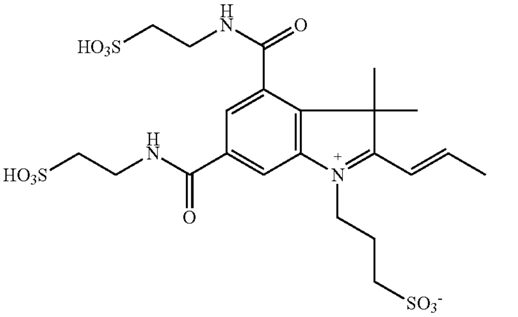
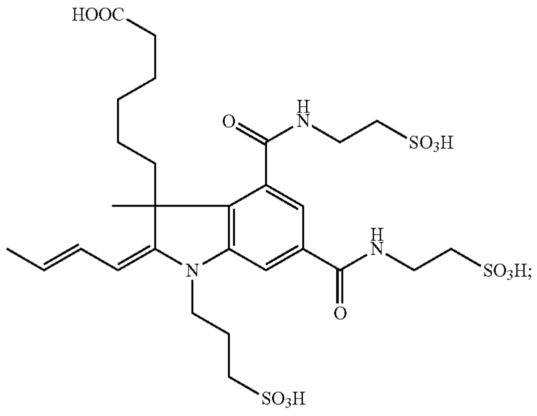

-continued
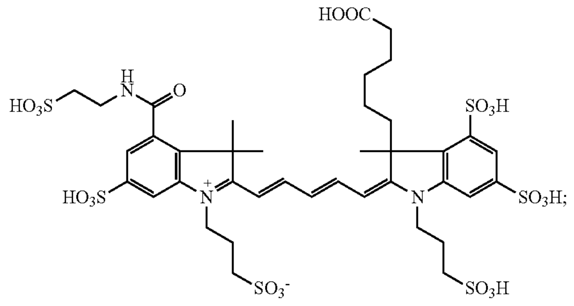
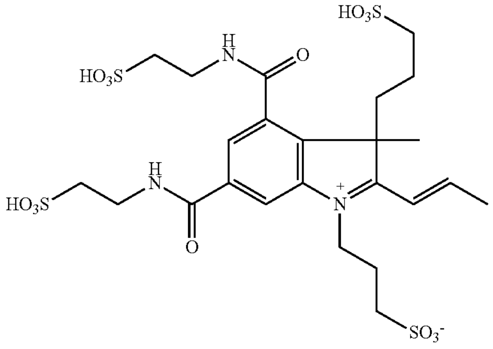
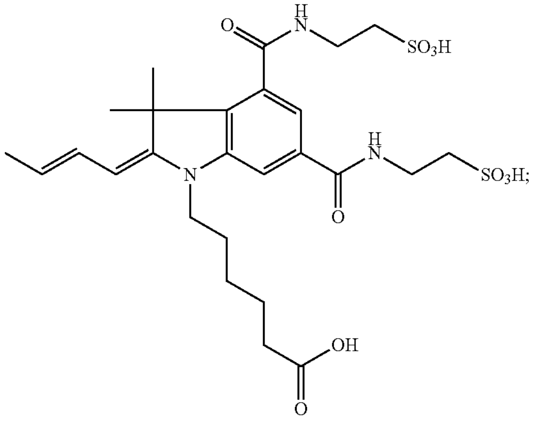
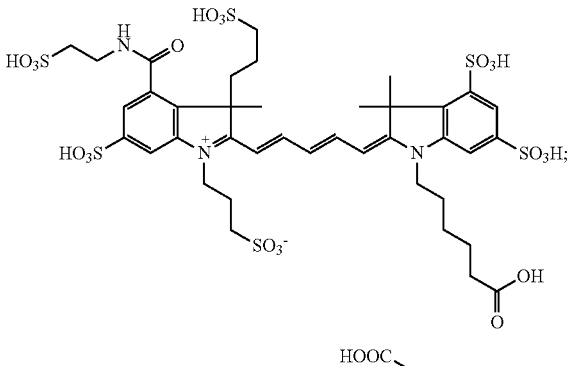
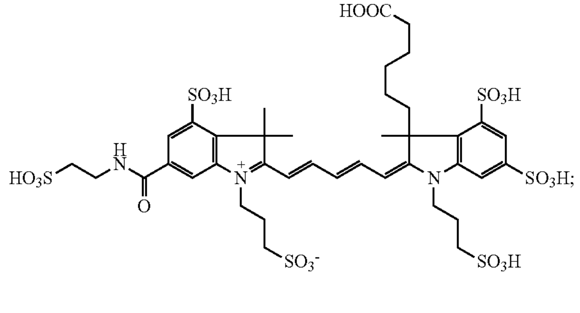
-continued
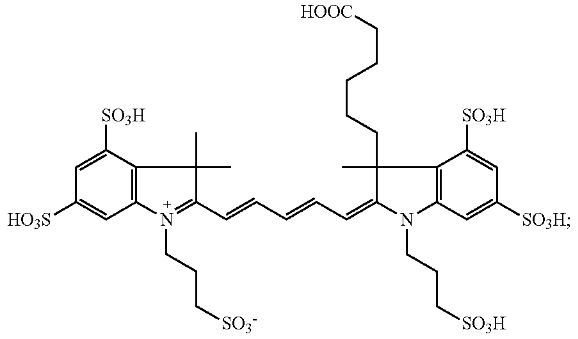
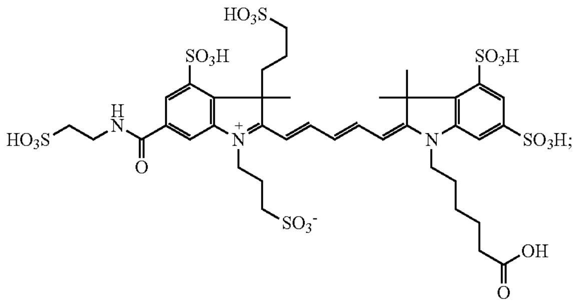
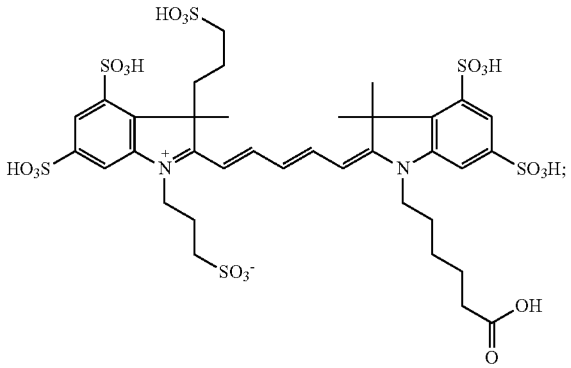
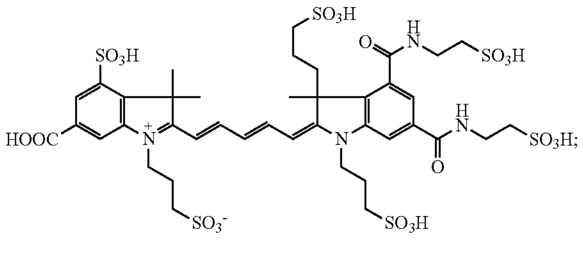
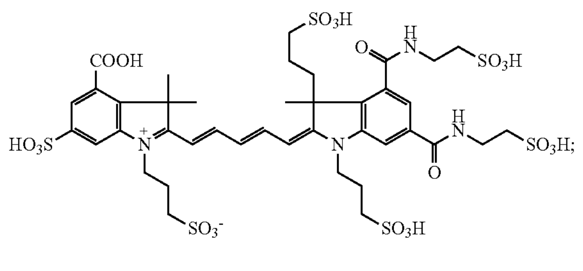

-continued
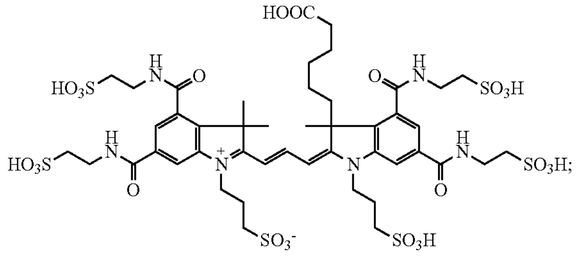
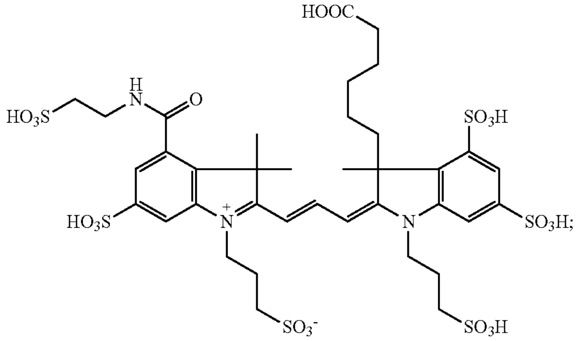
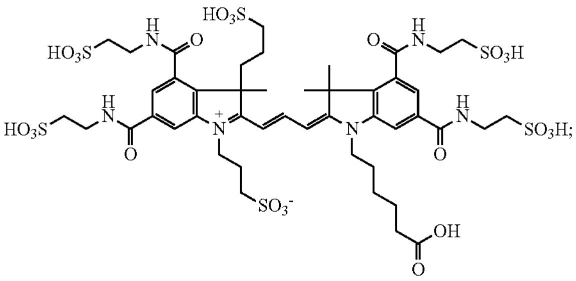
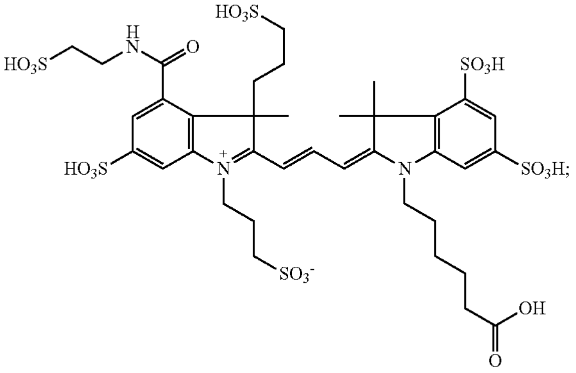
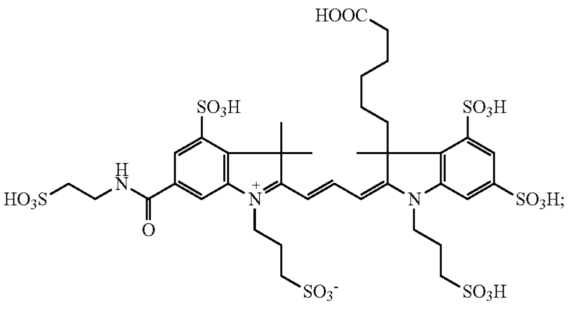
-continued
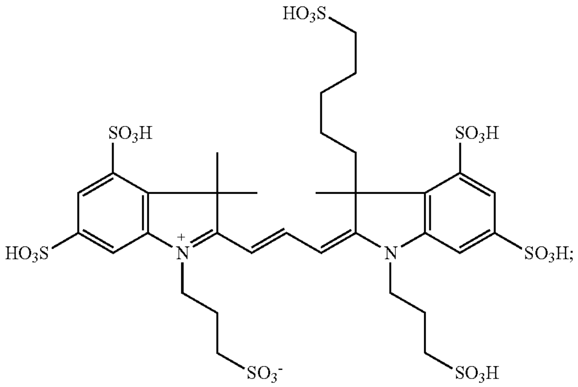
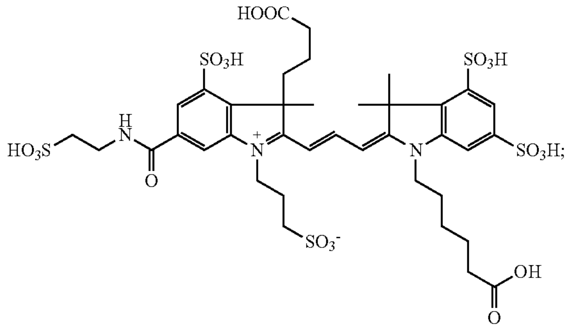
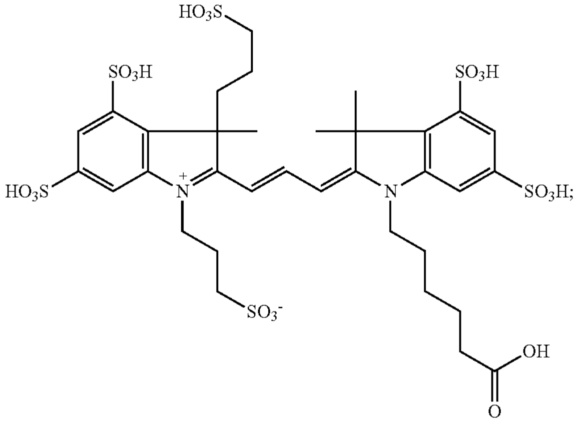
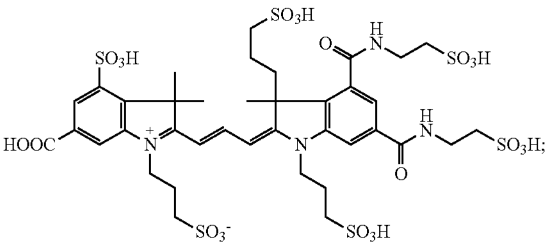
or
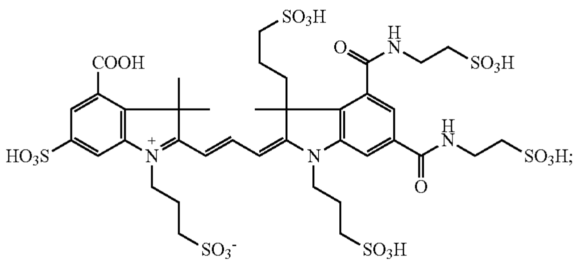
or an ionic derivative thereof, or a salt thereof.

2. A compound, wherein the compound is:
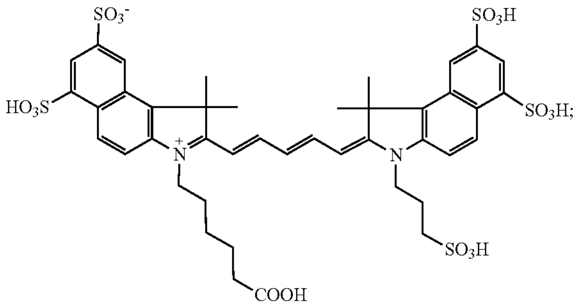
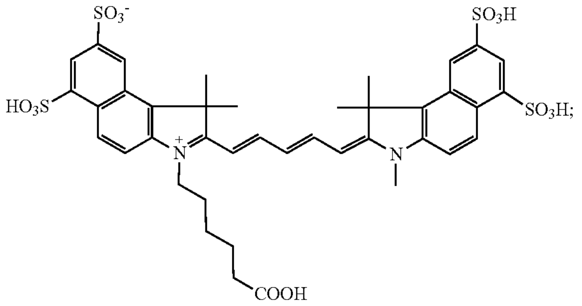
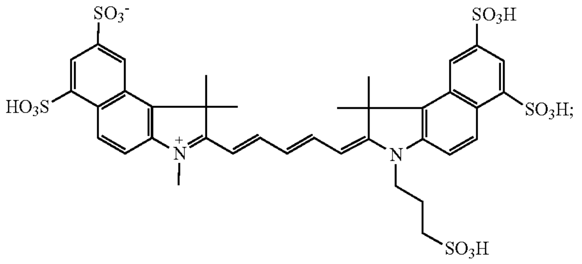
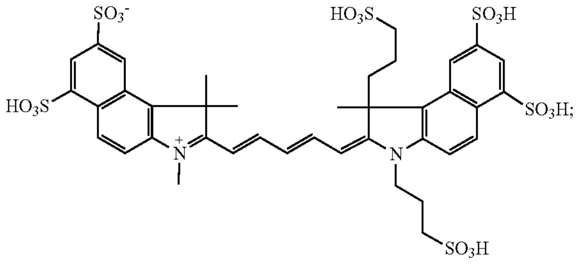
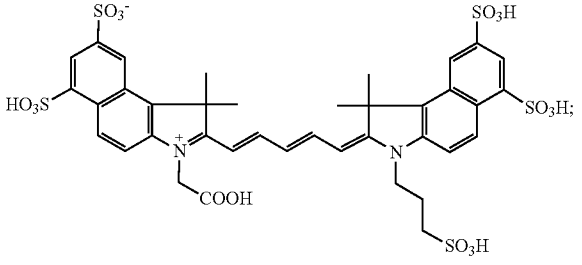
-continued
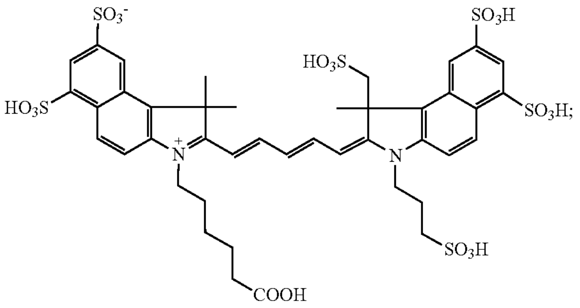
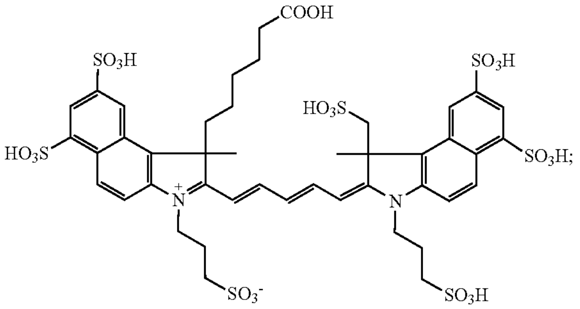
(Diastereomer 1)
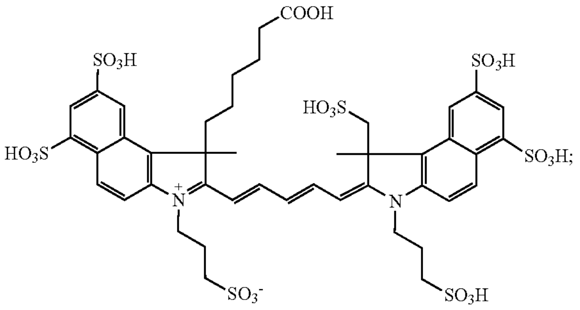
(Diastereomer 2)
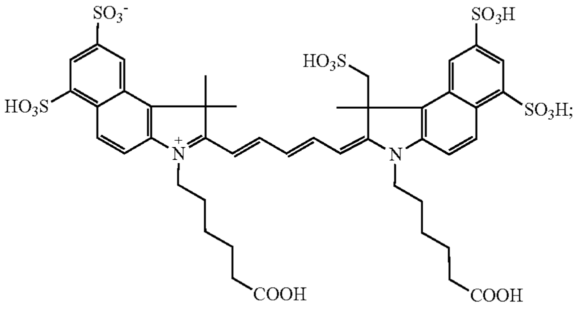
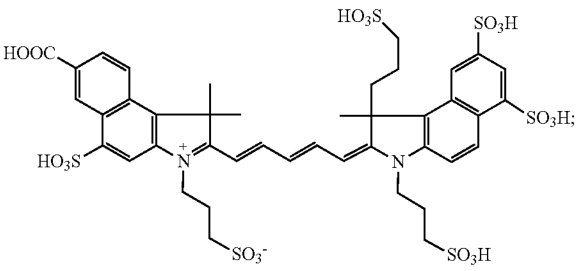

-continued
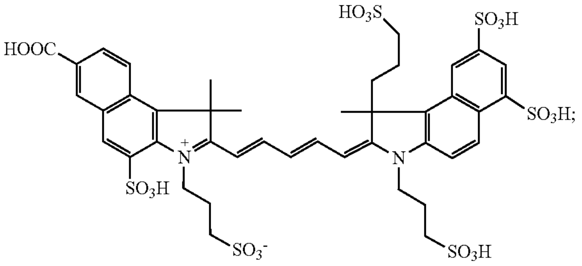
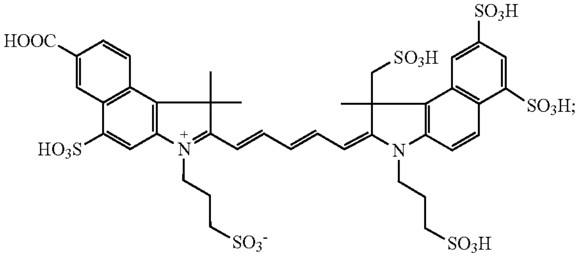
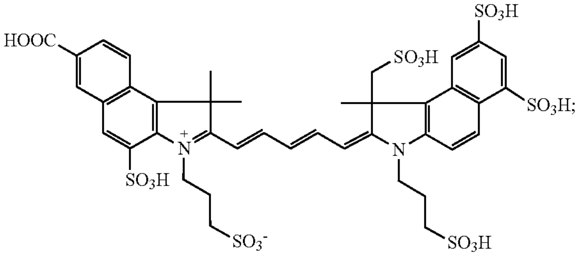
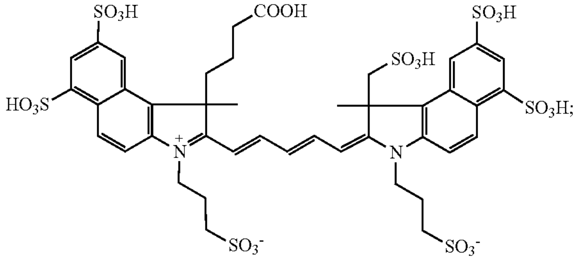
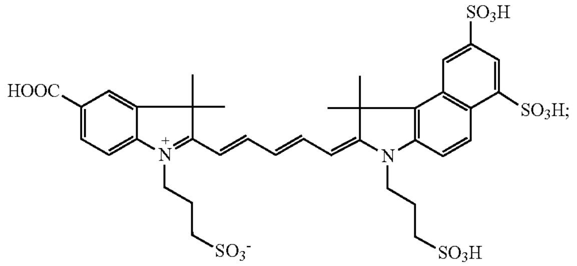
-continued
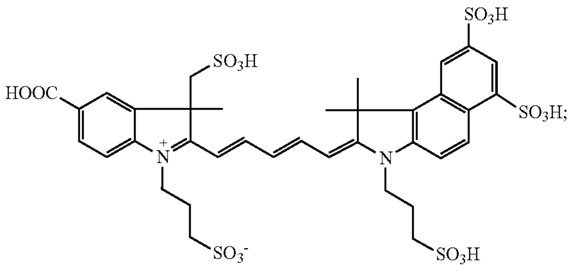
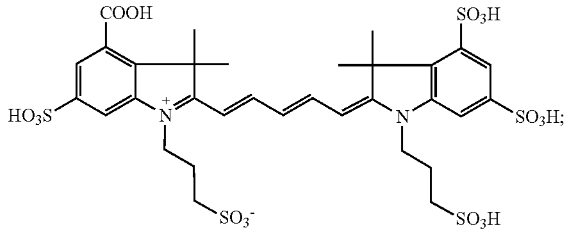
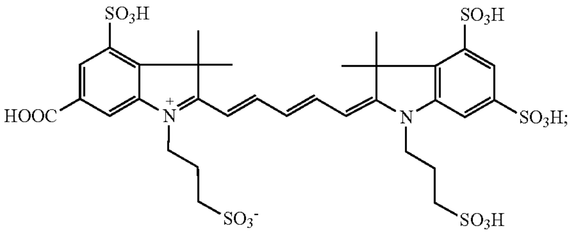
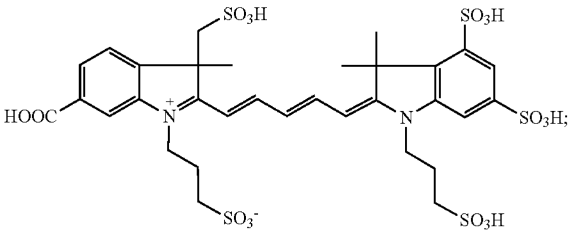
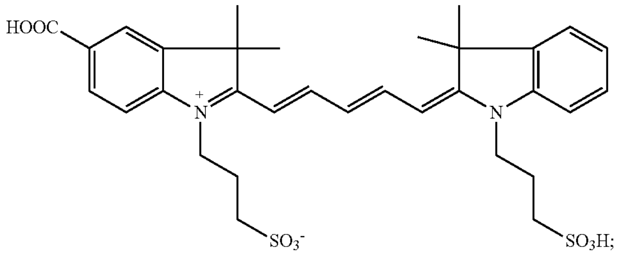

-continued
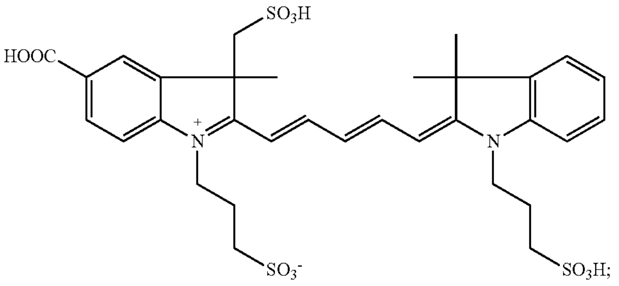
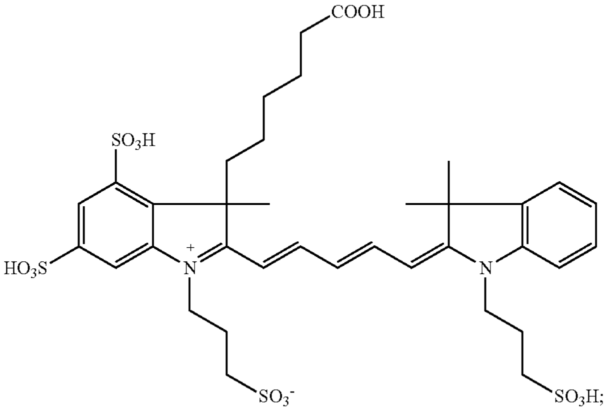
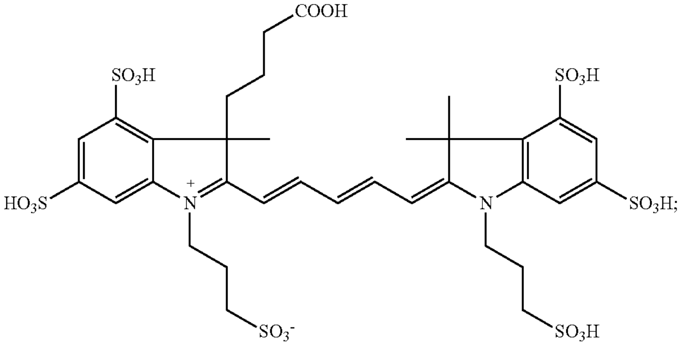
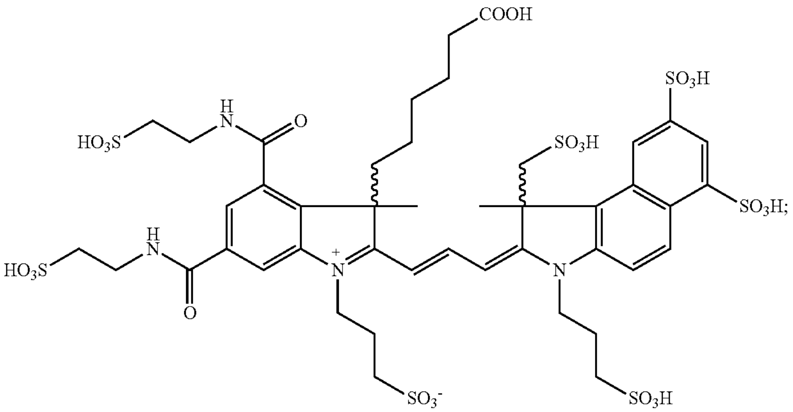

-continued
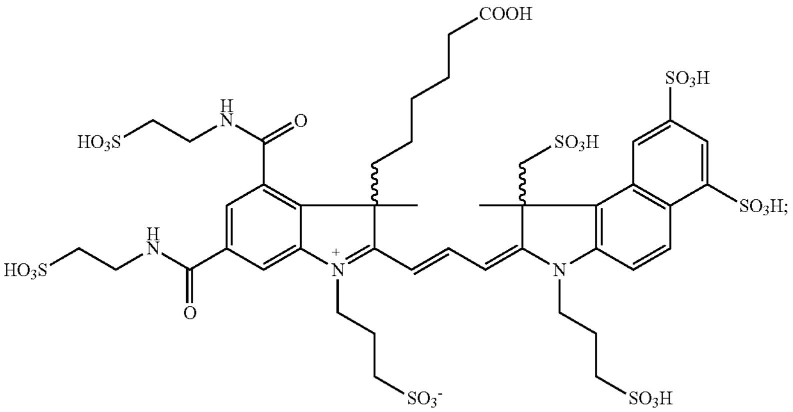
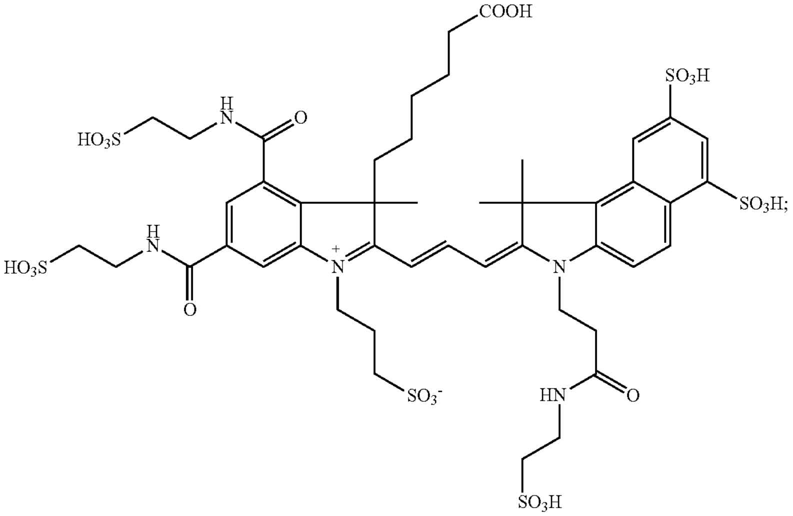
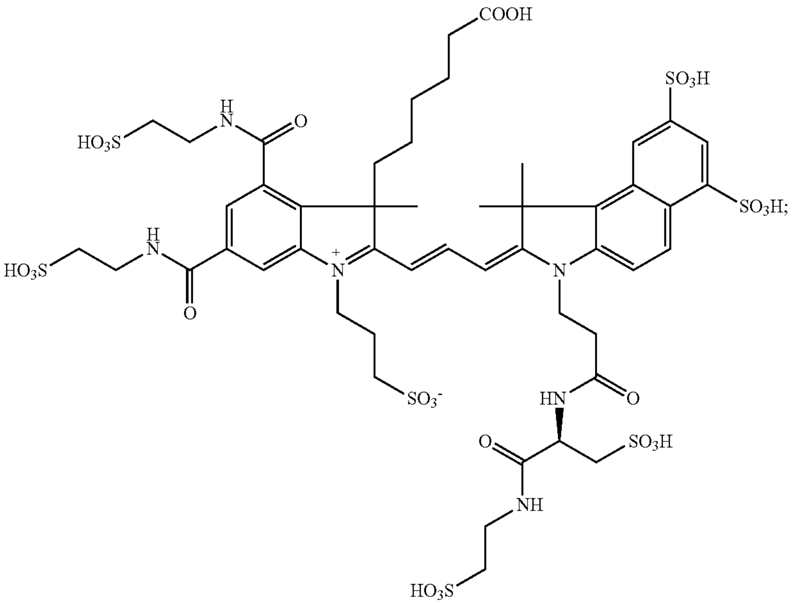

-continued
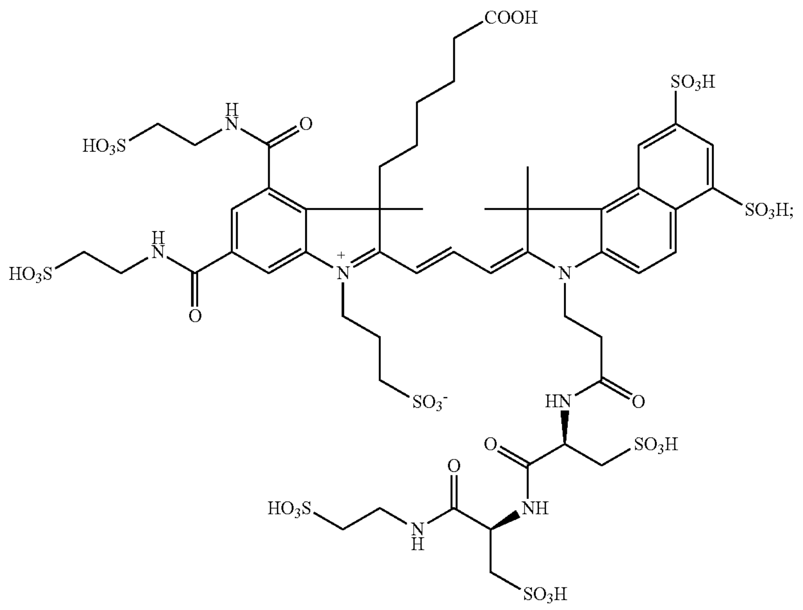
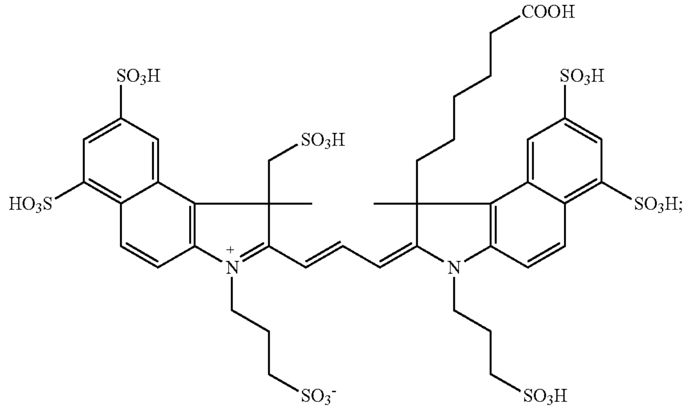
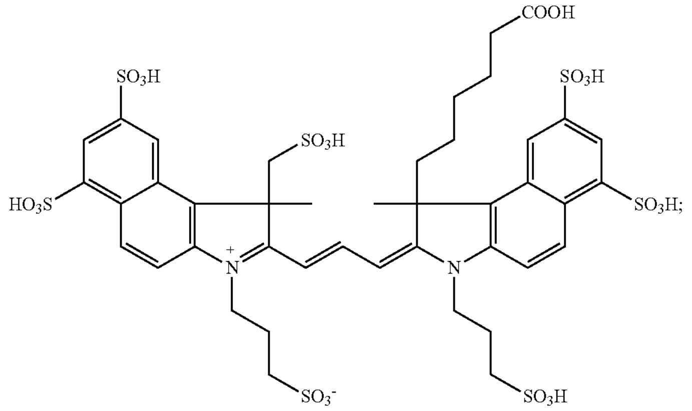

-continued
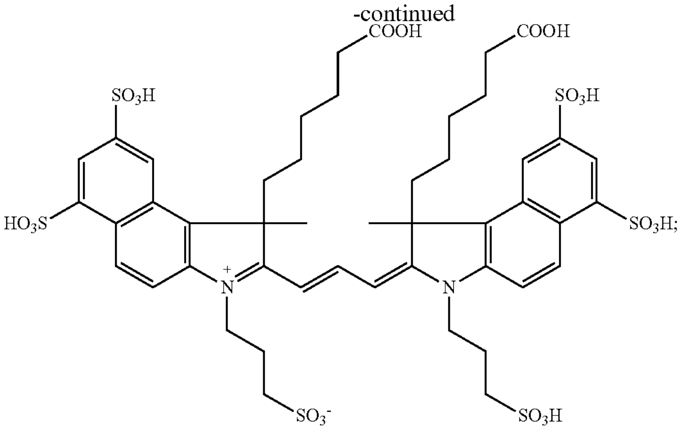
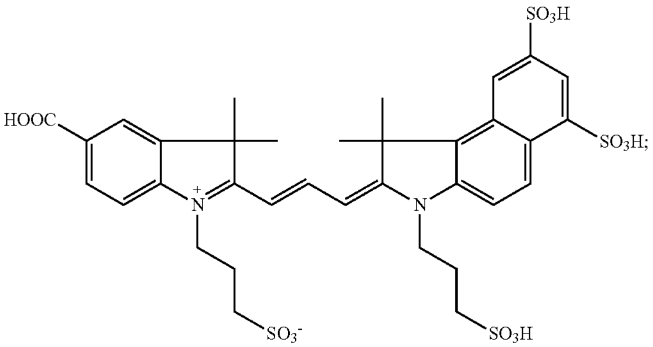
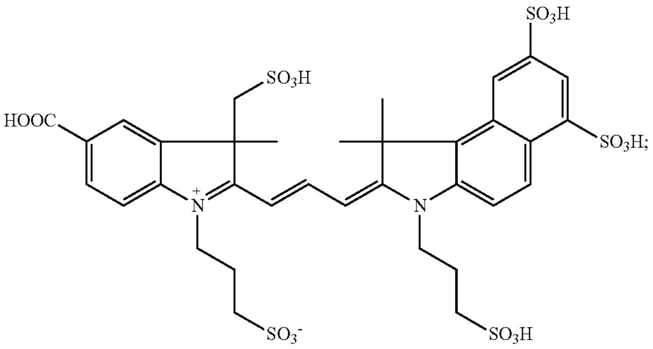
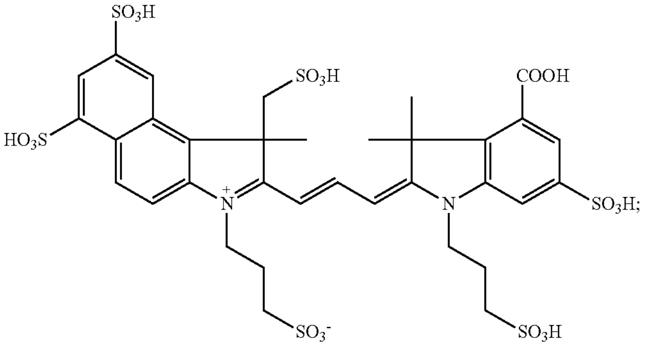

-continued
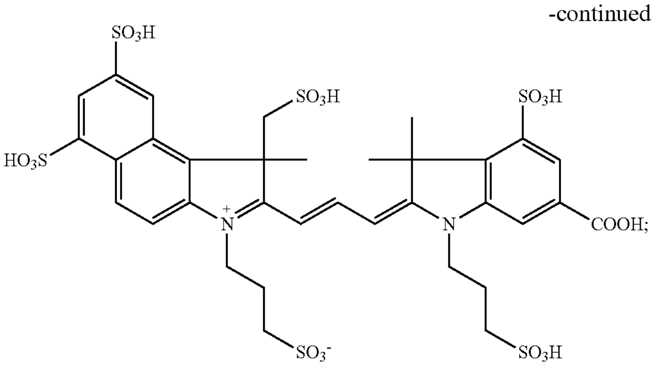
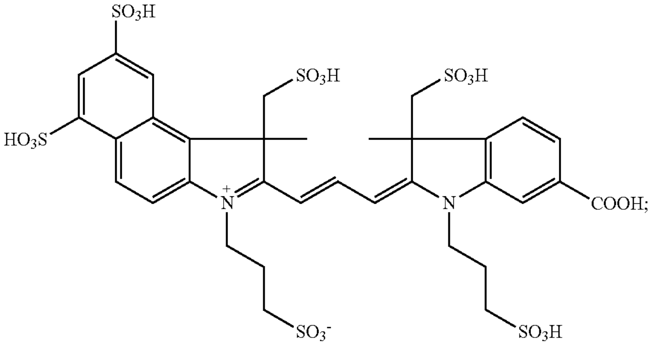
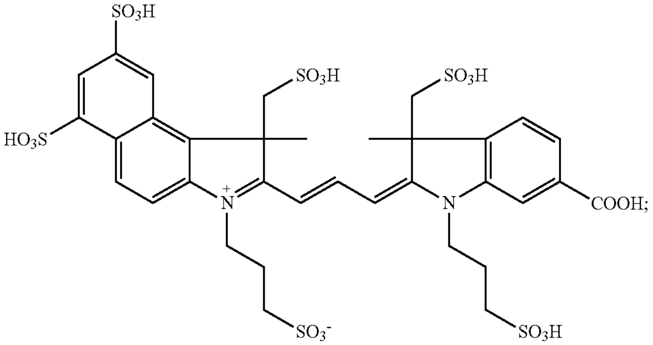
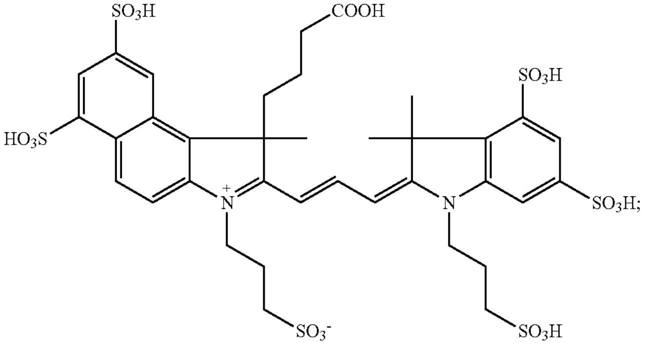
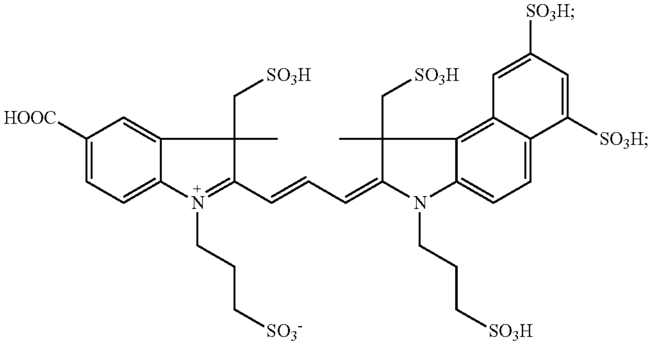

-continued
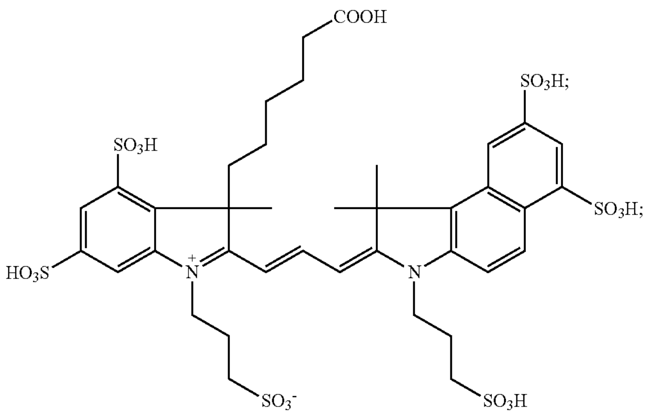
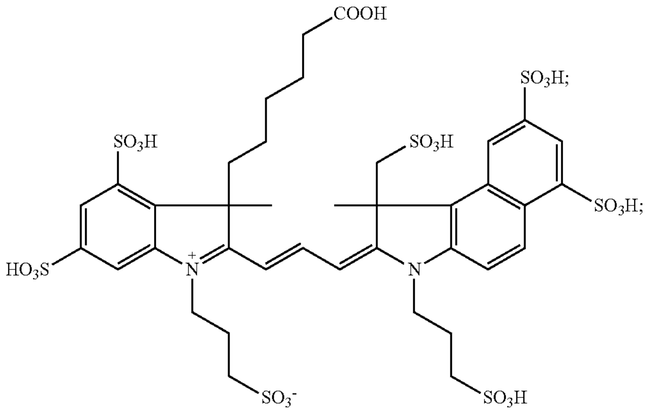
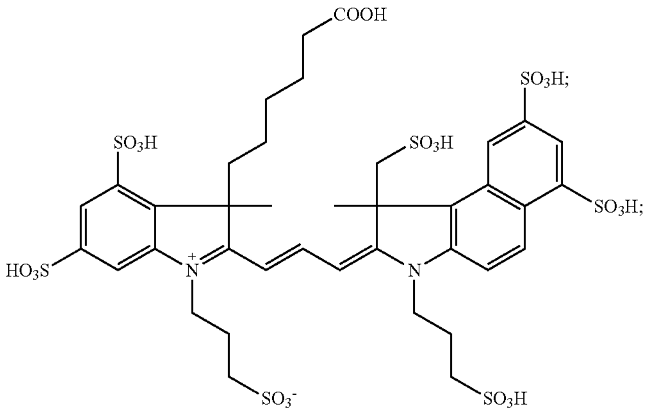
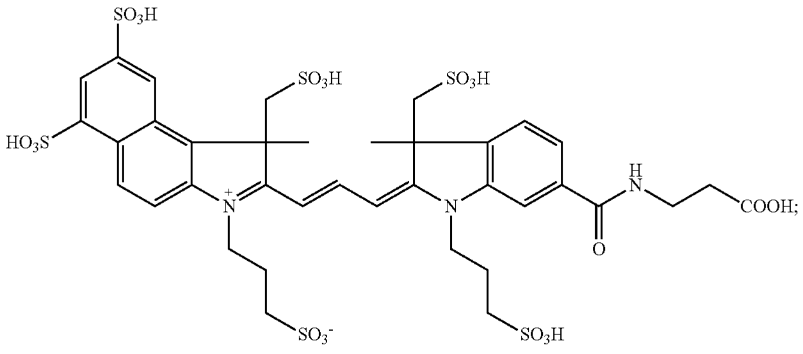

-continued
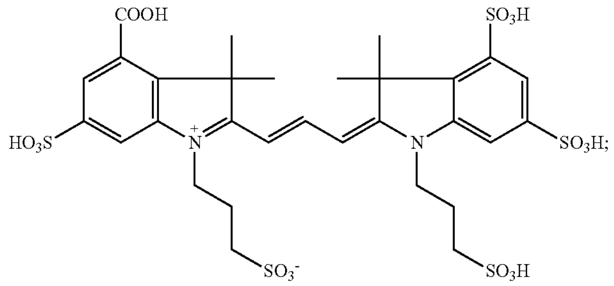
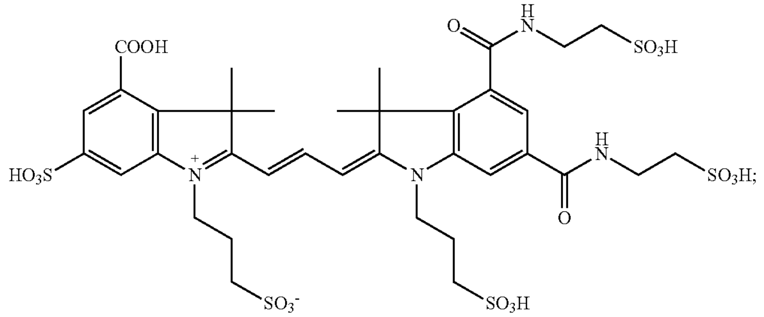
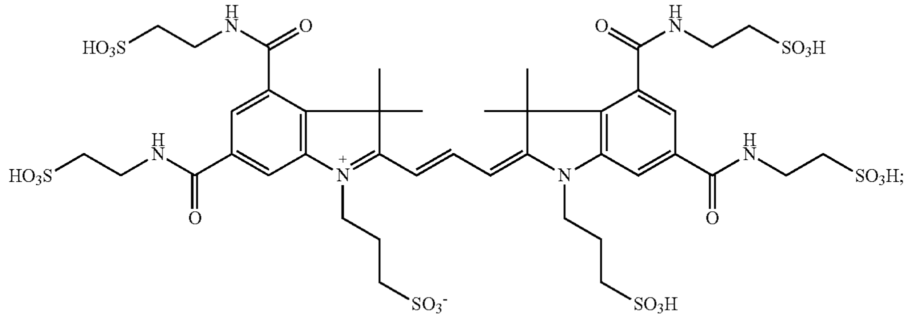
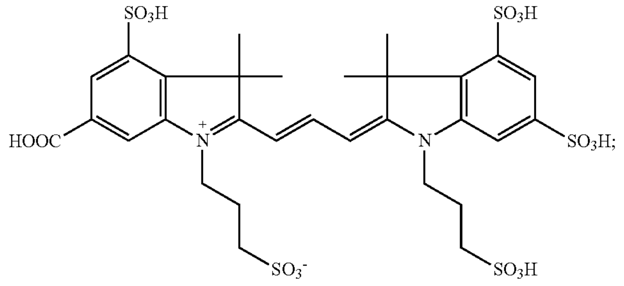
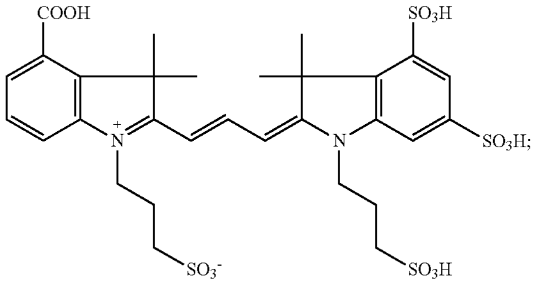
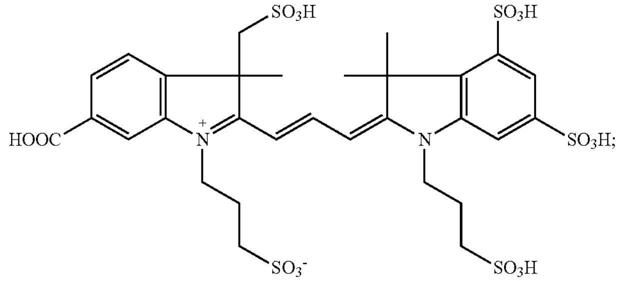

-continued
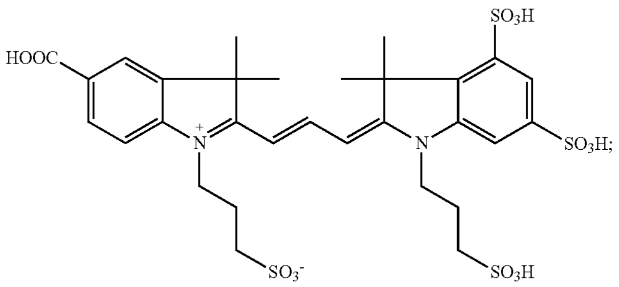
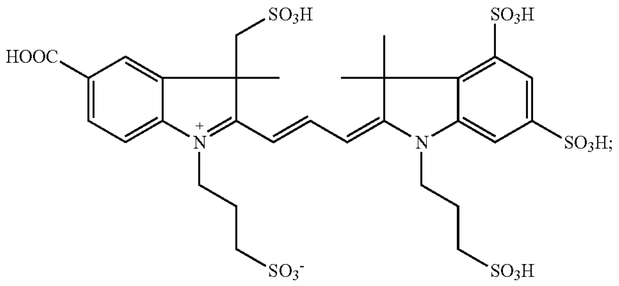
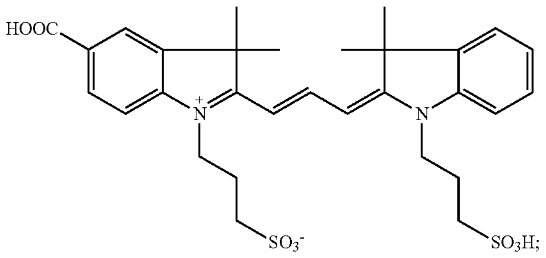
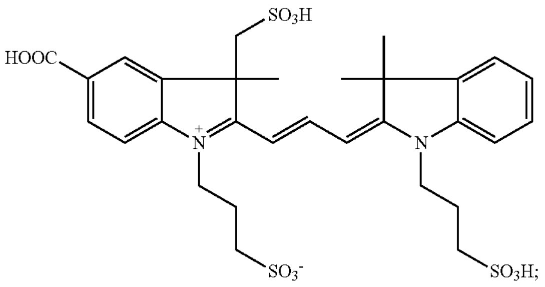
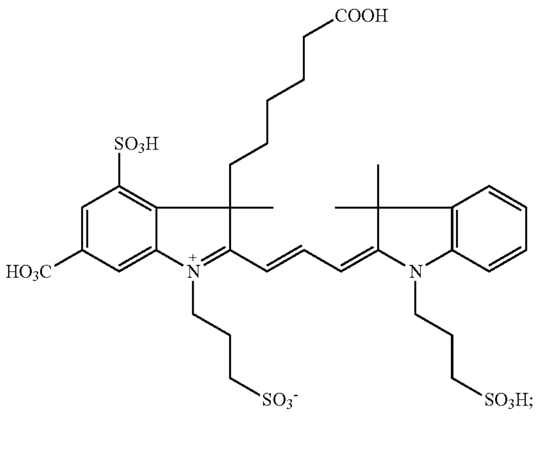
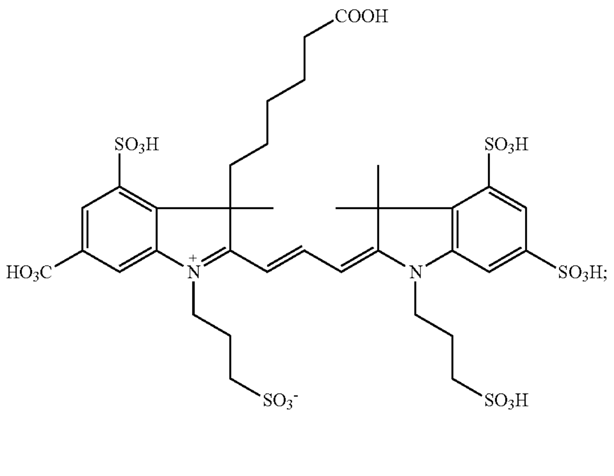

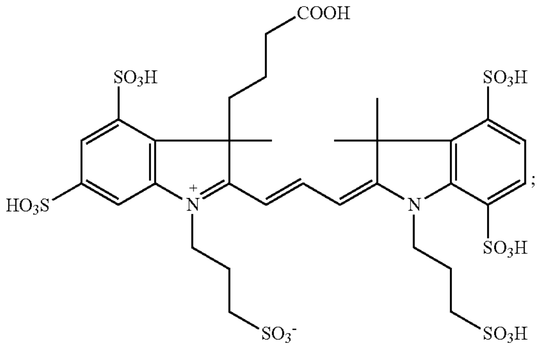
;
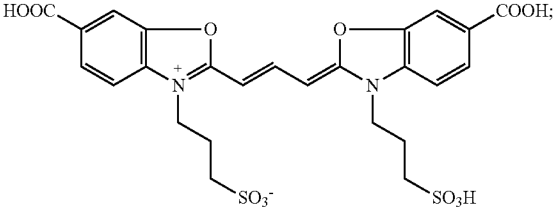
;
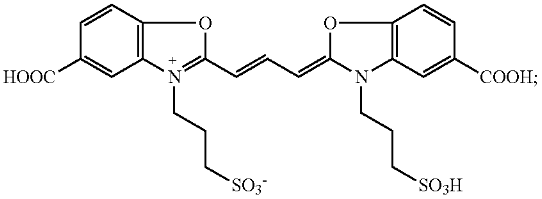
;
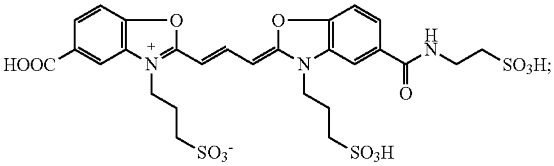
;
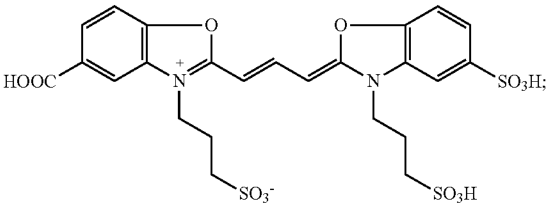
;
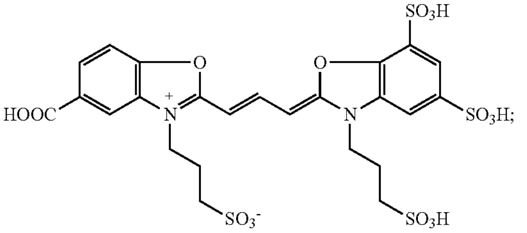
; or
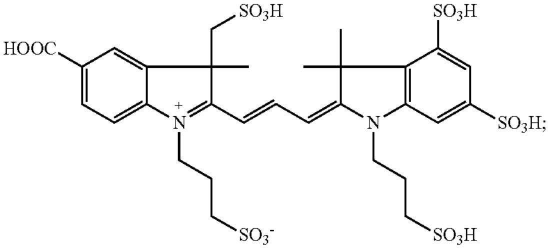
;

or an ionic derivative thereof, or a salt thereof.

3. A method of sequencing comprising:

(a) contacting (i) a plurality of polymerases, (ii) a plurality of nucleic acid template molecules and (iii) a plurality of nucleic acid sequencing primers under conditions suitable to form a plurality of complexes comprising a polymerase bound to a nucleic acid duplex, wherein the nucleic acid duplex comprises a nucleic acid template molecule hybridized to a primer;

(b) contacting the plurality of complexes with a plurality of nucleotides under conditions suitable for binding at least one nucleotide to one of the polymerases bound to a nucleic acid duplex; and (c) incorporating at least one nucleotide into the 3' end of an extendible primer of at least one of the complexes, wherein at least one nucleotide in the plurality of nucleotides is labeled with the compound of claim 1.

4. A method of sequencing comprising:

(a) contacting (i) a plurality of sequencing polymerases, (ii) a first plurality of nucleic acid template molecules and (iii) a plurality of nucleic acid sequencing primers under conditions suitable to form a plurality of complexes comprising a first polymerase bound to a nucleic acid duplex, wherein the nucleic acid duplex comprises a nucleic acid template molecule hybridized to a nucleic acid sequencing primer;

(b) contacting the plurality of complexes with a plurality of multivalent molecules to form a plurality of complexes, each complex comprising one or more polymerases, nucleic acid templates and sequencing primers, wherein the nucleic acid templates and the sequencing primers are associated in a duplex, wherein individual multivalent molecules comprise a core attached to multiple nucleotide arms and each nucleotide arm is attached to a nucleotide unit; and wherein individual multivalent molecules in the plurality comprise the compound of claim 1; and (c) detecting the plurality of multivalent-complexed polymerases.

5. A method of sequencing comprising:

(a) contacting (i) a plurality of polymerases, (ii) a plurality of nucleic acid template molecules and (iii) a plurality of nucleic acid sequencing primers under conditions suitable to form a plurality of complexes comprising a polymerase bound to a nucleic acid duplex, wherein the nucleic acid duplex comprises a nucleic acid template molecule hybridized to a primer;

(b) contacting the plurality of complexes with a plurality of nucleotides under conditions suitable for binding at least one nucleotide to one of the polymerases bound to a nucleic acid duplex; and (c) incorporating at least one nucleotide into the 3' end of an extendible primer of at least one of the complexes, wherein at least one nucleotide in the plurality of nucleotides is labeled with the compound of claim 2.

6. A method of sequencing comprising:

(a) contacting (i) a plurality of sequencing polymerases, (ii) a first plurality of nucleic acid template molecules and (iii) a plurality of nucleic acid sequencing primers under conditions suitable to form a plurality of complexes comprising a first polymerase bound to a nucleic acid duplex, wherein the nucleic acid duplex comprises a nucleic acid template molecule hybridized to a nucleic acid sequencing primer;

(b) contacting the plurality of complexes with a plurality of multivalent molecules to form a plurality of complexes, each complex comprising one or more polymerases, nucleic acid templates and sequencing primers, wherein the nucleic acid templates and the sequencing primers are associated in a duplex, wherein individual multivalent molecules comprise a core attached to multiple nucleotide arms and each nucleotide arm is attached to a nucleotide unit; and wherein individual multivalent molecules in the plurality comprise the compound of claim 2; and (c) detecting the plurality of multivalent-complexed polymerases.

7. A compound, wherein the compound is

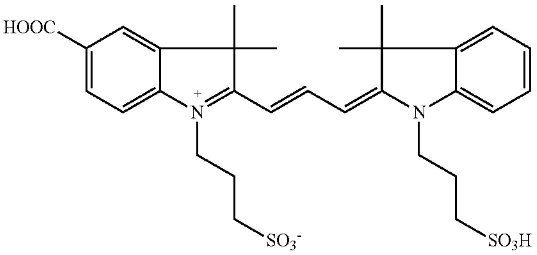

;

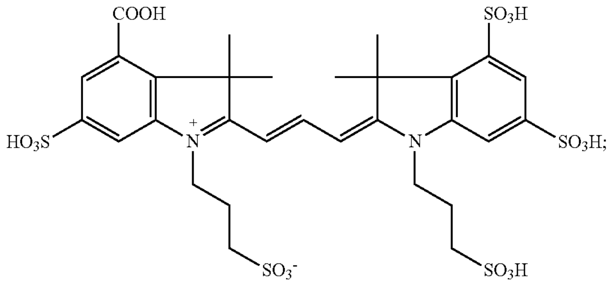

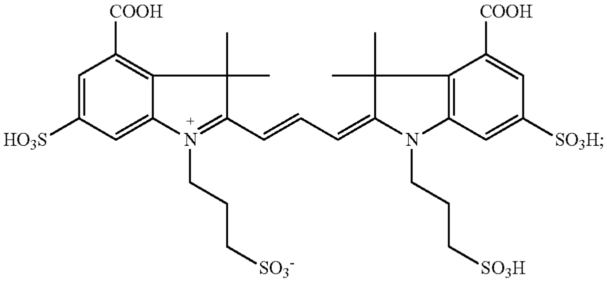

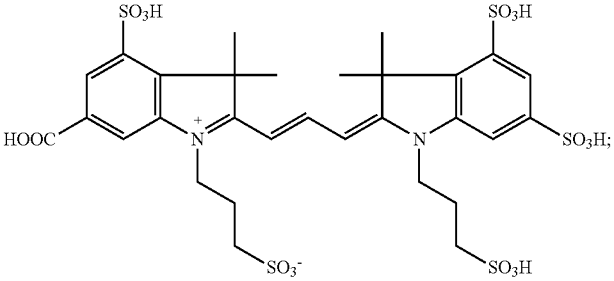

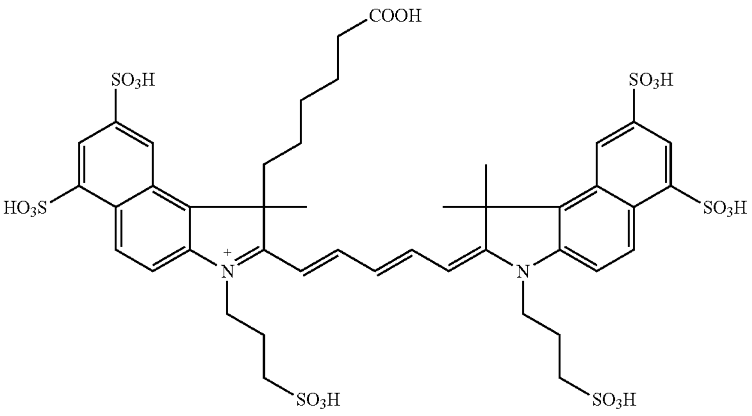

-continued
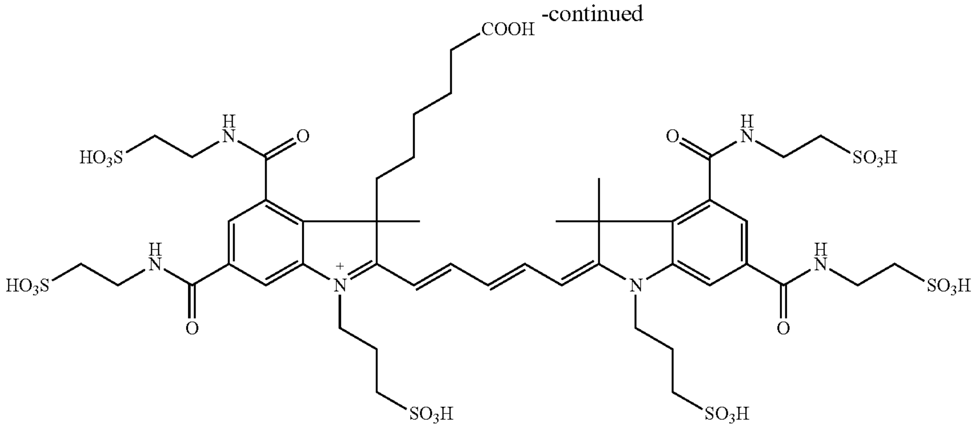
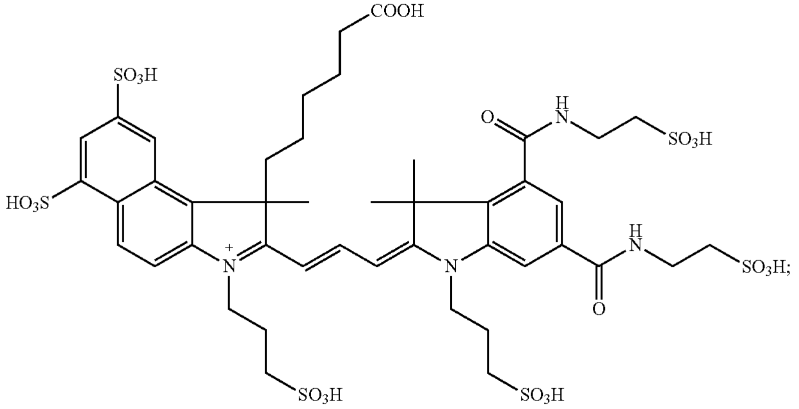
or
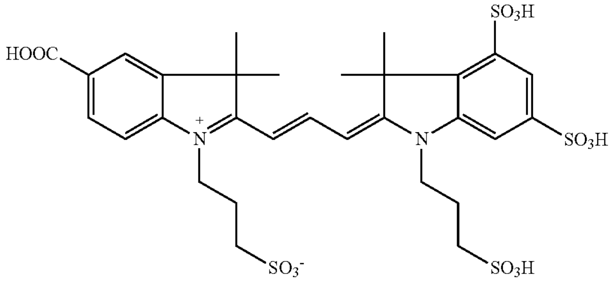
or an ionic derivative thereof, or a salt thereof.
8. The compound of claim 7, wherein the compound is:
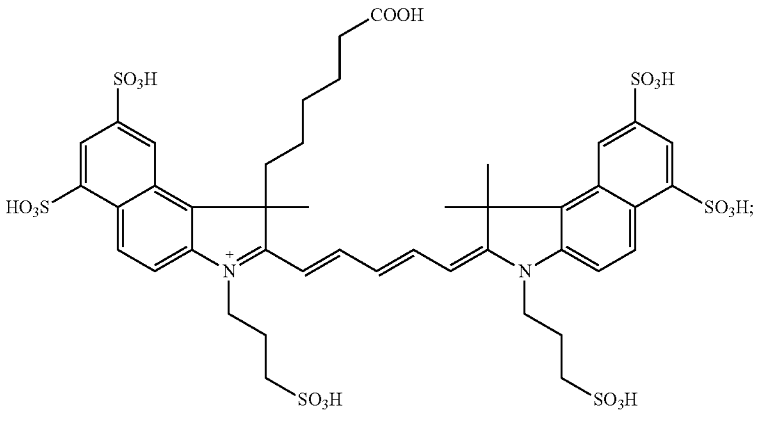

-continued

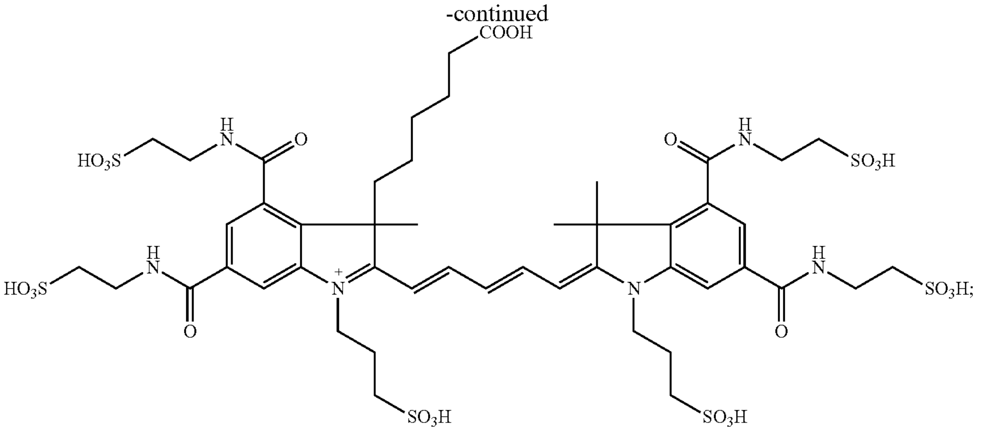

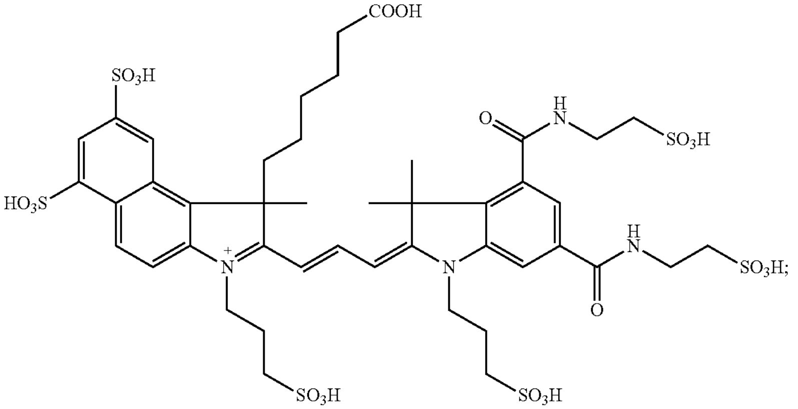

or

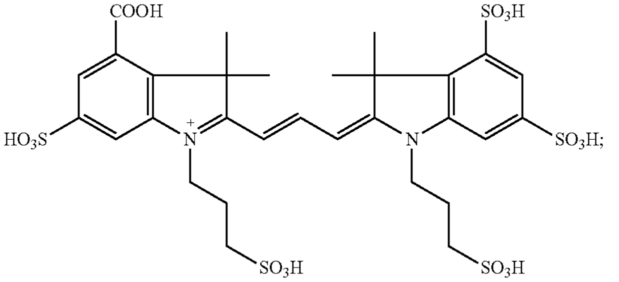

or an ionic derivative thereof, or a salt thereof.

9. A method of sequencing comprising:

(a) contacting (i) a plurality of polymerases, (ii) a plurality of nucleic acid template molecules and (iii) a plurality of nucleic acid sequencing primers under conditions suitable to form a plurality of complexes comprising a polymerase bound to a nucleic acid duplex, wherein the nucleic acid duplex comprises a nucleic acid template molecule hybridized to a primer;

(b) contacting the plurality of complexes with a plurality of nucleotides under conditions suitable for binding at least one nucleotide to one of the polymerases bound to a nucleic acid duplex; and (c) incorporating at least one nucleotide into the 3' end of an extendible primer of at least one of the complexes, wherein at least one nucleotide in the plurality of nucleotides is labeled with the compound of claim 7.

10. A method of sequencing comprising:

(a) contacting (i) a plurality of sequencing polymerases, (ii) a first plurality of nucleic acid template molecules and (iii) a plurality of nucleic acid sequencing primers under conditions suitable to form a plurality of complexes comprising a first polymerase bound to a nucleic acid duplex, wherein the nucleic acid duplex comprises a nucleic acid template molecule hybridized to a nucleic acid sequencing primer;

(b) contacting the plurality of complexes with a plurality of multivalent molecules to form a plurality of complexes, each complex comprising one or more polymerases, nucleic acid templates and sequencing primers, wherein the nucleic acid templates and the sequencing primers are associated in a duplex, wherein individual multivalent molecules comprise a core attached to multiple nucleotide arms and each nucleotide arm is attached to a nucleotide unit; and wherein individual multivalent molecules in the plurality comprise the compound of claim 7; and (c) detecting the plurality of multivalent-complexed polymerases.

11. A compound, wherein the compound is

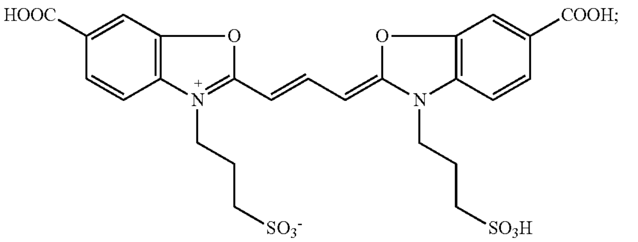

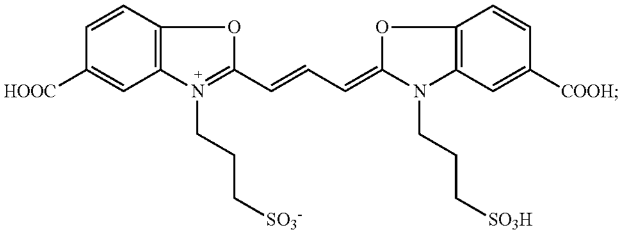

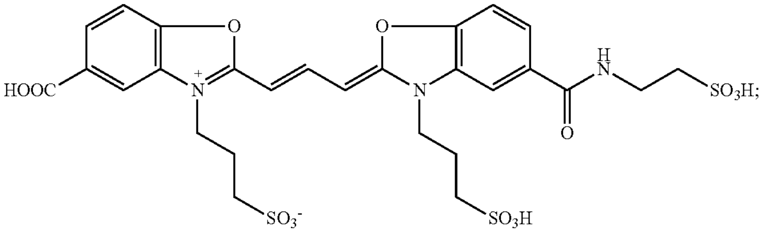

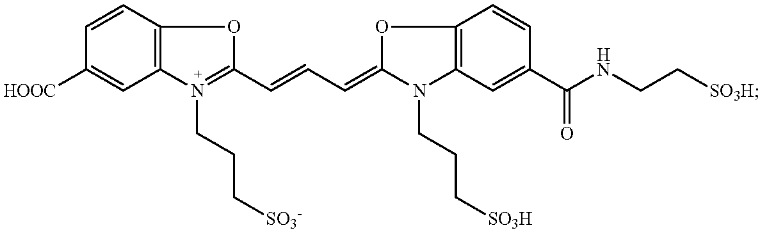

or

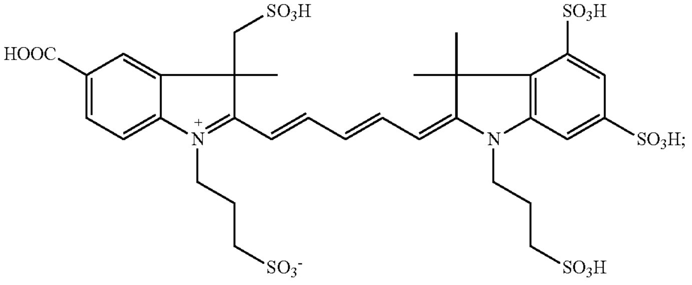

or an ionic derivative thereof, or a salt thereof.

12. A method of sequencing comprising:

(a) contacting (i) a plurality of polymerases, (ii) a plurality of nucleic acid template molecules and (iii) a plurality of nucleic acid sequencing primers under conditions suitable to form a plurality of complexes comprising a polymerase bound to a nucleic acid duplex, wherein the nucleic acid duplex comprises a nucleic acid template molecule hybridized to a primer;

(b) contacting the plurality of complexes with a plurality of nucleotides under conditions suitable for binding at least one nucleotide to one of the polymerases bound to a nucleic acid duplex; and (c) incorporating at least one nucleotide into the 3' end of an extendible primer of at least one of the complexes, wherein at least one nucleotide in the plurality of nucleotides is labeled with the compound of claim 11.

13. A method of sequencing comprising:

(a) contacting (i) a plurality of sequencing polymerases, (ii) a first plurality of nucleic acid template molecules and (iii) a plurality of nucleic acid sequencing primers under conditions suitable to form a plurality of complexes comprising a first polymerase bound to a nucleic acid duplex, wherein the nucleic acid duplex comprises a nucleic acid template molecule hybridized to a nucleic acid sequencing primer;

(b) contacting the plurality of complexes with a plurality of multivalent molecules to form a plurality of complexes, each complex comprising one or more polymerases, nucleic acid templates and sequencing primers, wherein the nucleic acid templates and the sequencing primers are associated in a duplex, wherein individual multivalent molecules comprise a core attached to multiple nucleotide arms and each nucleotide arm is attached to a nucleotide unit; and wherein individual multivalent molecules in the plurality comprise the compound of claim 11; and (c) detecting the plurality of multivalent-complexed polymerases.

14. The compound of claim 1, wherein the compound is

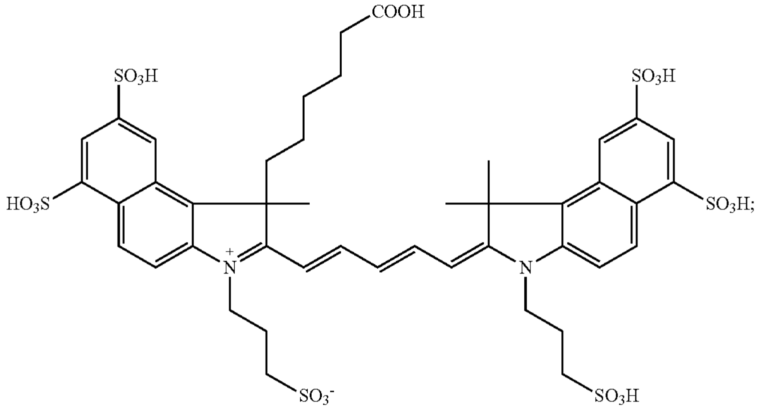

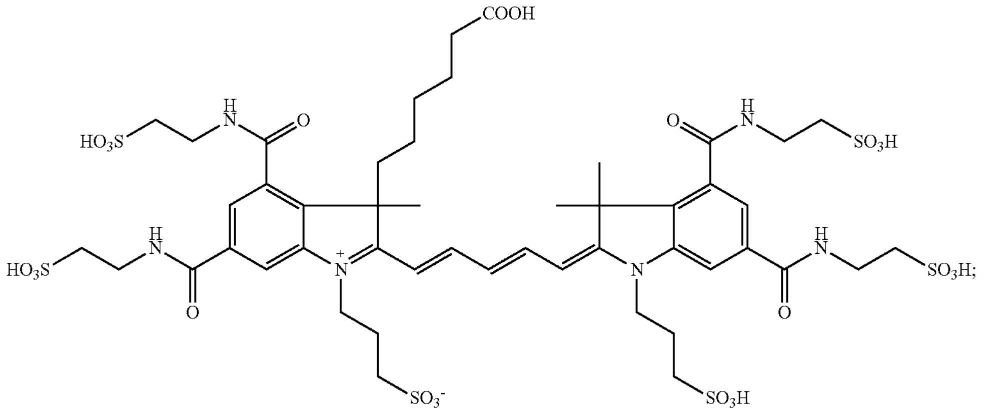

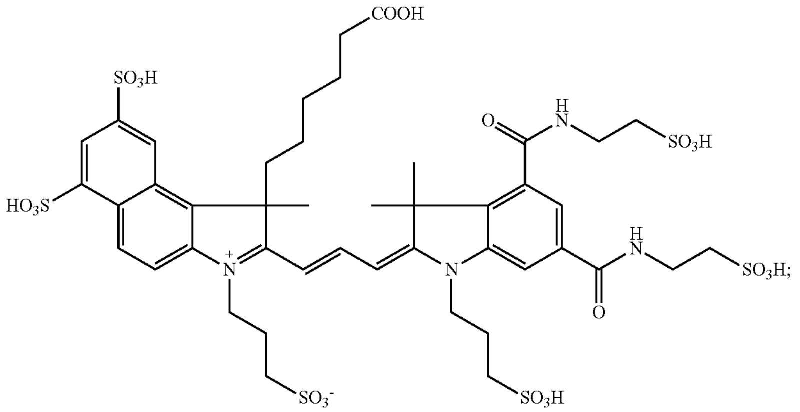

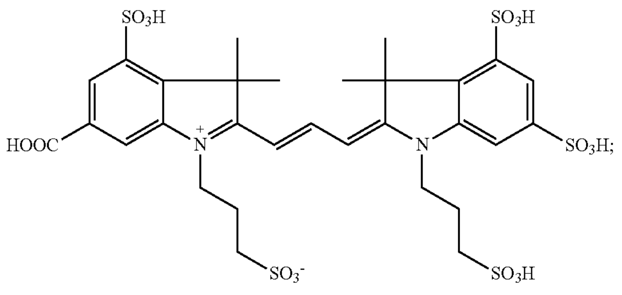

-continued
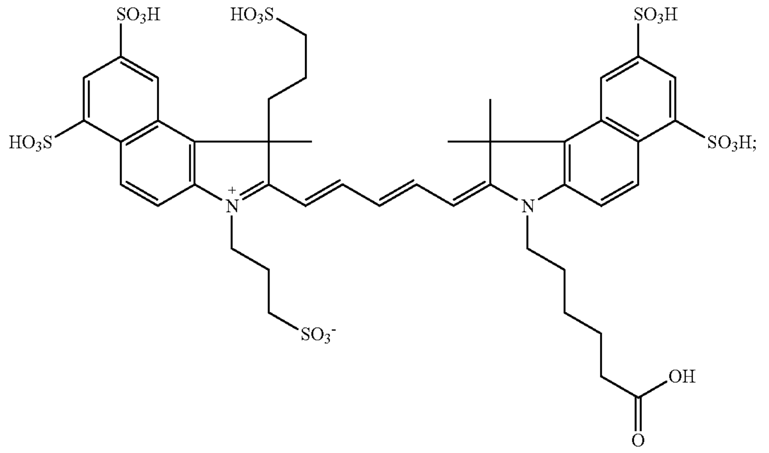
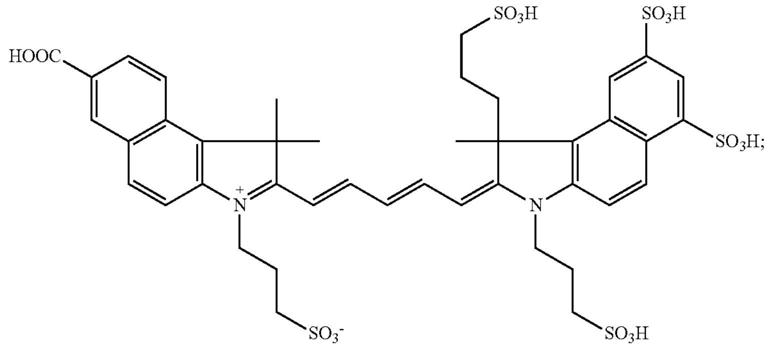
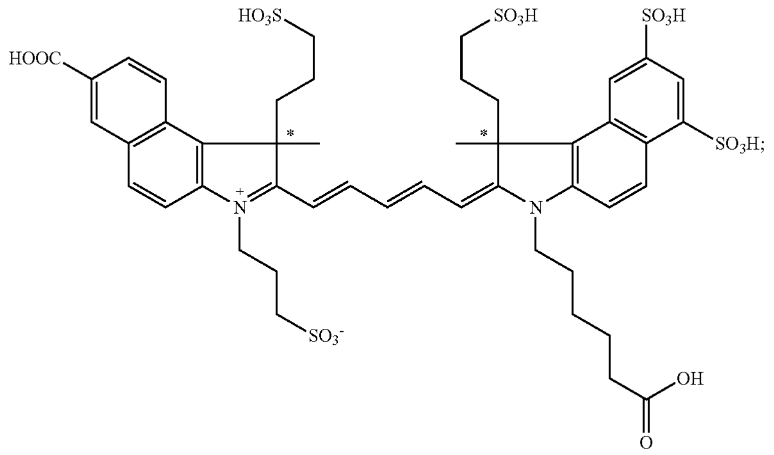
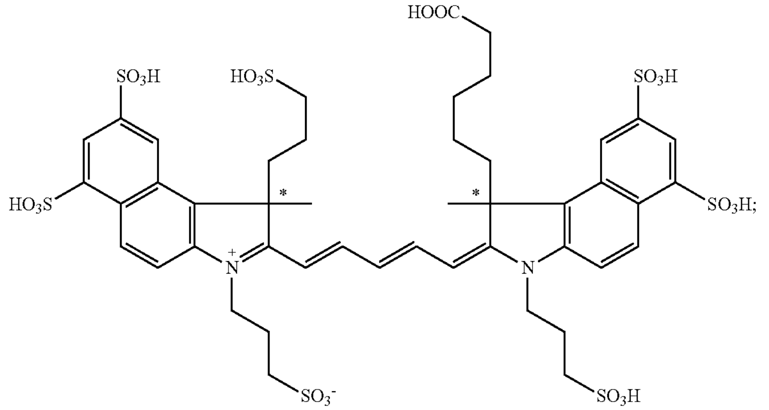

-continued
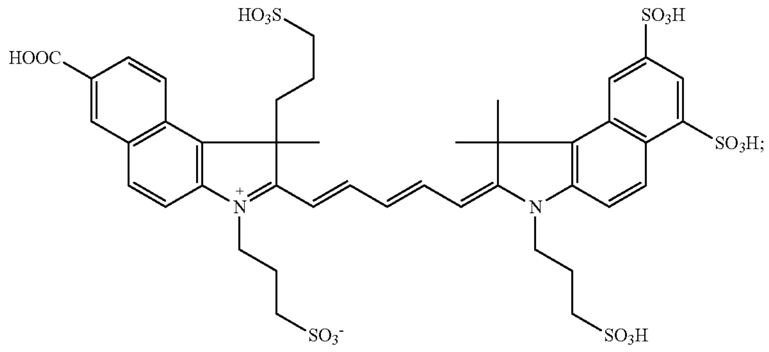
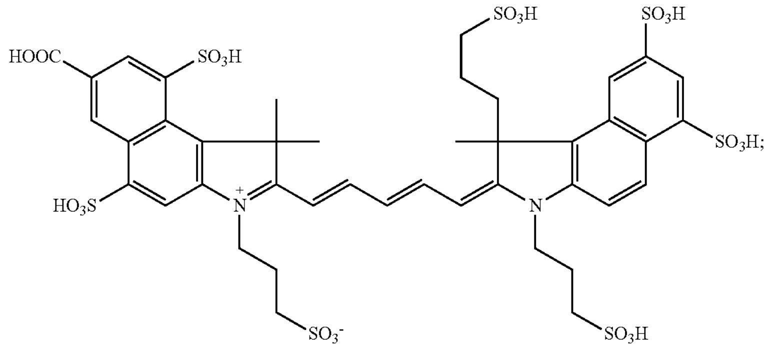
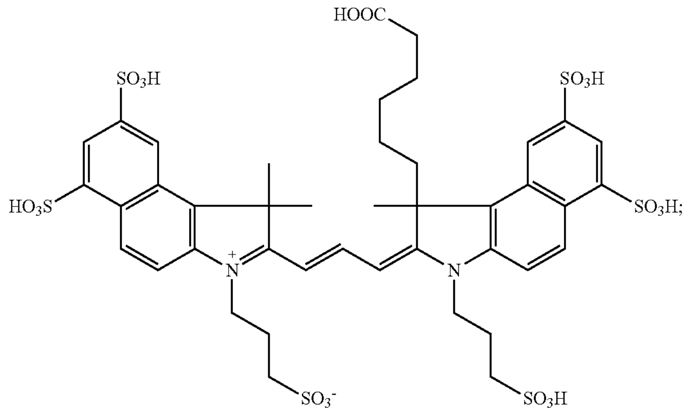
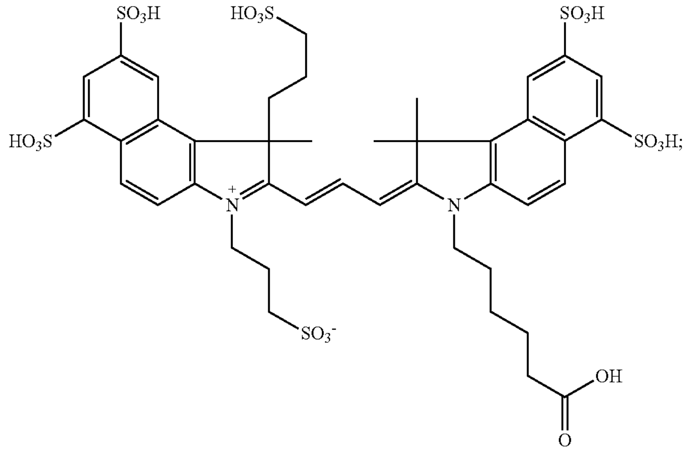

-continued
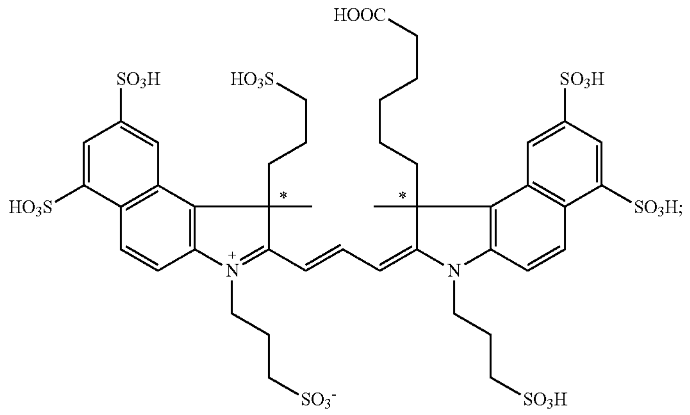
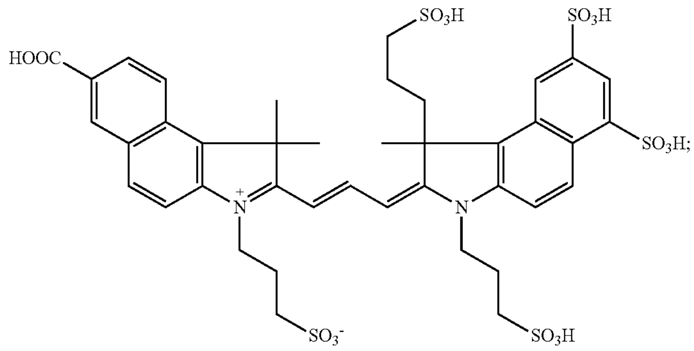
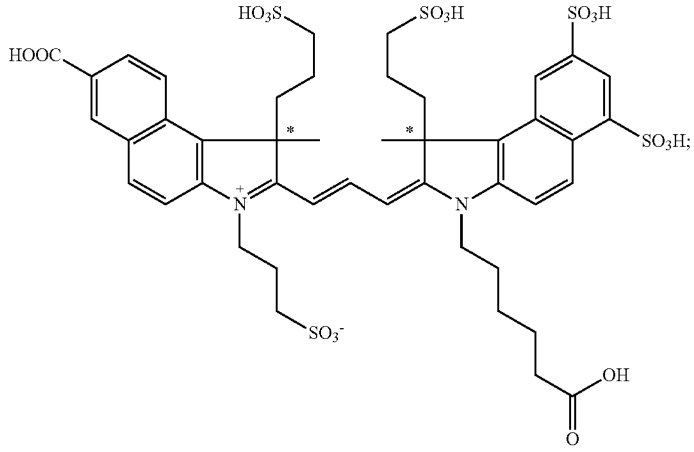
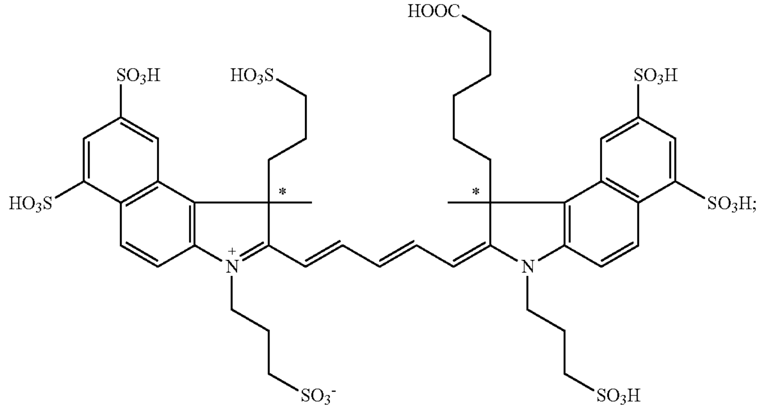

-continued
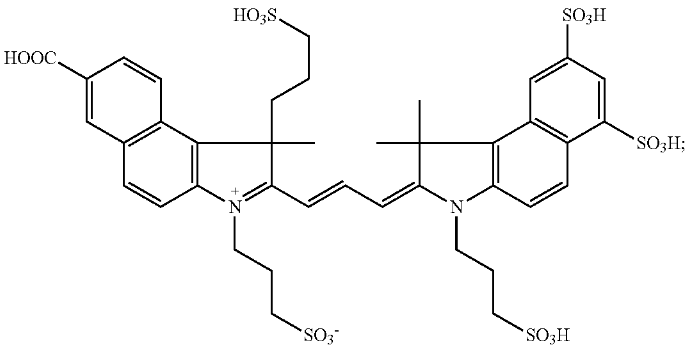
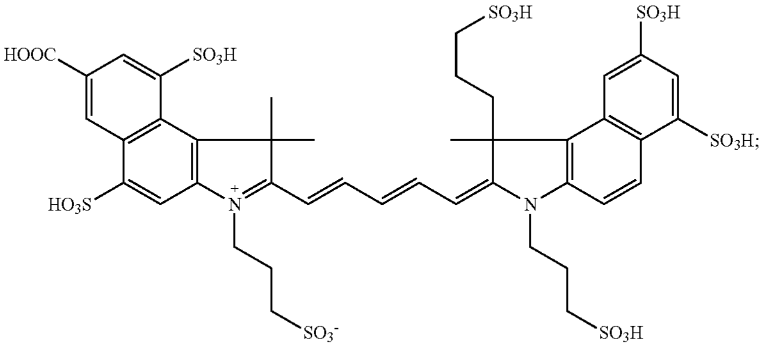
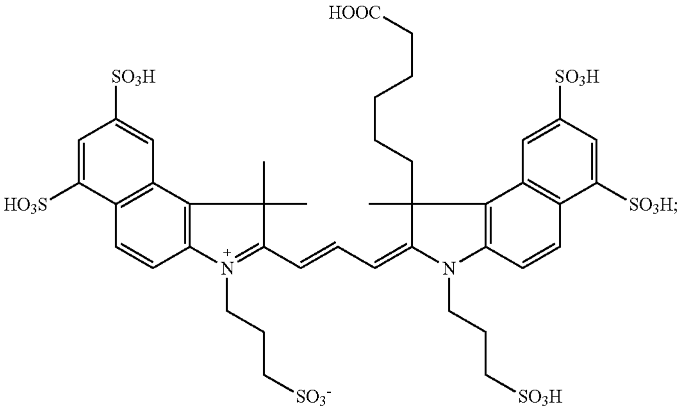
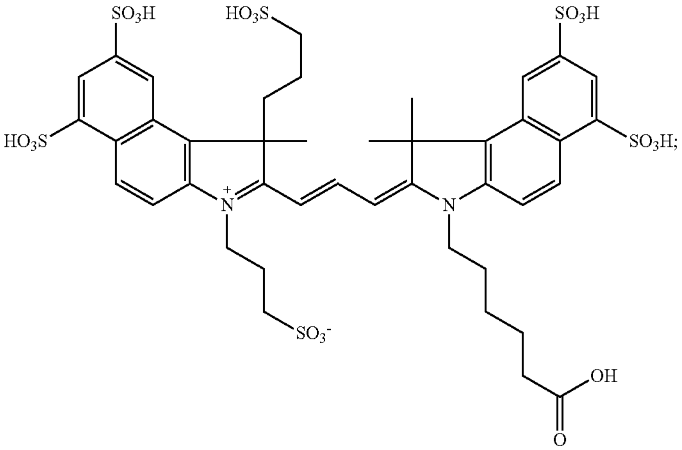

-continued
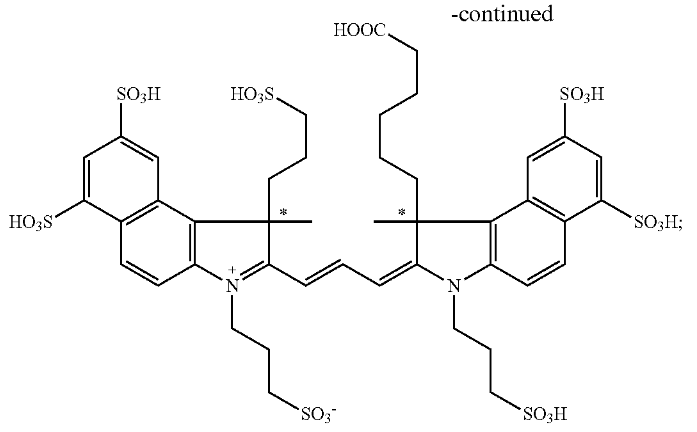
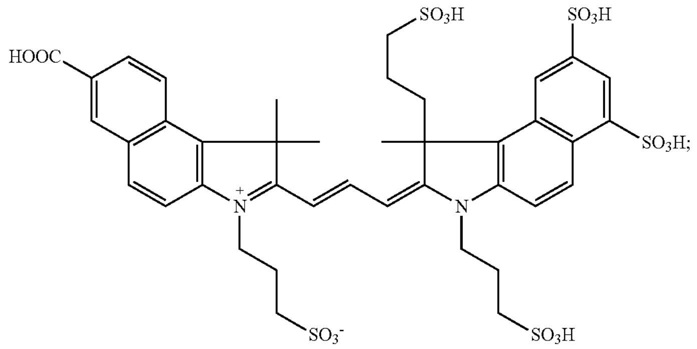
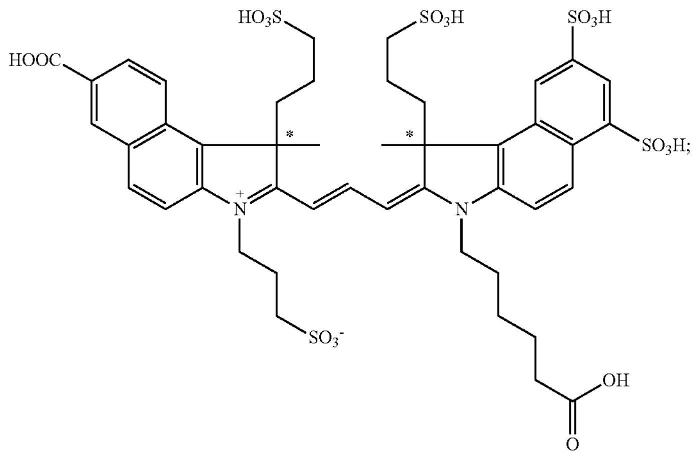

-continued
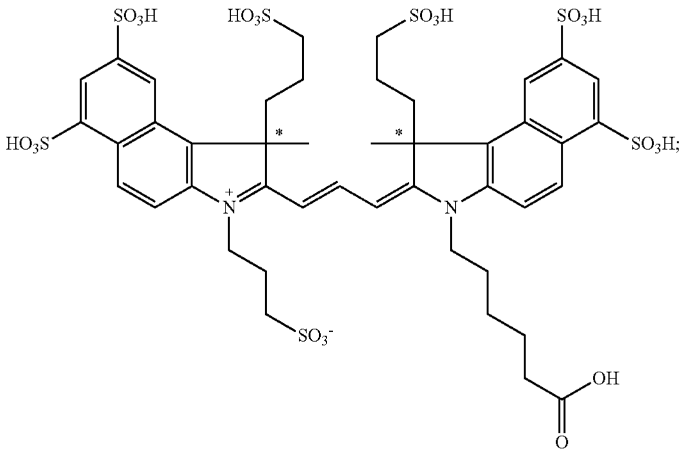
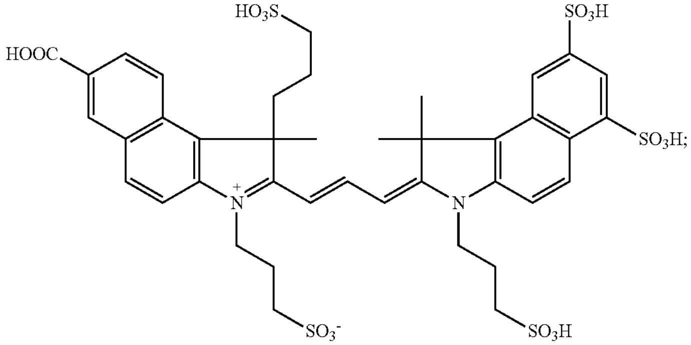
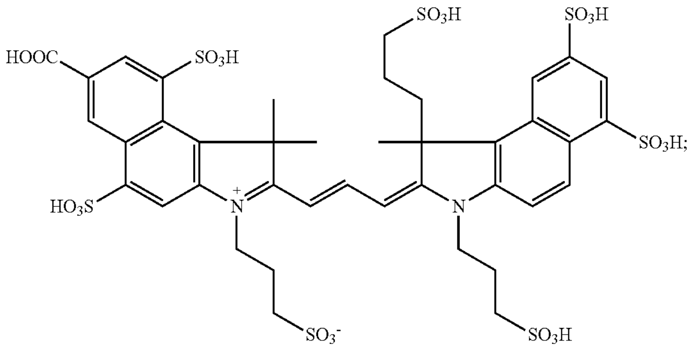
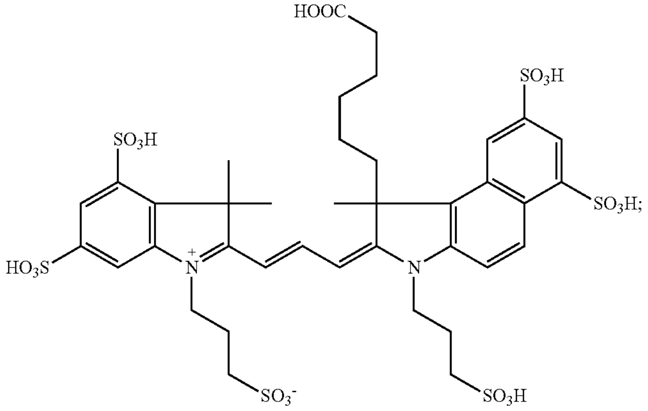

-continued
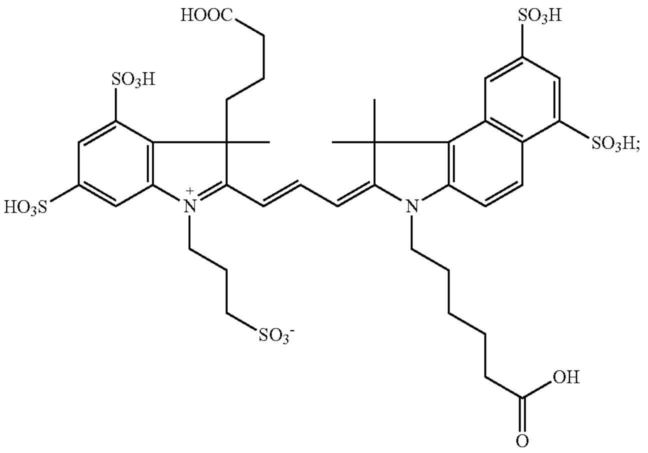
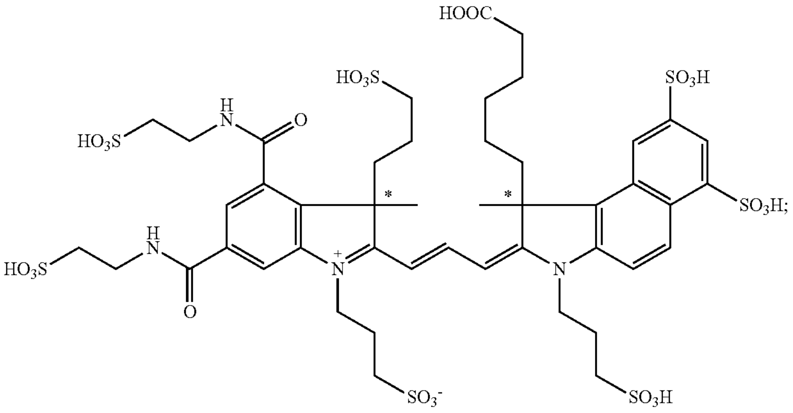
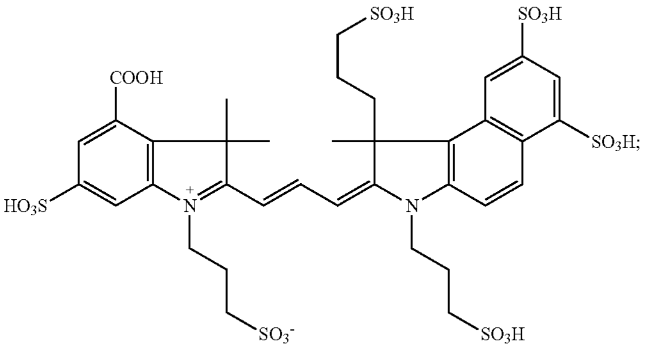
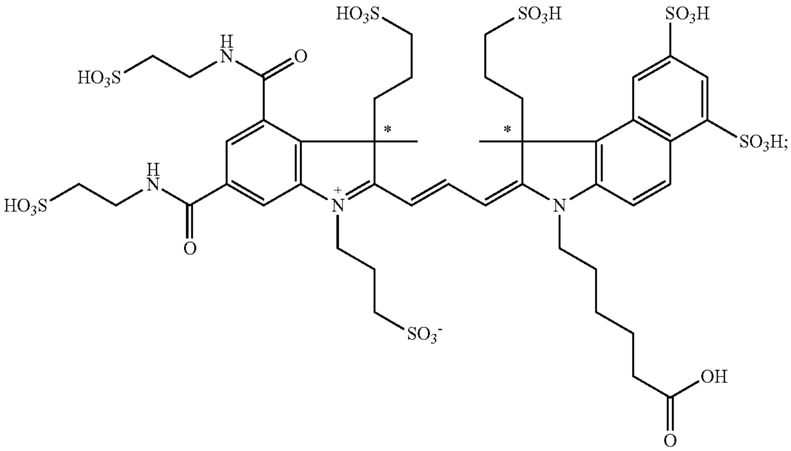

-continued
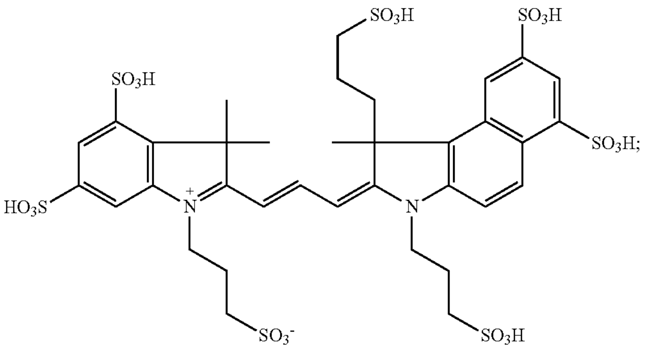
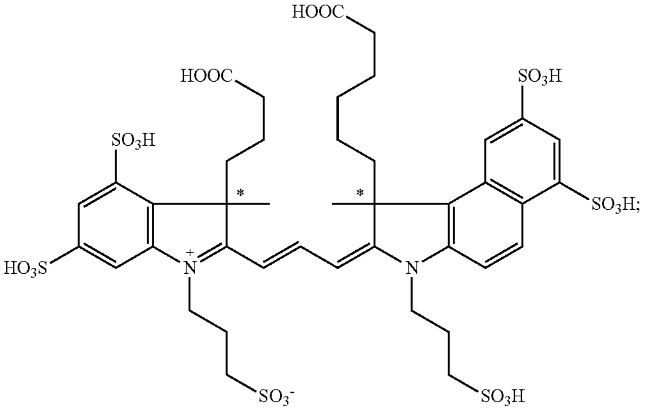
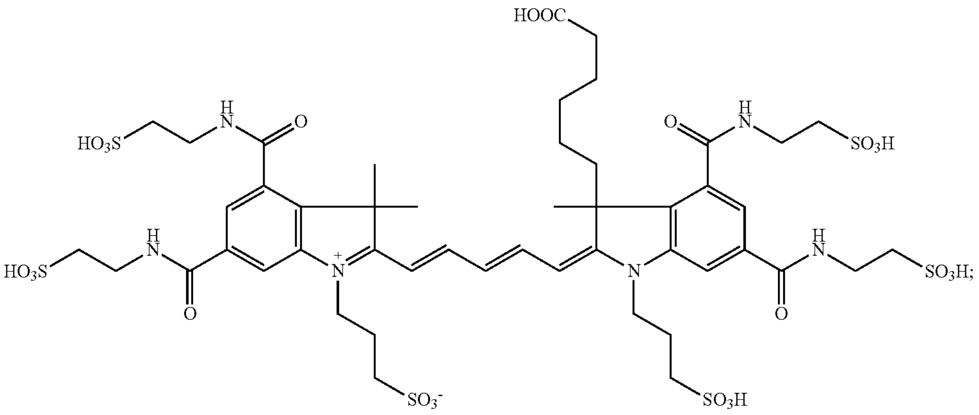
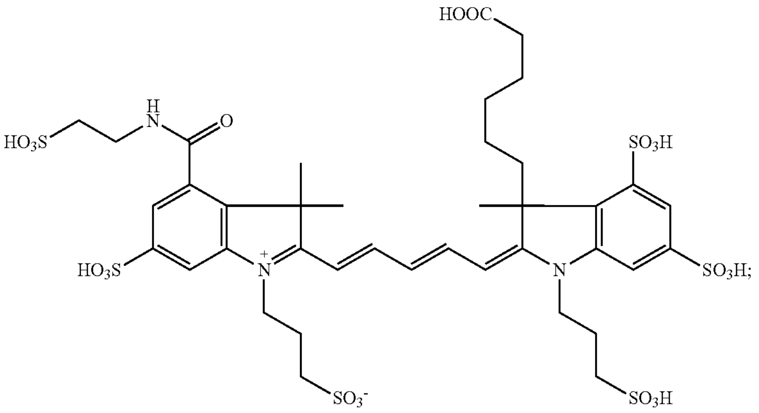

-continued
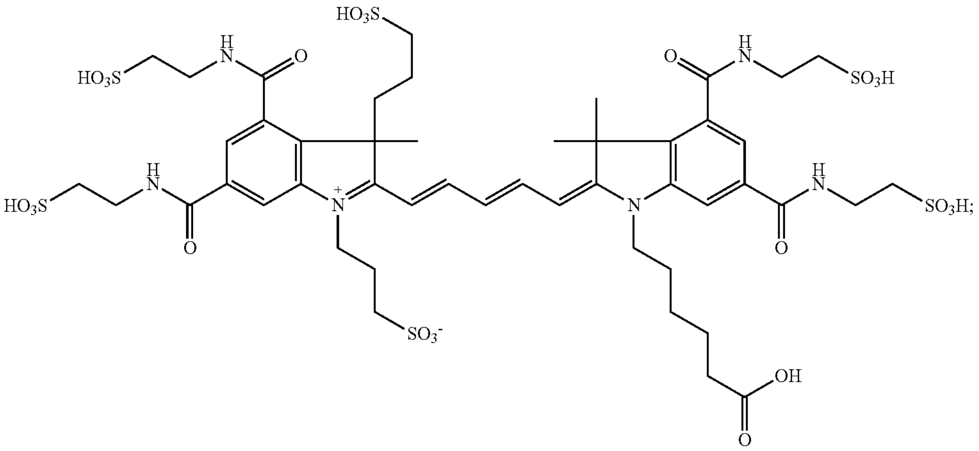
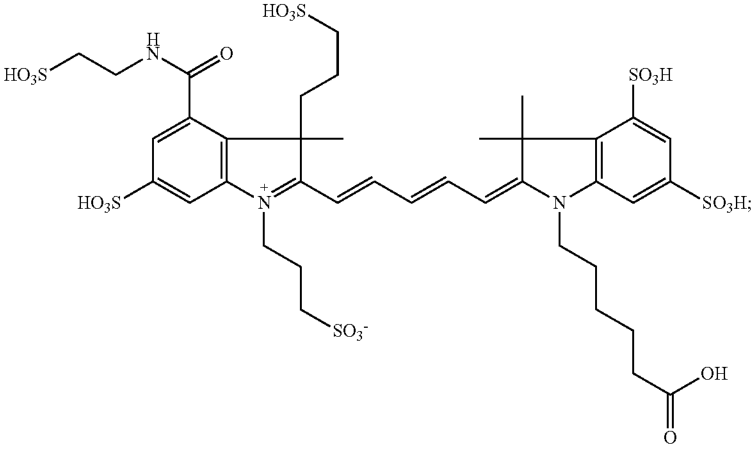
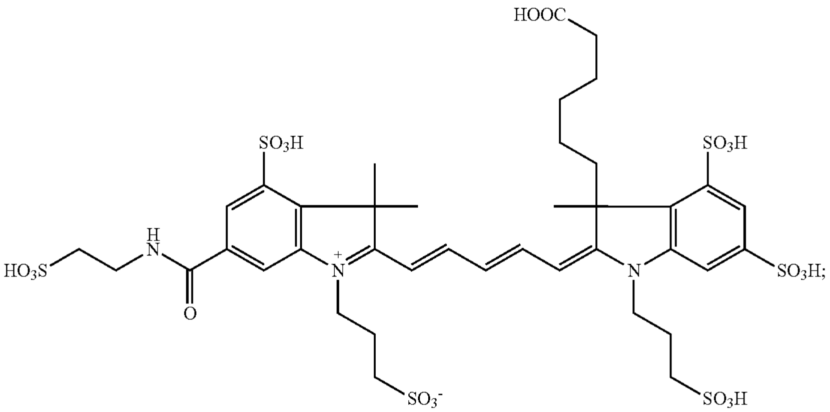
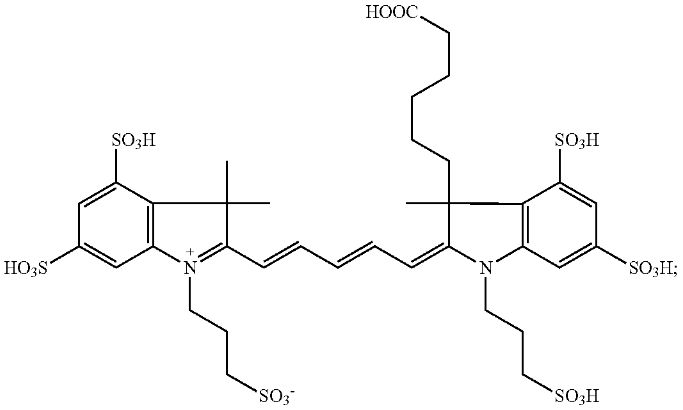

-continued
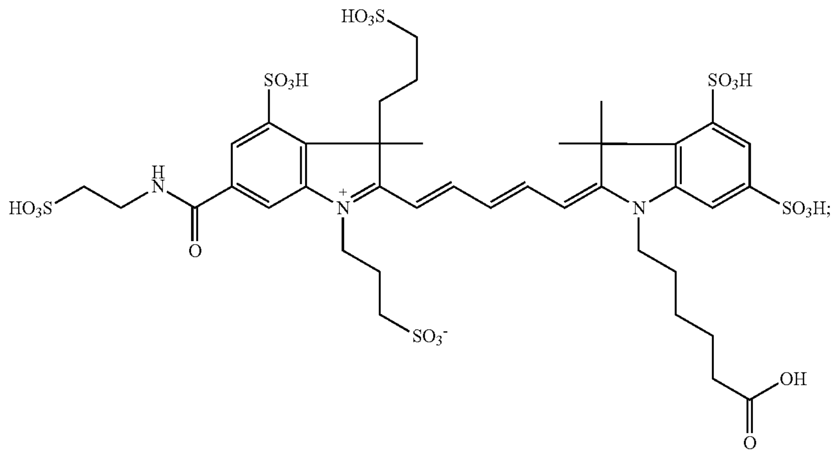
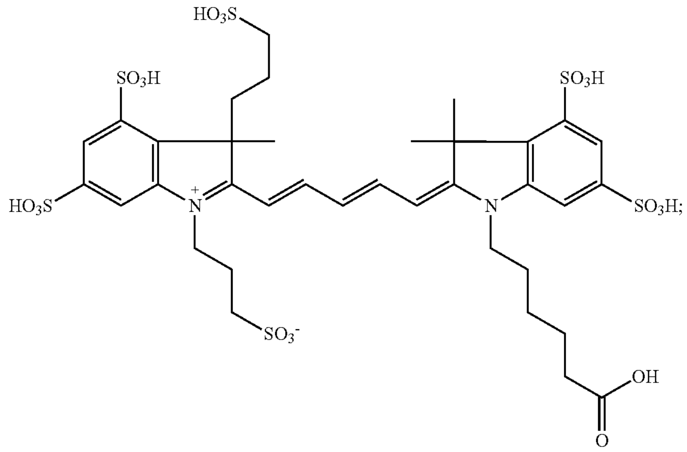
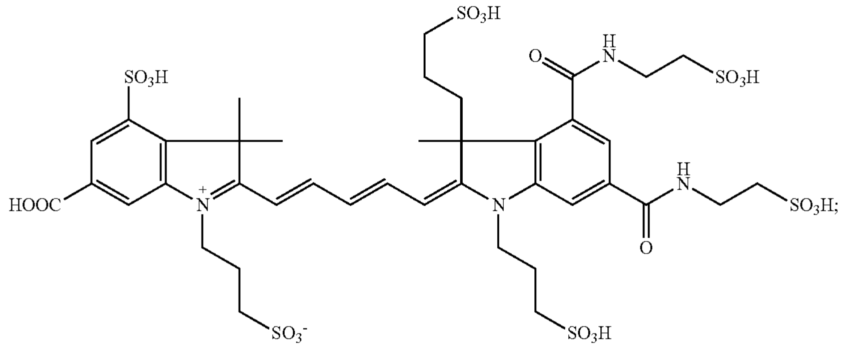
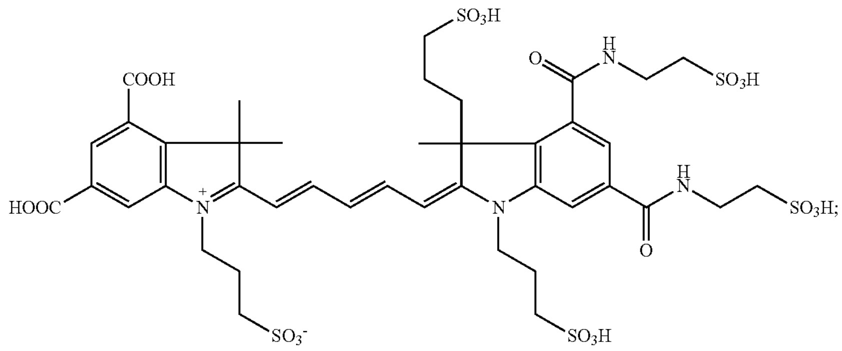

-continued
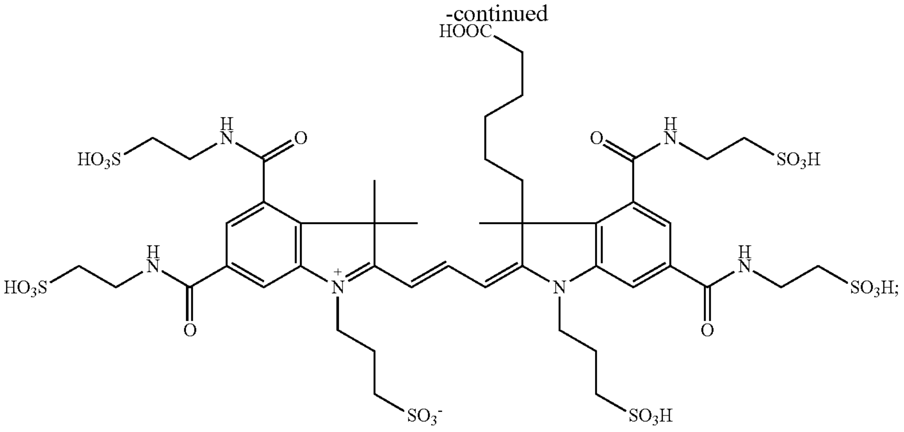
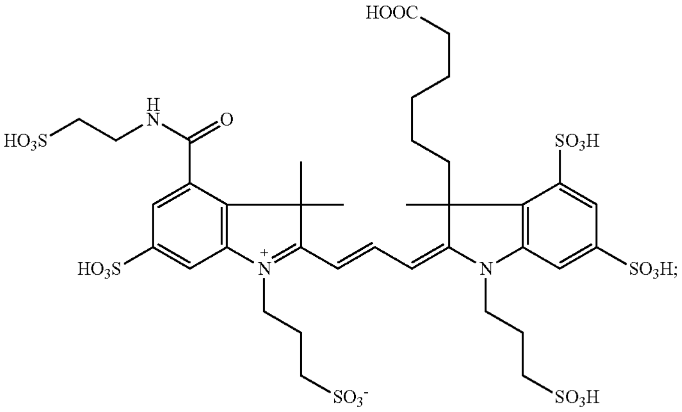
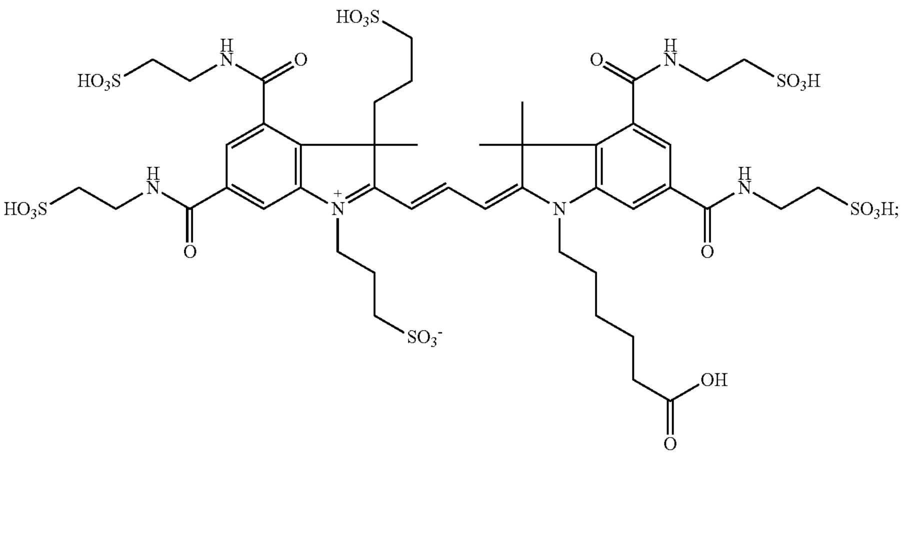

-continued
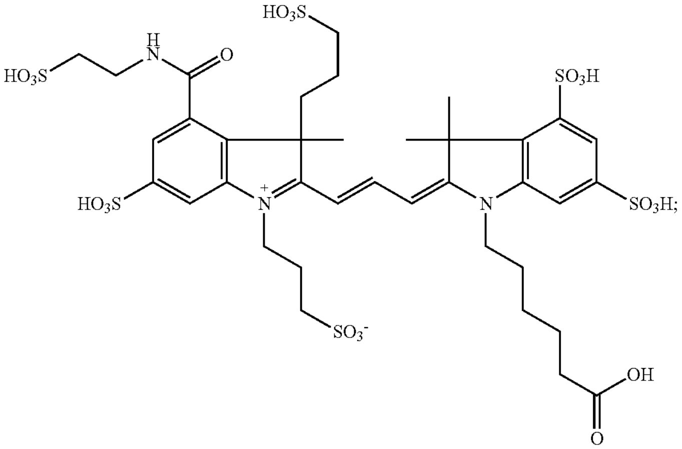
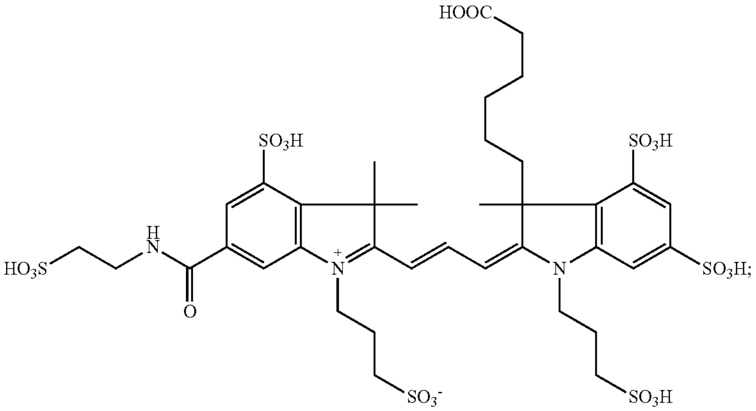
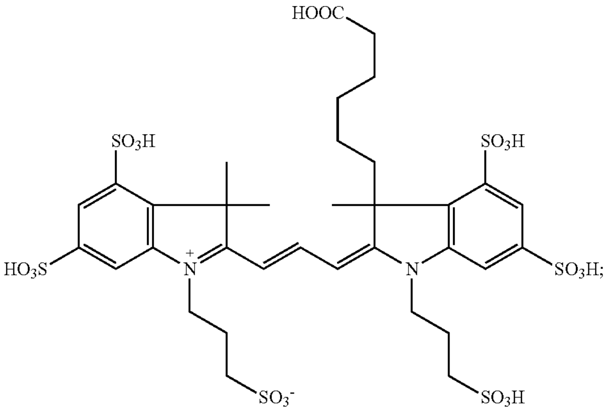
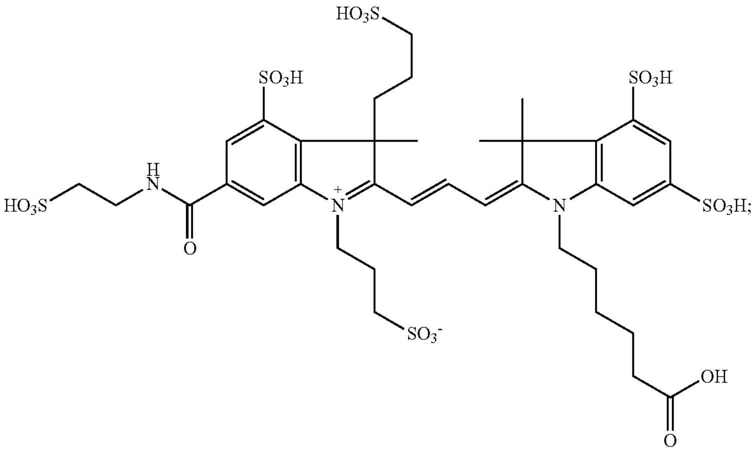

-continued
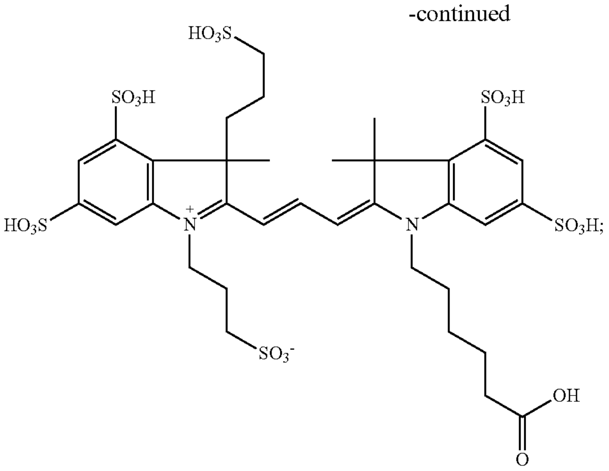
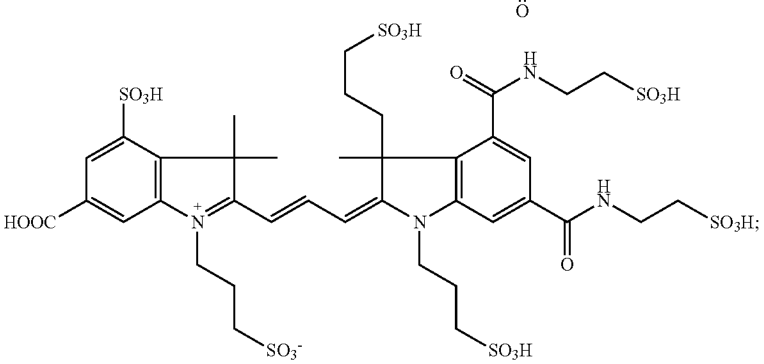
or
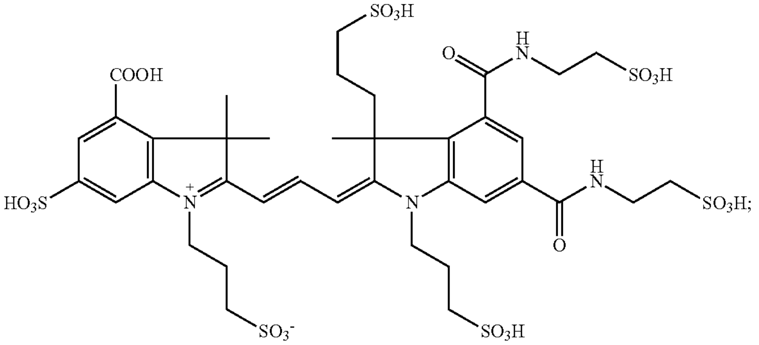
or a salt thereof.
15. The compound of claim 1, wherein the compound is
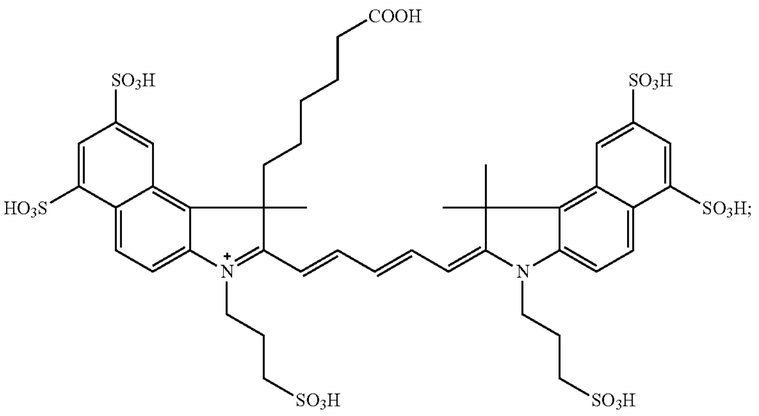

-continued
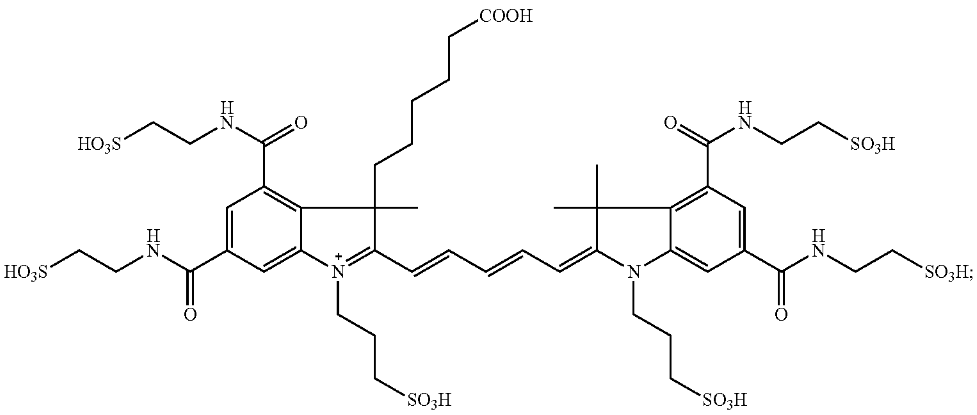
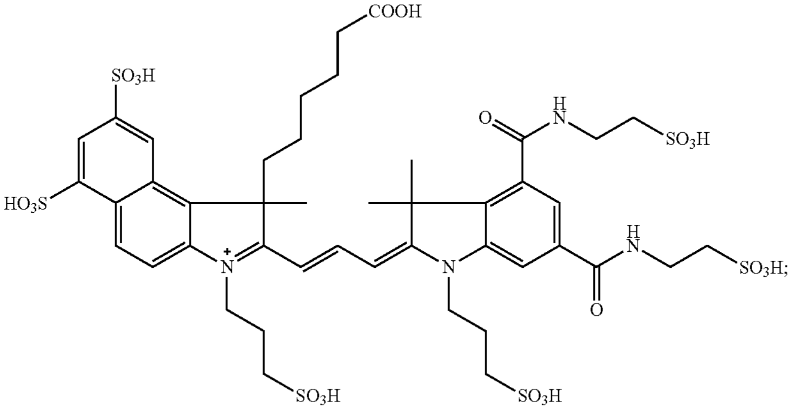
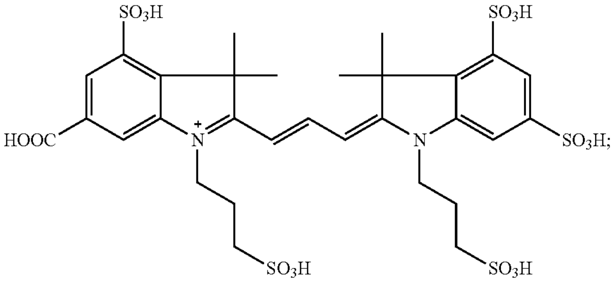
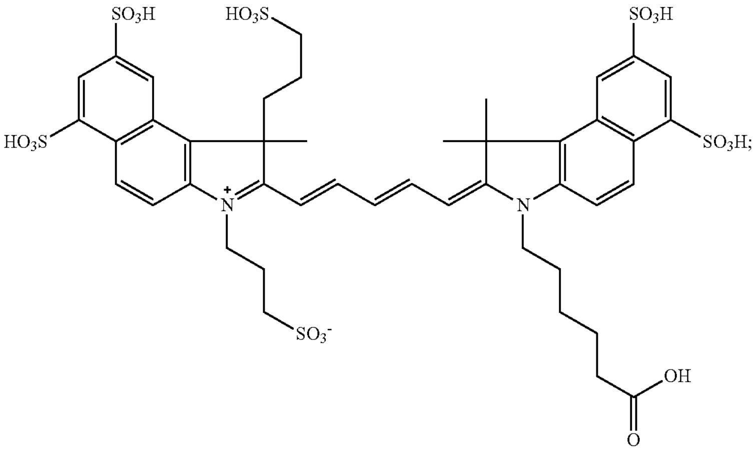

-continued
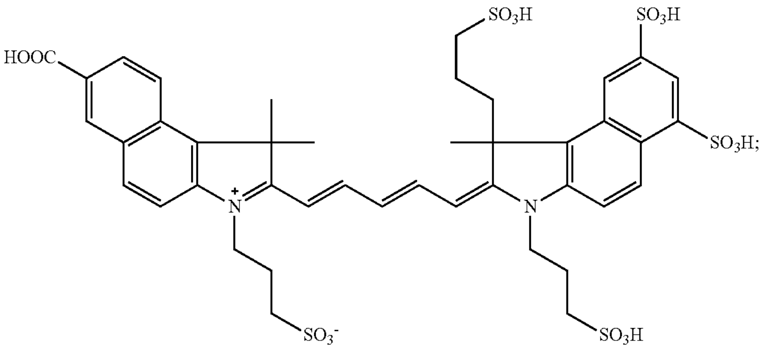
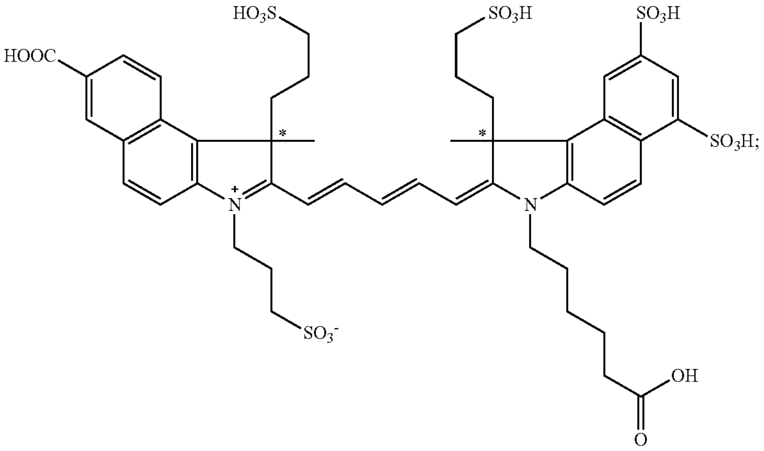
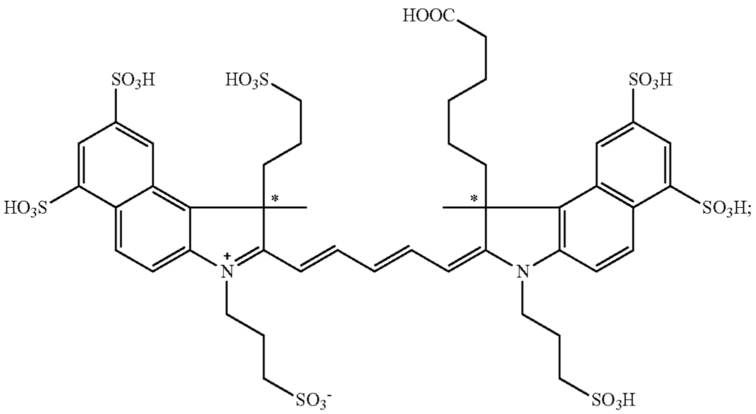
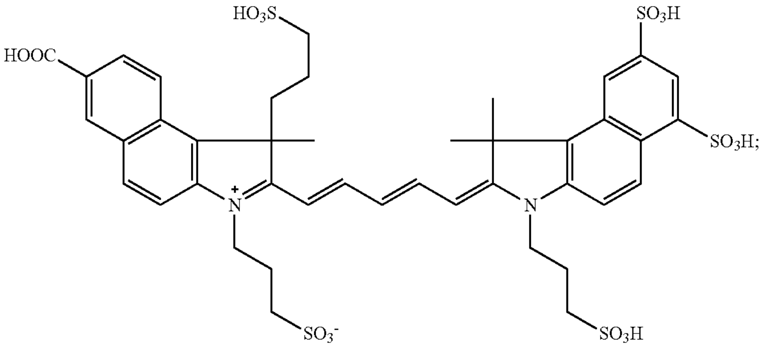

-continued
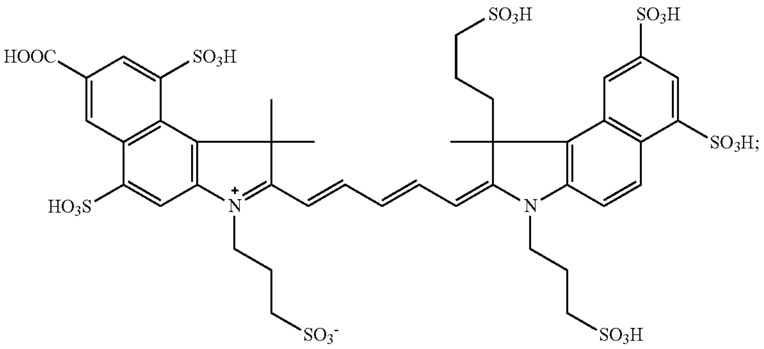
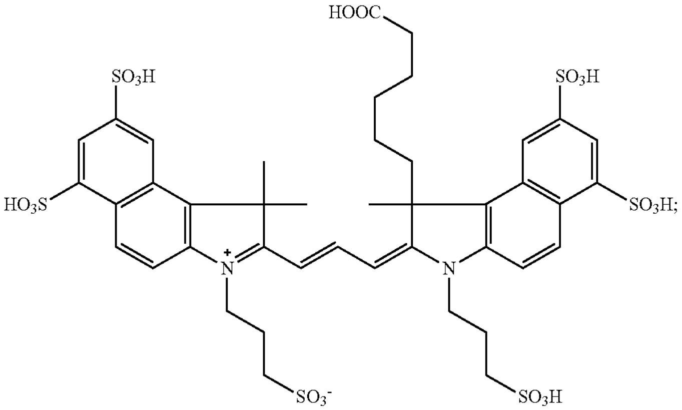
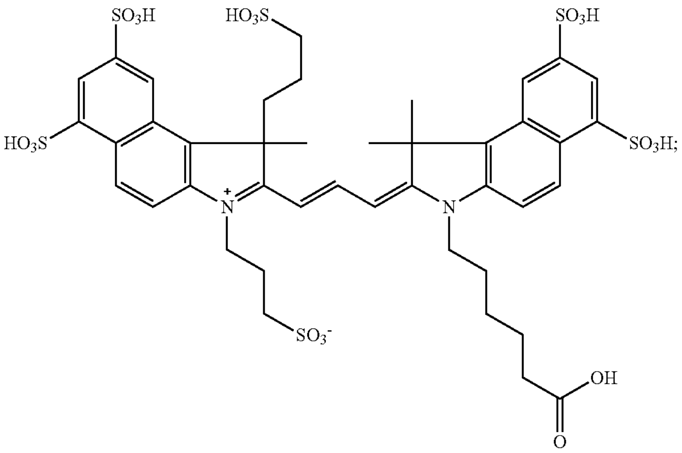
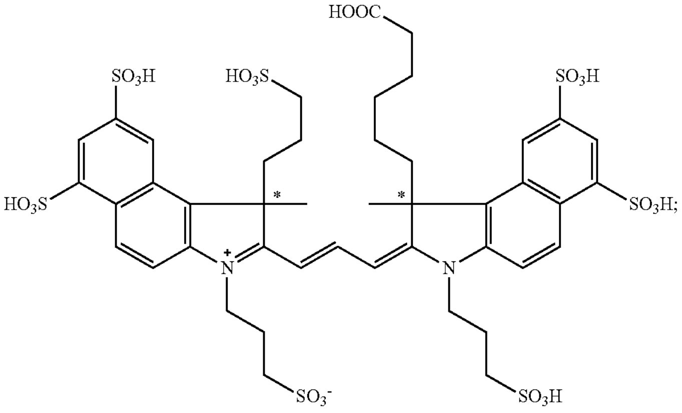

-continued
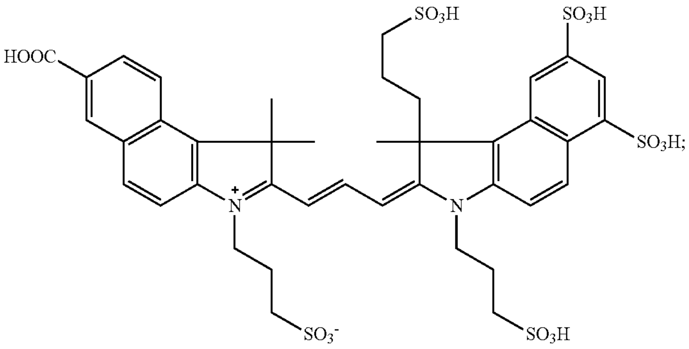
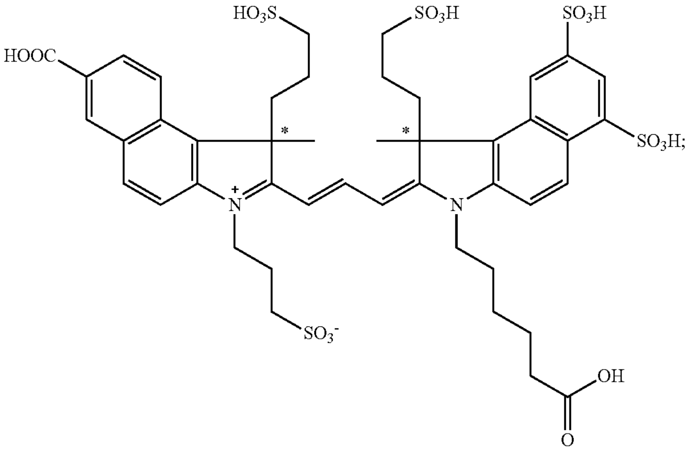
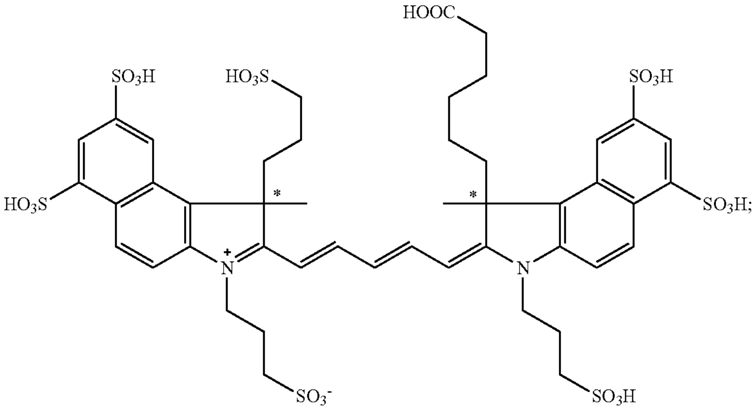
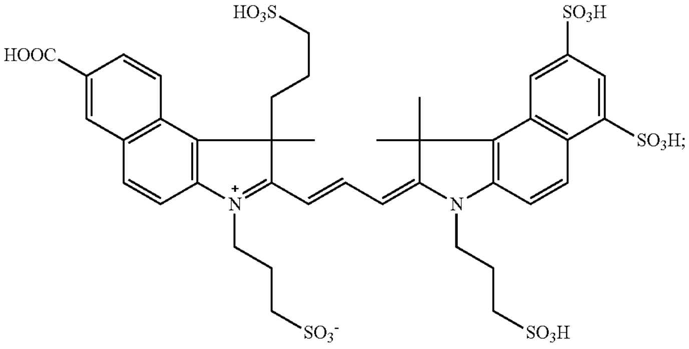

-continued
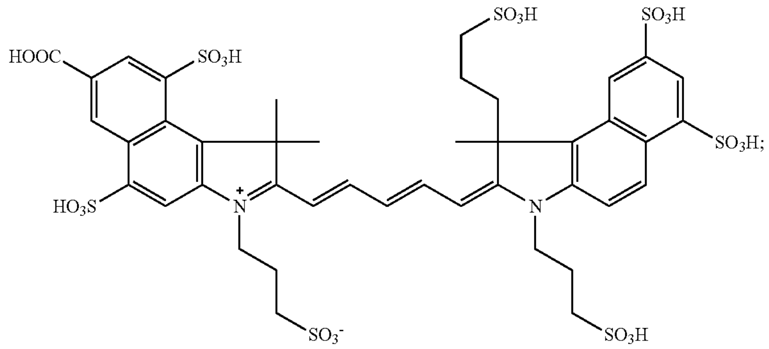
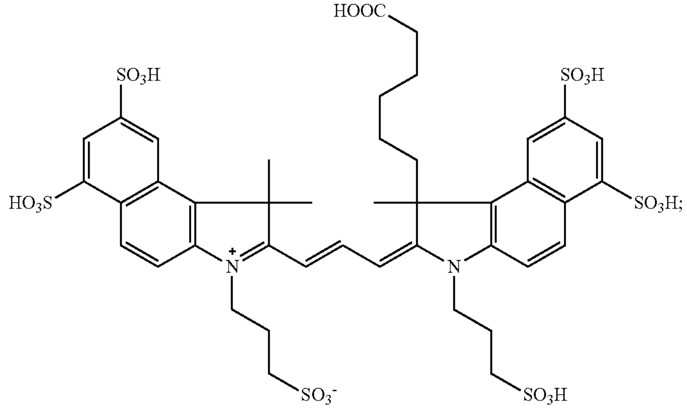
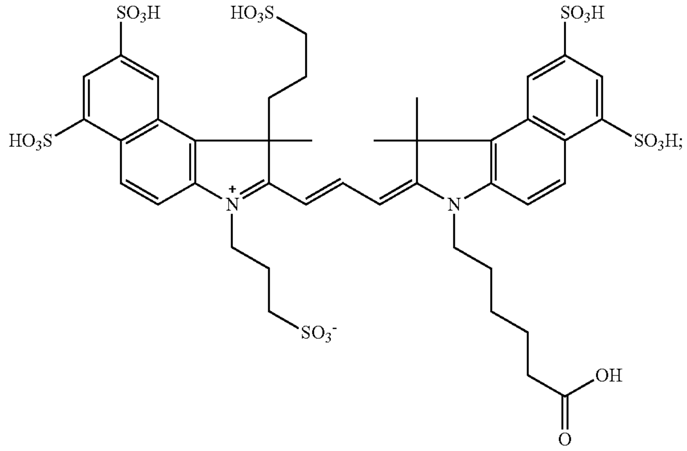
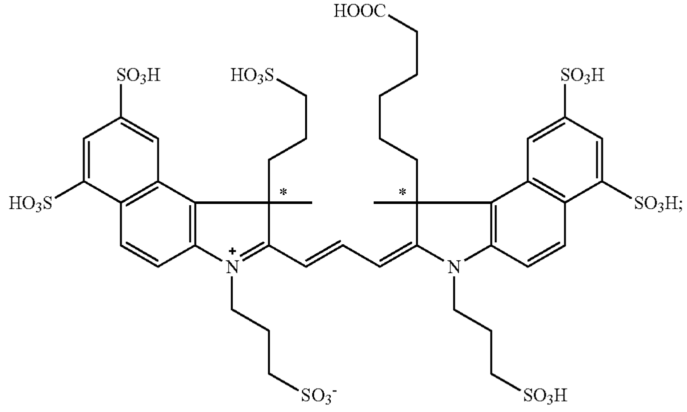

-continued
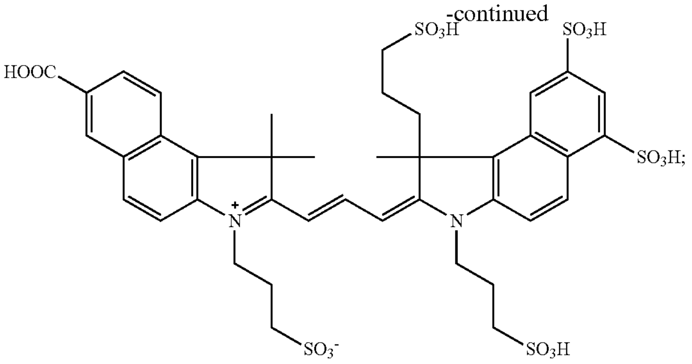
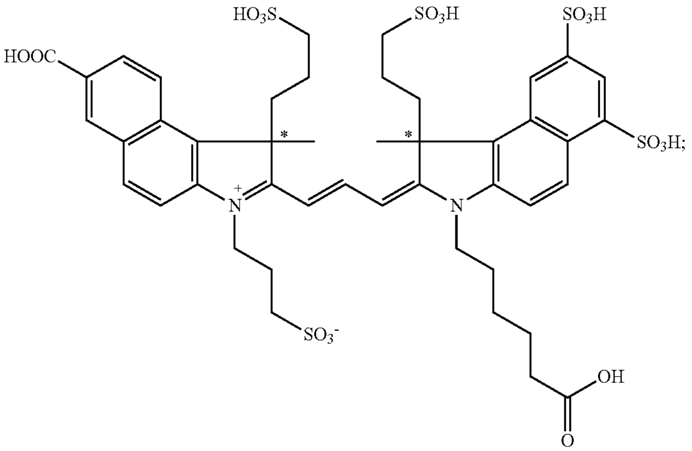
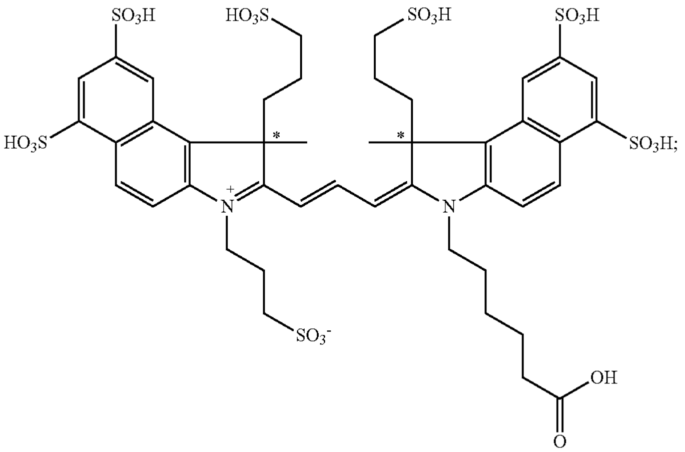
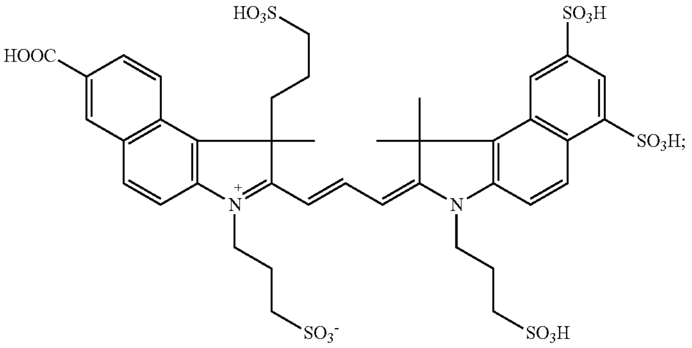

-continued
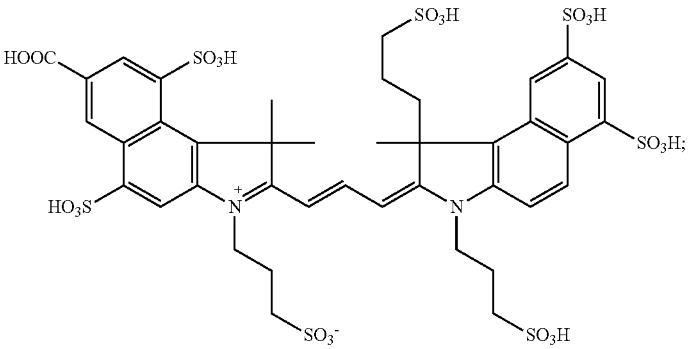
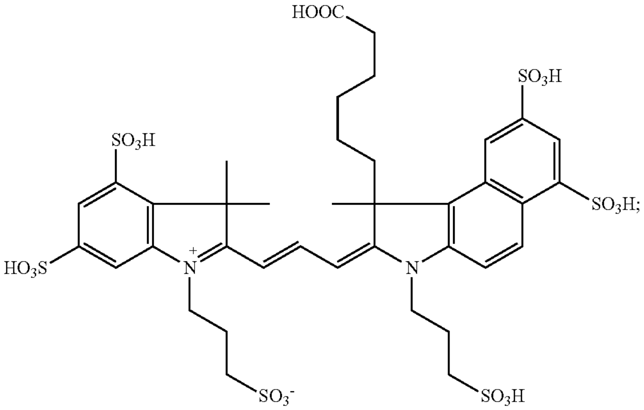
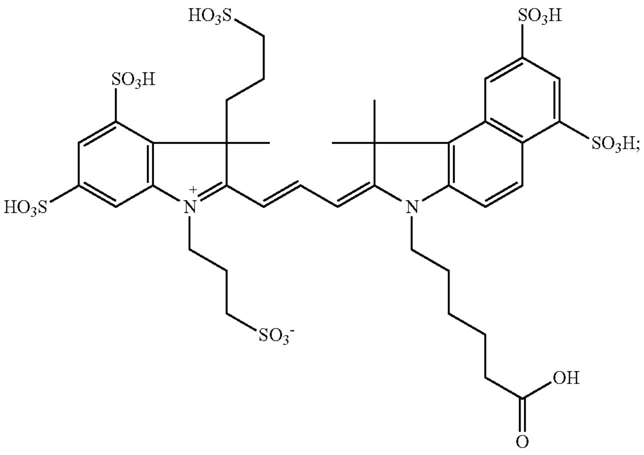
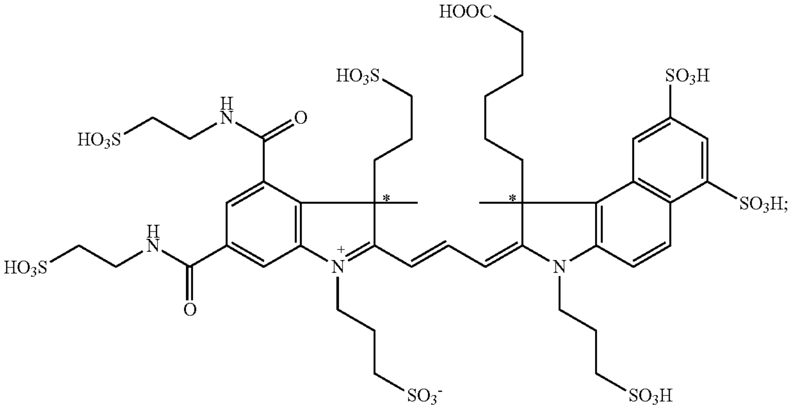

-continued
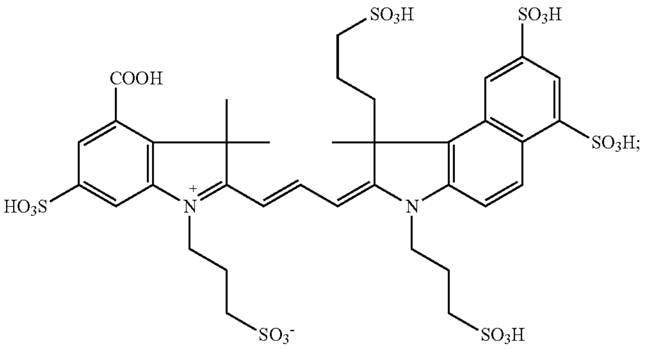
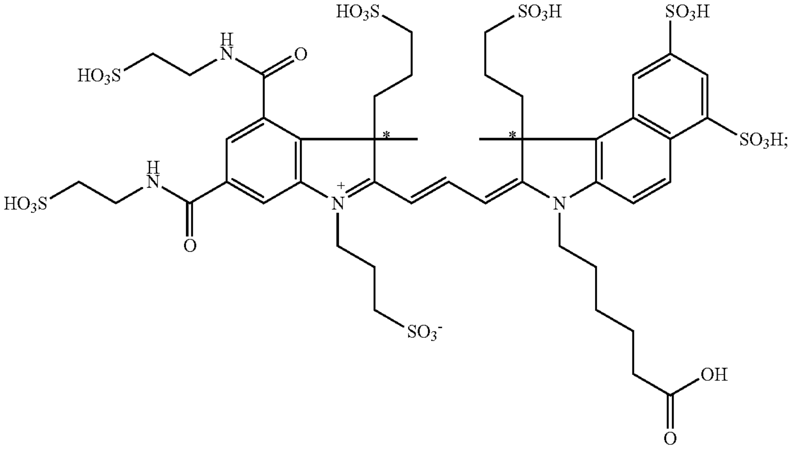
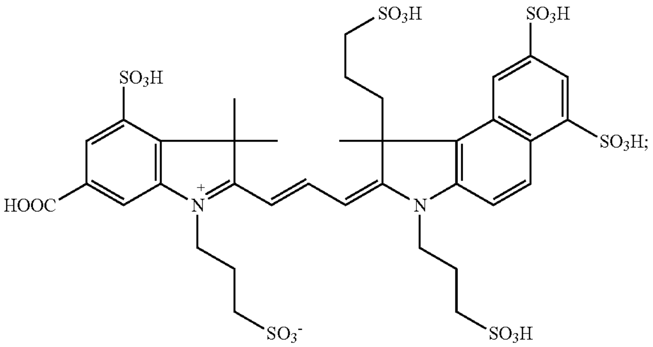
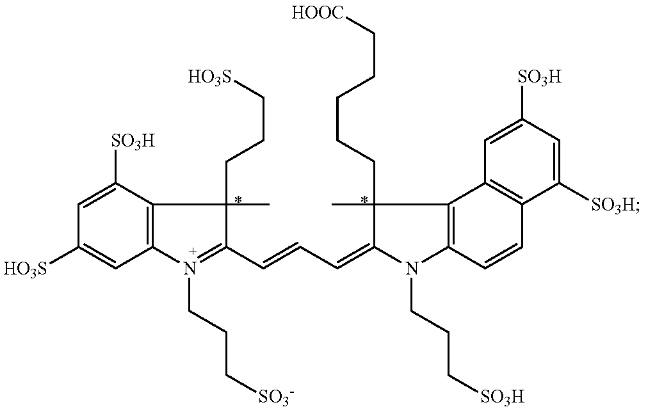

-continued
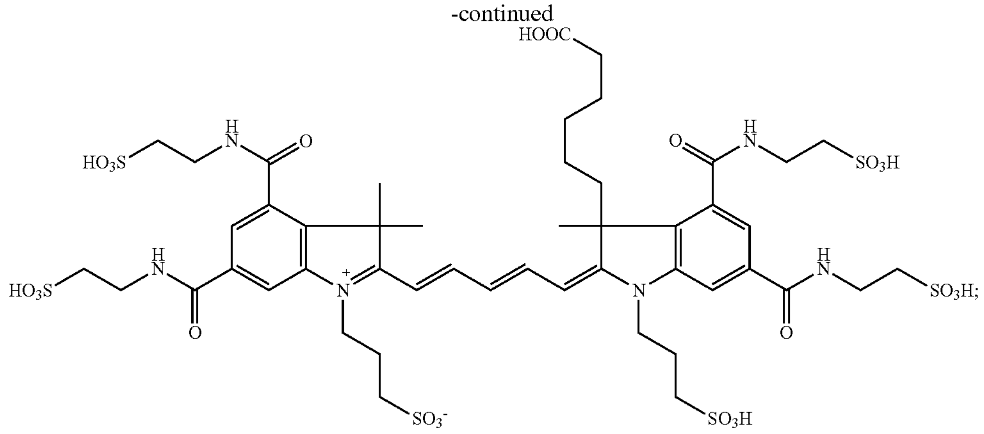
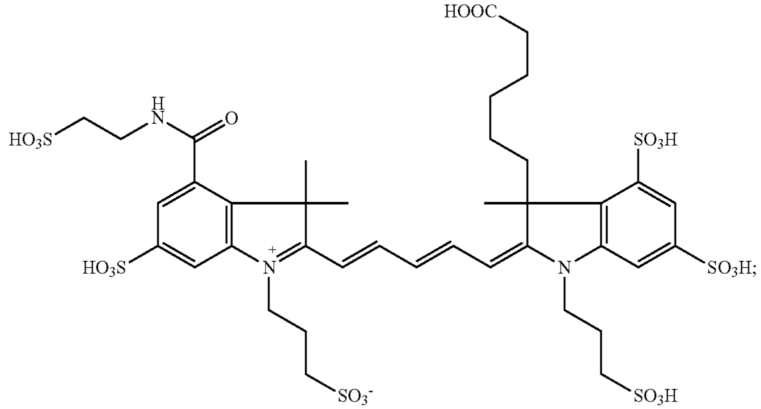
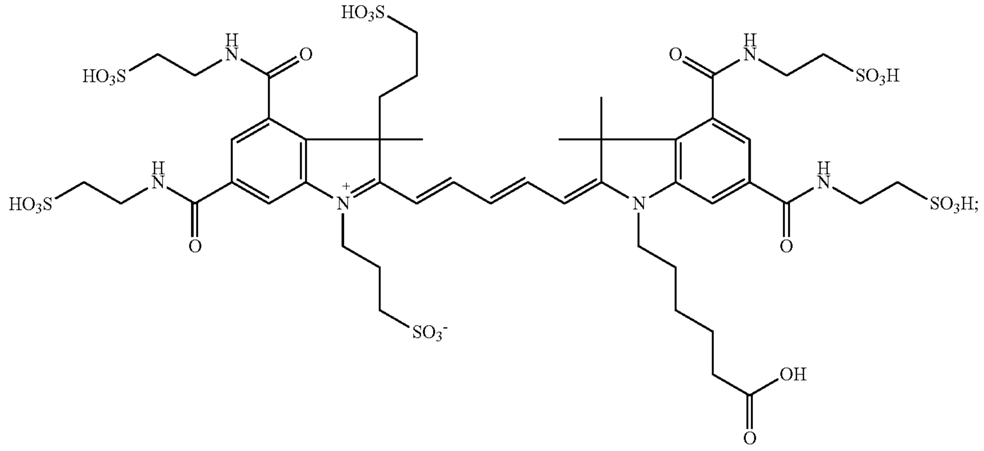
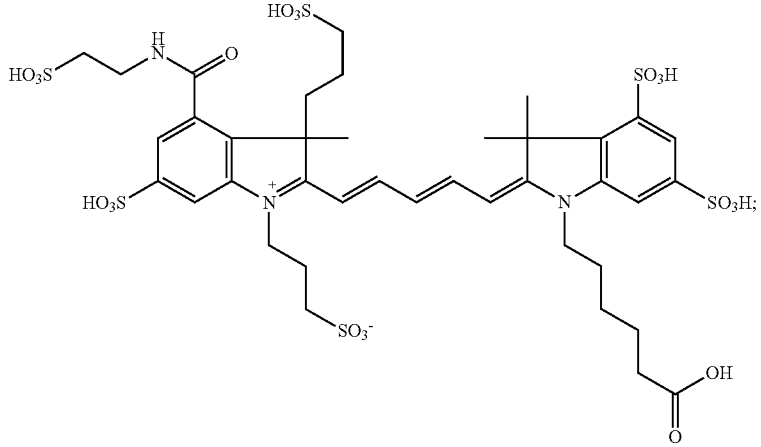

-continued
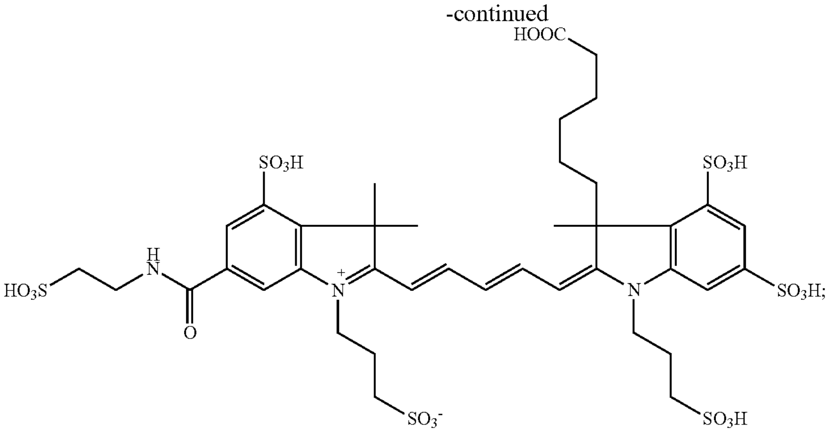
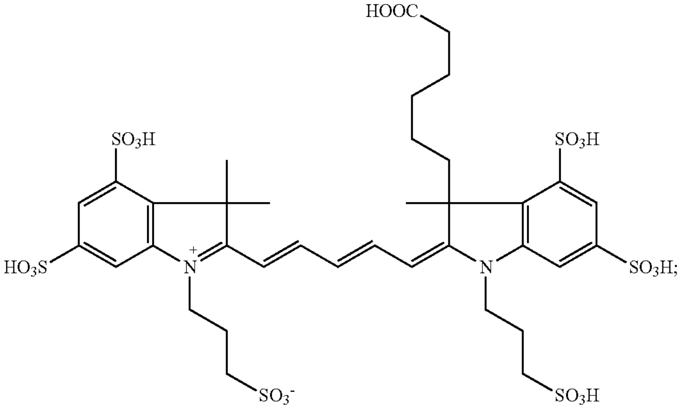
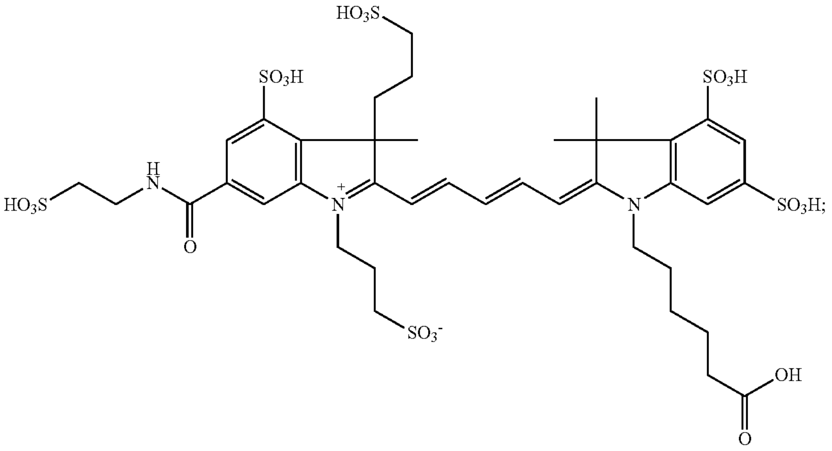
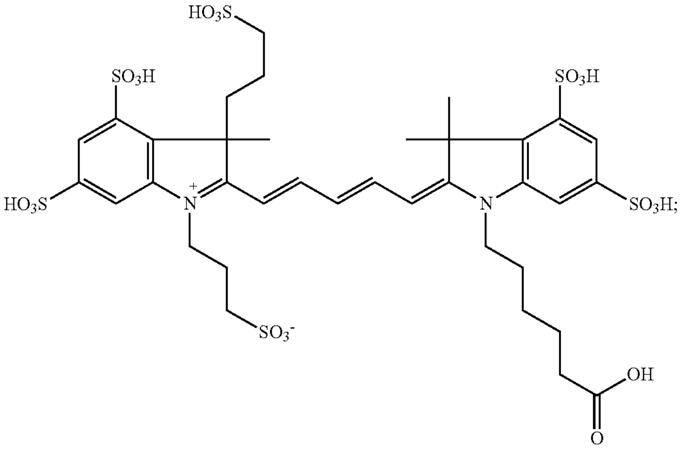

-continued
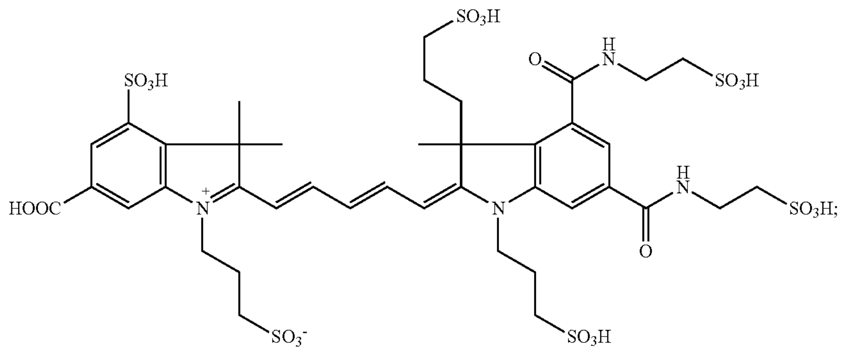
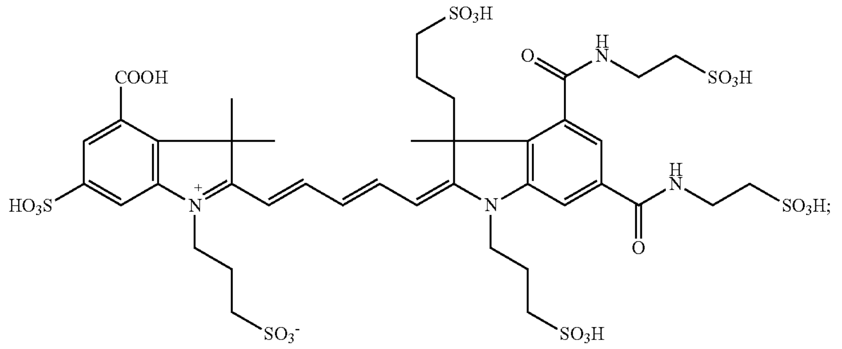
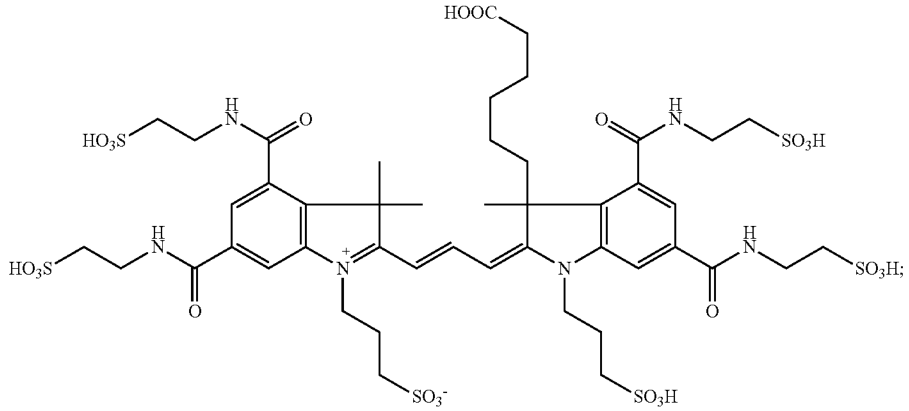
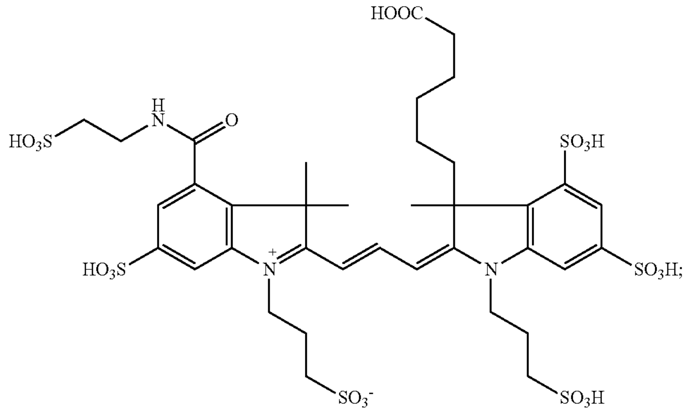

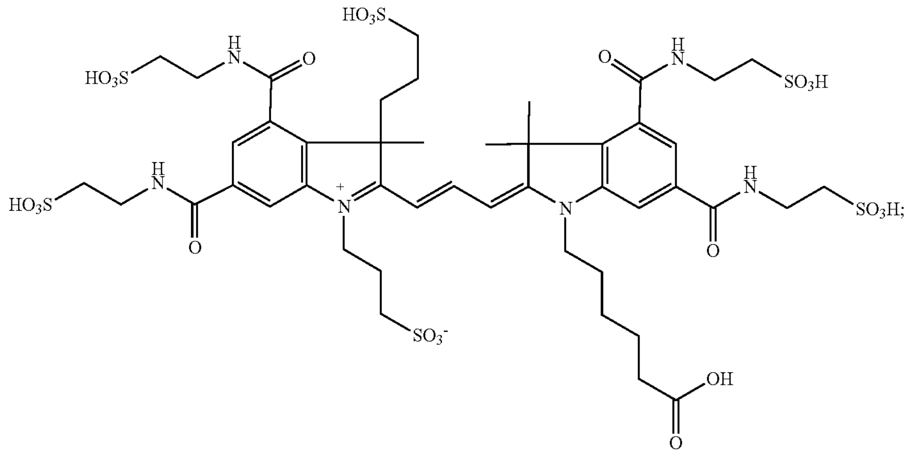
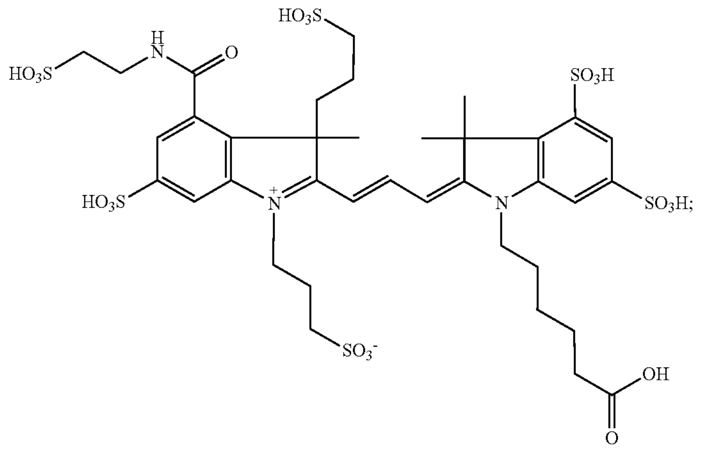
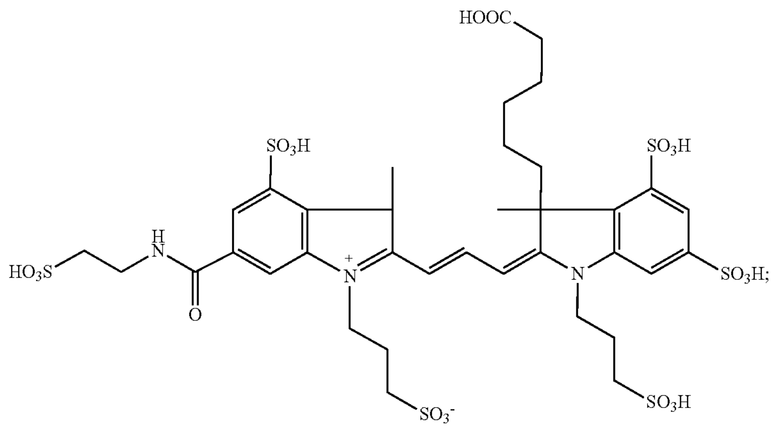

-continued
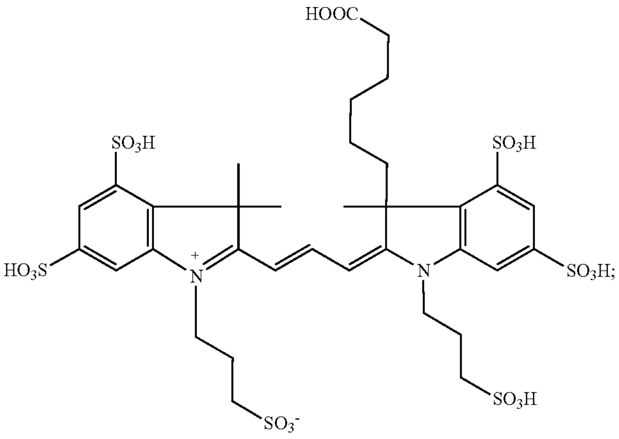
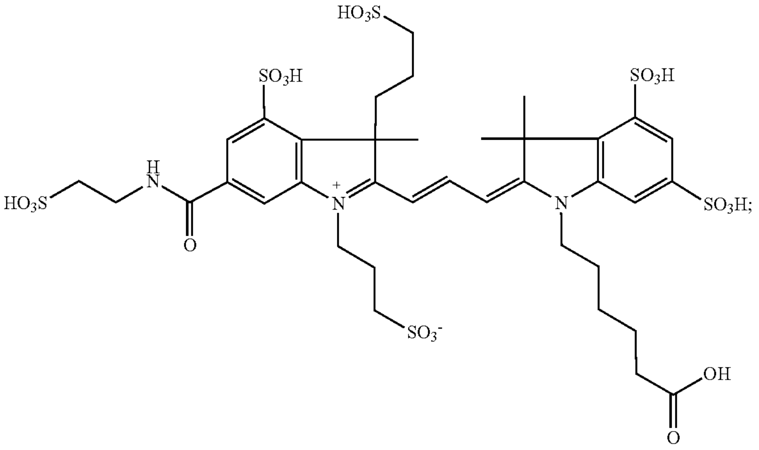
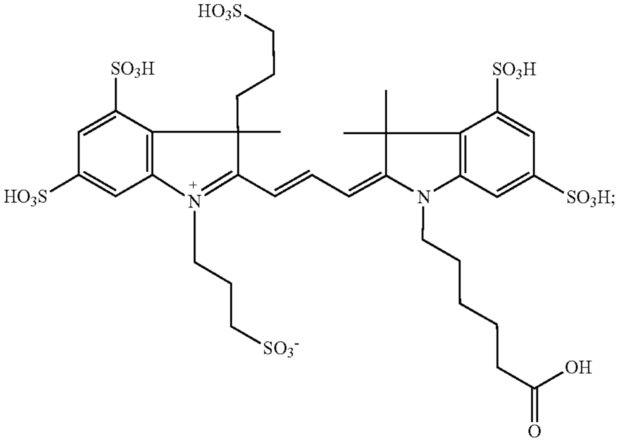
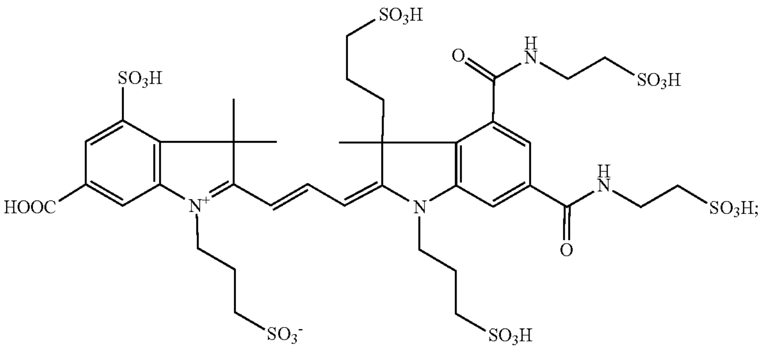 or

-continued
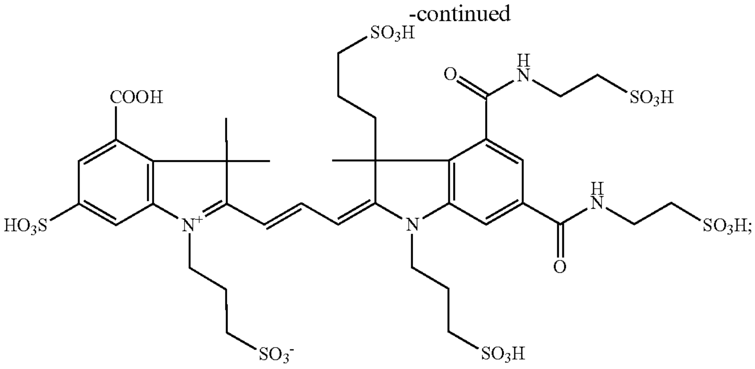
or an ionic derivative thereof.
16. The compound of claim 1, wherein the compound is
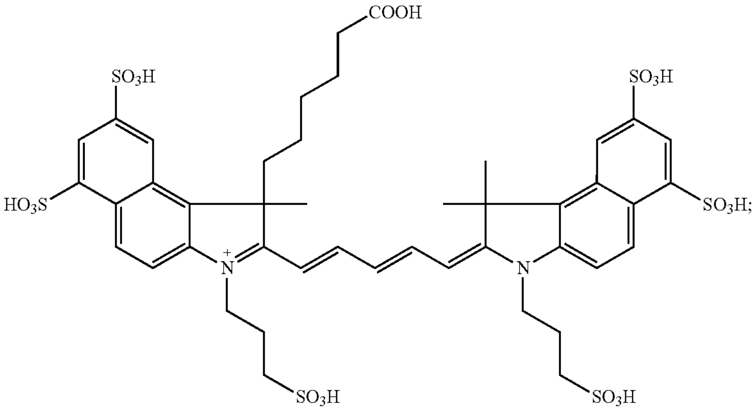
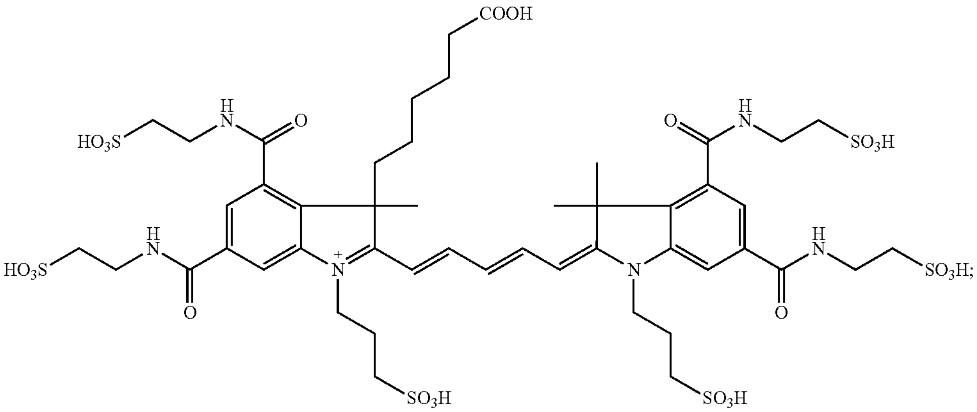
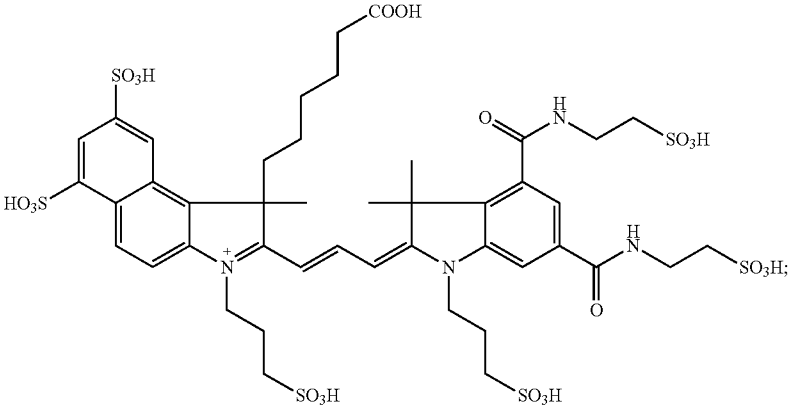

-continued
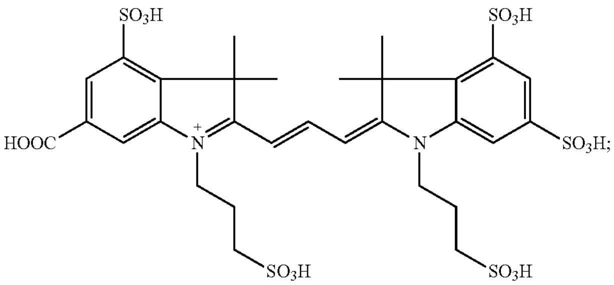
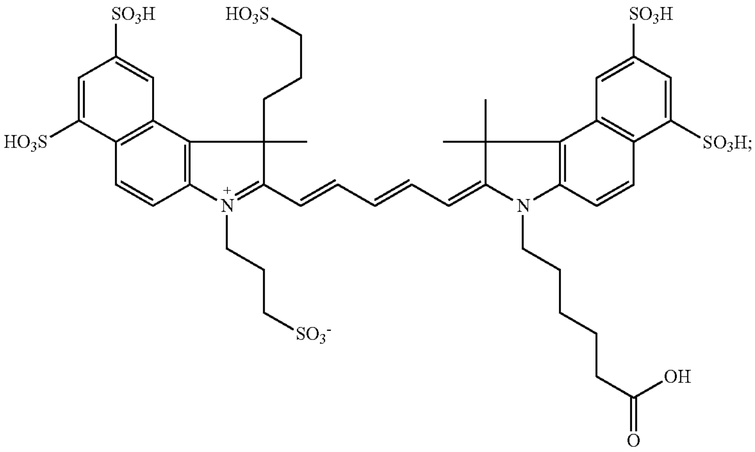
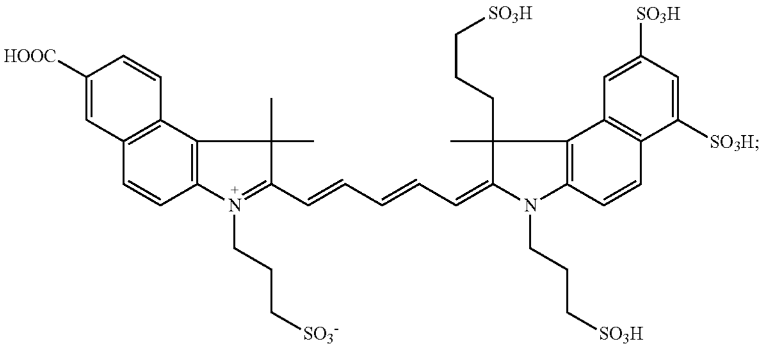
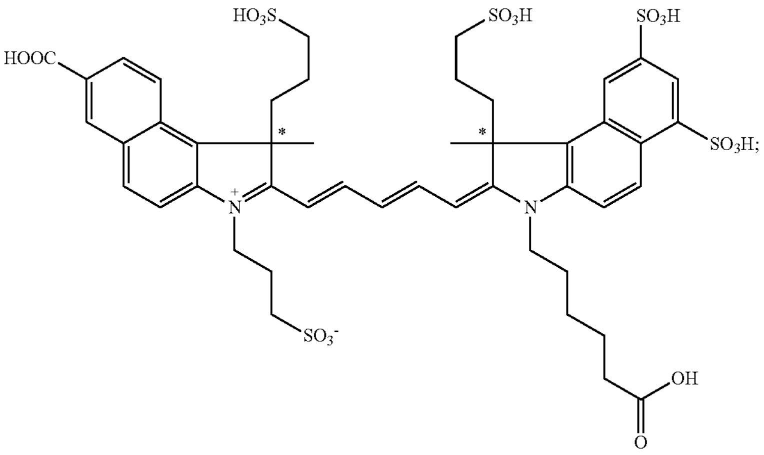

-continued
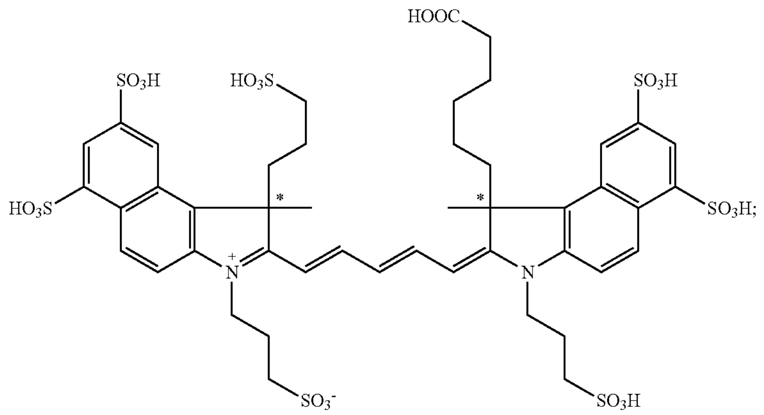
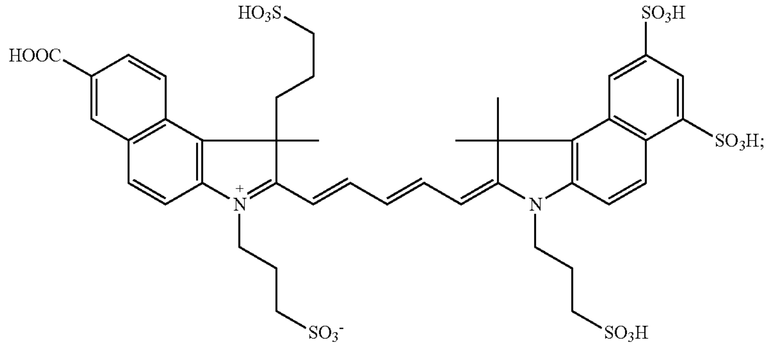
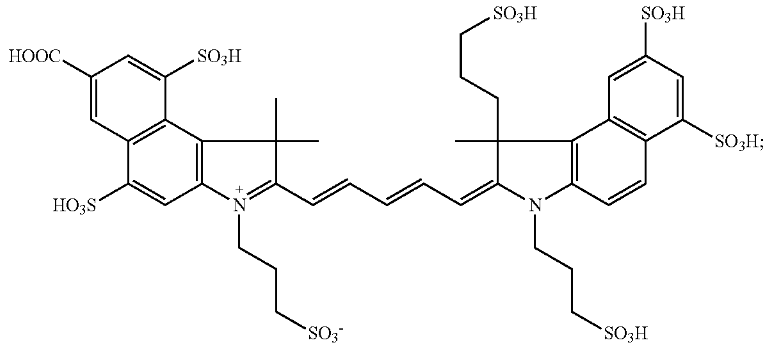
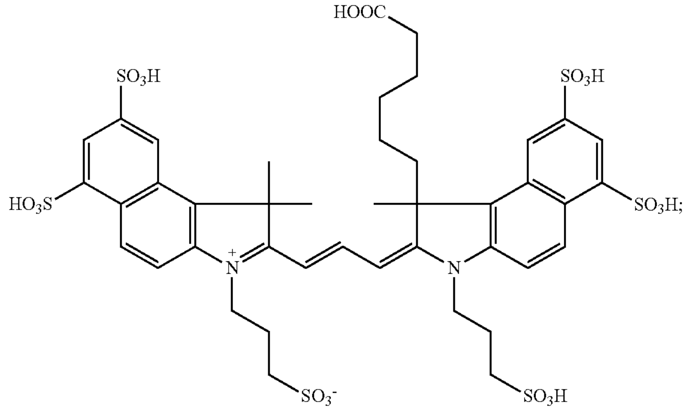

-continued
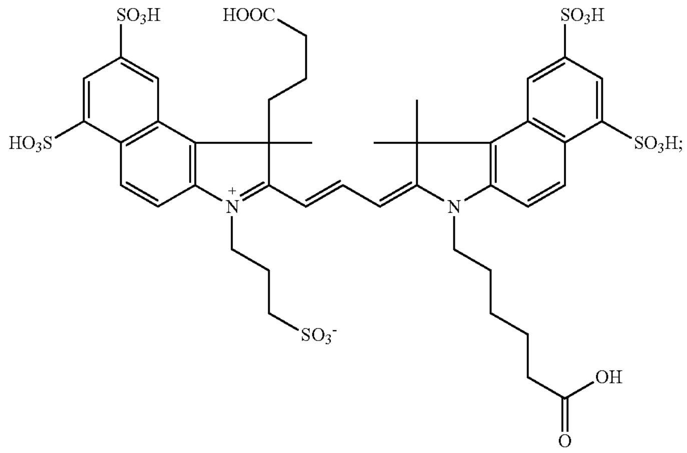
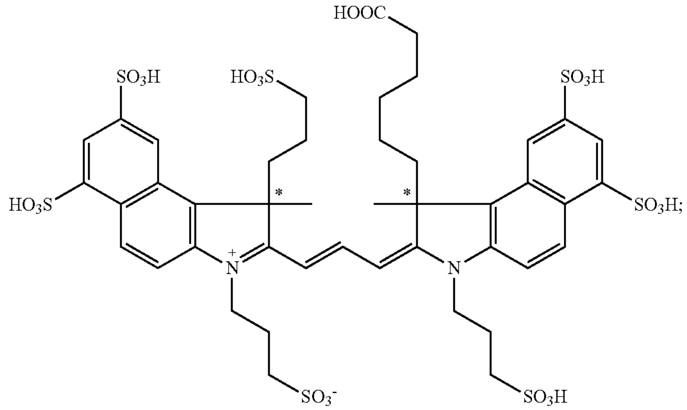
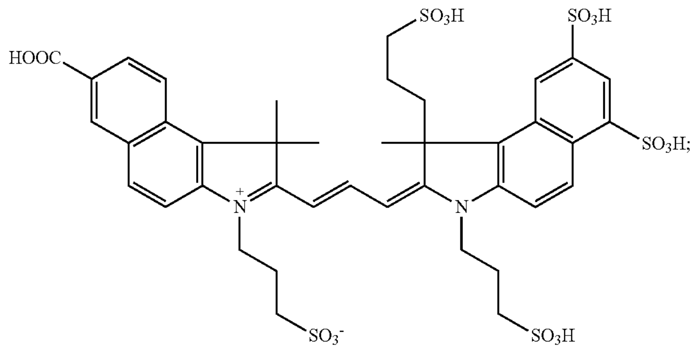
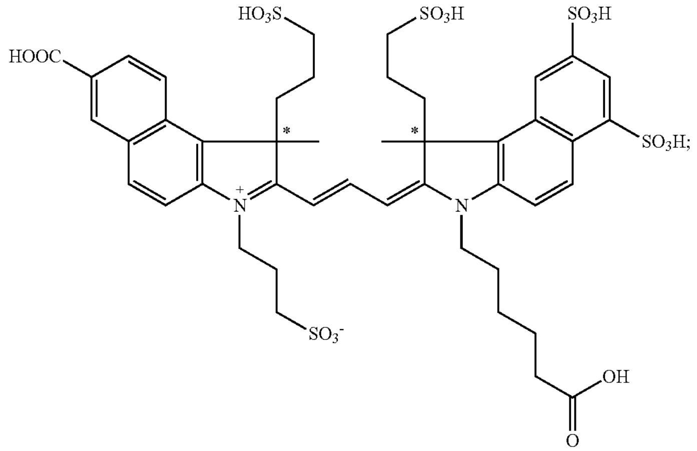

-continued
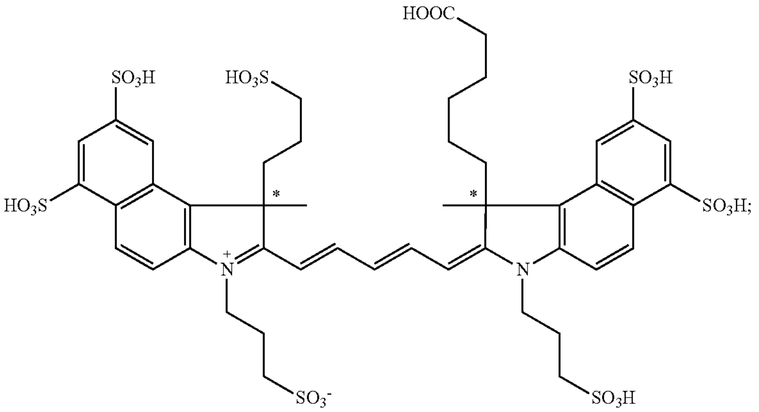
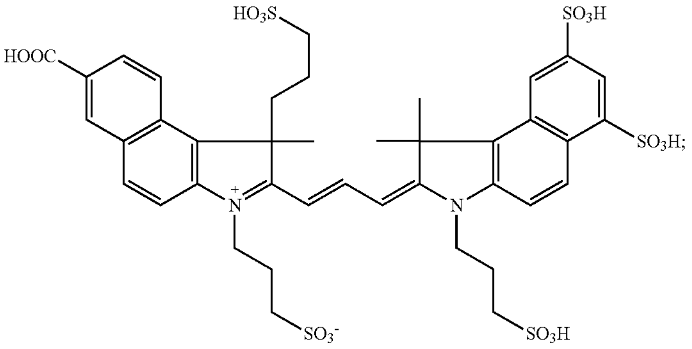
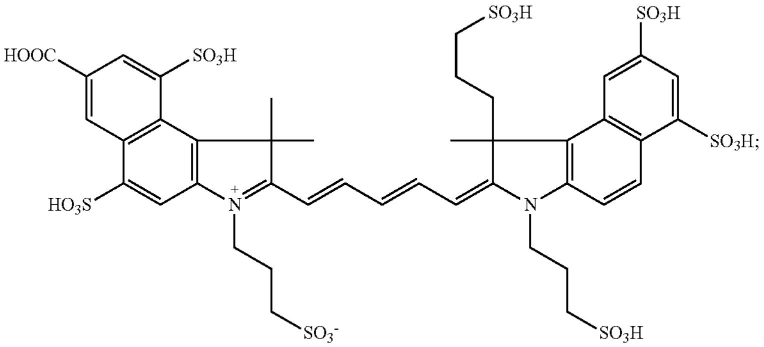
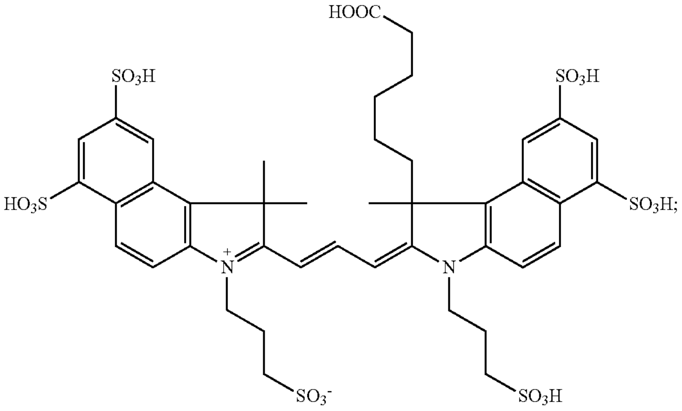

-continued
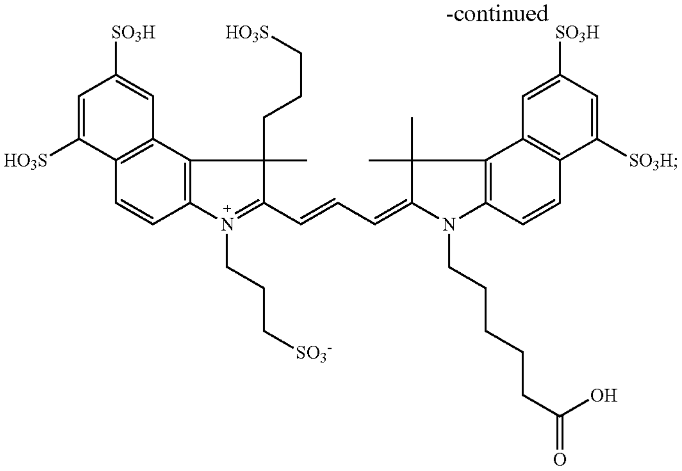
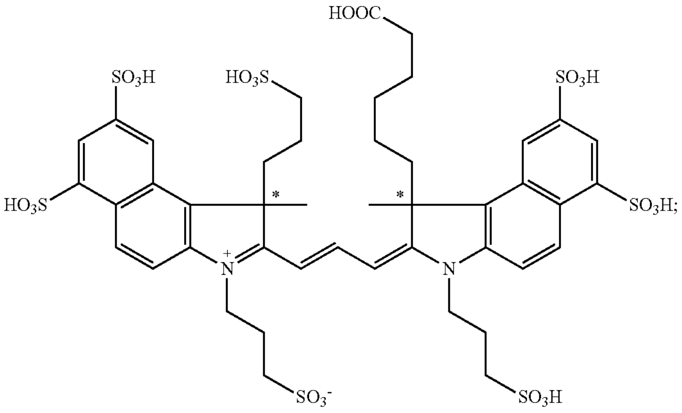
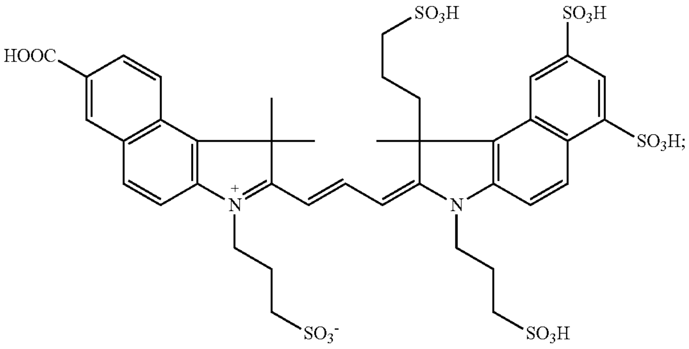

-continued
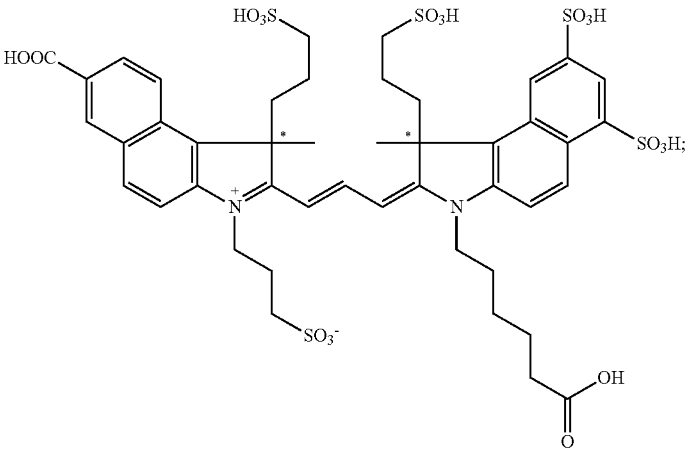
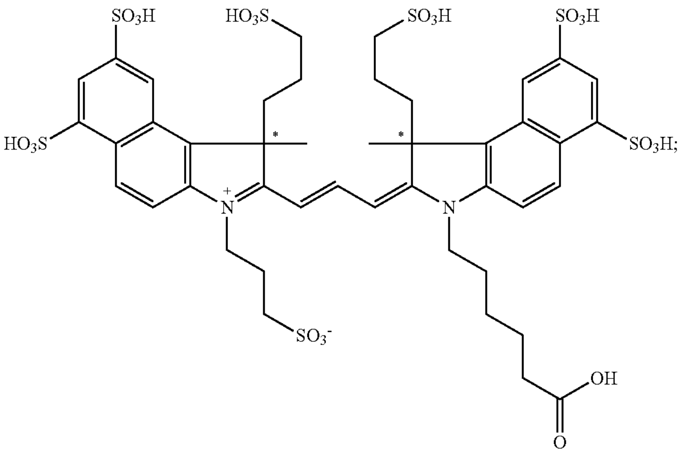
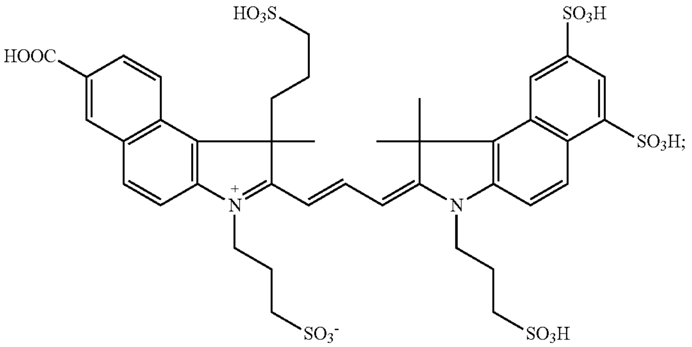
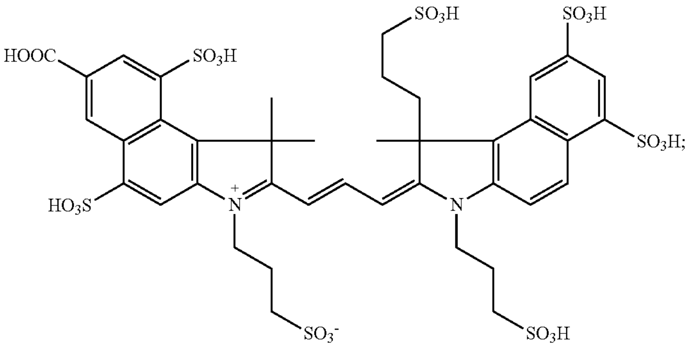

-continued
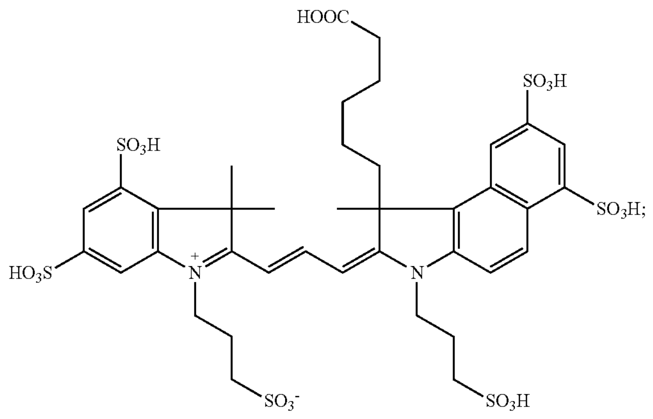
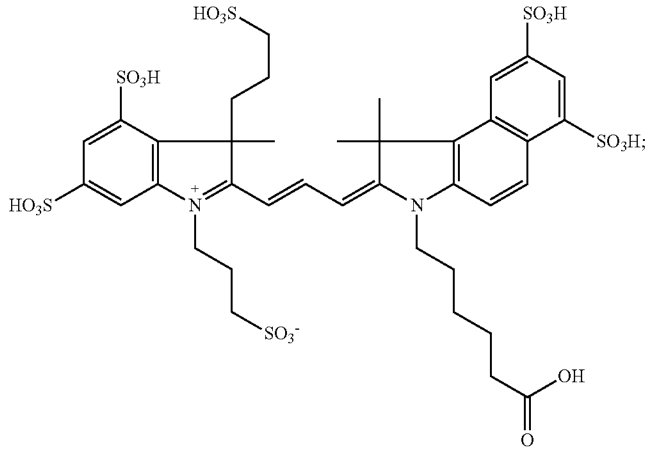
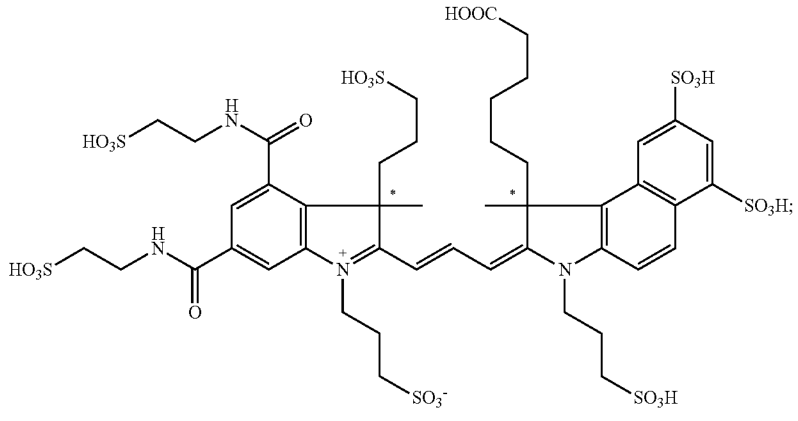

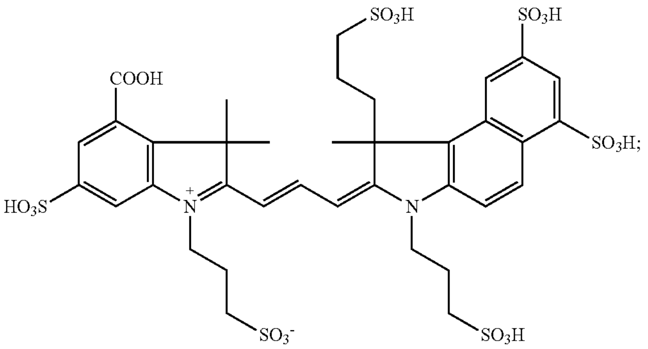
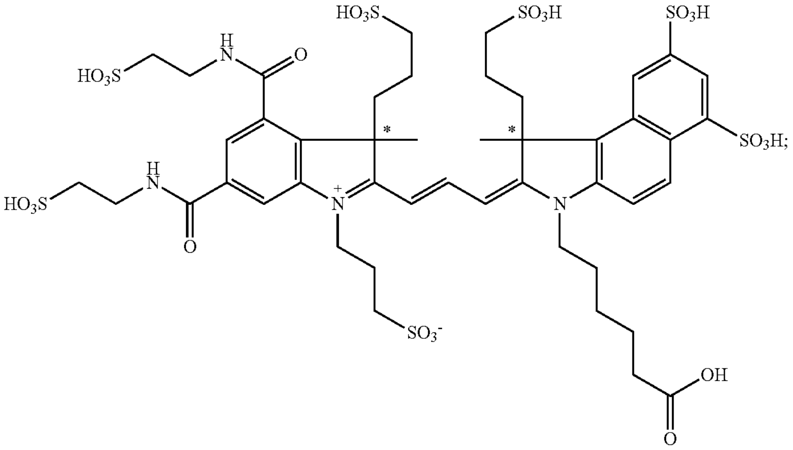
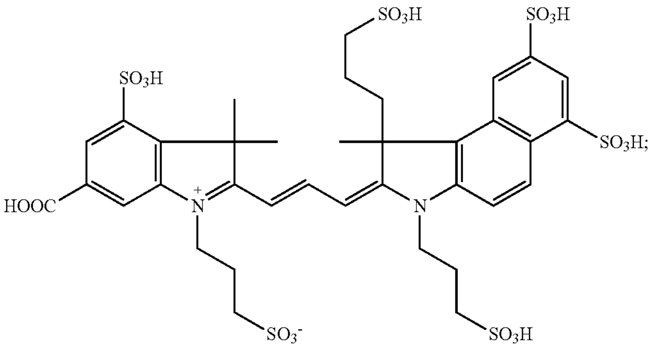
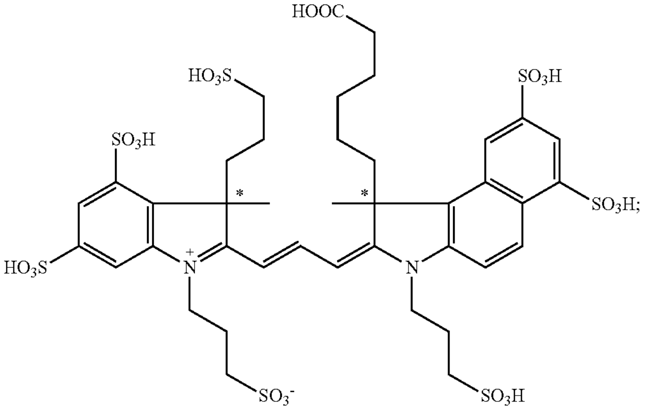

-continued
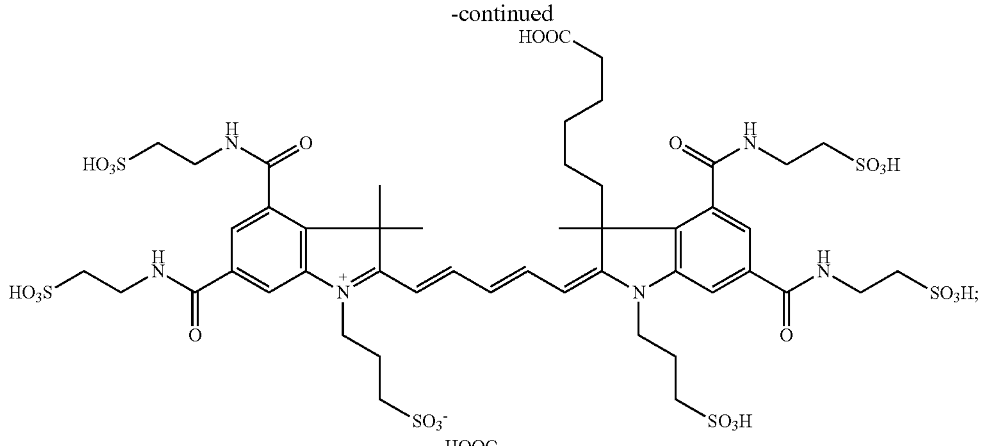
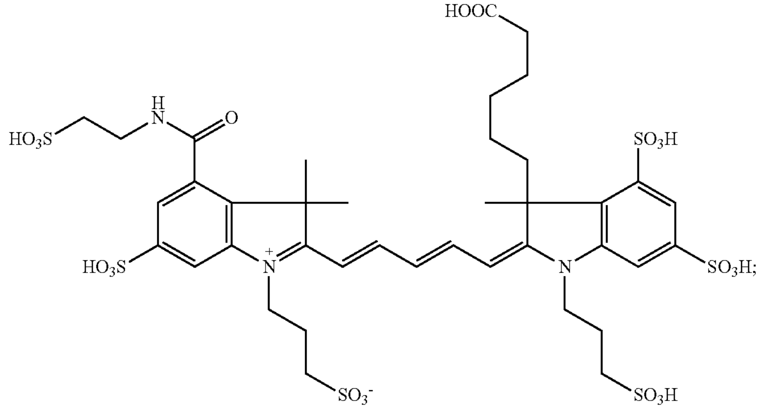
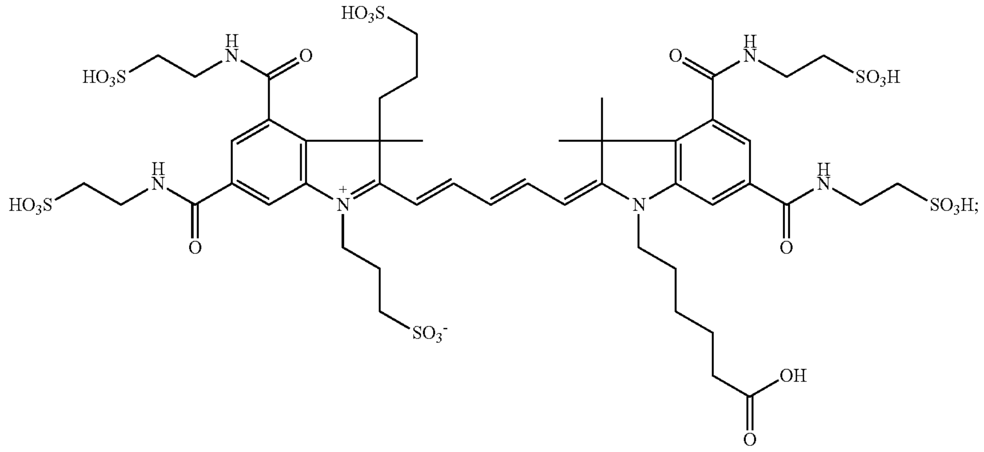
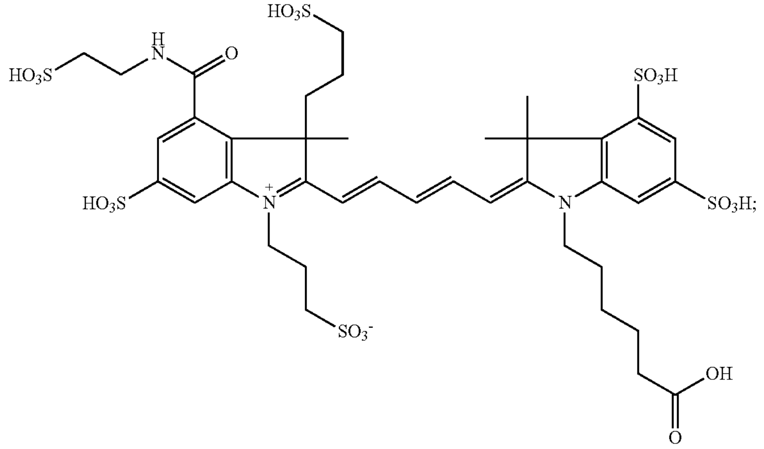

-continued
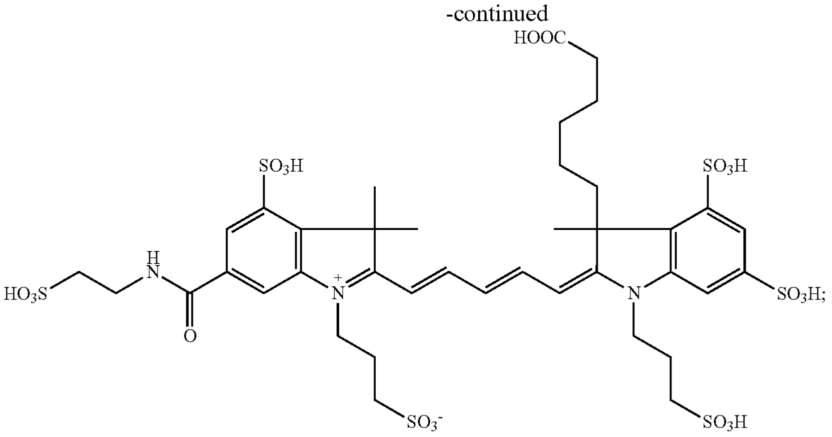
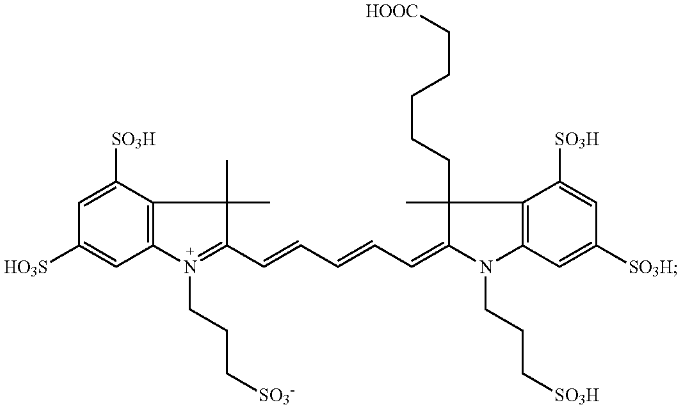
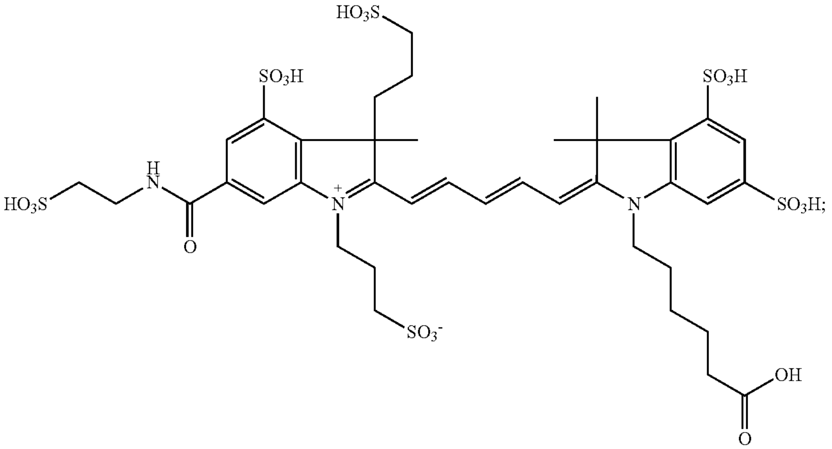
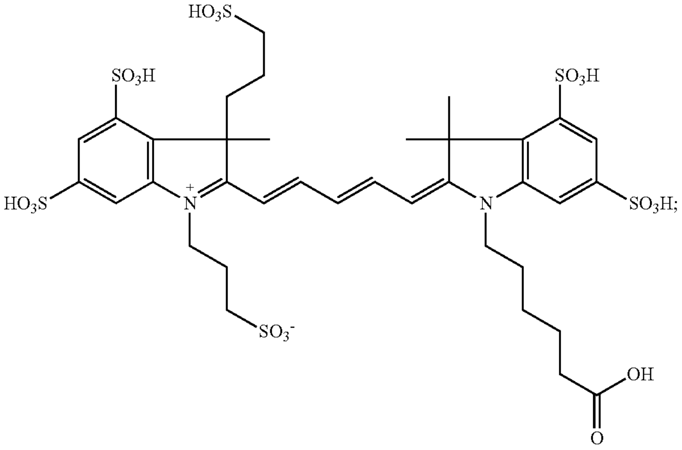

-continued
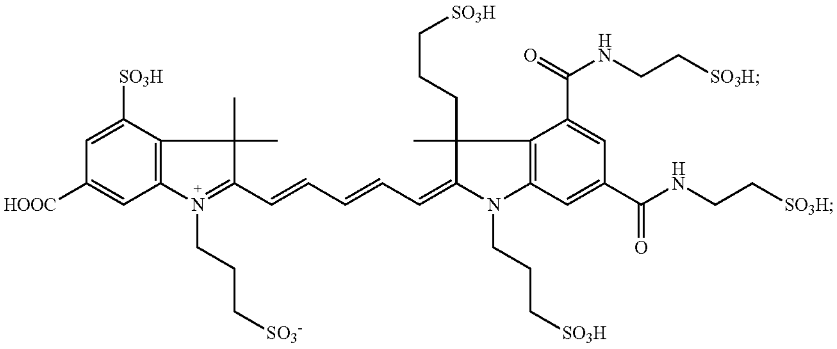
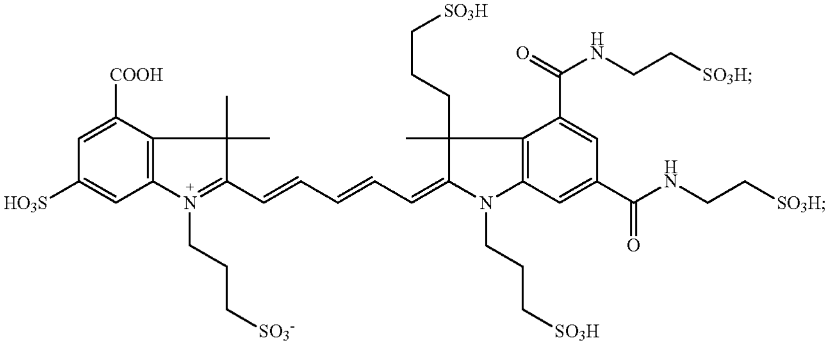
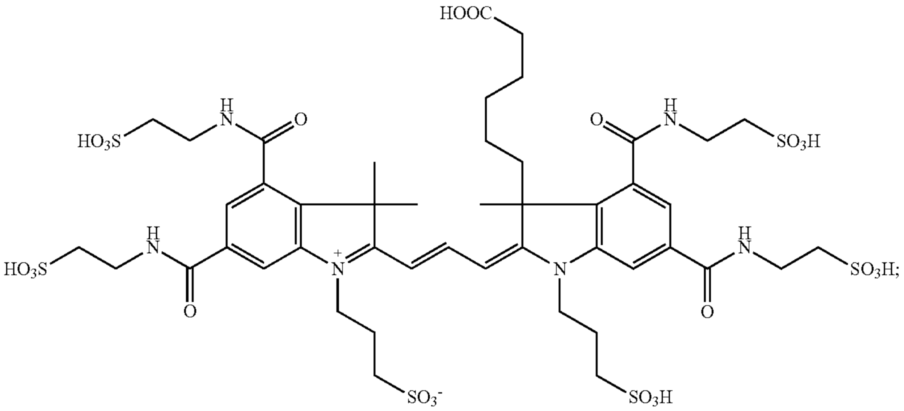
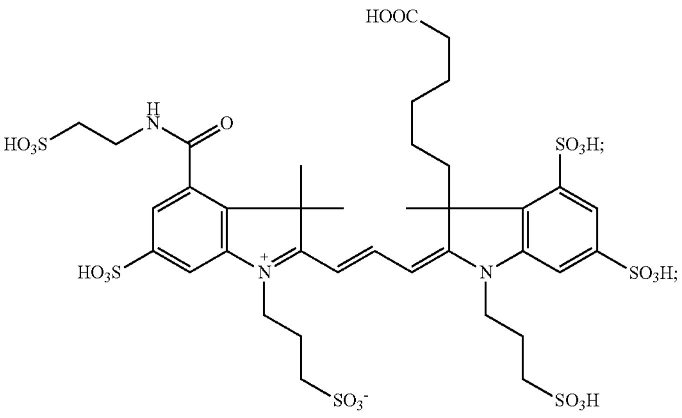

-continued
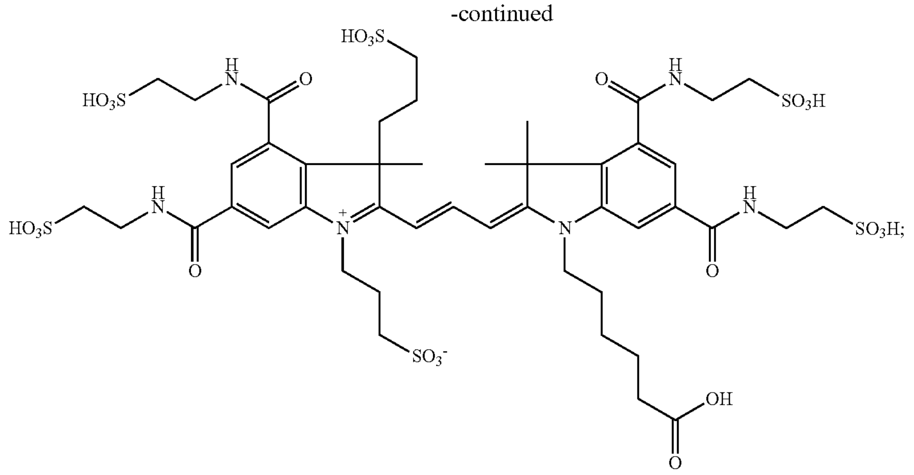
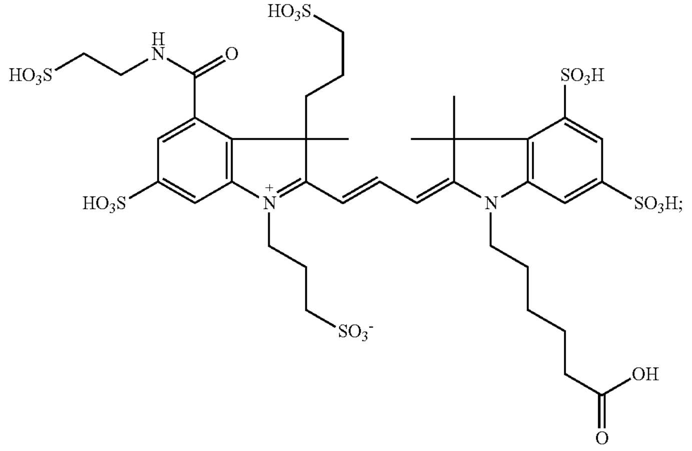
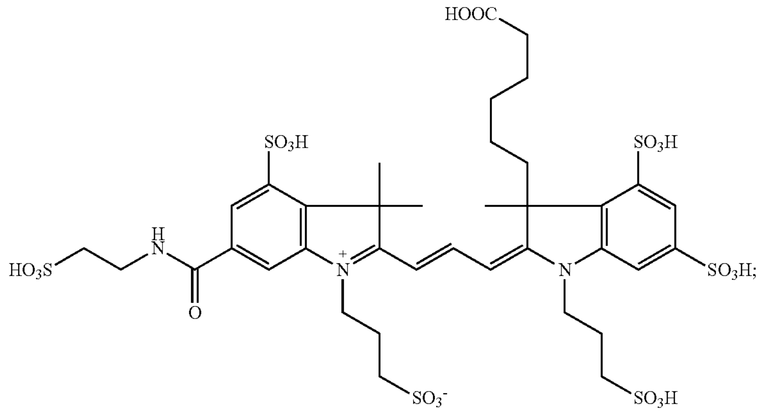
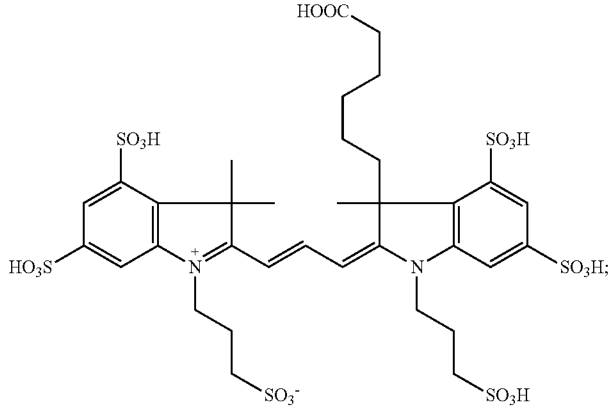

-continued
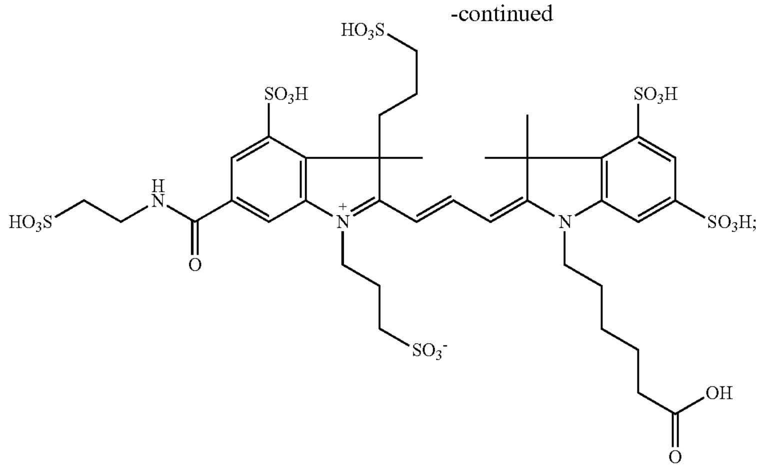
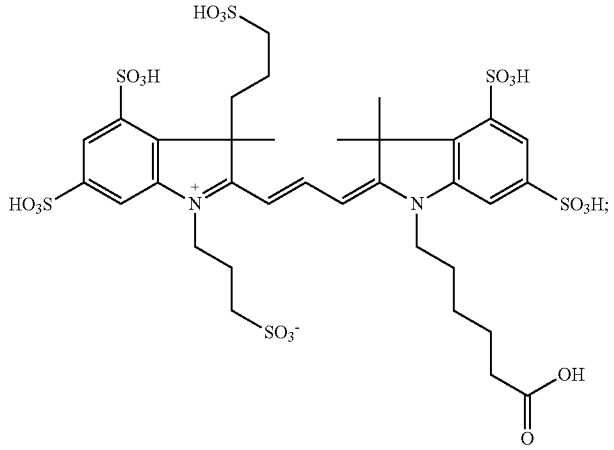
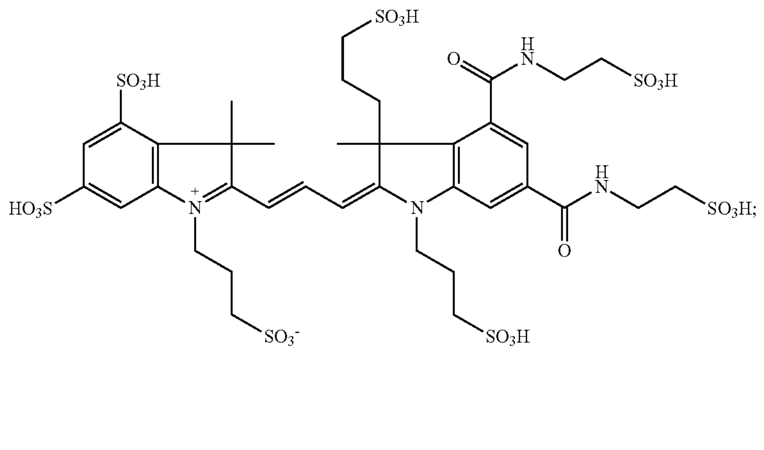
or

-continued
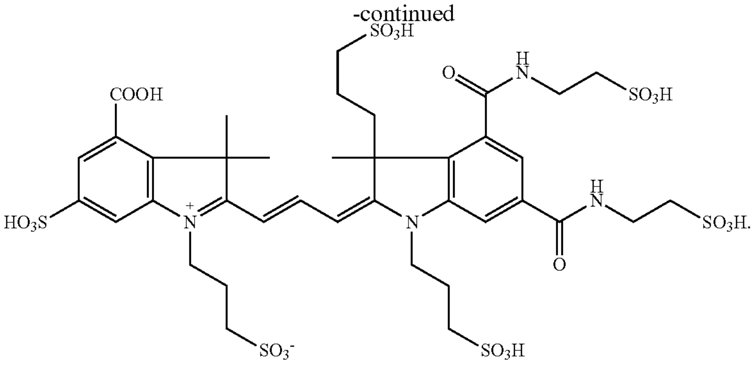
17. The compound of claim 2, wherein the compound is:
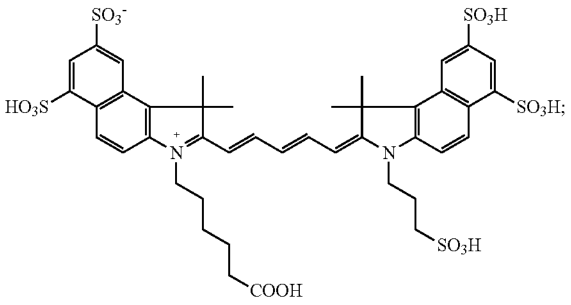
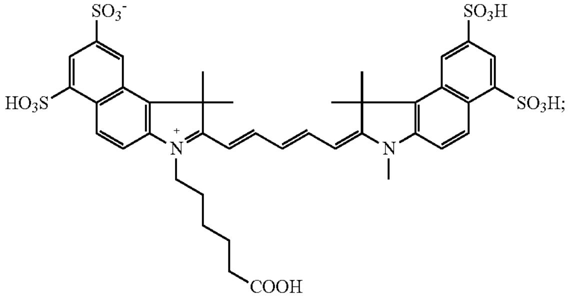
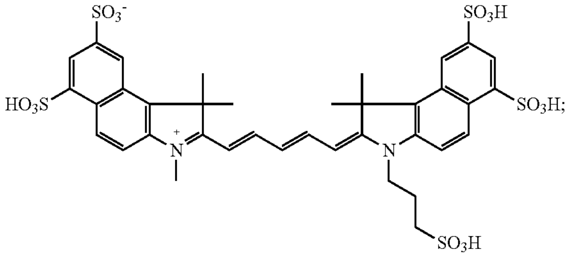
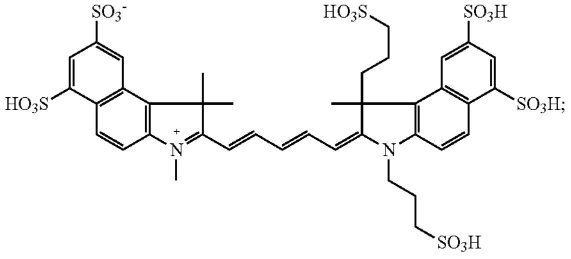
-continued
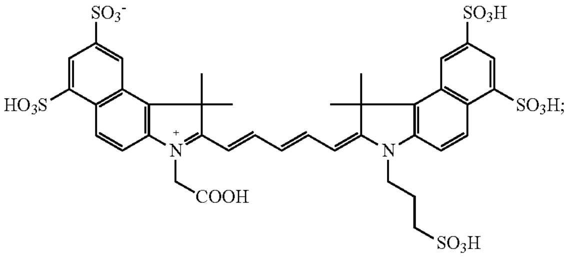
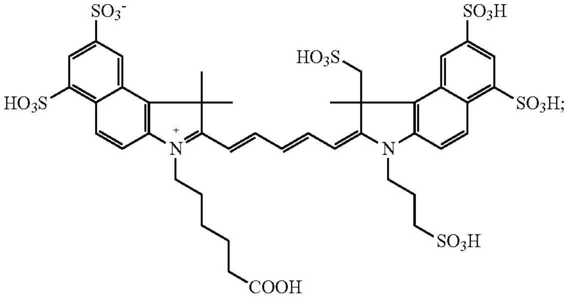
(Diastereomer 1)
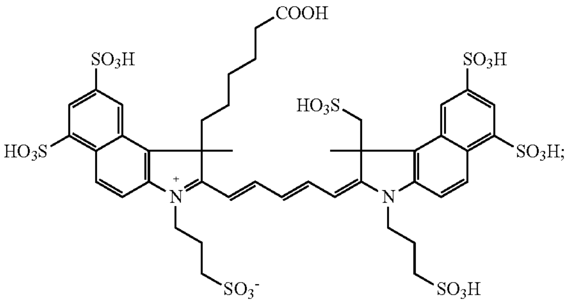
(Diastereomer 2)
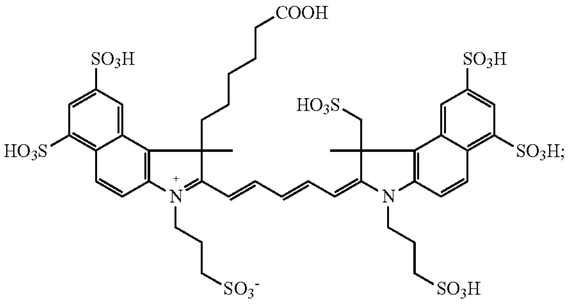

-continued
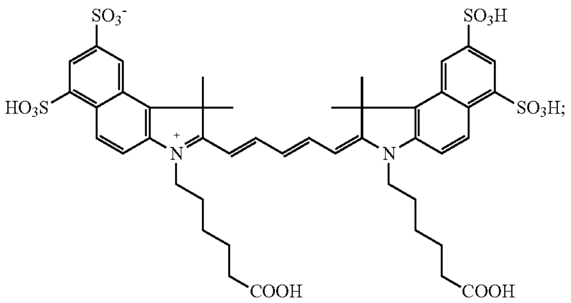
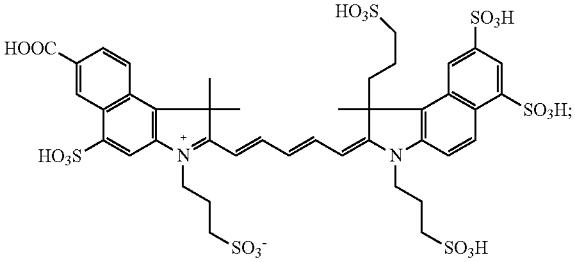
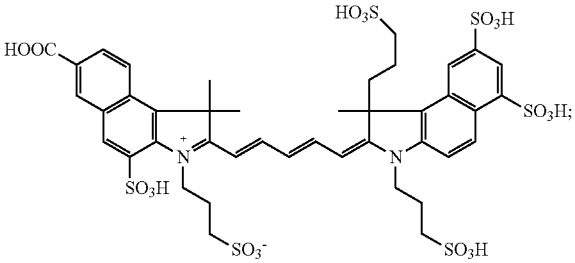
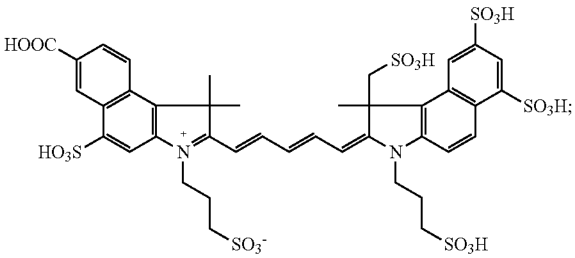
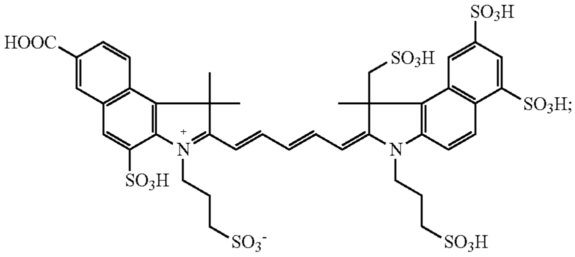
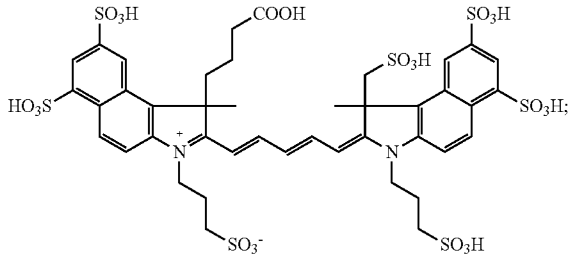
-continued
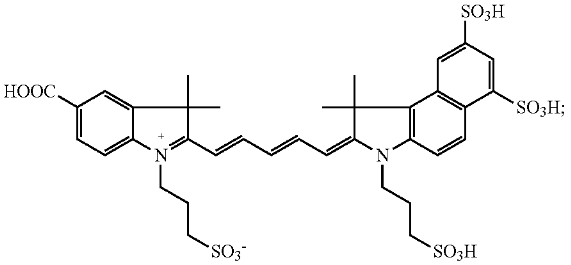
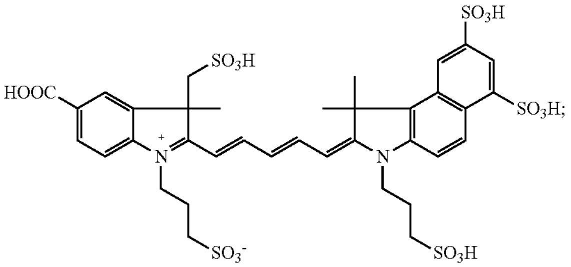
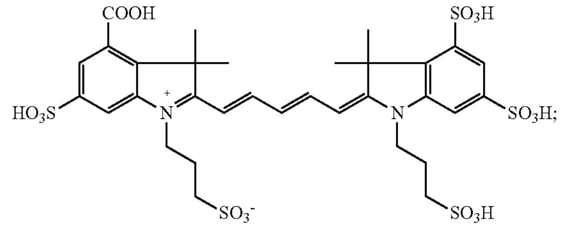
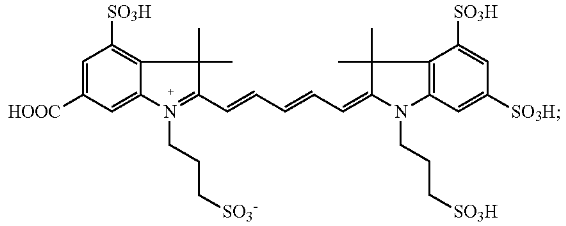
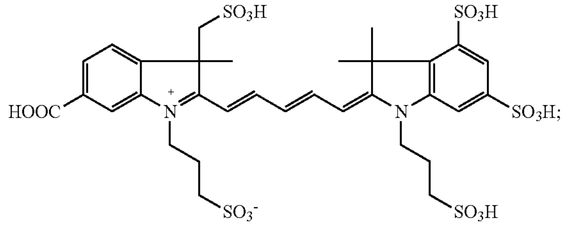
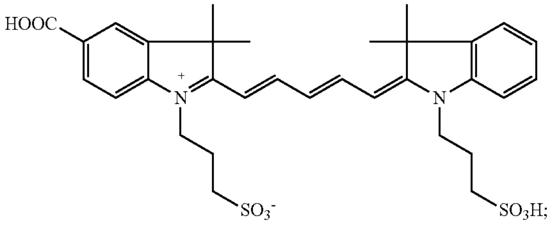
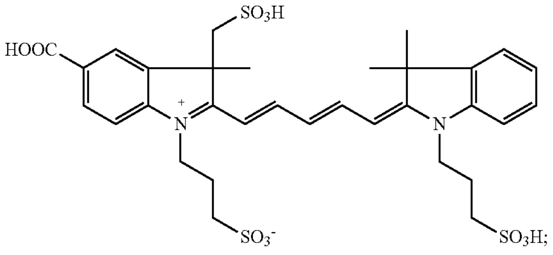

-continued
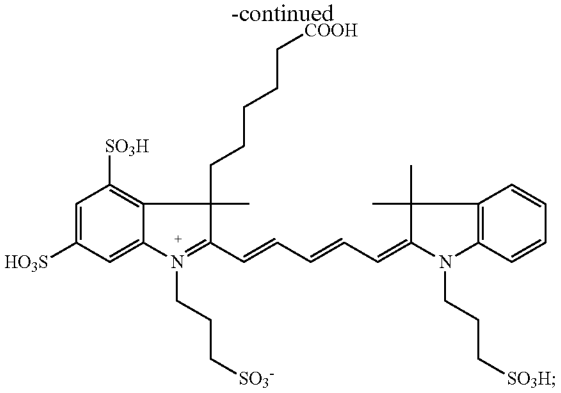
-continued
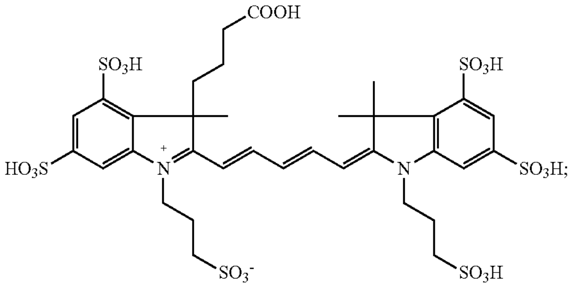
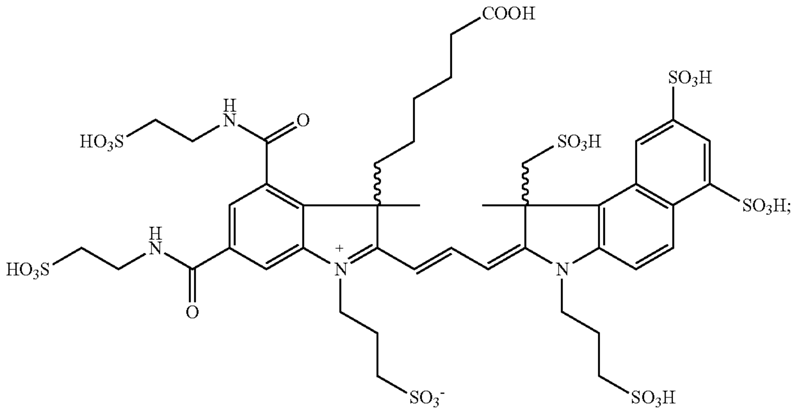
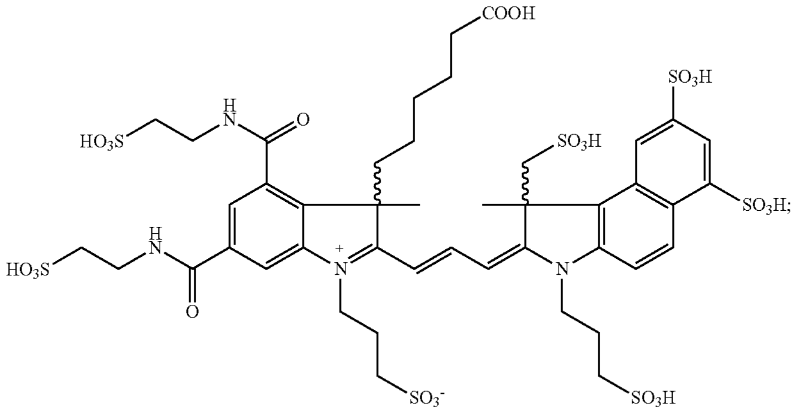

-continued
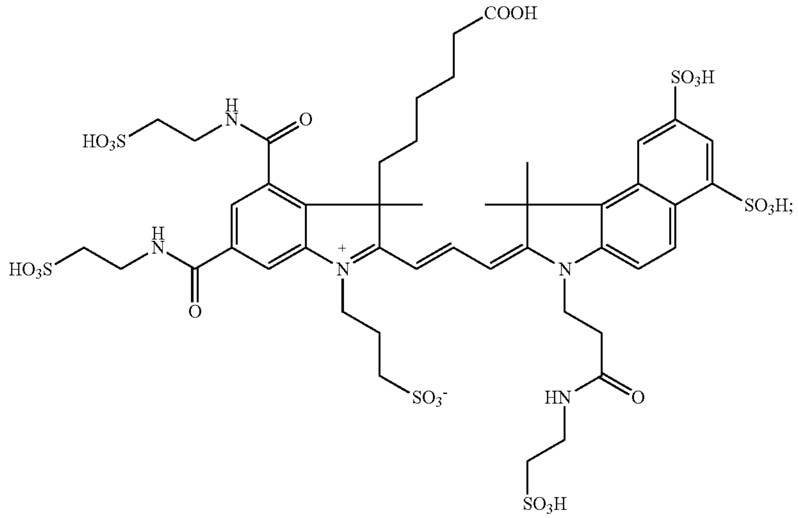
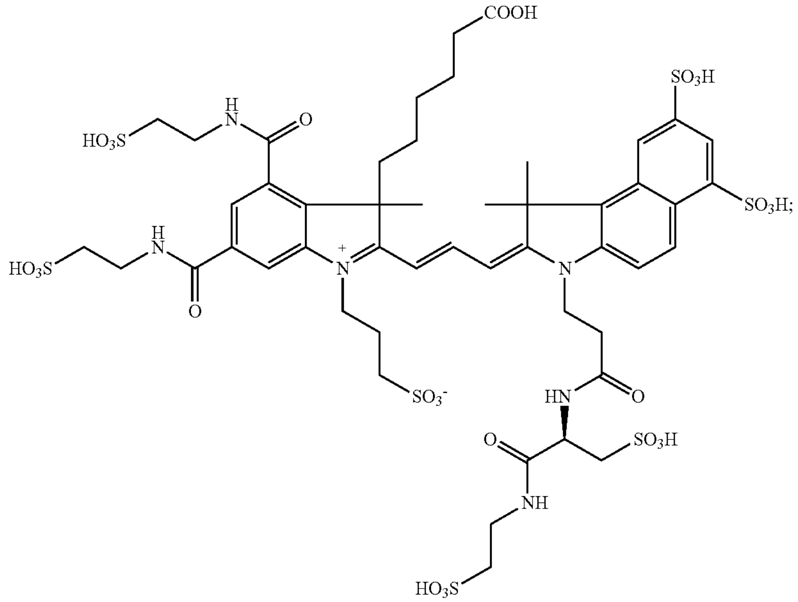
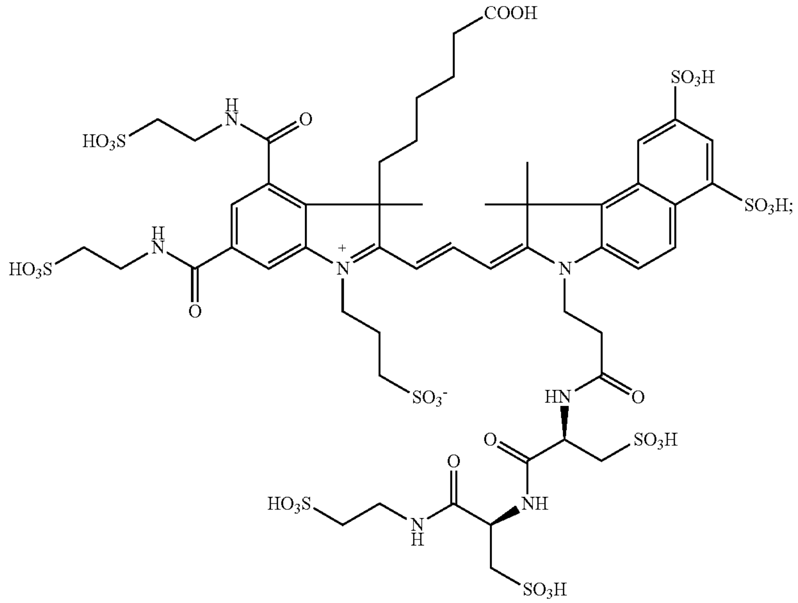

-continued
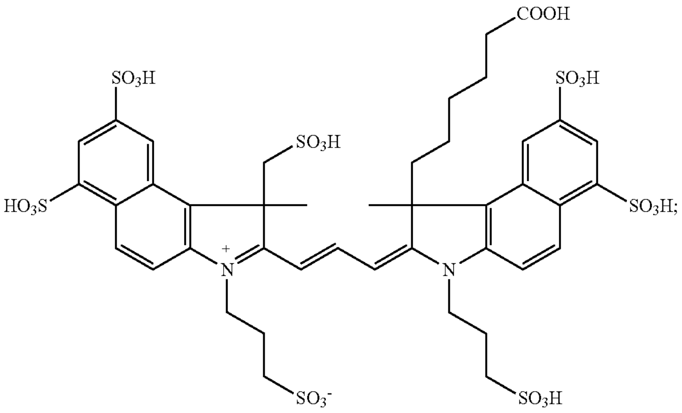
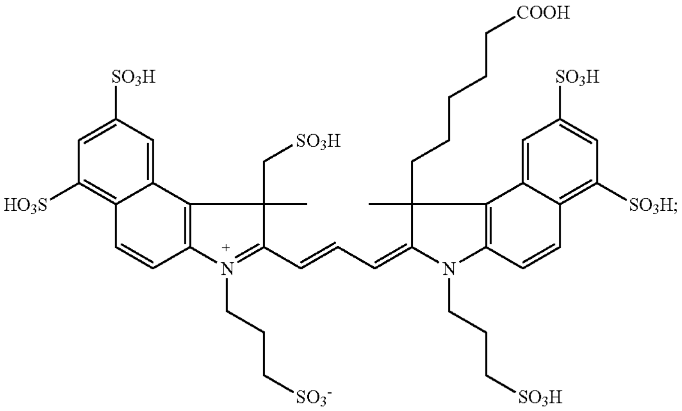
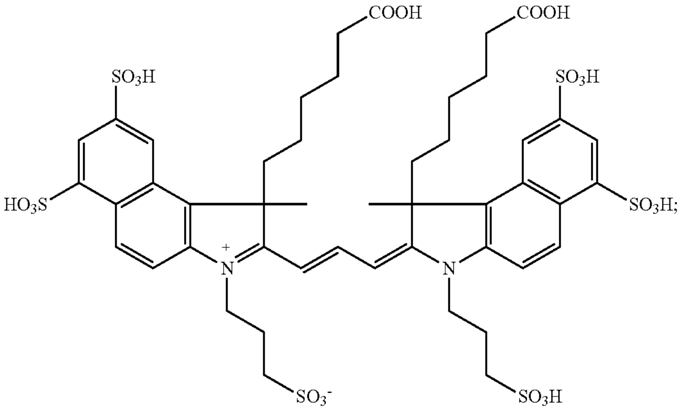
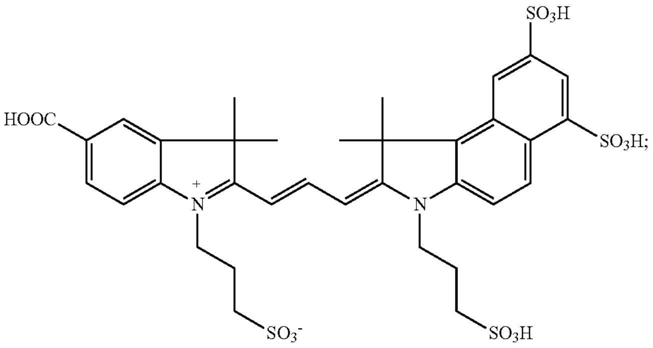

-continued
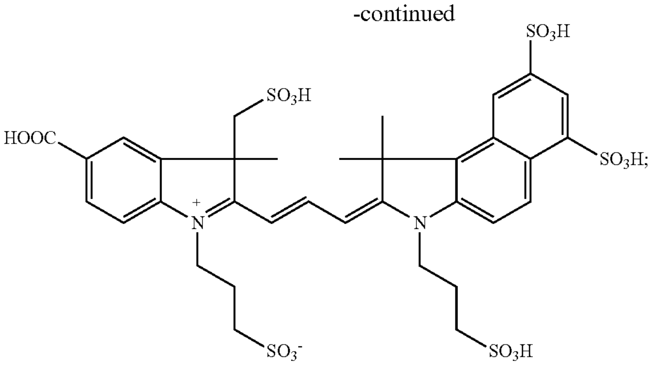
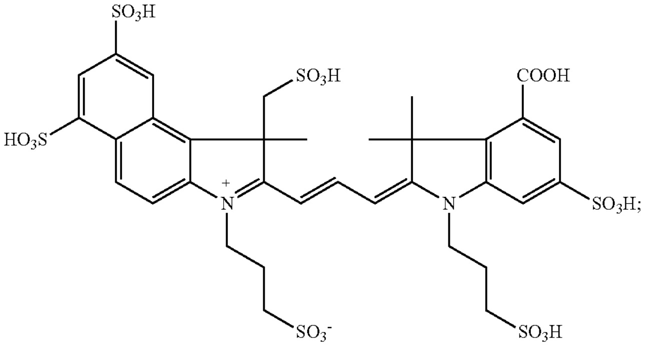
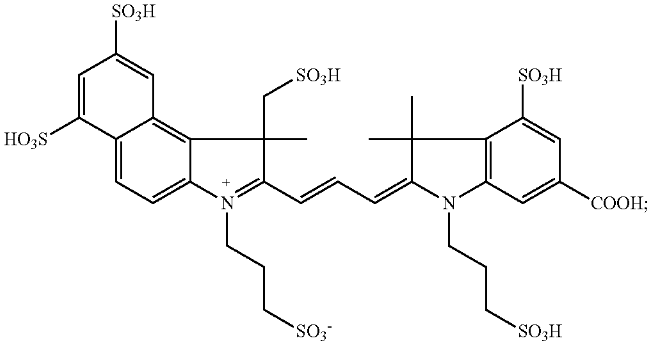
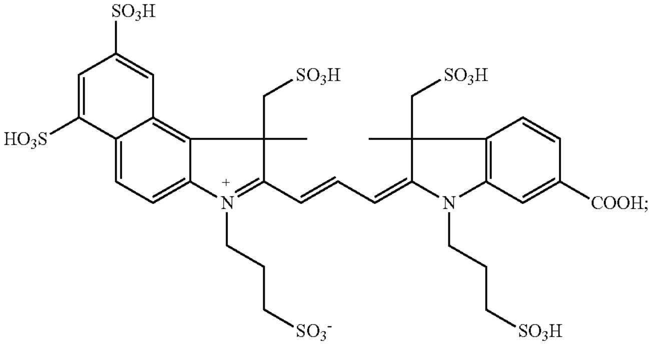
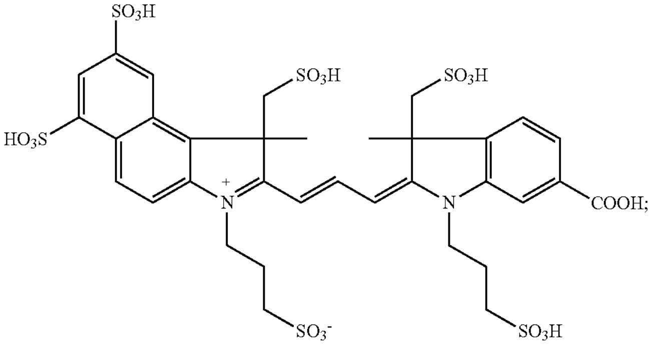

-continued
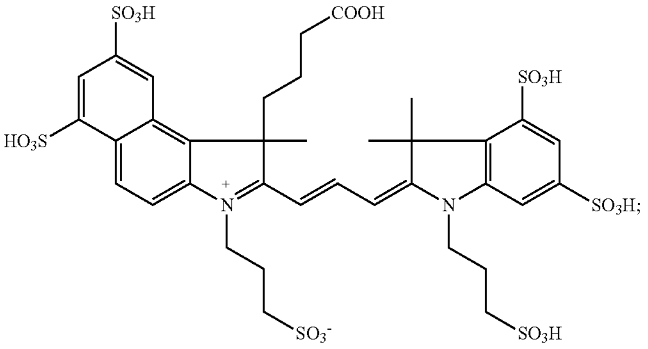
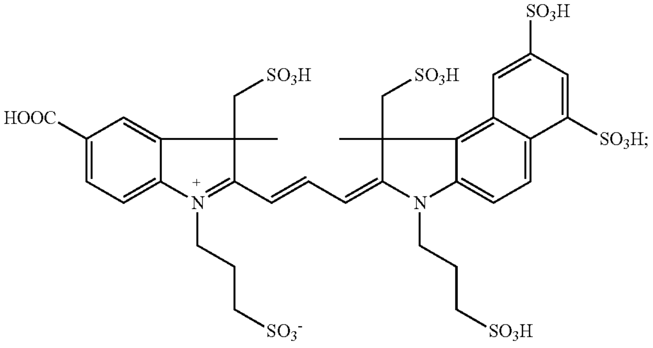
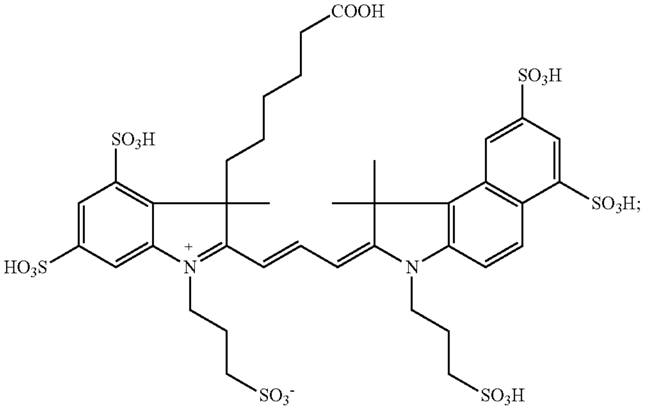
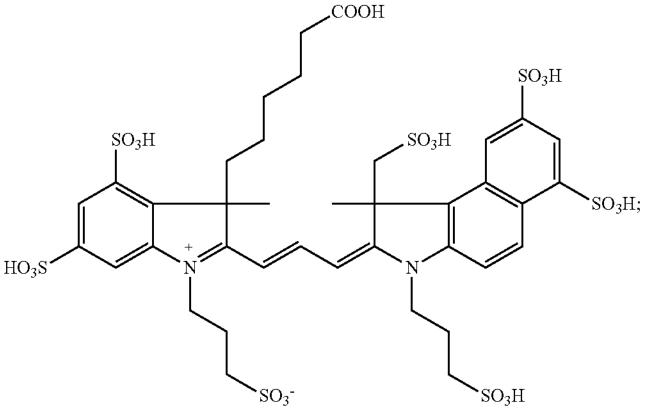

-continued
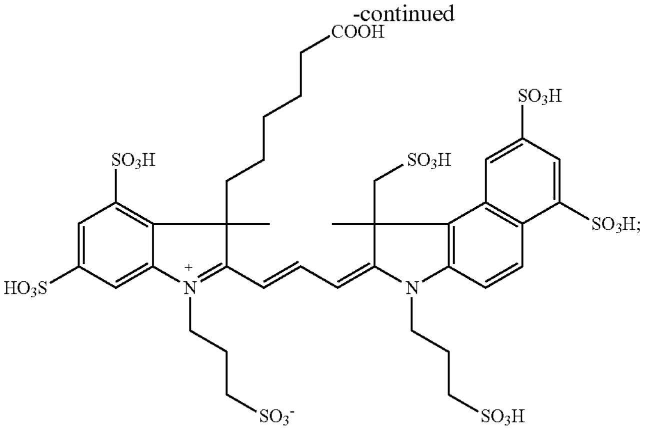
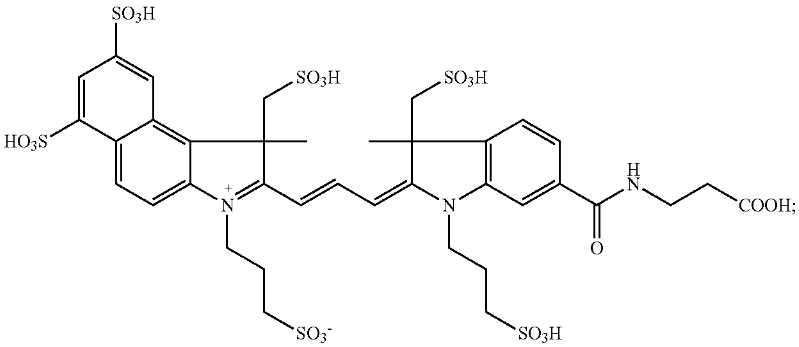
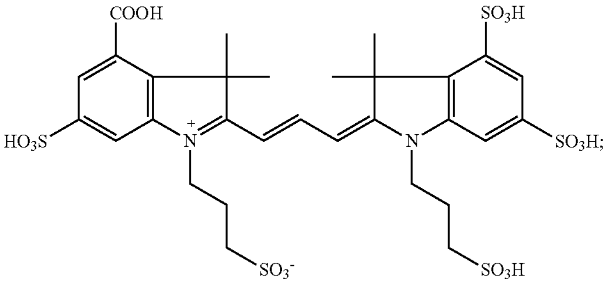
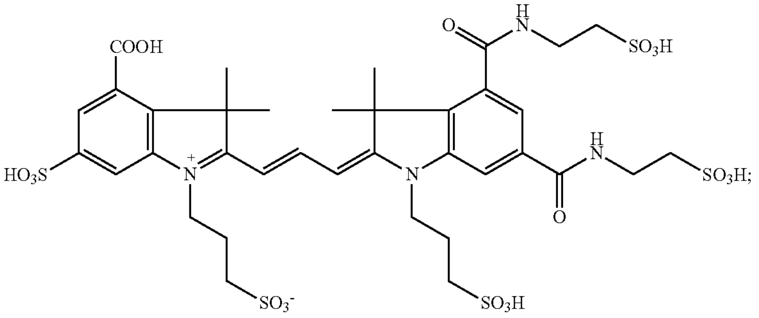

-continued
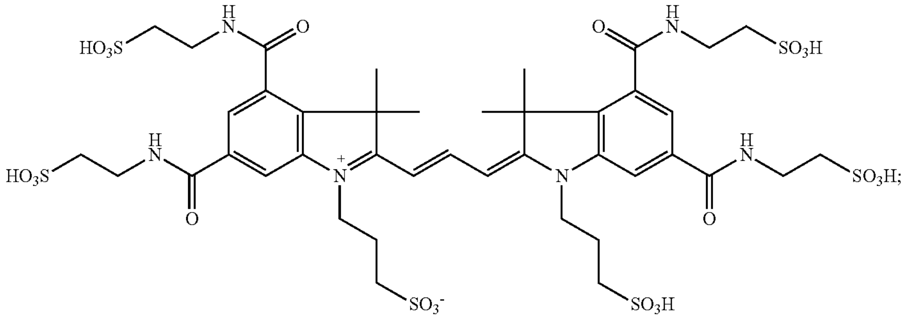
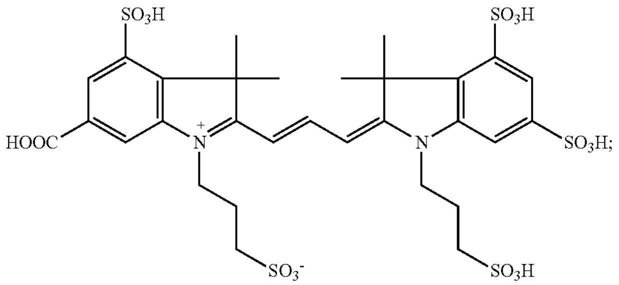
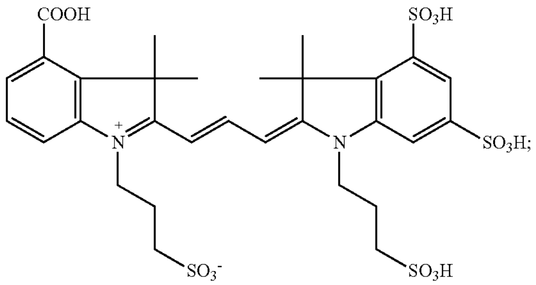
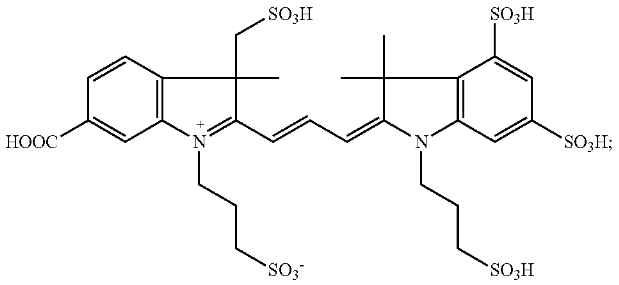
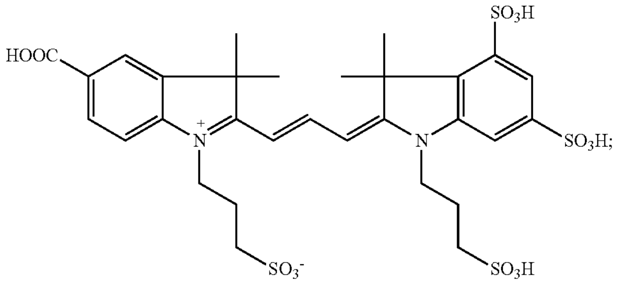
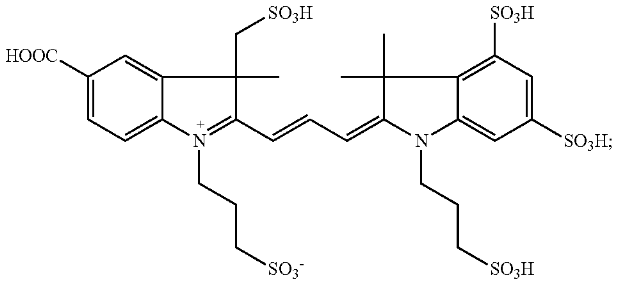
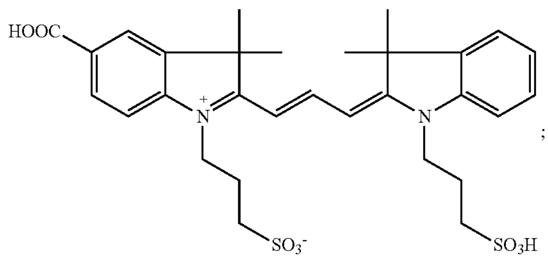
;

-continued
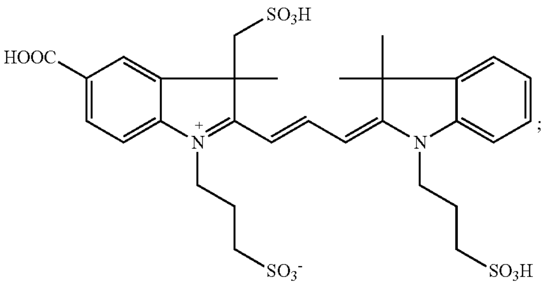
;
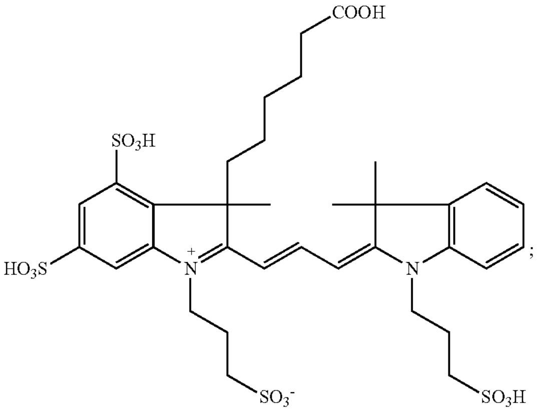
;
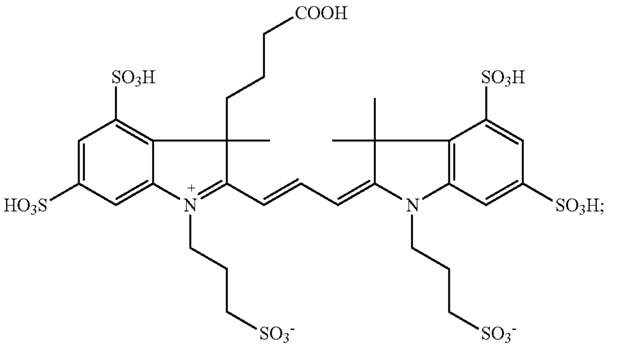
;
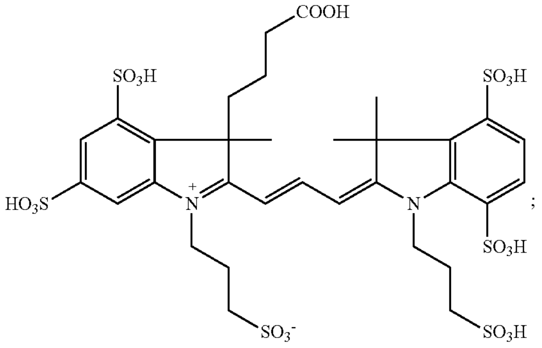
;
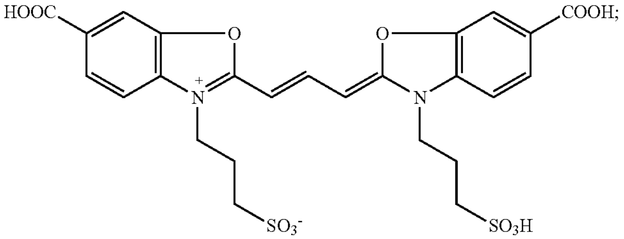
;
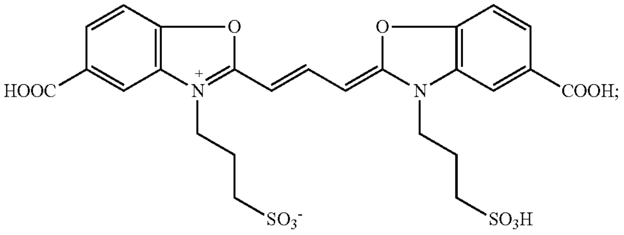
;
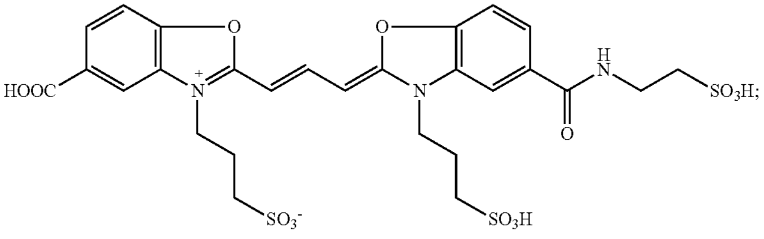
;
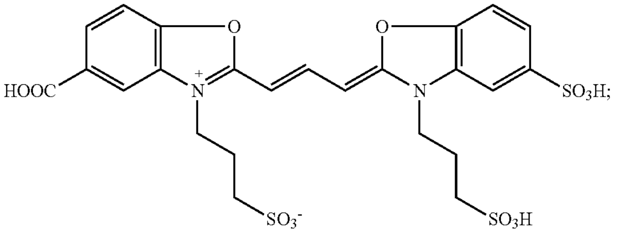
;

-continued
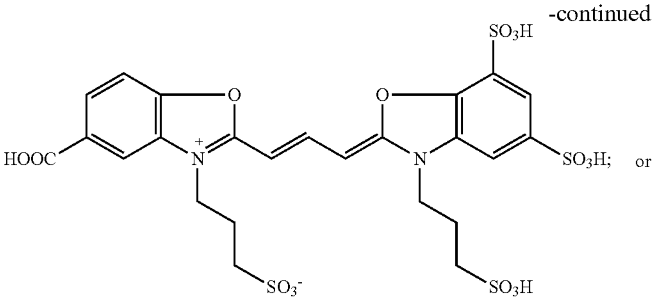
or
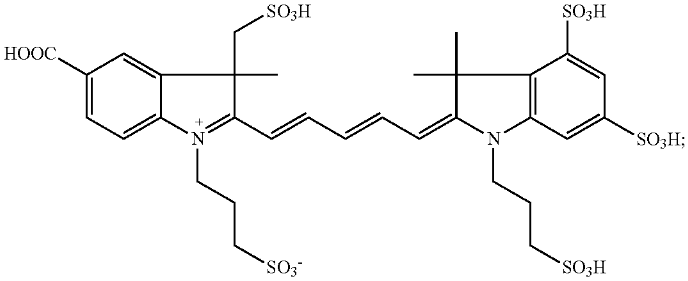
or a salt thereof.
18. The compound of claim 2, wherein the compound is
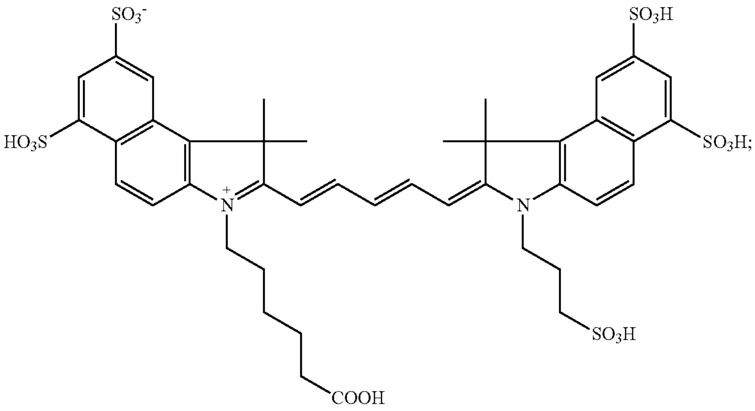
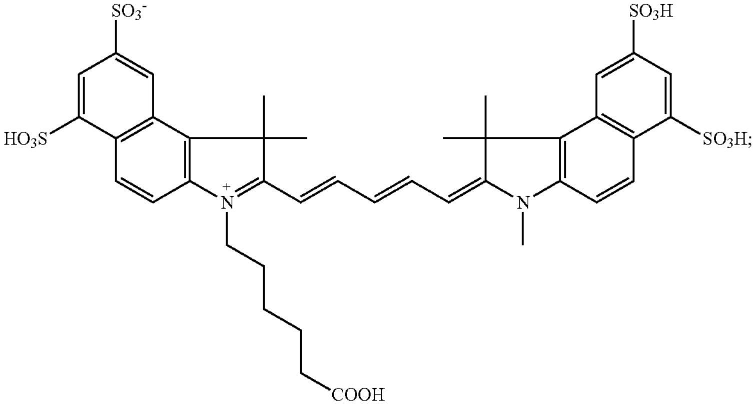

-continued
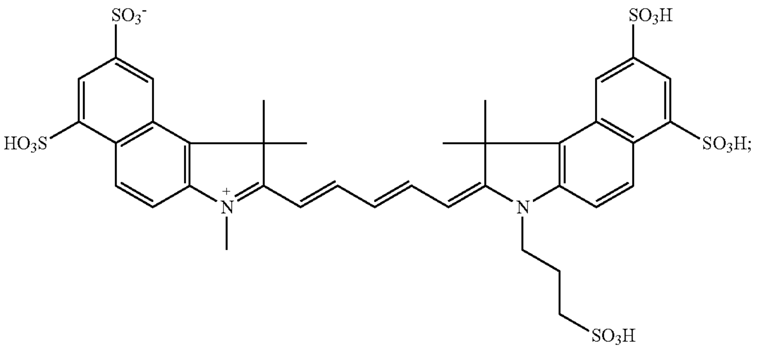
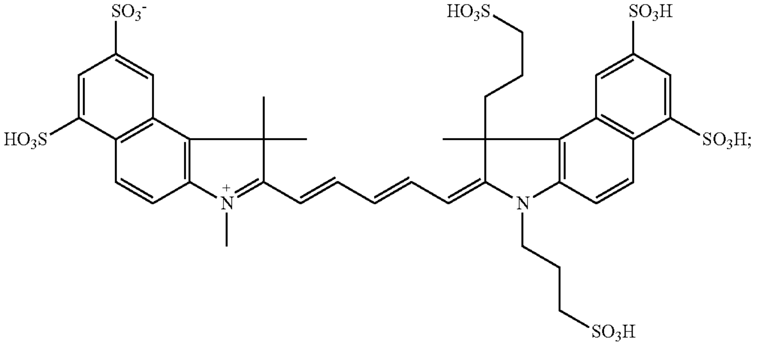
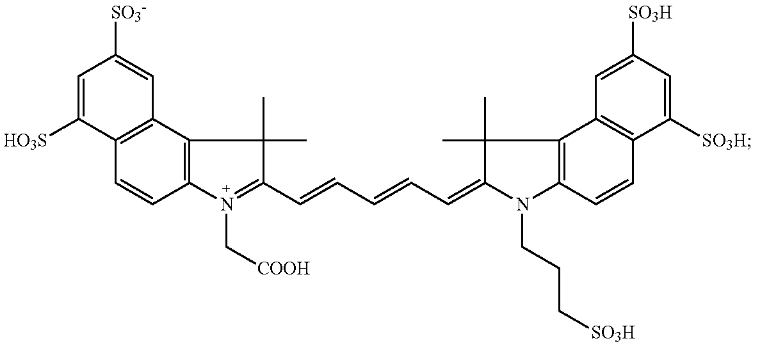
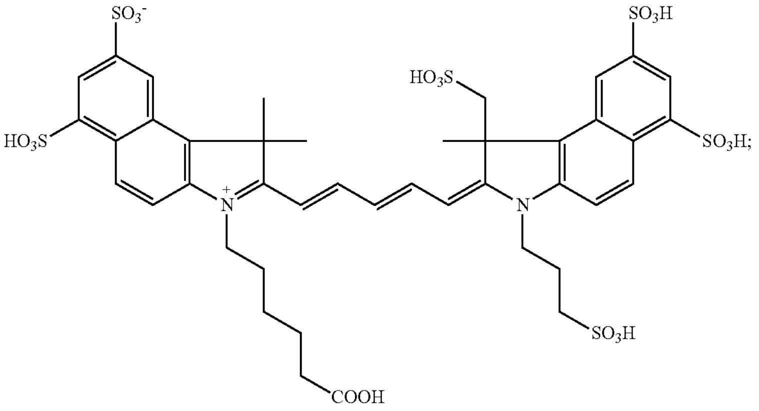

-continued
(Diasteromer 1)
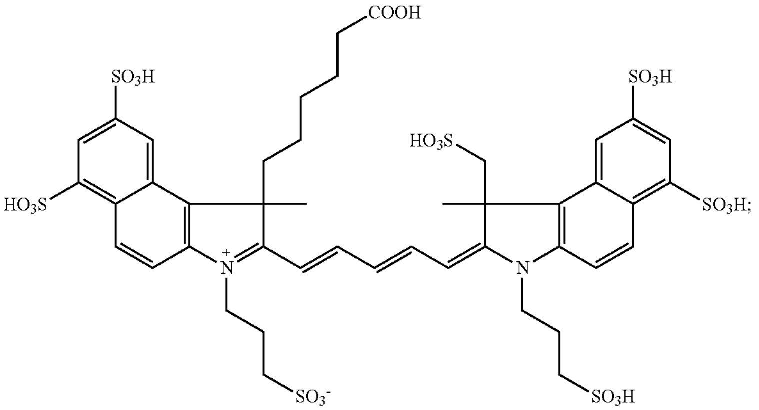
(Diasteromer 2)
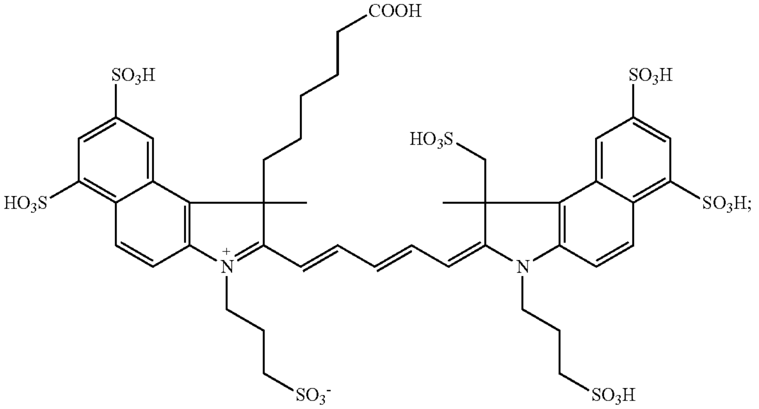
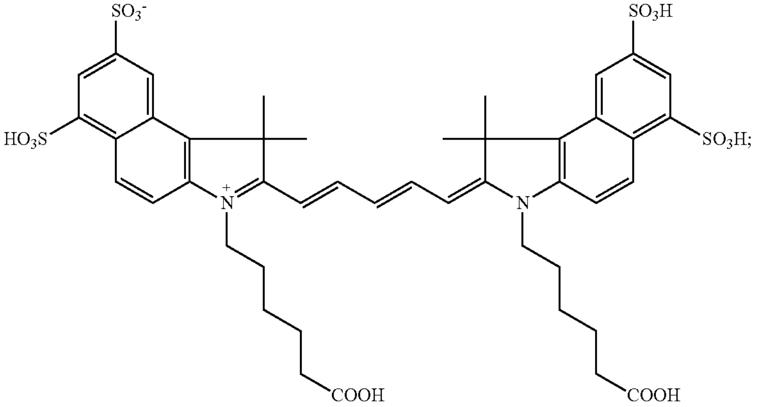
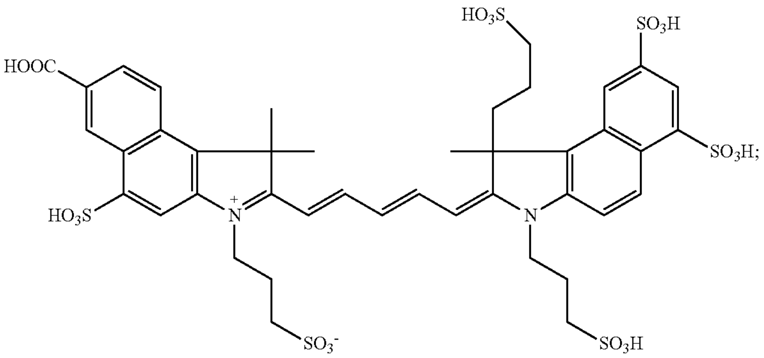

-continued
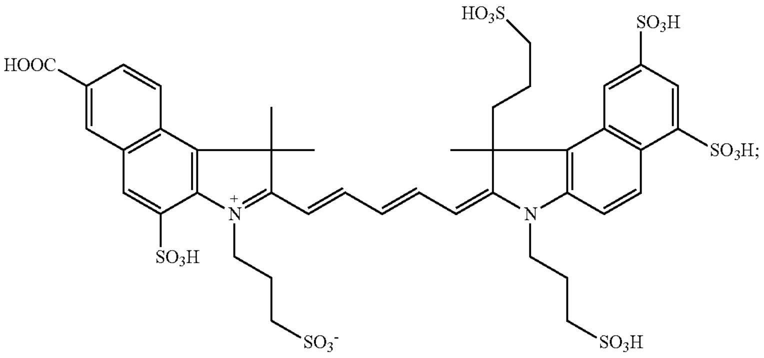
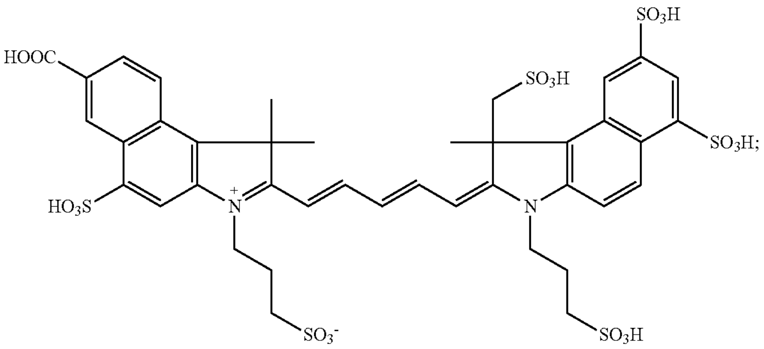
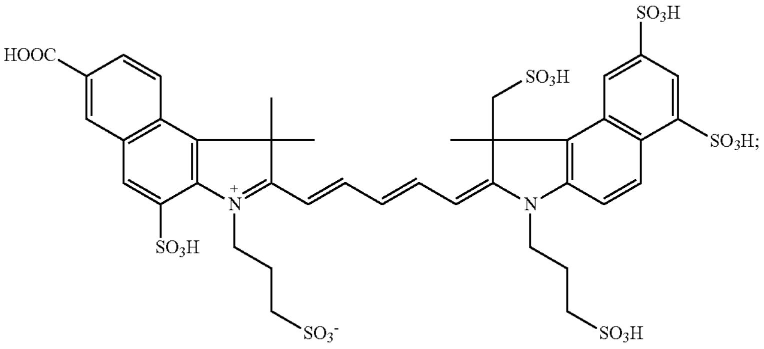
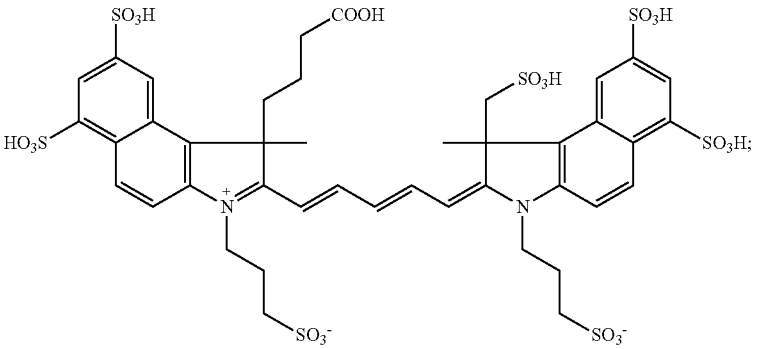

-continued
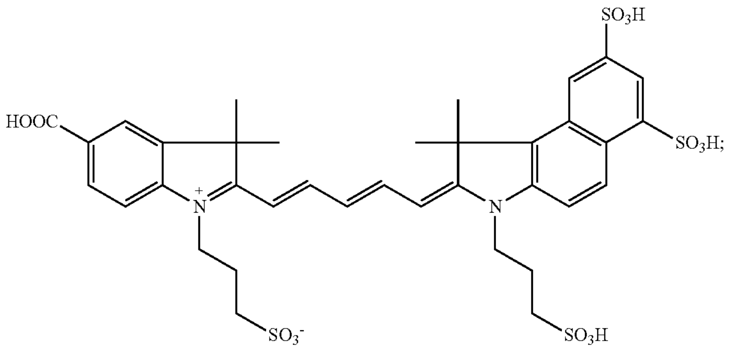
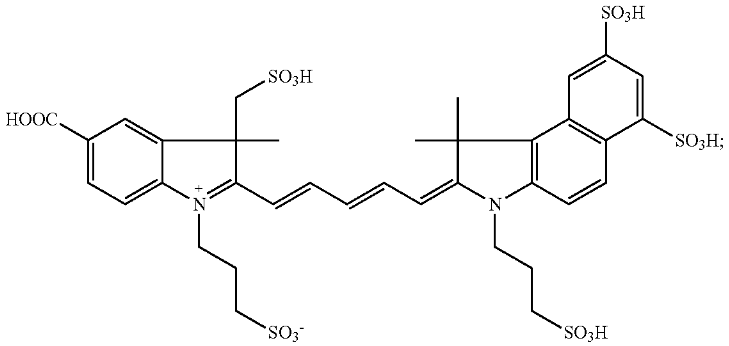
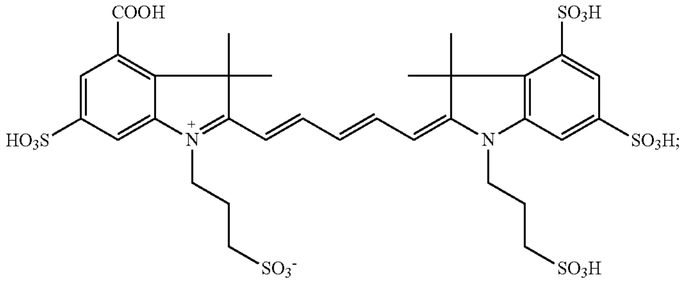
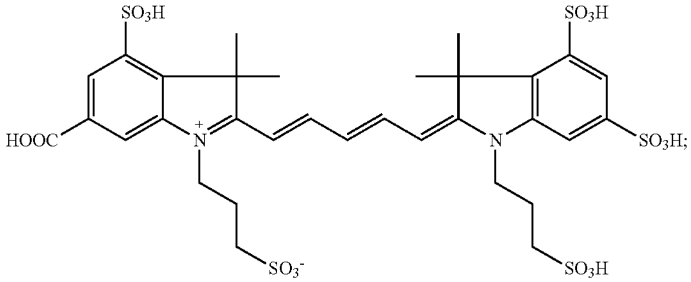
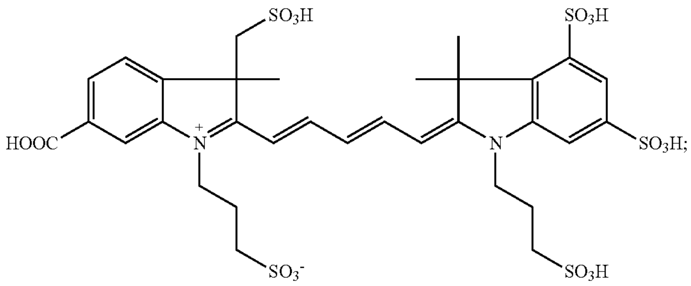

-continued
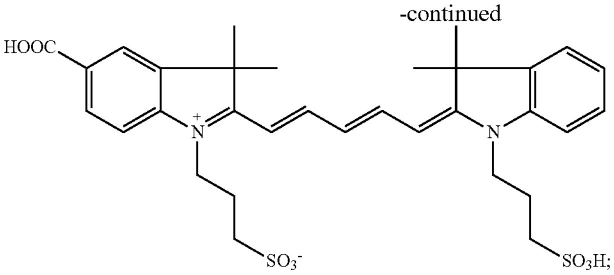
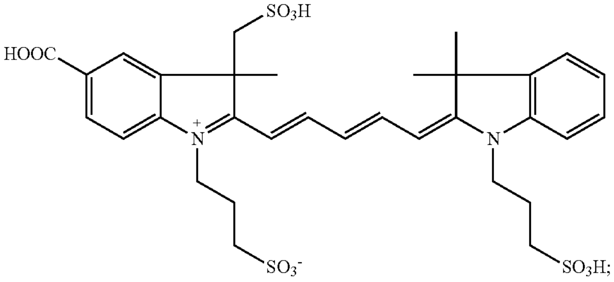
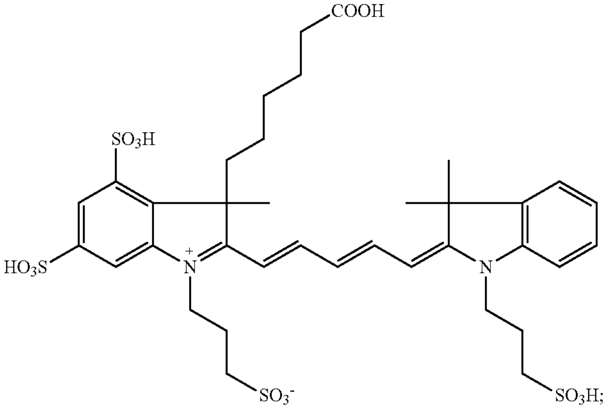
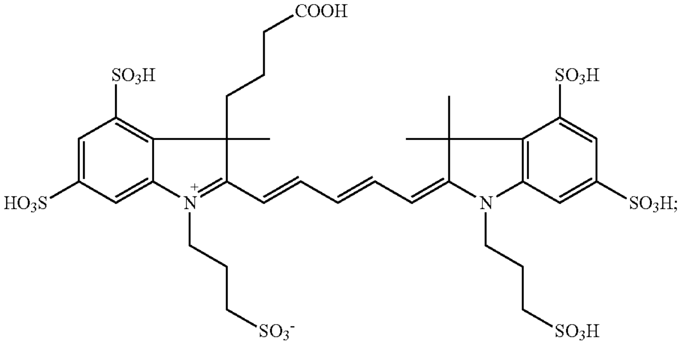

-continued
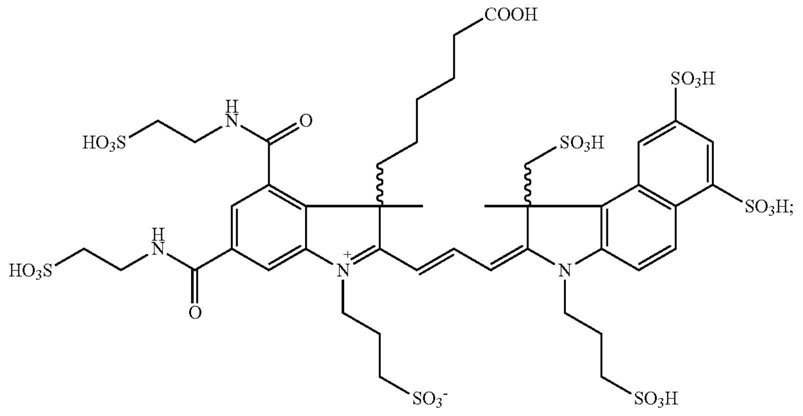
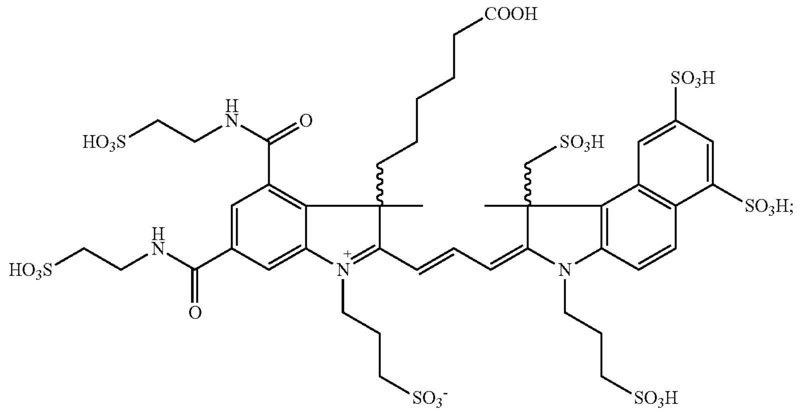
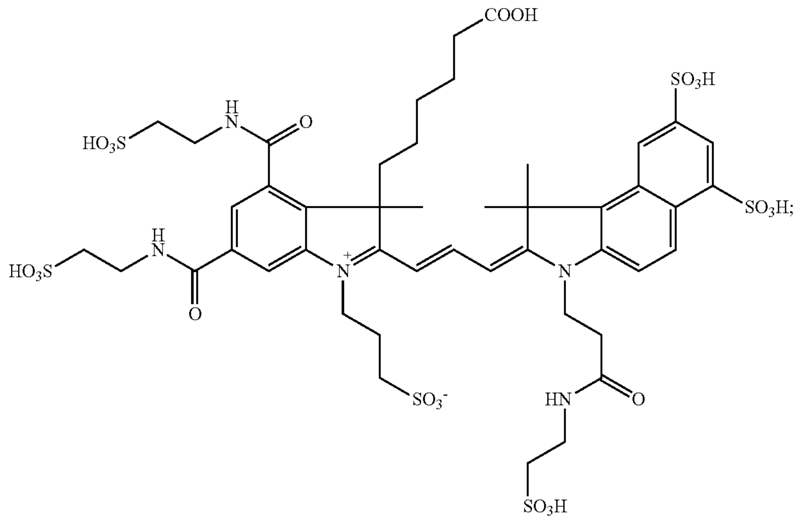

-continued
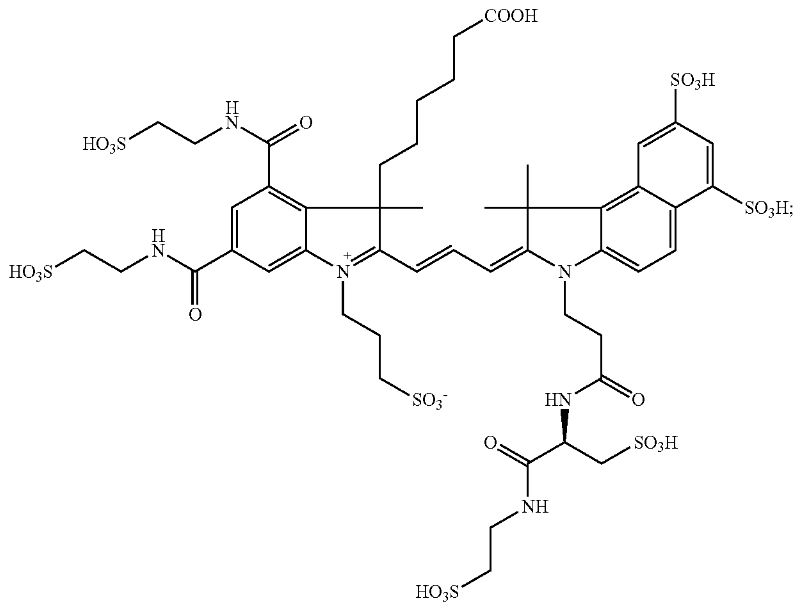
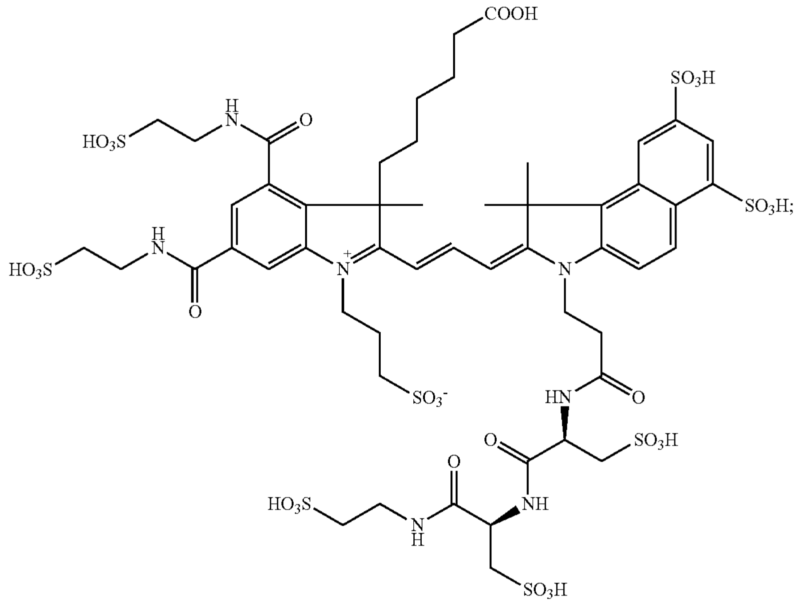
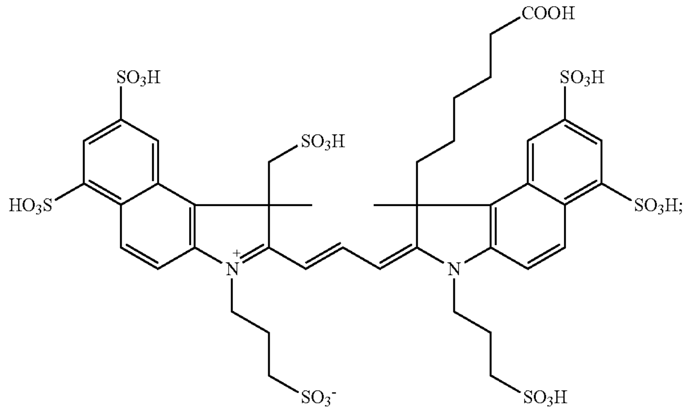

-continued
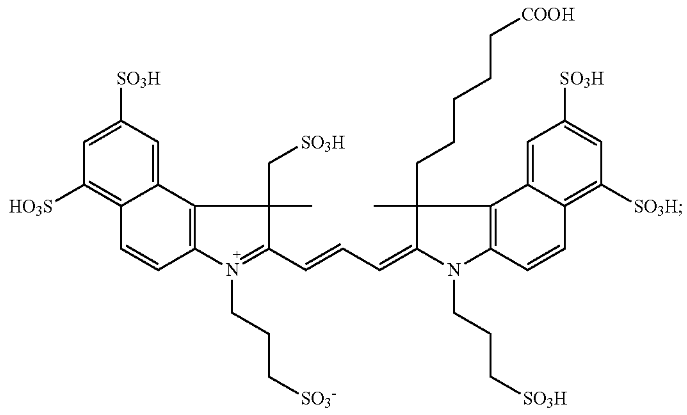
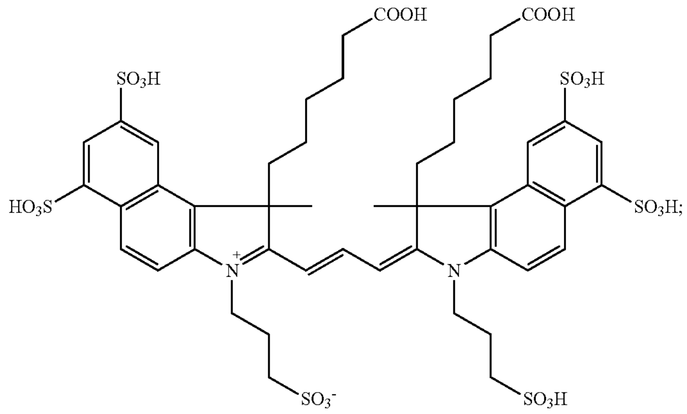
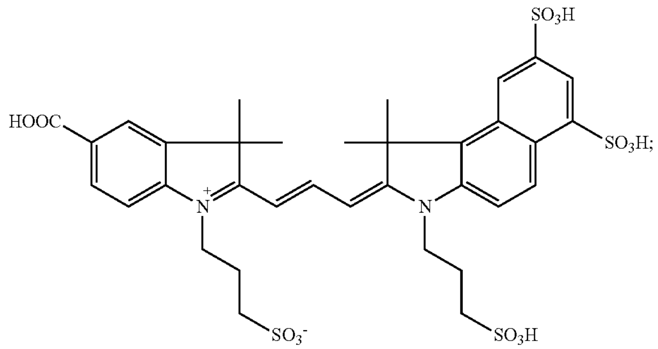
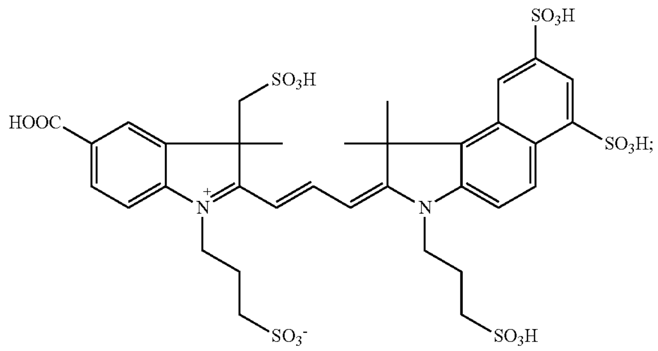

-continued
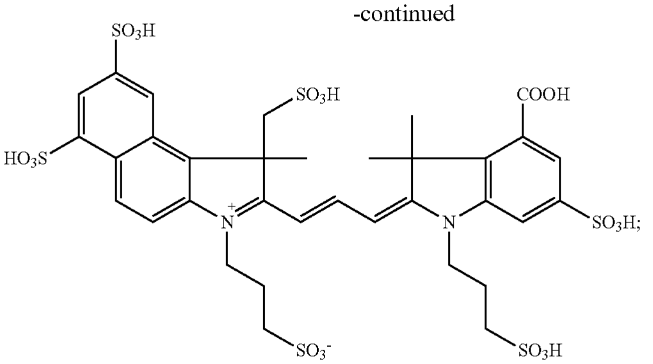
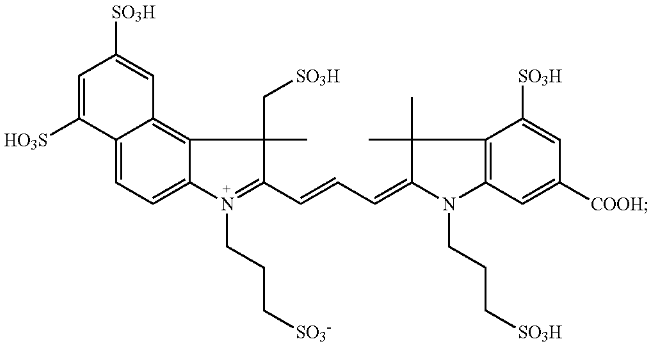
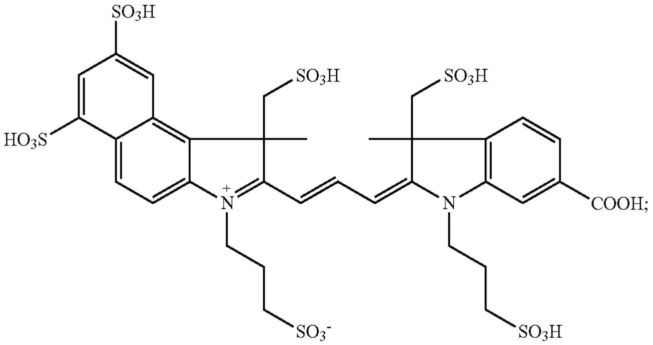
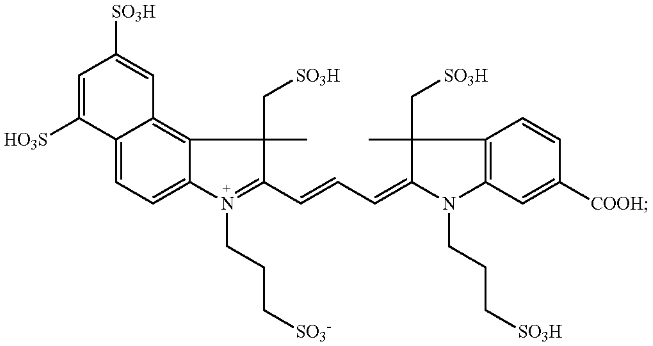

-continued
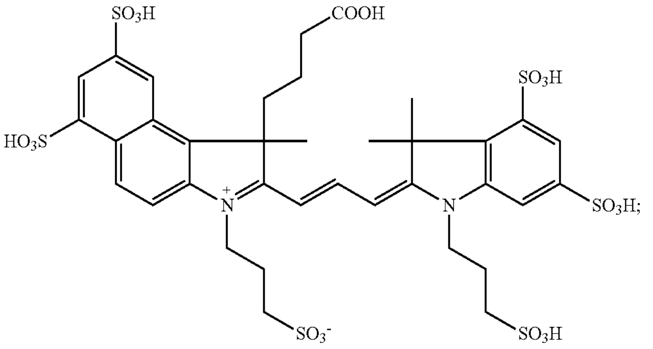
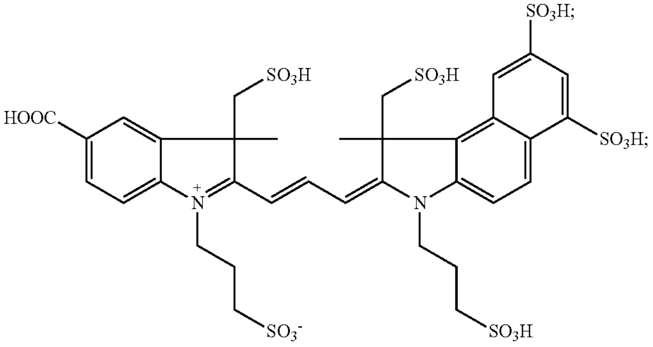
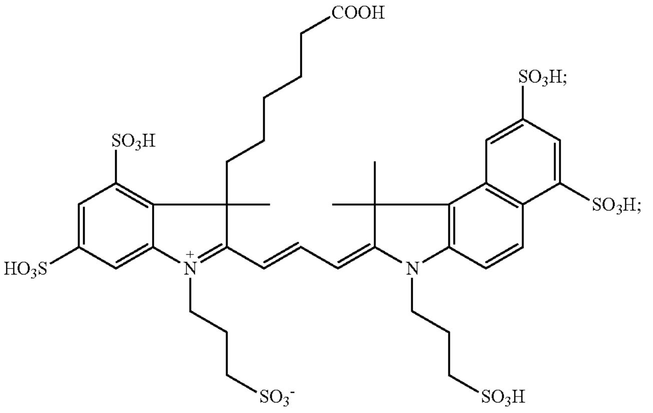
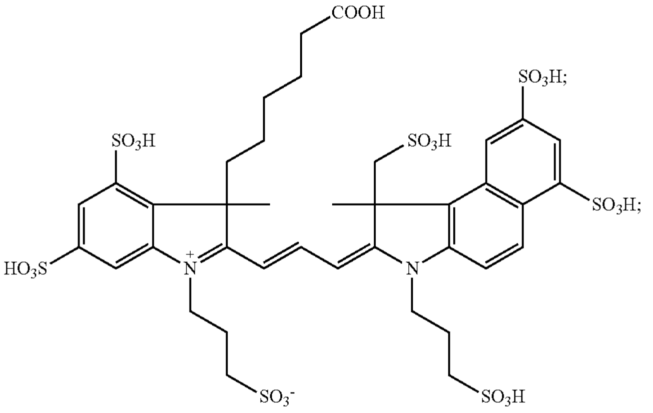

-continued
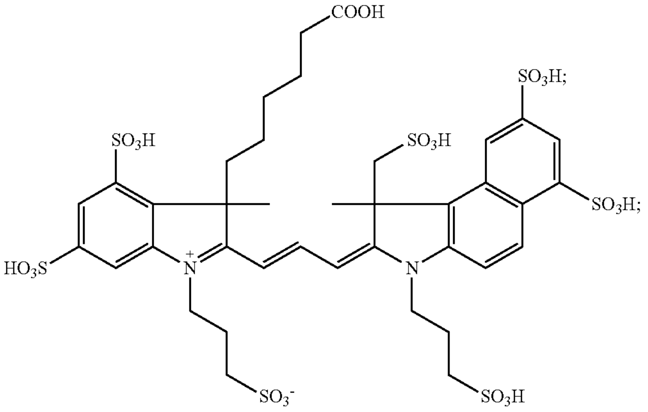
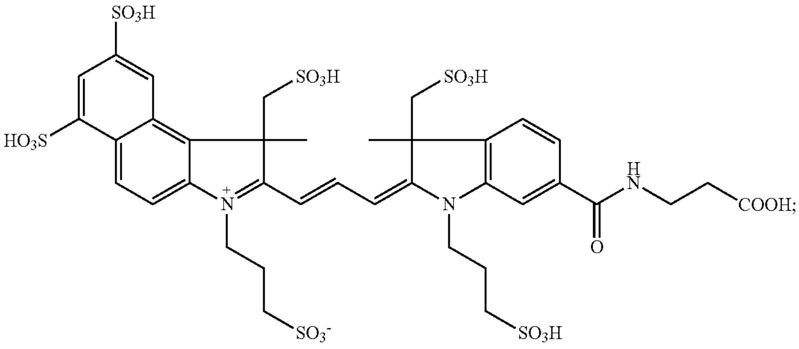
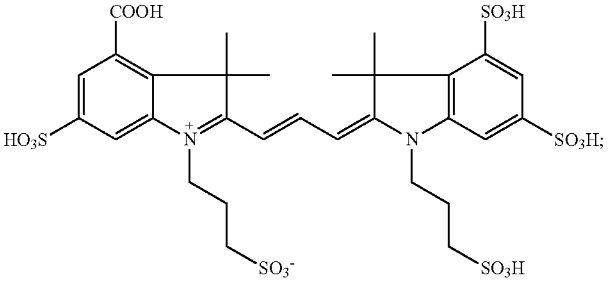
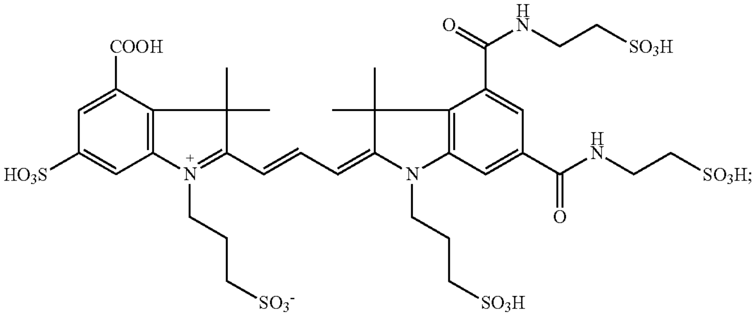
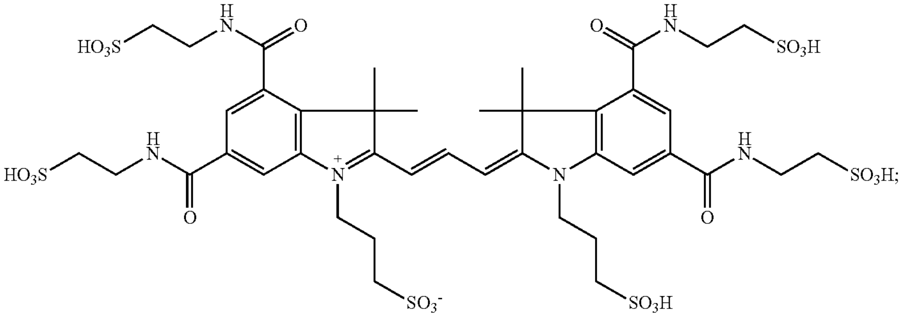

-continued
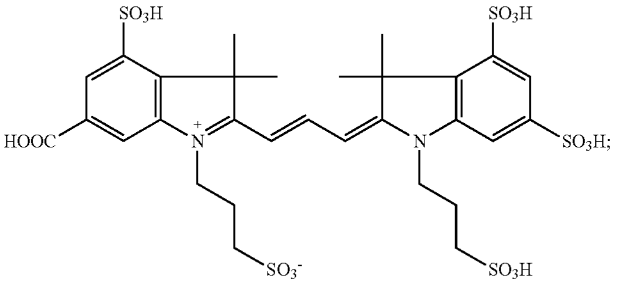
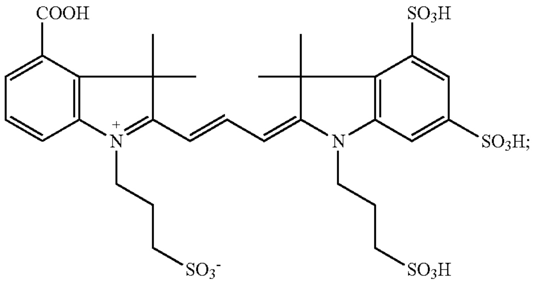
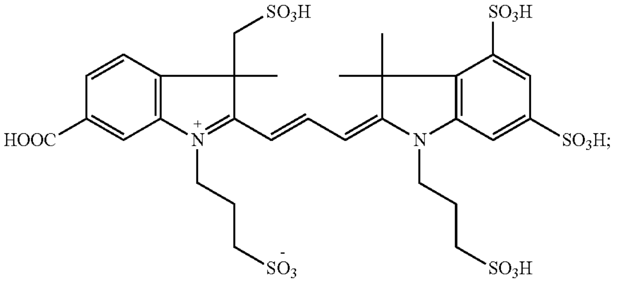
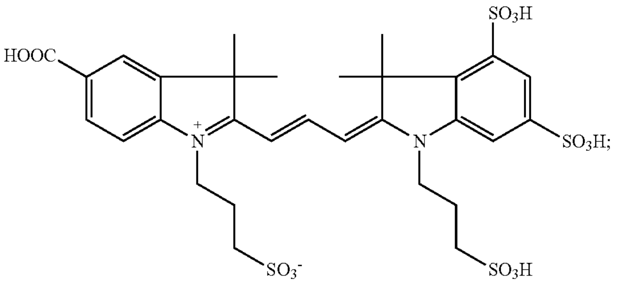
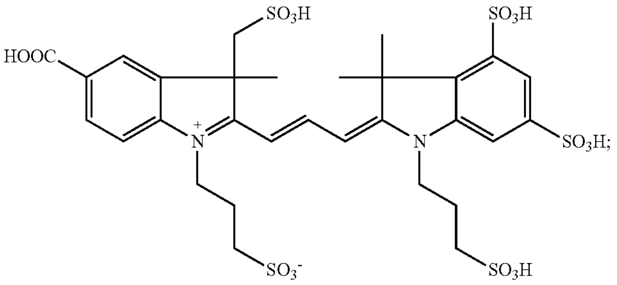
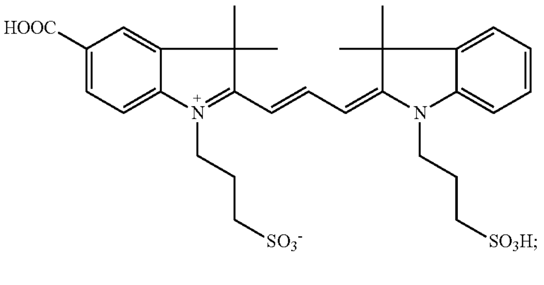
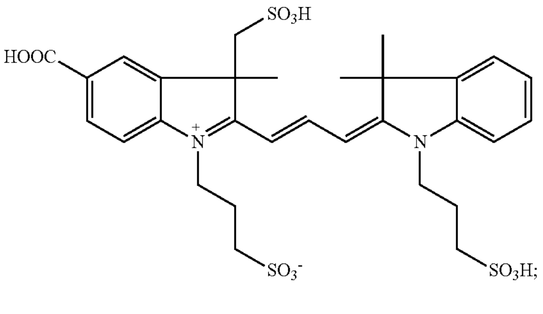

-continued
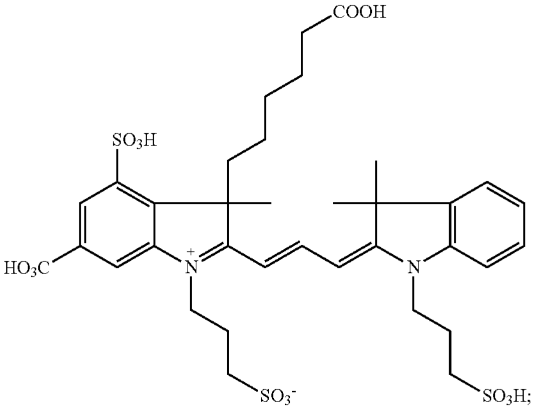
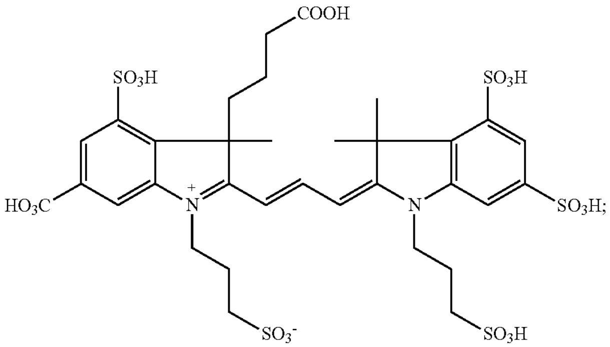
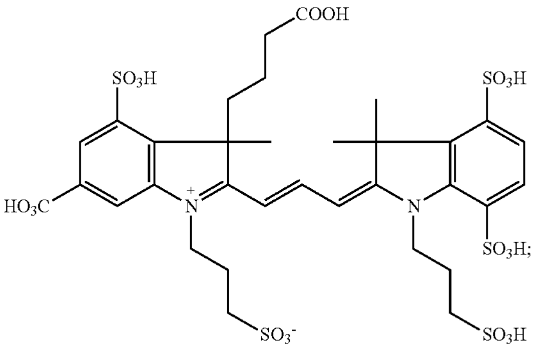
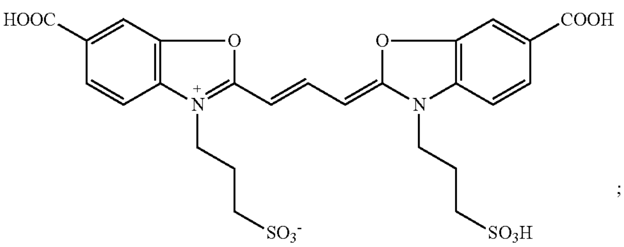
;
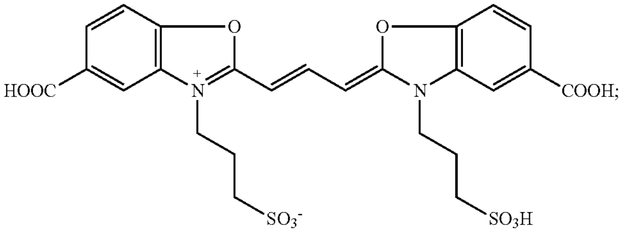
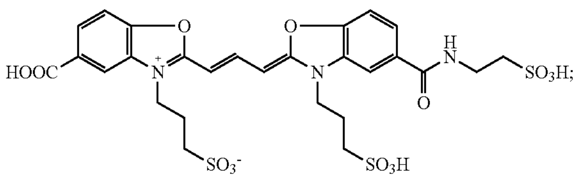
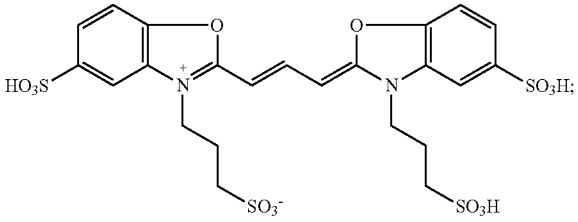
-continued
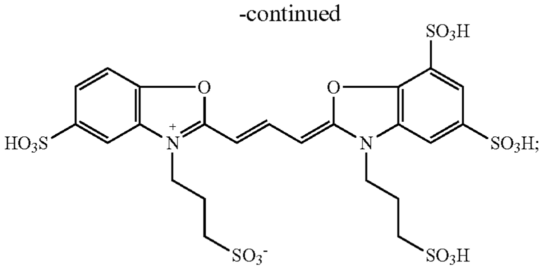
or
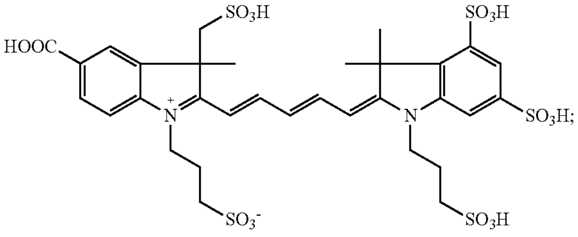
or an ionic derivative thereof.

19. The compound of claim 2, wherein the compound is
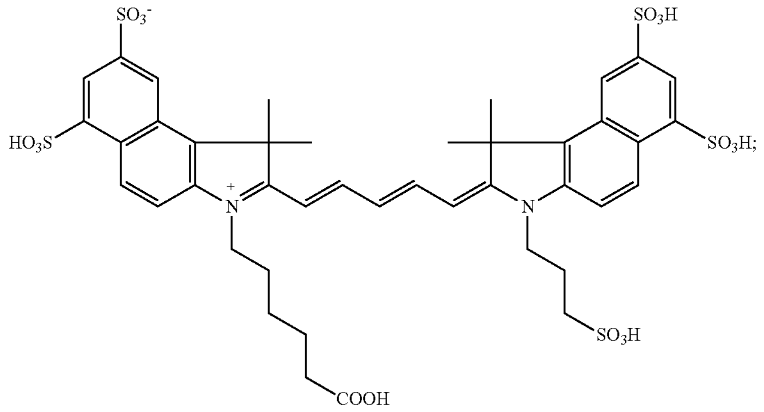
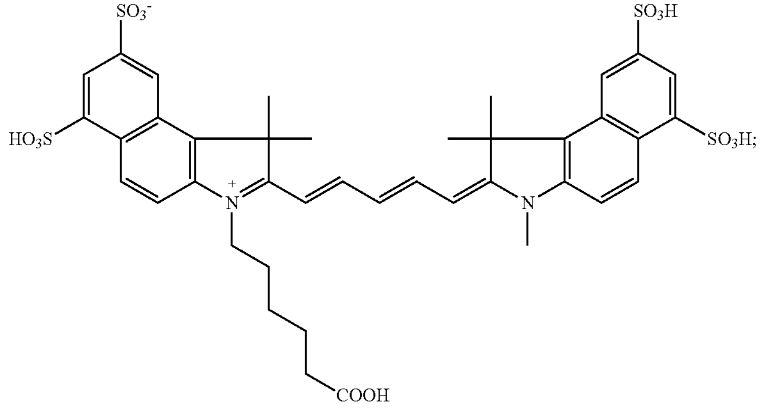
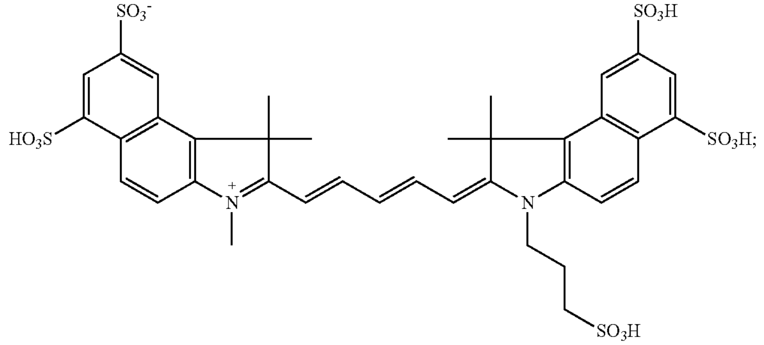
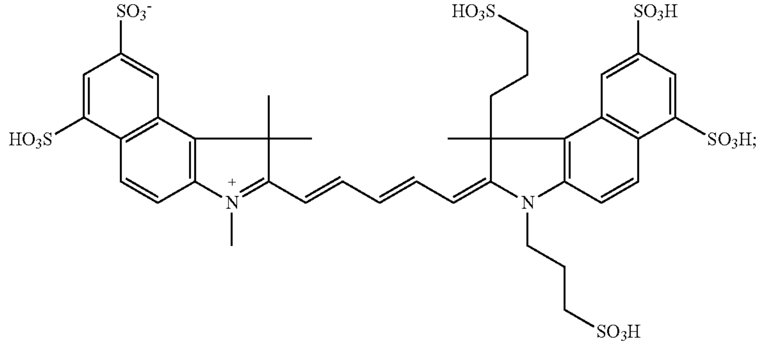

-continued
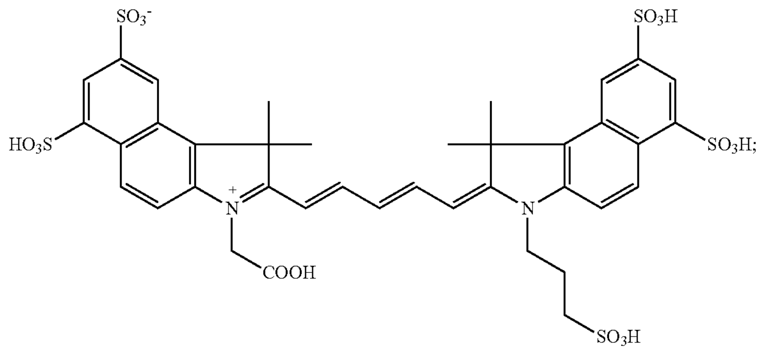
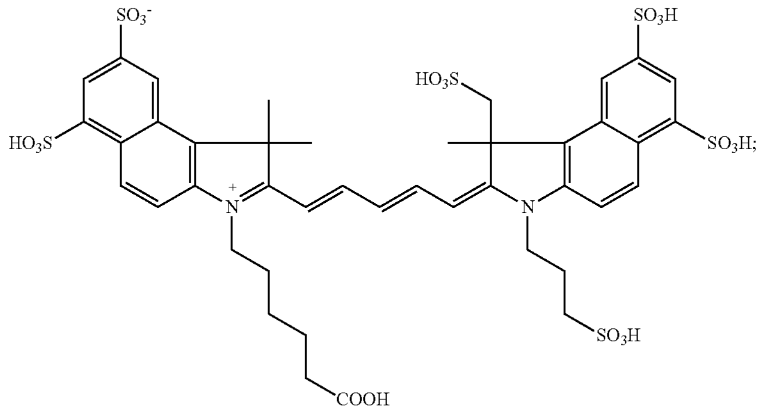
(Diastereomer 1)
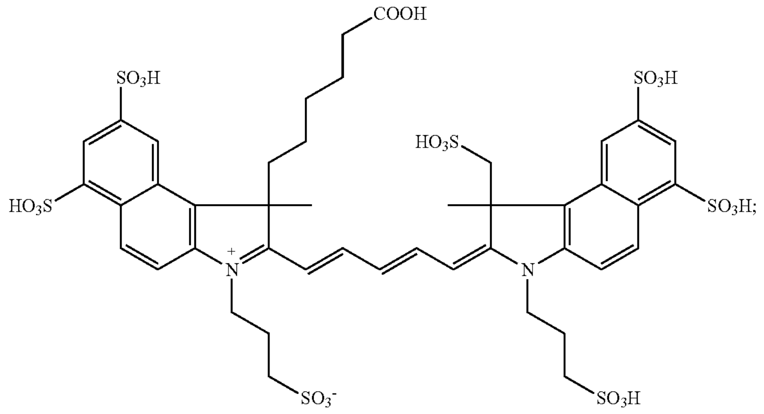
(Diastereomer 2)
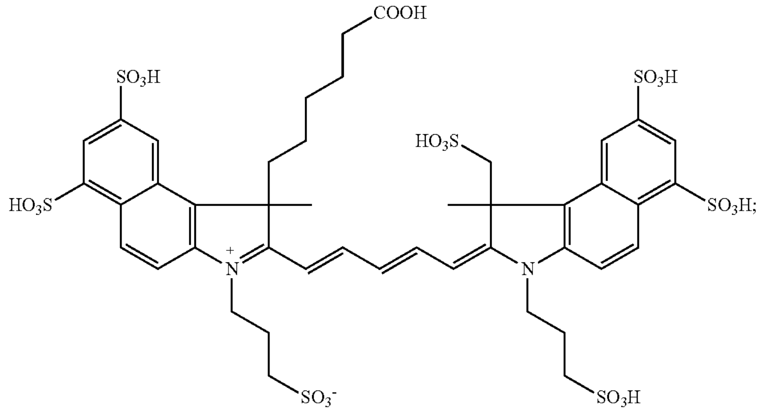

-continued
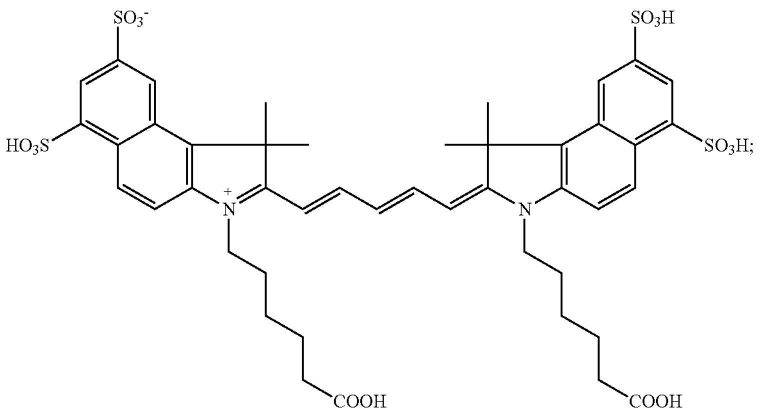
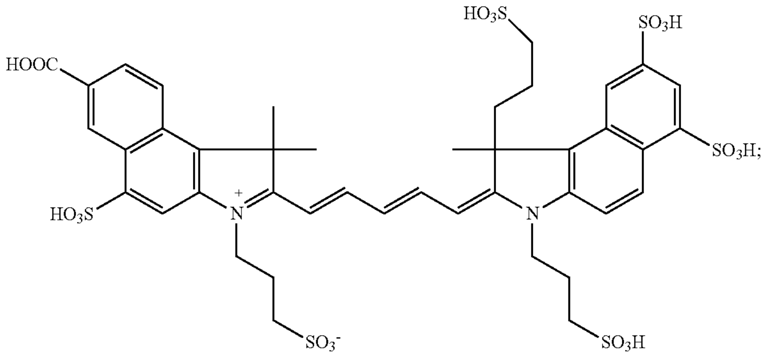
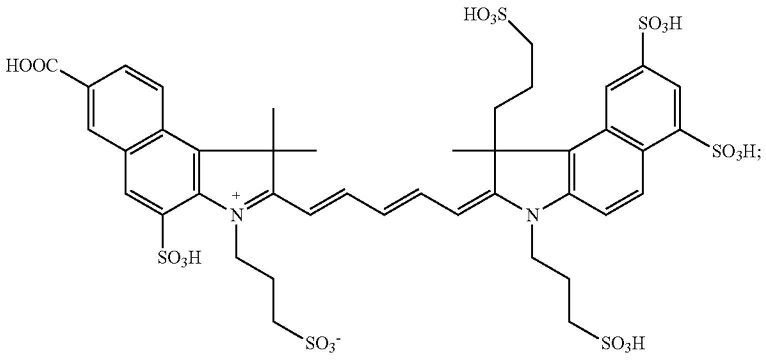
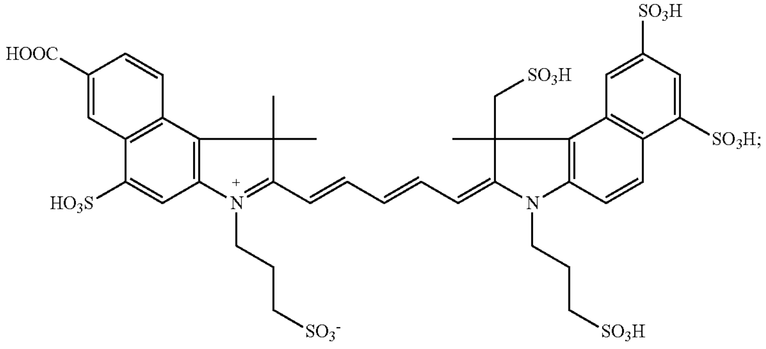

-continued
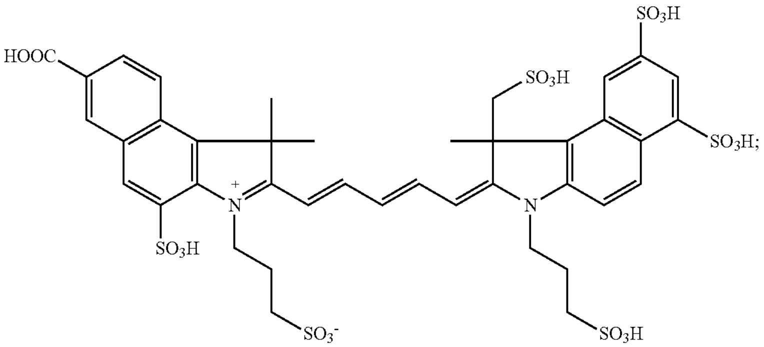
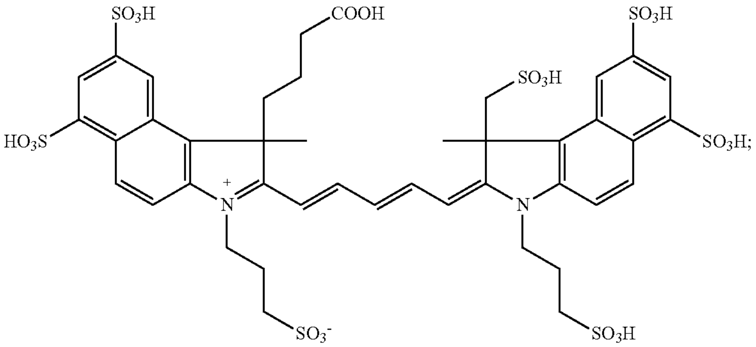
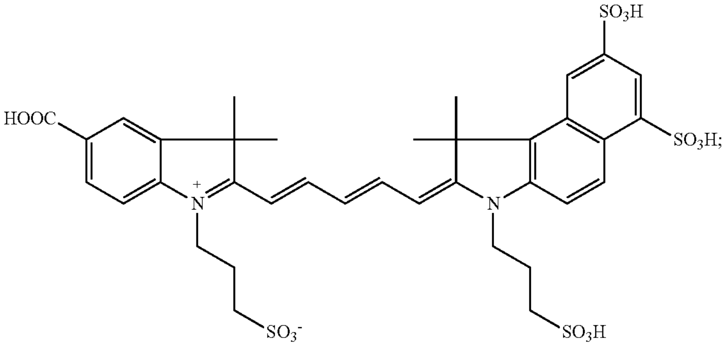
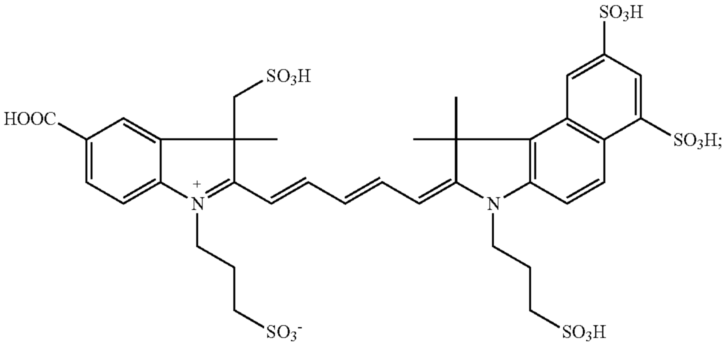
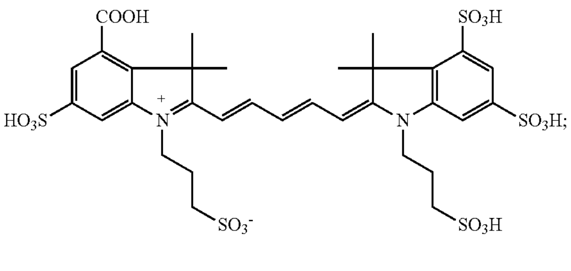
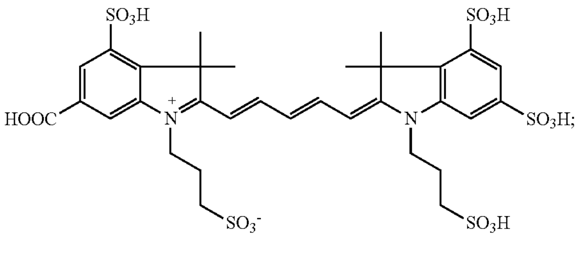

-continued
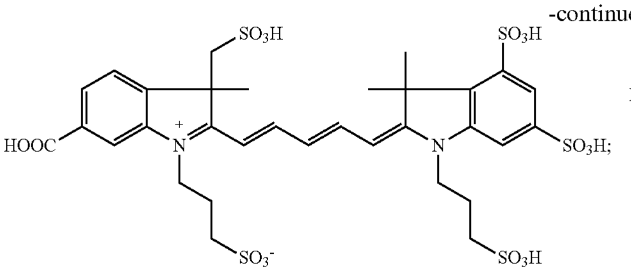
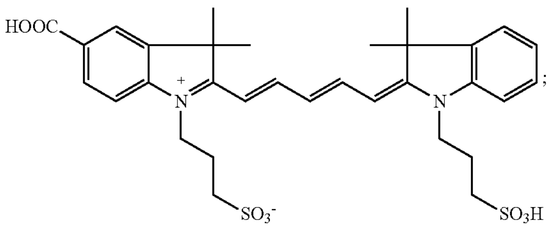
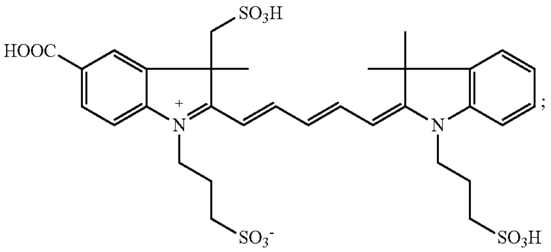
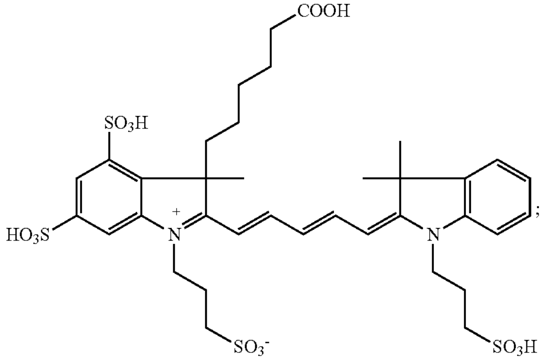
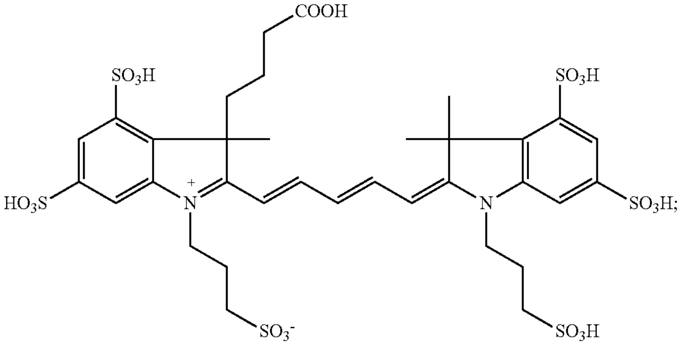
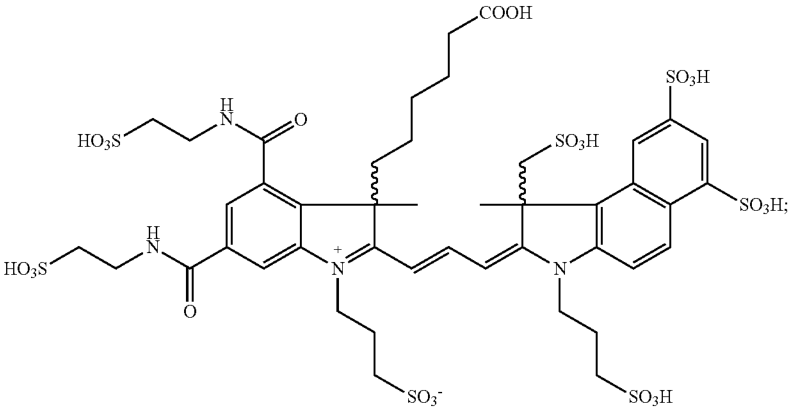

-continued
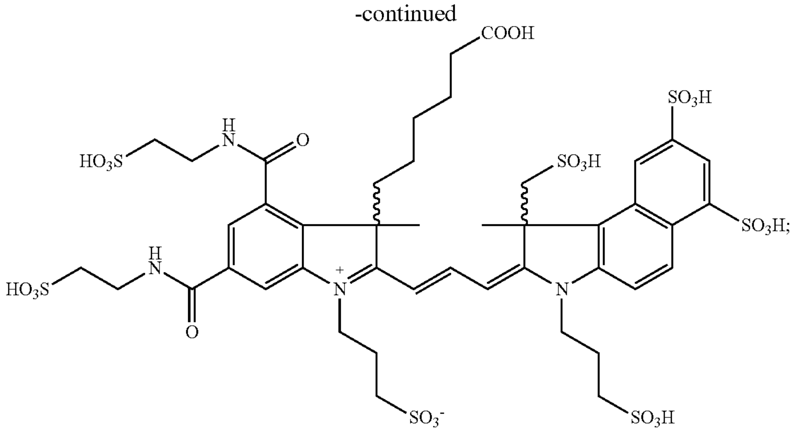
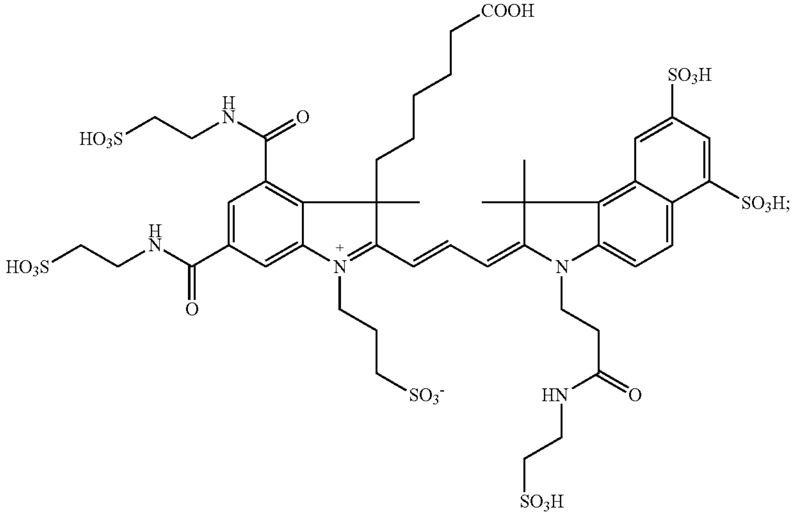
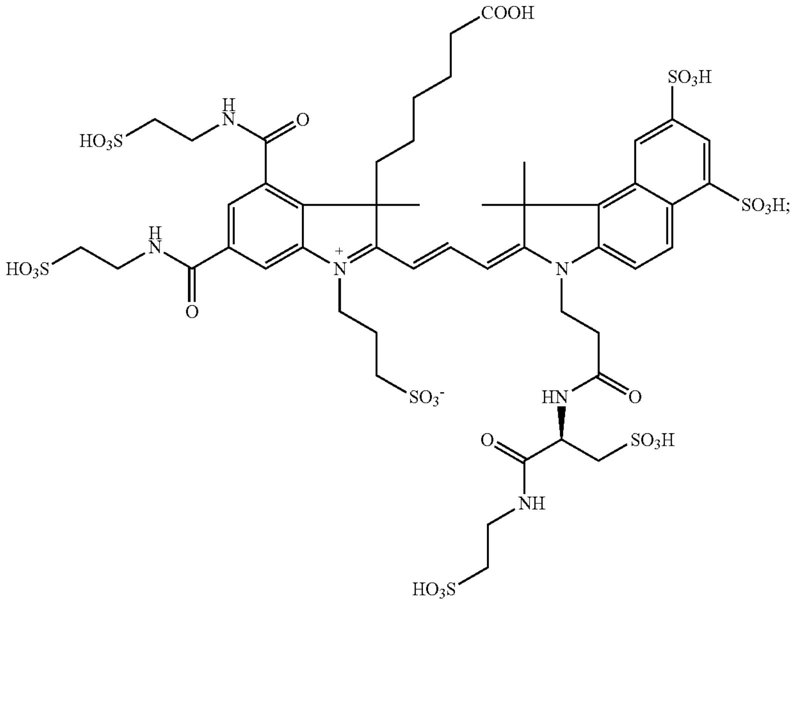

-continued
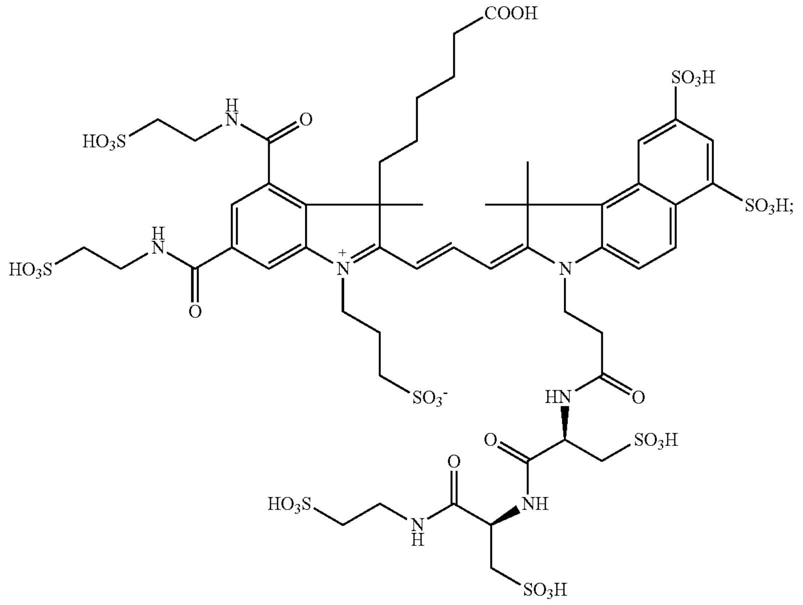
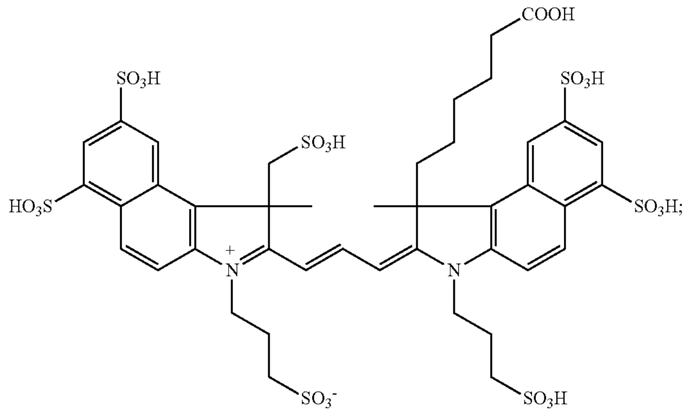
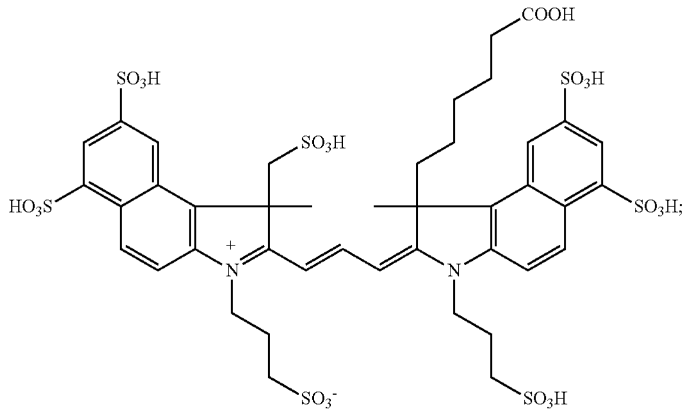

-continued
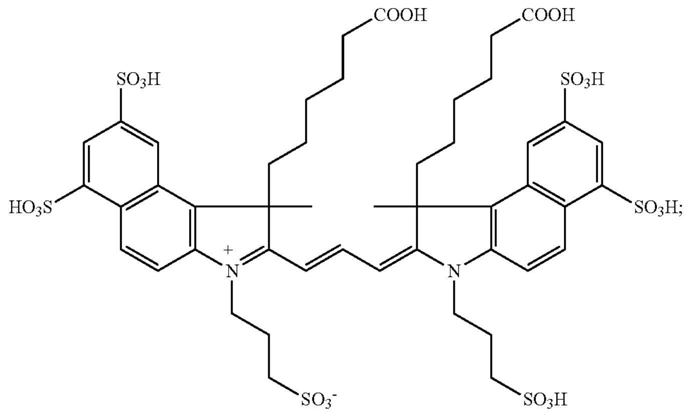
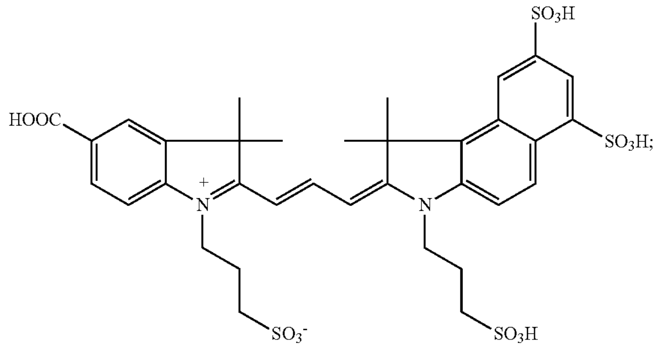
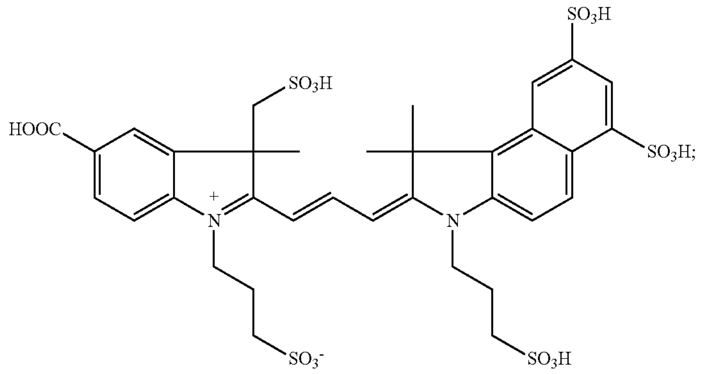
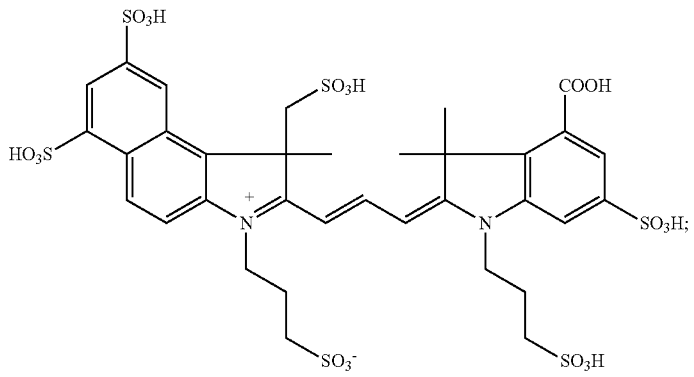

-continued
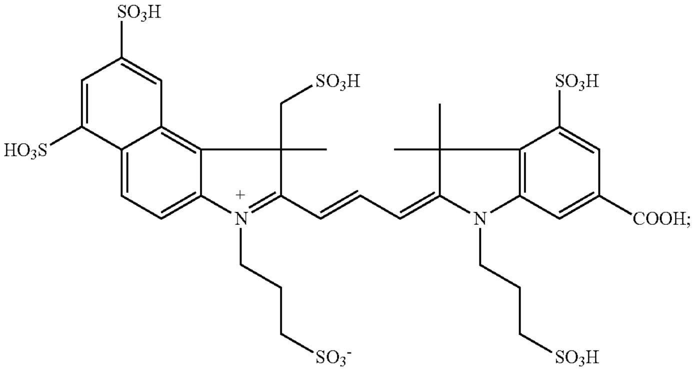
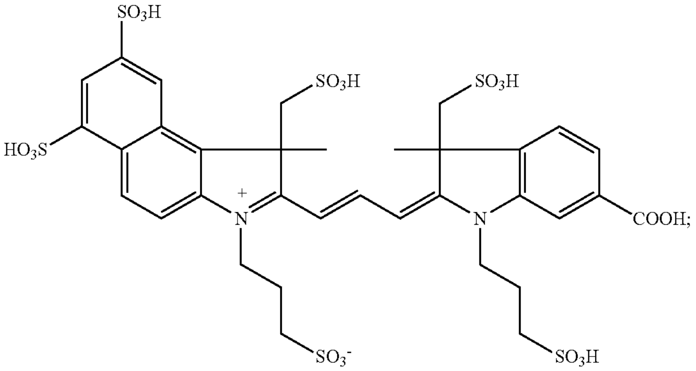
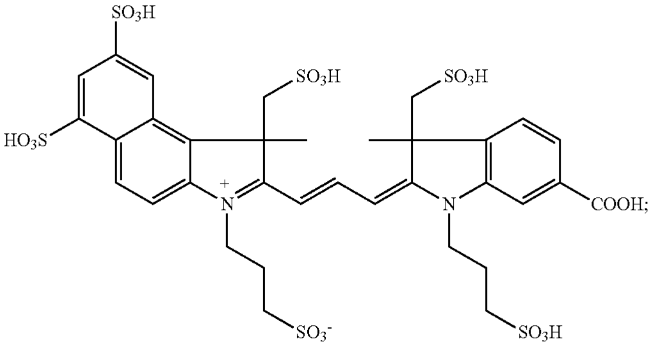
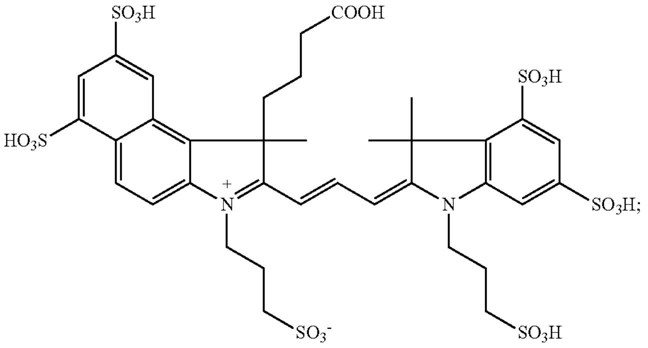

-continued
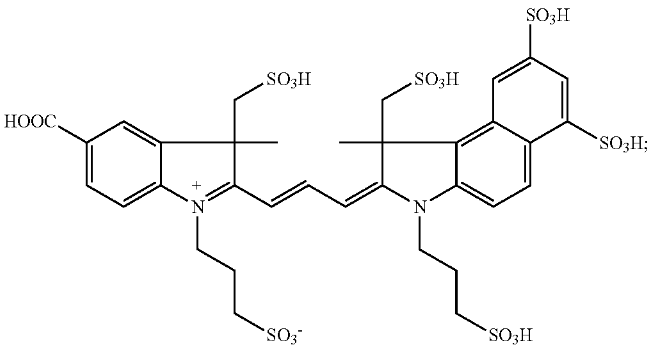
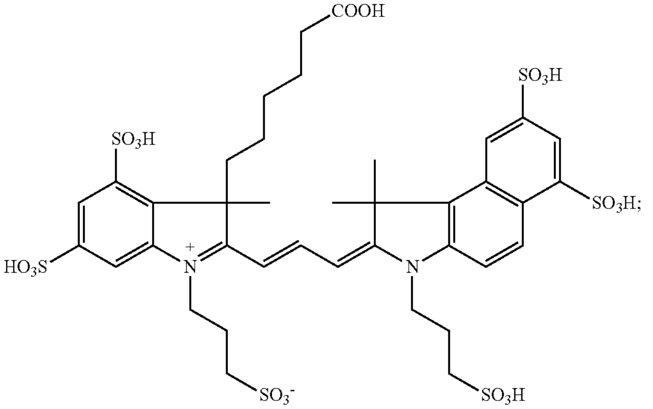
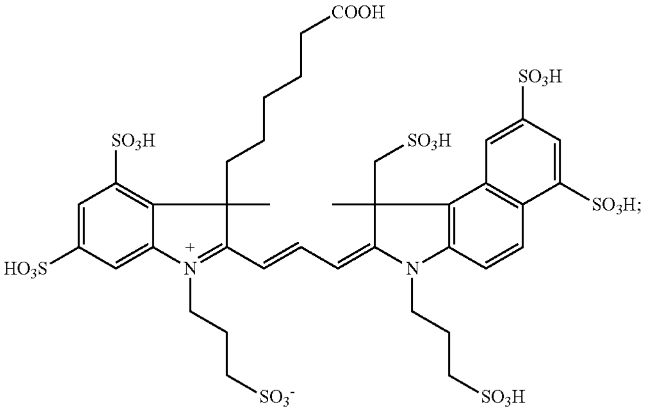
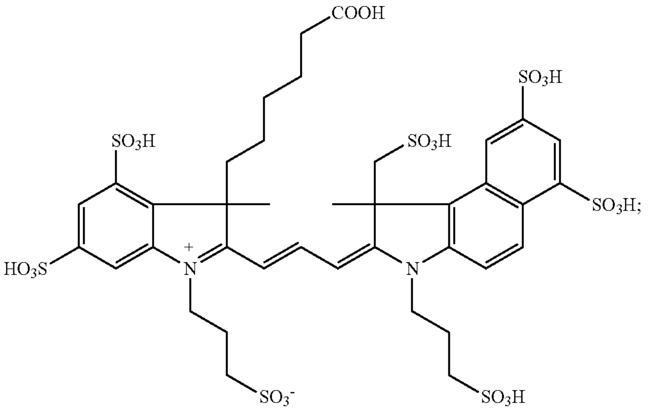

-continued
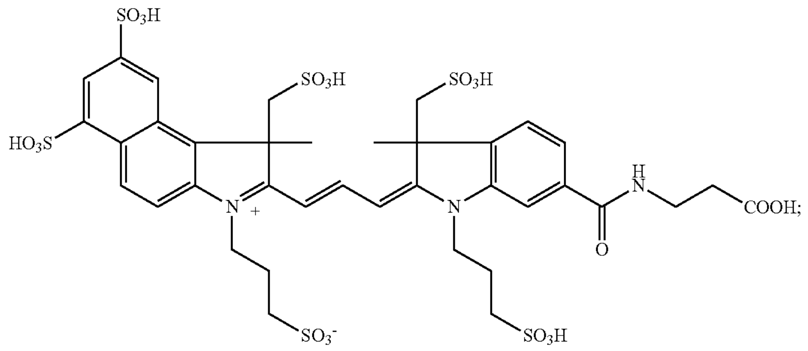
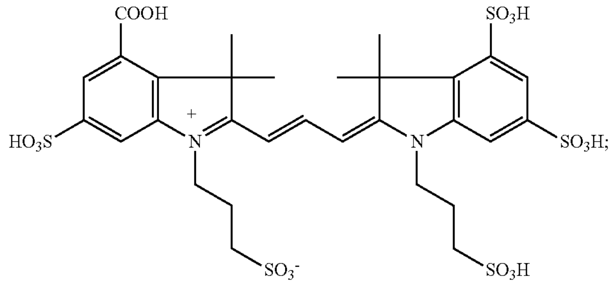
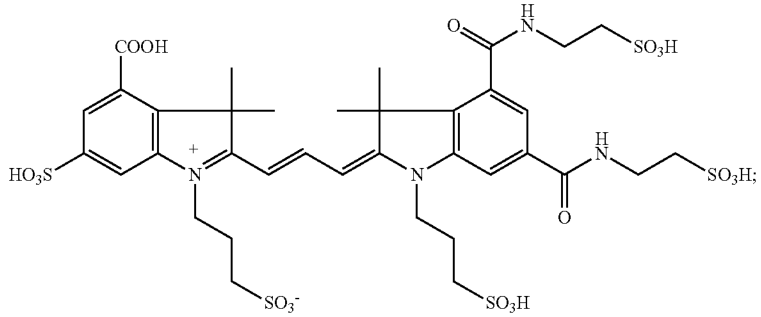
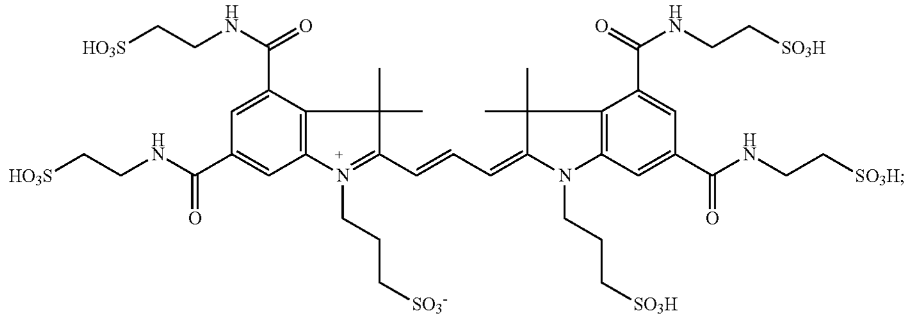
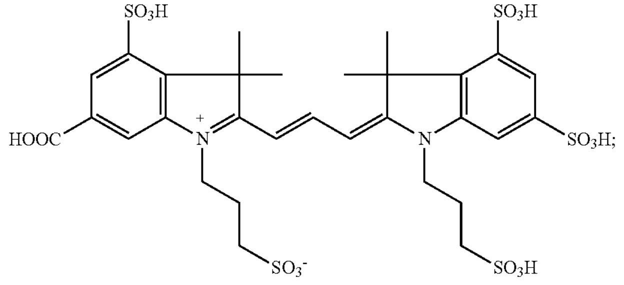

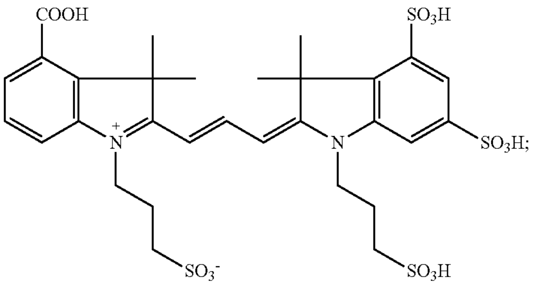
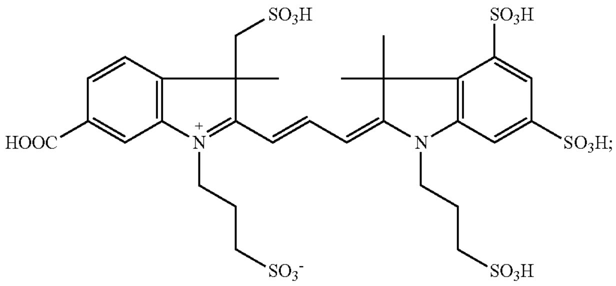
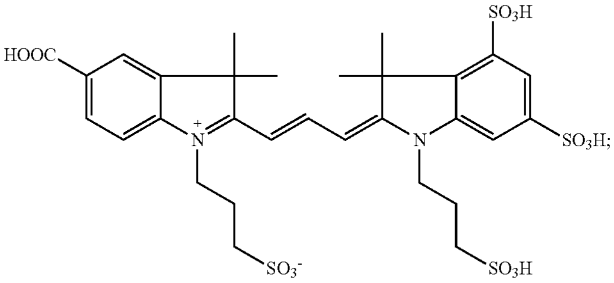
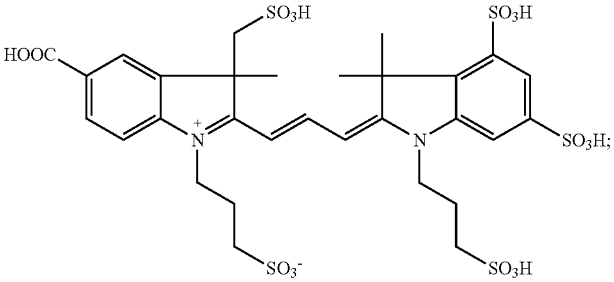
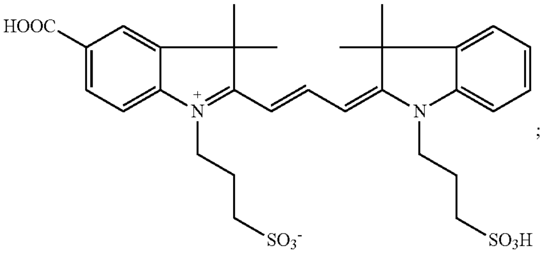
;
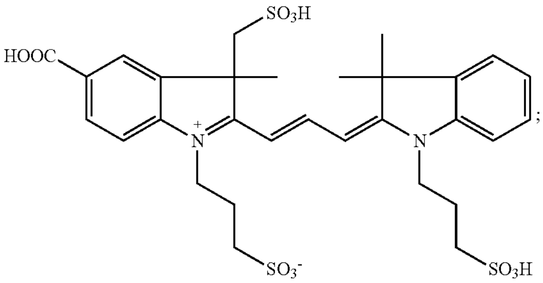
;
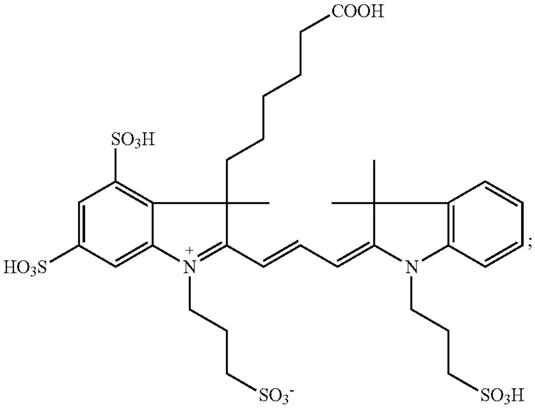
;
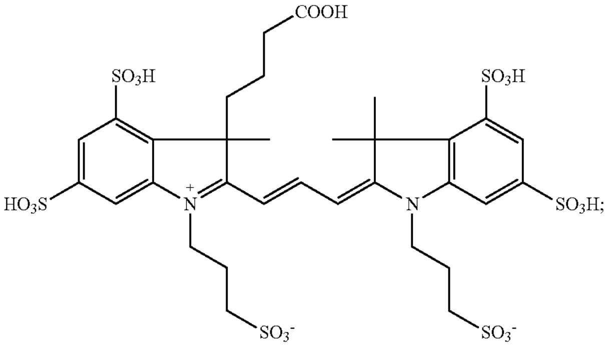
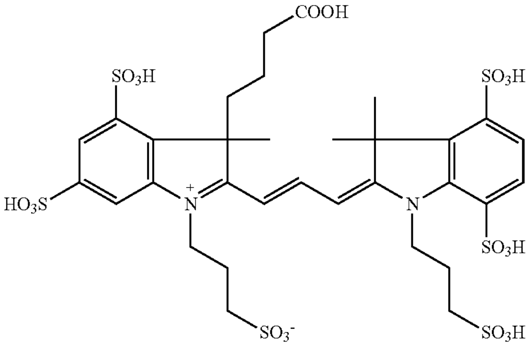
;

-continued
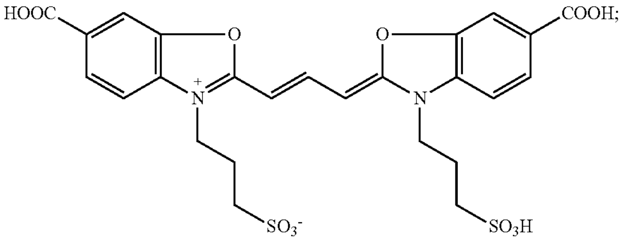
;
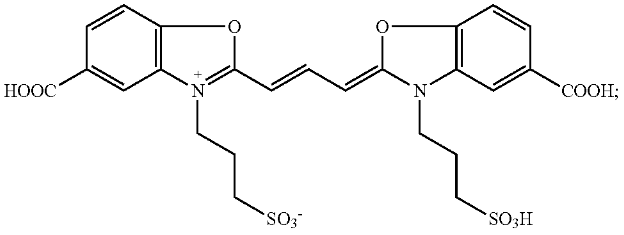
;
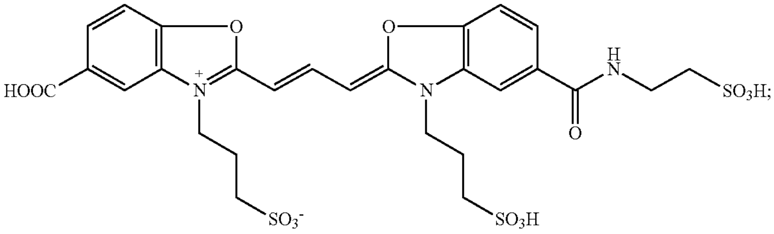
;
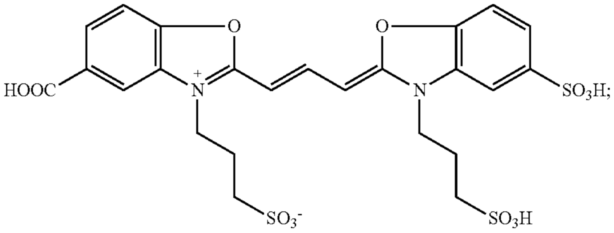
;
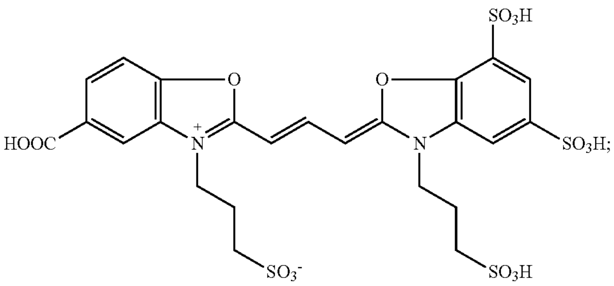
; or
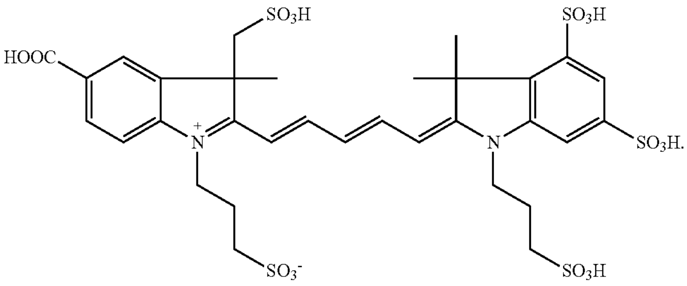
.

20. The compound of claim 7, wherein the compound is
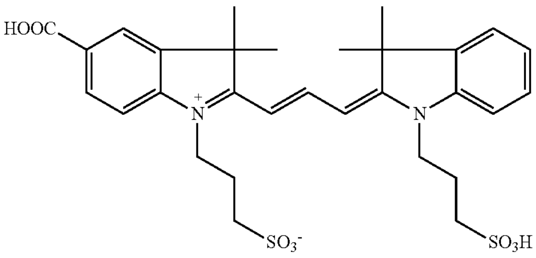
;
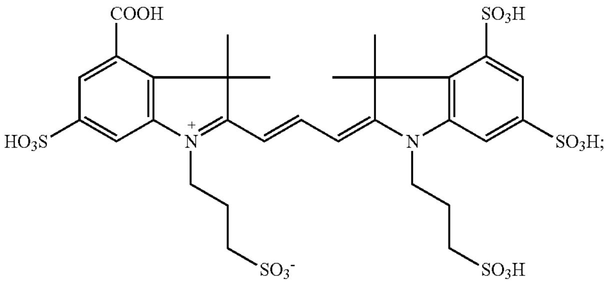
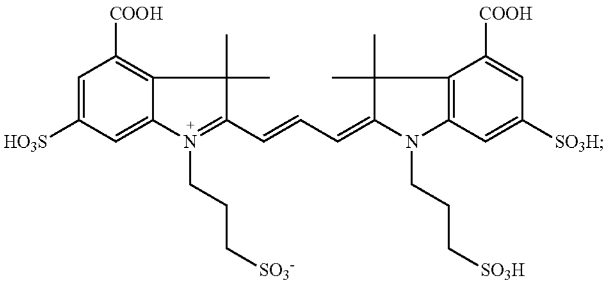
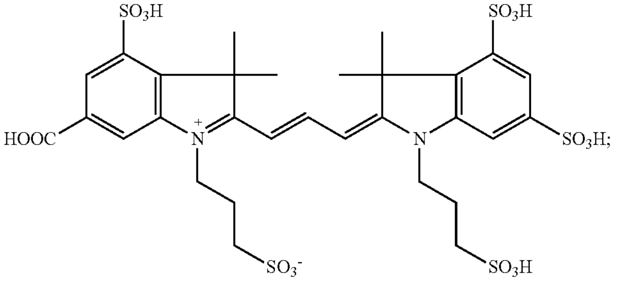
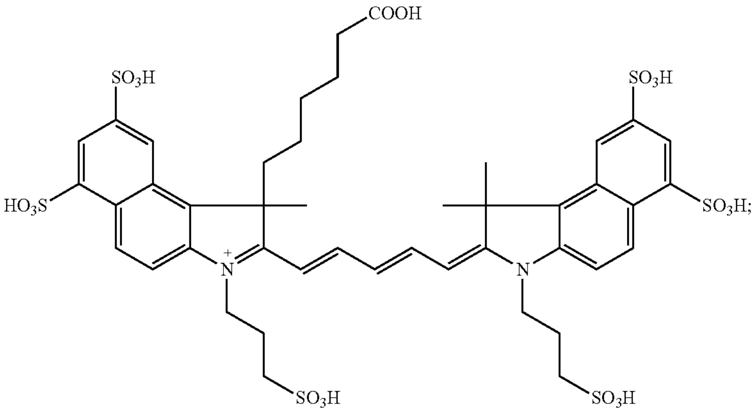
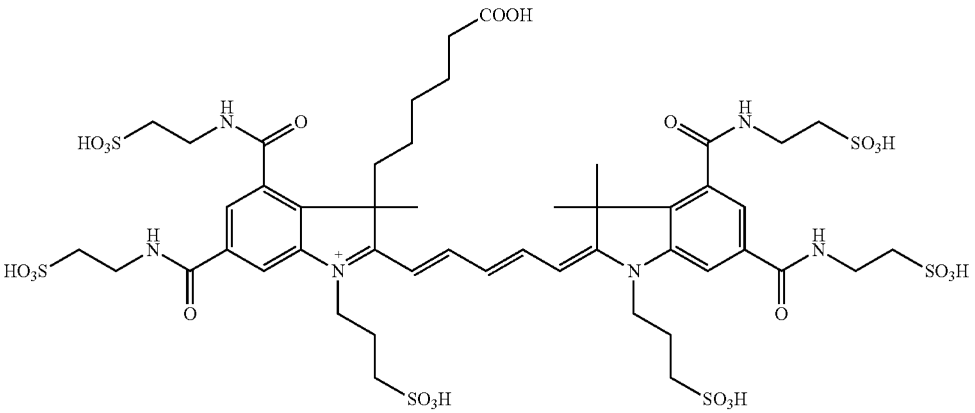

-continued
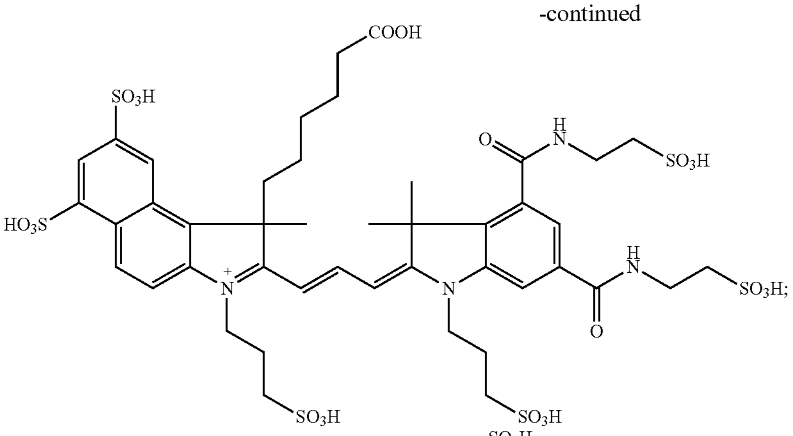
or
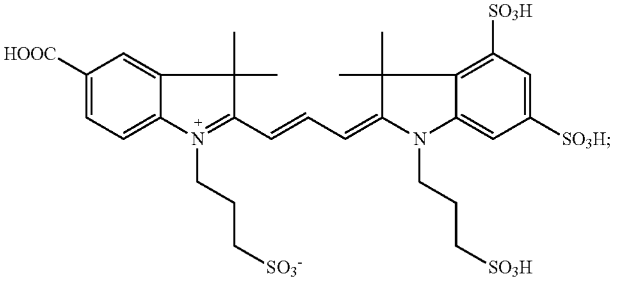
or a salt thereof.
21. The compound of claim 7, wherein the compound is
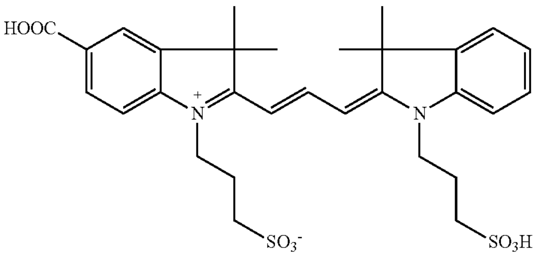
;
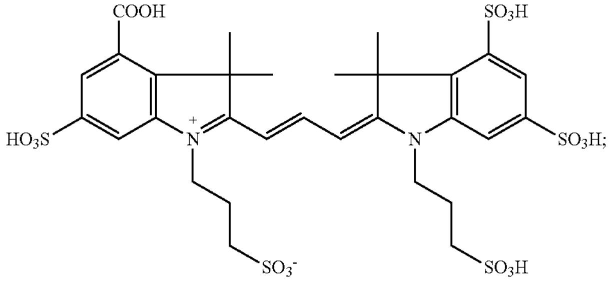
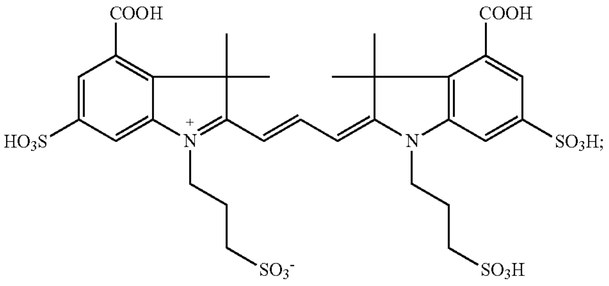
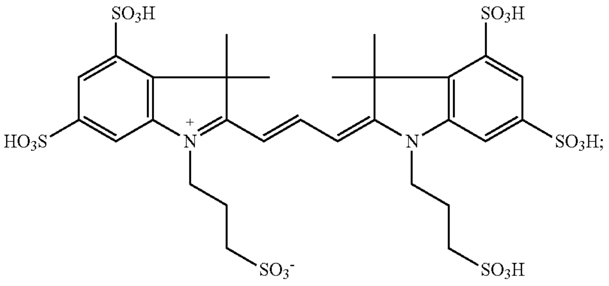

-continued
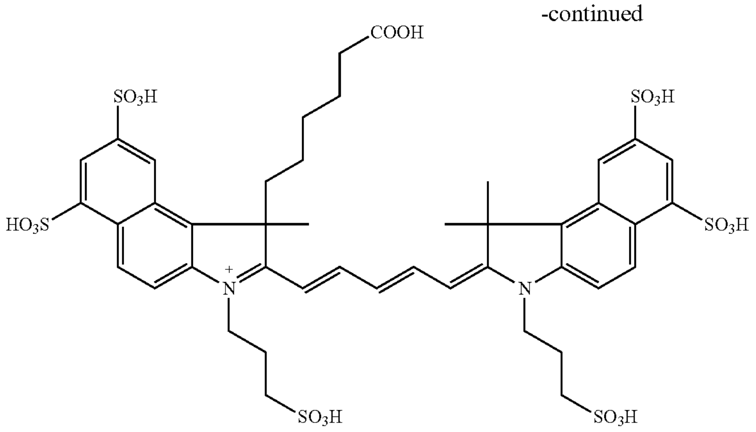
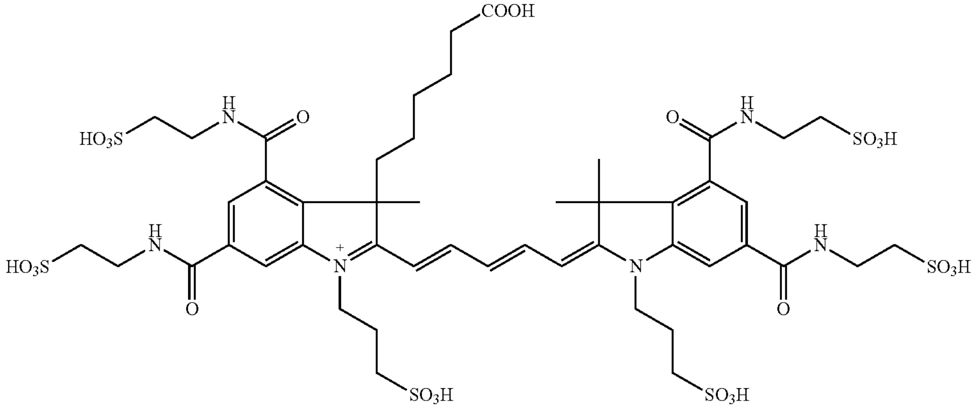
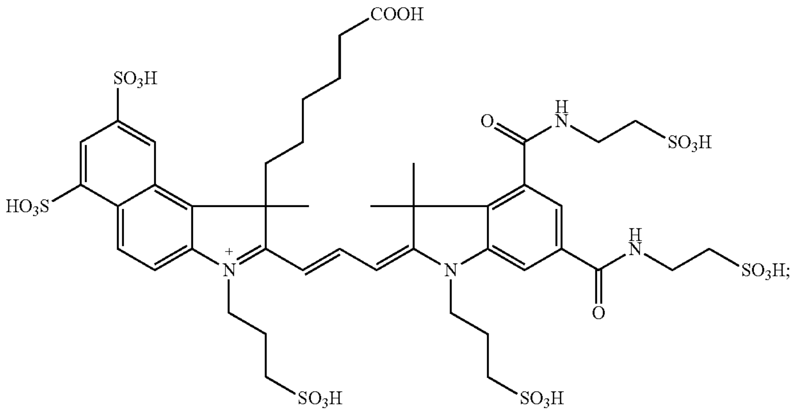
or
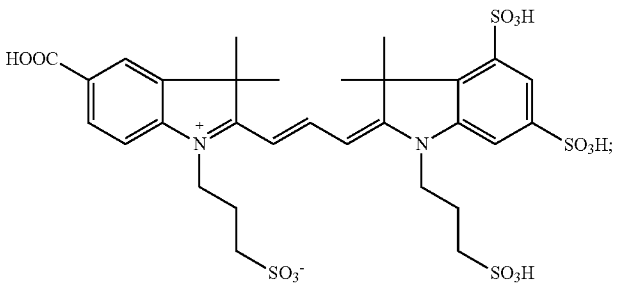
or an ionic derivative thereof.

22. The compound of claim 7, wherein the compound is
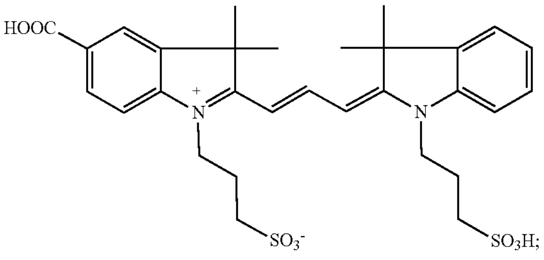
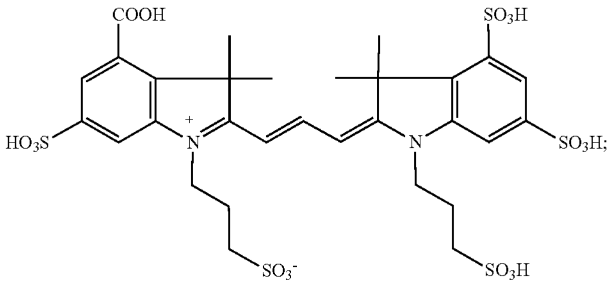
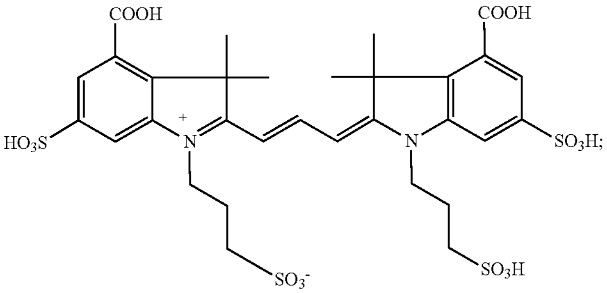
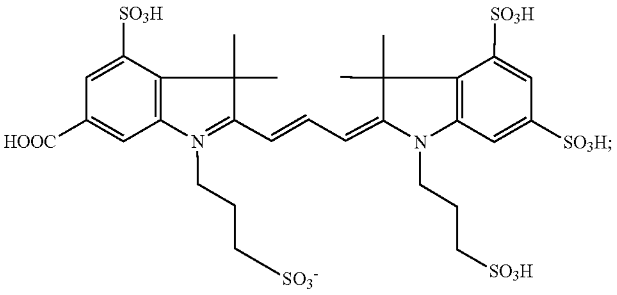
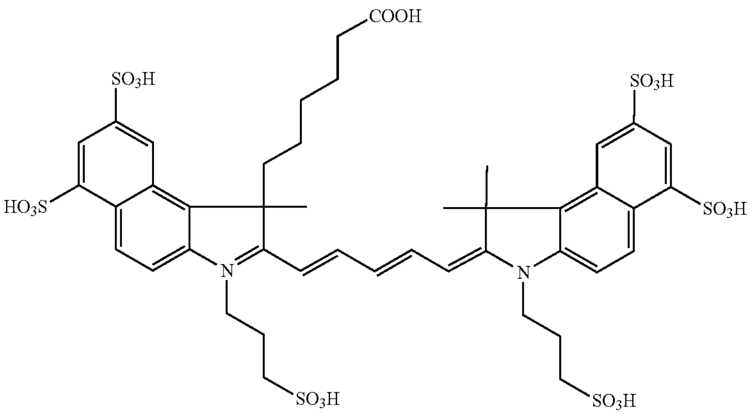

-continued
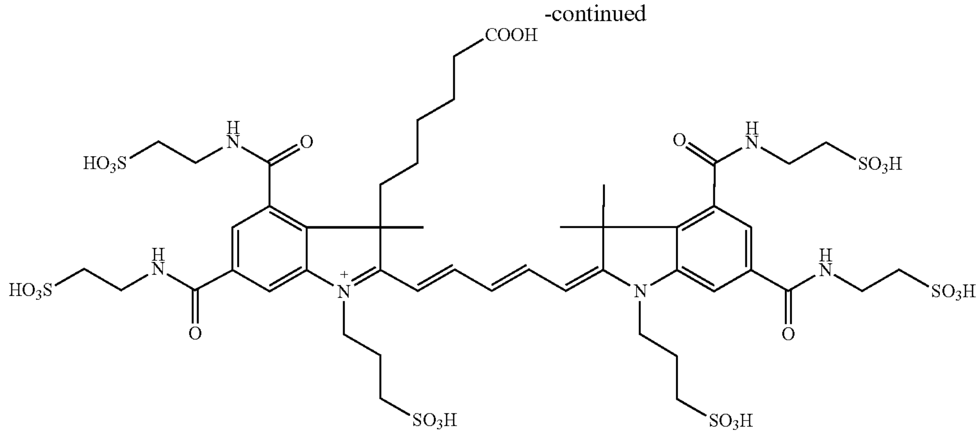
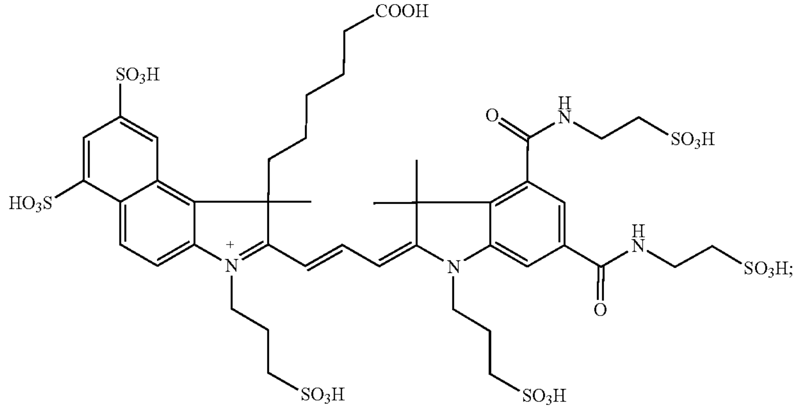
or
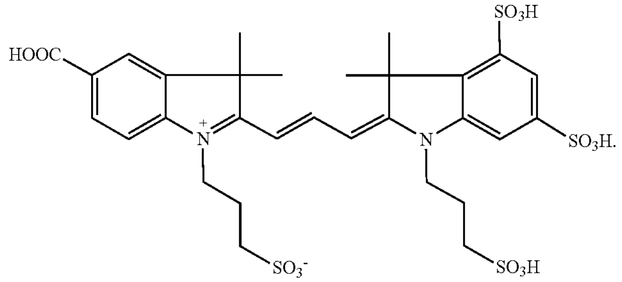
23. The compound of claim 8, wherein the compound is
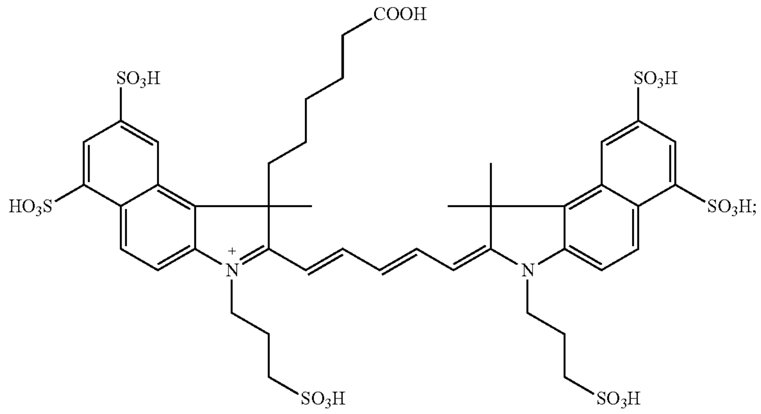

-continued
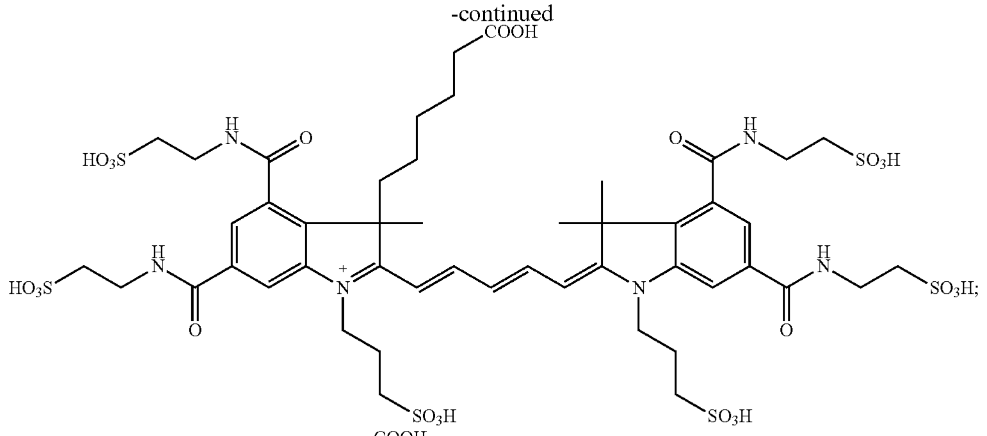
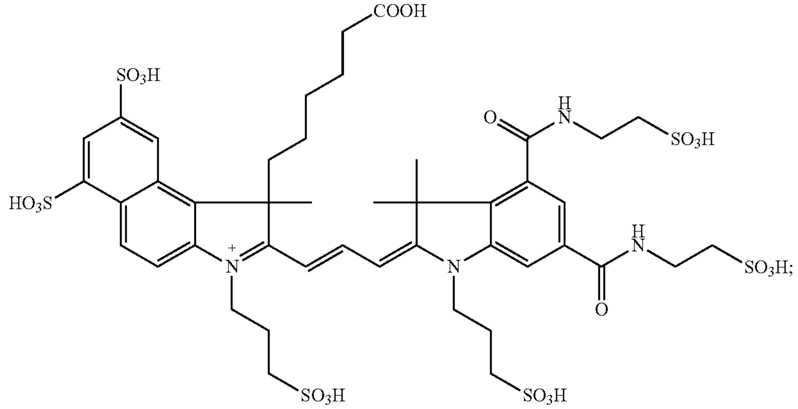
or
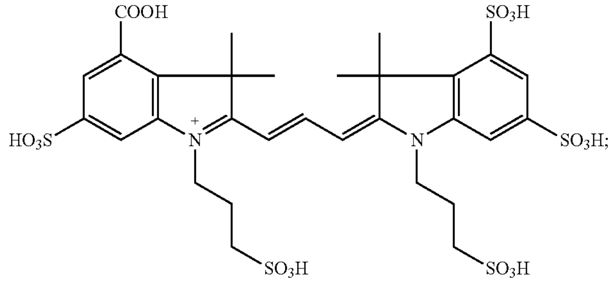
or a salt thereof.
24. The compound of claim 8, wherein the compound is
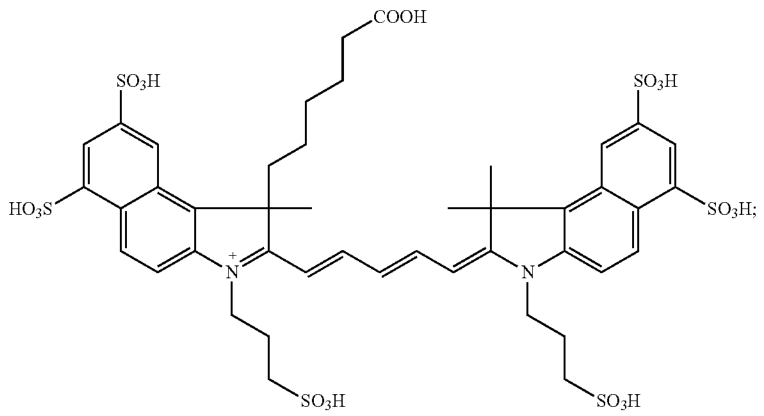

-continued
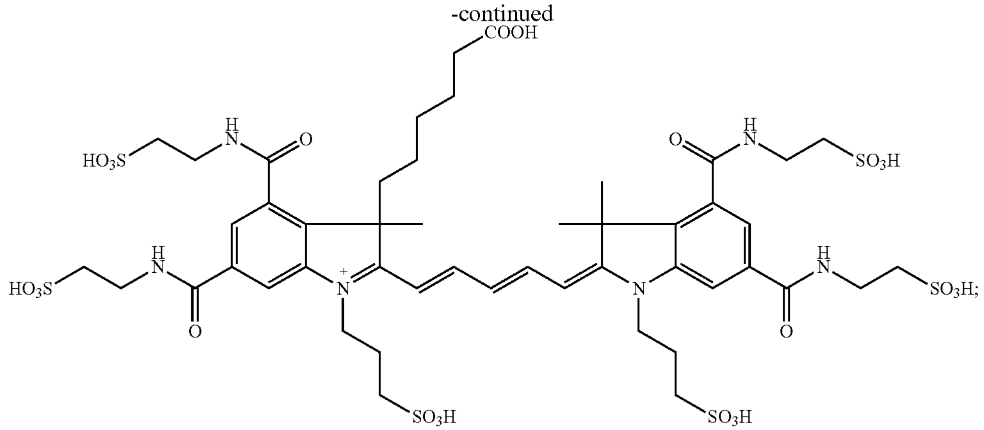
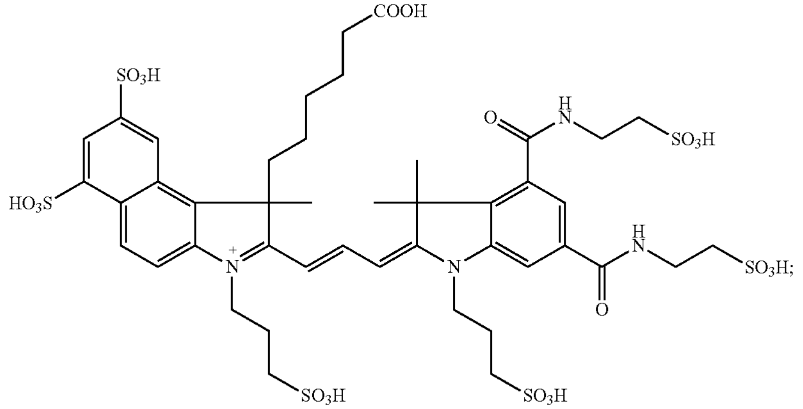
or
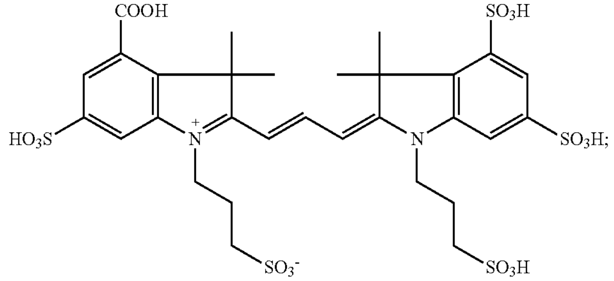
or an ionic derivative thereof.
25. The compound of claim 8, wherein the compound is
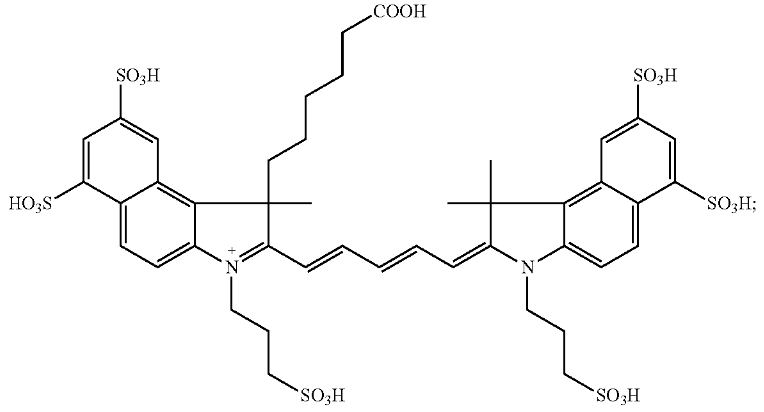

-continued
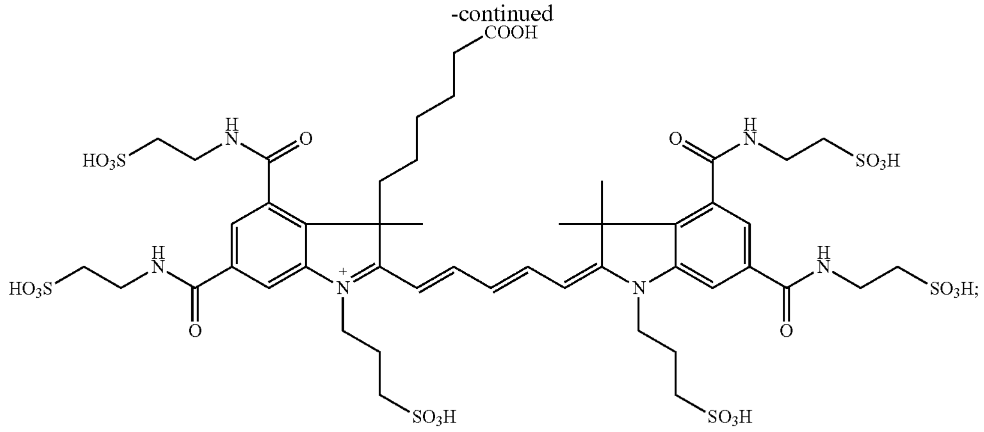
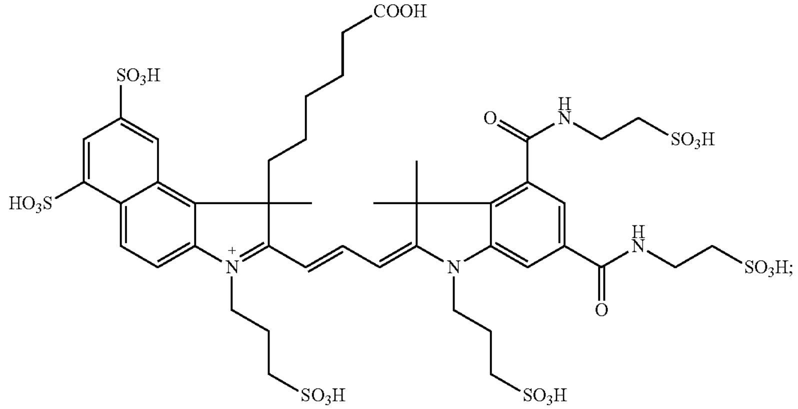
or
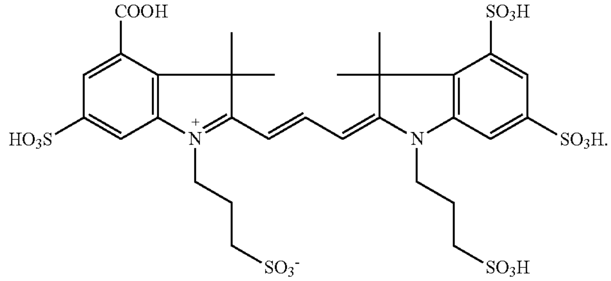
26. The compound of claim 11, wherein the compound is
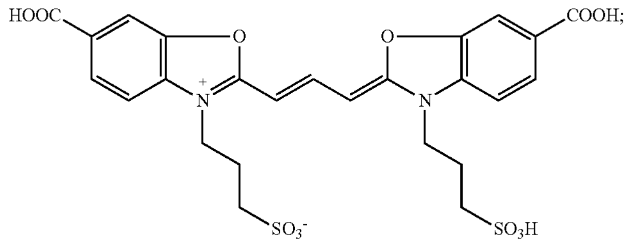
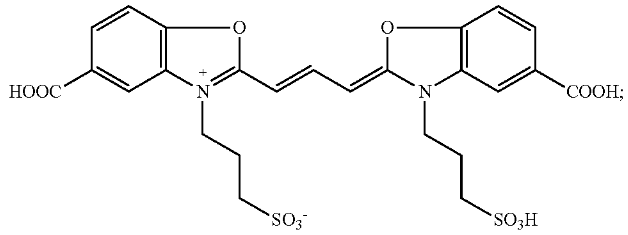

-continued
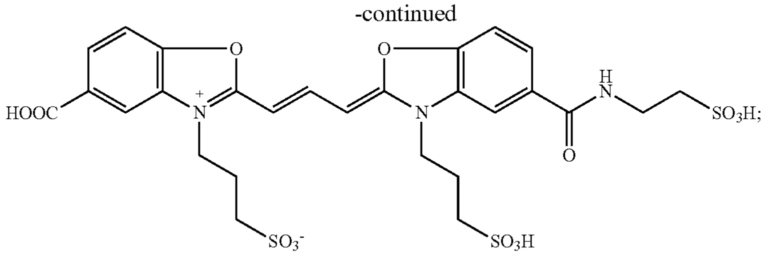
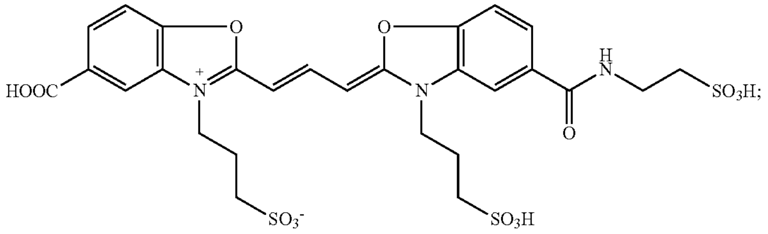
or
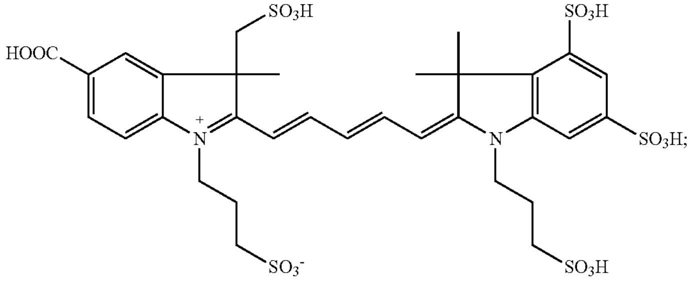
or a salt thereof.
27. The compound of claim 11, wherein the compound is
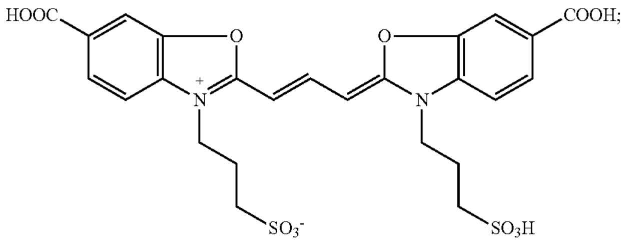
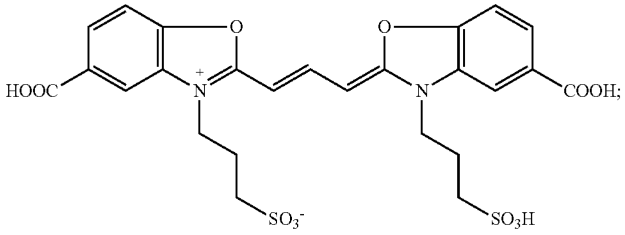
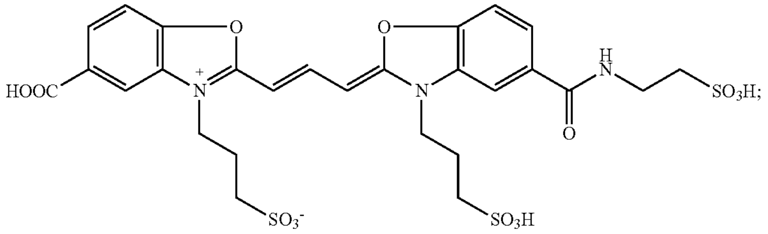

-continued
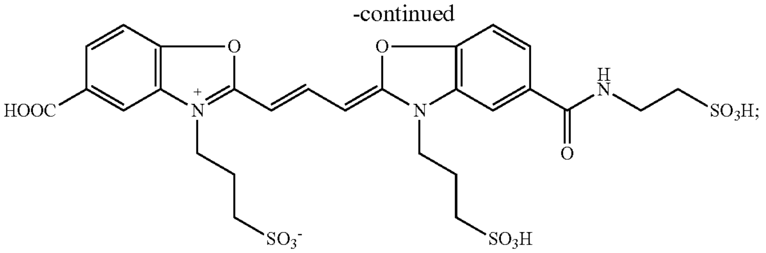
or
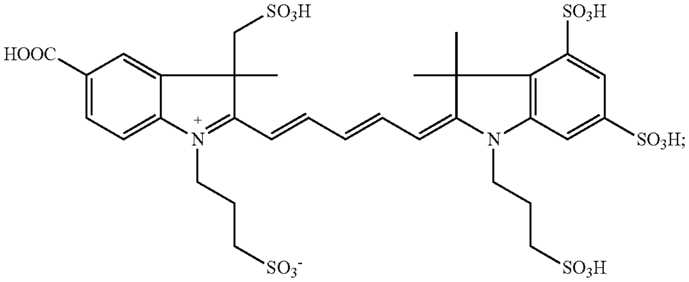
or an ionic derivative thereof.
28. The compound of claim 11, wherein the compound is
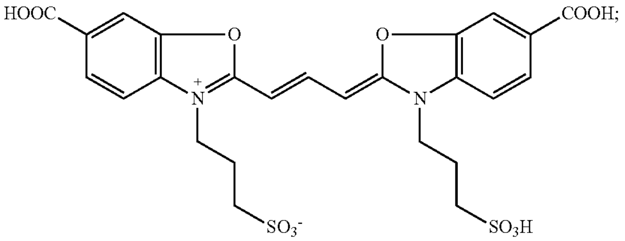
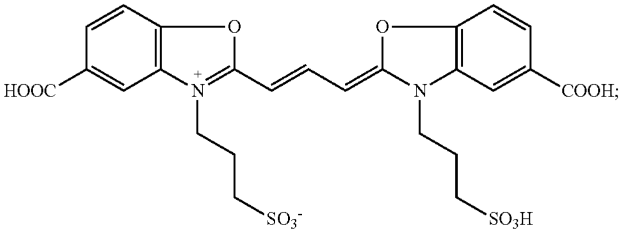
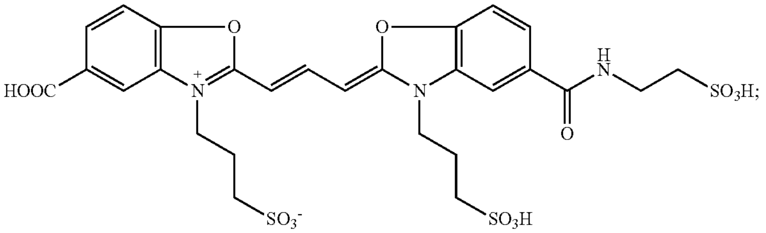
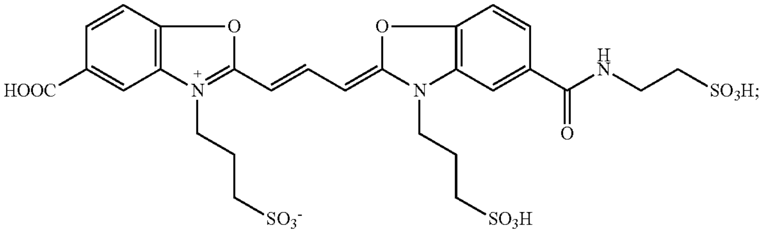
or -continued
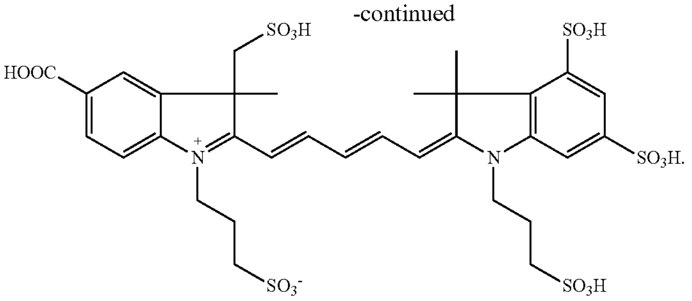
* * * * *